(12) United States Patent
Keung et al.

(10) Patent No.: US 8,129,538 B1
(45) Date of Patent: Mar. 6, 2012

(54) RENIN INHIBITORS

(75) Inventors: Walter Keung, Carlsbad, CA (US); Zhe Li, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 1000 days.

(21) Appl. No.: 12/055,510

(22) Filed: Mar. 26, 2008

Related U.S. Application Data

(60) Provisional application No. 60/908,583, filed on Mar. 28, 2007.

(51) Int. Cl.
*C07D 213/56* (2006.01)
*A61K 31/4418* (2006.01)

(52) U.S. Cl. ........................................ 546/316; 514/356

(58) Field of Classification Search .................. None
See application file for complete search history.

(56) References Cited

FOREIGN PATENT DOCUMENTS

| | | |
|---|---|---|
| WO | WO92/05174 | 4/1992 |
| WO | WO2006/021401 A2 | 3/2006 |
| WO | WO2006/021402 A1 | 3/2006 |
| WO | WO2006/021403 A1 | 3/2006 |
| WO | WO2006/058546 A1 | 6/2006 |
| WO | WO2006/059304 A2 | 6/2006 |
| WO | WO2006/061791 A2 | 6/2006 |
| WO | WO2006/064484 A1 | 6/2006 |
| WO | WO2006/074924 A1 | 7/2006 |
| WO | WO2006/079988 A1 | 8/2006 |
| WO | WO2006/094763 A1 | 9/2006 |
| WO | WO2006/125621 A1 | 11/2006 |
| WO | WO2006/128659 A2 | 12/2006 |
| WO | WO2006/129237 A2 | 12/2006 |
| WO | WO2006/131884 A2 | 12/2006 |
| WO | WO2006/131884 A3 | 12/2006 |
| WO | WO2007/034406 A1 | 3/2007 |
| WO | WO2007/034445 A2 | 3/2007 |
| WO | WO2007/049224 A1 | 5/2007 |
| WO | WO2007/077005 A1 | 7/2007 |
| WO | WO2007/088514 A1 | 8/2007 |
| WO | WO2007/099509 A2 | 9/2007 |
| WO | WO2007/099509 A3 | 9/2007 |
| WO | WO2007/102127 A2 | 9/2007 |
| WO | WO2008/058387 A1 | 5/2008 |

*Primary Examiner* — Kamal Saeed
*Assistant Examiner* — Nyeemah A Grazier
(74) *Attorney, Agent, or Firm* — Matthew J. Russo; C. Amy Smith

(57) ABSTRACT

The invention relates to compounds having the formula:

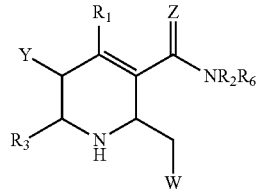

wherein the variables are as defined herein. The invention further relates to methods of making and using these compounds, and pharmaceutical compositions, kits and articles of manufacture comprise the compounds.

81 Claims, 1 Drawing Sheet

FIGURE 1

DNA Sequence Encoding First PCR Primer [SEQ ID NO: 1]

AAGCTTATGG ATGGATGGAG A

DNA Sequence Encoding Second PCR Primer [SEQ ID NO: 2]

GGATCCTCAG CGGGCCAAGG C

SEQUENCE LISTING

<160> NUMBER OF SEQ ID NOS: 2

<210> SEQ ID NO 1
<211> LENGTH: 21
<212> TYPE: DNA
<213> ORGANISM: Artificial
<220> FEATURE:
<223> OTHER INFORMATION: Synthetic Primers

<400> SEQUENCE: 1
aagcttatgg atggatggag a                    21

<210> SEQ ID NO 2
<211> LENGTH: 21
<212> TYPE: DNA
<213> ORGANISM: Artificial
<220> FEATURE:
<223> OTHER INFORMATION: Synthetic Primers

<400> SEQUENCE: 2
ggatcctcag cgggccaagg c                    21

RENIN INHIBITORS

RELATED APPLICATION

This application claims the benefit of U.S. Provisional Application Ser. No. 60/908,583, filed Mar. 28, 2007; the disclosure of which is incorporated herein by reference in its entirety.

FIELD OF THE INVENTION

The present invention relates to compounds that may be used to inhibit renin, as well as compositions of matter and kits comprising these compounds. The invention also relates to methods for inhibiting renin and treatment methods using compounds according to the present invention.

BACKGROUND OF THE INVENTION

The renin-angiotensin-aldosterone system ("RAAS") is one of the hormonal mechanisms involved in regulating pressure/volume homeostasis and also in the development of hypertension, a condition that can progress to more serious cardiovascular diseases such as congestive heart failure. Activation of RAAS begins with secretion of the enzyme renin from juxtaglomerular cells in the kidney.

Renin, a member of the aspartyl protease family, passes from the kidneys into the blood where it cleaves angiotensinogen to generate the decapeptide angiotensin I. Angiotensin I is then cleaved in the lungs, the kidneys and other organs by the angiotensin-converting enzyme (ACE) to form the octapeptide angiotensin II. Angiotensin II, which is known to work on at least two receptor subtypes ($AT_1$ and $AT_2$), increases blood pressure both directly by arterial vasoconstriction and indirectly by liberating from the adrenal glands the sodium-ion-retaining hormone aldosterone. Angiotensin II also produces other physiological effects such as promoting sodium and fluid retention, inhibiting renin secretion, increasing sympathetic nervous system activity, stimulating vasopressin secretion, causing a positive cardiac inotropic effect and modulating other hormonal systems.

Modulation of the RAAS represents a major advance in the treatment of cardiovascular diseases. In particular, the rationale to develop renin inhibitors lies in its specificity (Kleinert H. D., *Cardiovasc. Drugs*, 1995, 9, 645). The only substrate known for renin is angiotensinogen, which can only be processed (under physiological conditions) by renin. Inhibitors of the enzymatic activity of renin are therefore expected to bring about a reduction in the formation of angiotensin I and angiotensin II.

In view of the foregoing, renin is an attractive target for the discovery of new therapeutics for cardiovascular disease, hypertension, congestive heart failure, myocardial infarction, renal protection, inflammation, neurological diseases, cancer and other diseases. Accordingly, there is a need to find new renin inhibitors for use as therapeutic agents to treat human diseases.

SUMMARY OF THE INVENTION

The present invention relates to compounds that have activity for inhibiting renin. The present invention provides compounds, pharmaceutical compositions, articles of manufacture and kits comprising these compounds, and also methods of using and method of preparing these compounds.

In one aspect, the invention is directed to compounds having the formula:

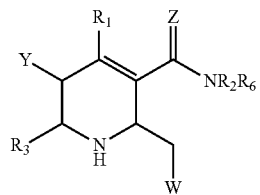

or a hydrate, solvate, tautomer, enantiomer, or pharmaceutically acceptable salt thereof, wherein Z is selected from the group consisting of O, S;

W is selected from the group consisting of cyano, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thio-carbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, $(C_{9-12})$bicycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{4-12})$bicycloaryl and hetero$(C_{4-12})$bicycloaryl, each unsubstituted or substituted;

Y is selected from the group consisting of hydrogen, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_1$ is a cyclyl moiety, unsubstituted or substituted;

$R_2$ is selected from the group consisting of hydrogen, $(C_{1-10})$alkoxy, $(C_{4-12})$aryloxy, hetero$(C_{1-10})$aryloxy, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_3$ is selected from the group consisting of hydrogen, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted; and $R_6$ is selected from the group consisting of hydrogen, $(C_{1-10})$alkoxy, $(C_{4-12})$aryloxy, hetero$(C_{1-10})$aryloxy, $(C_{1-10})$ alkyl, $(C_{1-10})$alkenyl, $(C_{1-10})$alkynyl, halo$(C_{1-40})$alkyl, hydroxy$(C_{1-10})$alkyl, carbonyl$(C_{1-10})$alkyl, thiocarbonyl $(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$ alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted.

In another aspect, the invention relates to pharmaceutical compositions that comprise a renin inhibitor according to the present invention as an active ingredient and a pharmaceutical acceptable excipient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

In another aspect, the invention provides kits and other articles of manufacture for treating disease states associated with renin. In one embodiment, a kit is provided that comprises a composition comprising at least one renin inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another aspect, the invention provides an article of manufacture that comprises a composition comprising at least one renin inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The article of manufacture may also optionally comprise additional components, such as syringes for administration of the composition. The article of manufacture may comprise the composition in single or multiple dose forms.

In another aspect, the invention is related to methods for preparing the compounds, compositions and kits according to the present invention. For example, several synthetic schemes are provided herein for synthesizing compounds according to the present invention.

In another aspect, the invention is related to reagents that may be used in the preparation of the compounds according to the invention.

In another aspect, the invention is related to methods for using compounds, compositions, kits and articles of manufacture according to the present invention. In one embodiment, the compounds, compositions, kits and articles of manufacture are used to inhibit renin.

In one embodiment, the compounds, compositions, kits and articles of manufacture are used to treat a disease state for which renin possess activity that contributes to the pathology and/or symptomology of the disease state. In another embodiment, a compound is administered to a subject wherein renin activity within the subject is altered, preferably reduced.

In another embodiment, a prodrug of a compound is administered to a subject that is converted to the compound in vivo where it inhibits renin.

In another embodiment, a method of inhibiting renin is provided that comprises contacting a renin with a compound according to the present invention.

In another embodiment, a method of inhibiting renin is provided that comprises causing a compound according to the present invention to be present in a subject in order to inhibit renin in vivo.

In another embodiment, a method of inhibiting renin is provided that comprises administering a first compound to a subject that is converted in vivo to a second compound wherein the second compound inhibits renin in vivo. It is noted that the compounds of the present invention may be the first or second compounds.

In another embodiment, a therapeutic method is provided that comprises administering a compound according to the present invention.

In another embodiment, a method of treating a condition in a patient that is known to be mediated by renin, or which is known to be treated by renin inhibitors, comprising administering to the patient a therapeutically effective amount of a compound according to the present invention.

In another embodiment, a method is provided for treating a disease state for which renin possess activity that contributes to the pathology and/or symptomology of the disease state, the method comprising: causing a compound according to the present invention to be present in a subject in a therapeutically effective amount for the disease state.

In another embodiment, a method is provided for treating a disease state for which renin possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which renin possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state that is known to be mediated by renin, or that is known to be treated by renin inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound of or having the formula" is intended to encompass the compound and all pharmaceutically acceptable ionized forms and solvates, all possible stereoisomers, all possible resonance forms and tautomers, all pharmaceutically acceptable salts and their polymorphs, unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibit renin and thus may themselves be prodrugs for another compound. Such prodrugs of another compound may or may not themselves independently have renin inhibitory activity.

BRIEF DESCRIPTION OF THE FIGURES

FIG. 1 illustrates SEQ ID NO: 1 and SEQ ID NO: 2 referred to in this application.

DEFINITIONS

Unless otherwise stated, the following terms used in the specification and claims shall have the following meanings for the purposes of this Application.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with $C_{3-8}$ rings such as cyclopropane, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkoxy" means the radical —O-alkyl; the alkyl group is as defined in this Application and can be optionally substituted.

"Alkyl" represented by itself means a straight or branched, saturated or unsaturated, aliphatic radical having a chain of carbon atoms, optionally with oxygen (See "oxaalkyl") or nitrogen atoms (See "azaalkyl") between the carbon atoms. $C_X$ alkyl and $C_{X-Y}$ alkyl are typically used where X and Y indicate the number of carbon atoms in the chain. For example, $C_{1-6}$ alkyl includes alkyls that have a chain of between 1 and 6 carbons (e.g., methyl, ethyl, propyl, isopropyl, butyl, sec-butyl, isobutyl, tert-butyl, pentyl, hexyl, vinyl, allyl, 1-propenyl, isopropenyl, 1-butenyl, 2-butenyl, 3-butenyl, 2-methylallyl, ethynyl, 1-propynyl, 2-propynyl, ethyloxymethyl, (—CH$_2$—O—CH$_2$CH$_3$), ethylaminomethyl (—CH$_2$—NH—CH$_2$CH$_3$) and the like). Alkyl represented along with another radical (e.g., as in arylalkyl, heteroarylalkyl) means a straight or branched, saturated or unsaturated aliphatic divalent radical having the number of atoms indicated or when no atoms are indicated means a bond (e.g., $(C_{6-10})$aryl$(C_{1-3})$alkyl includes, benzyl, phenylethyl, 1-phenylethyl, 3-phenylpropyl, 2-thienylmethyl, 2-pyridinylmethyl and the like).

"Alkenyl" means a straight or branched, carbon chain that contains at least one carbon-carbon double bond. Examples of alkenyl include vinyl, allyl, isopropenyl, pentenyl, hexenyl, heptenyl, 1-propenyl, 2-butenyl, 2-methyl-2-butenyl, and the like.

"Alkynyl" means a straight or branched, carbon chain that contains at least one carbon-carbon triple bond. Examples of alkynyl include ethynyl, propargyl, 3-methyl-1-pentynyl, 2-heptynyl and the like.

"Alkylene", unless indicated otherwise, means a straight or branched, saturated or unsaturated, aliphatic, divalent radical. $C_X$alkylene and $C_{X-Y}$alkylene are typically used where X and Y indicate the number of carbon atoms in the chain. For example, $C_{1-6}$alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—), 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like.

"Alkenylene" means a straight or branched, divalent carbon chain having one or more carbon-carbon double bonds. Examples of alkenylene include ethene-1,2-diyl, propene-1,3-diyl, methylene-1,1-diyl, and the like.

"Alkynylene" means a straight or branched, divalent carbon chain having one or more carbon-carbon triple bonds. Examples of alkynylene include ethyne-1,2-diyl, propyne-1,3-diyl, and the like.

"Alkylidene" means a straight or branched saturated or unsaturated, aliphatic radical connected to the parent molecule by a double bond. $C_X$alkylidene and $C_{X-Y}$alkylidene are typically used where X and Y indicate the number of carbon atoms in the chain. For example, $C_{1-6}$ alkylidene includes methylidene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like.

"Amino" means the radical —NR$_a$R$_b$, where R$_a$ and R$_b$ are each independently hydrogen or a non-hydrogen substituent. Representative amino groups include, without limits, —NH$_2$, —NHCH$_3$, —N(CH$_3$)$_2$, —NH(C$_{1-10}$)alkyl, —N((C$_{1-10}$)alkyl)$_2$, —NHaryl, —NHheteroaryl, —N(aryl)$_2$, —N(heteroaryl)$_2$, and the like. Optionally, R$_a$ and R$_b$ together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, reptiles and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (see Heteroaryl).

"Aryl" means a monocyclic or polycyclic ring assembly where all the ring atoms are carbon atoms, and at least one of the rings comprising the ring assembly is an aromatic ring. If one or more ring atoms is not carbon (e.g., N, S), the ring assembly is a heteroaryl. $C_X$ aryl and $C_{X-Y}$ aryl are typically used where X and Y indicate the number of carbon atoms in the ring.

"Azaalkyl" means an alkyl, as defined above, except where one or more substituted or unsubstituted nitrogen atoms (—N—) are positioned between carbon atoms of the alkyl. For example, an ($C_{2-6}$) azaalkyl refers to a chain comprising between 2 and 6 carbons and one or more nitrogen atoms positioned between the carbon atoms.

"Bicyclic" means a two-ringed ring assembly where the two rings are fused together, linked by a single bond or linked by two bridging atoms.

"Bicycloalkyl" means a saturated or partially unsaturated fused bicyclic or bridged polycyclic ring assembly.

"Bicycloaryl" means a ring assembly of two rings, wherein the rings are linked by a single bond or fused and at least one of the rings comprising the ring assembly is an aromatic ring. $C_X$ bicycloaryl and $C_{X-Y}$ bicycloaryl are typically used where X and Y indicate the number of carbon atoms in the bicyclic ring assembly and directly attached to the ring.

"Bridging ring" as used herein refers to a ring that is bonded to another ring to form a compound having a bicyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NR$_a$R$_b$ where R$_a$ and R$_b$ are each independently hydrogen or a non-hydrogen substituent.

"Carbocycle" means a ring consisting of carbon atoms.

"Carbocyclic ketone derivative" means a carbocyclic derivative wherein the ring contains a —C(=O)— moiety.

"Carbonyl" typically means a divalent radical —C(=O)—. It is noted that the term "carbonyl" when referring to a monovalent substituent can alternatively refer to a substituted carbonyl or acyl group, —C(=O)R$_a$, where R$_a$ is hydrogen or a non-hydrogen substituent on the carbonyl carbon, forming different carbonyl-containing groups including acids, acid halides, aldehydes, amides, esters, and ketones.

"Carboxy" typically means a divalent radical —C(O)O—. It is noted that the term "carboxy" when referring to a monovalent substituent means a substituted carboxy, —C(O)OR$_a$, where R$_a$ is hydrogen or a non-hydrogen substituent on the carboxyl group forming different carboxy containing groups including acids and esters. It is further noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a radical comprising a non-aromatic, saturated or partially unsaturated, monocyclic, fused or bridged polycyclic ring assembly. $C_X$ cycloalkyl and $C_{X-Y}$ cycloalkyl are typically used where X and Y indicate the number of carbon atoms in the ring assembly. For example, $C_{3-10}$ cycloalkyl includes cyclopropyl, cyclobutyl, cyclopentyl, cyclohexyl, cyclohexenyl, 2,5-cyclohexadienyl, bicyclo [2.2.2]octyl, adamantan-1-yl, decahydronaphthyl, oxocyclohexyl, dioxocyclohexyl, thiocyclohexyl, 2-oxobicyclo[2.2.1] hept-1-yl, and the like.

"Cycloalkylene" means a divalent radical comprising a saturated or partially unsaturated, monocyclic or polycyclic ring assembly. $C_X$ cycloalkylene and $C_{X-Y}$ cycloalkylene are typically used where X and Y indicate the number of carbon atoms in the ring assembly.

"Cyclyl" means a mono- or polycyclic radical, typically a mono-, bi- or tricyclic, unsaturated, partially saturated or saturated ring system with typically 3 to 22, more typically 3 to 14, most typically 3-7, ring atoms and is unsubstituted or substituted by one or more substituents independently selected typically from the substituents as defined in this Application.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a multi-ring assembly wherein the rings comprising the ring assembly are so linked that the ring atoms that are common to two rings are directly bound to each other. The fused ring assemblies may be saturated, partially saturated, carbocyclics, heterocyclics, aromatics, heteroaromatics, and the like. Non-exclusive examples of common fused rings include decalin, naphthalene, anthracene, phenanthrene, indole, benzofuran, purine, quinoline, and the like.

"Halo" means fluoro, chloro, bromo or iodo.

"Halo-substituted alkyl", as an isolated group or part of a larger group, means "alkyl" substituted by one or more "halo" atoms, as such terms are defined in this Application. Halo-substituted alkyl includes haloalkyl, dihaloalkyl, trihaloalkyl, perhaloalkyl and the like (e.g., halo-substituted ($C_{1-3}$)alkyl includes chloromethyl, dichloromethyl, difluoromethyl, trifluoromethyl, 2,2,2-trifluoroethyl, perfluoroethyl, 2,2,2-trifluoro-1,1-dichloroethyl, and the like).

"Heteroalkyl" means alkyl, as defined in this Application, provided that one or more of the atoms within the alkyl chain is a heteroatom.

"Heteroaryl" means a monocyclic or polycyclic ring assembly wherein at least one ring atom is a heteroatom and the remaining ring atoms are carbon, and at least one of the rings comprising the ring assembly is an aromatic ring. Monocyclic heteroaryl groups include, but are not limited to, cyclic aromatic groups having five or six ring atoms, wherein at least one ring atom is a heteroatom and the remaining ring atoms are carbon. The nitrogen atoms of such heteroaryl rings can be optionally quaternerized and the sulfur atoms of such heteroaryl rings can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes polycyclic ring assemblies, wherein a heteroaromatic ring is fused or linked by a bond to one or more rings independently selected from the group consisting of an aromatic ring, a cycloalkyl ring, a cycloalkenyl ring, a heterocycloalkyl ring and another heteroaromatic ring. Bicyclic or tricyclic heteroaryls include, but are not limited to, those derived from benzo[b]furan, benzo[b]thiophene, benzimidazole, imidazo [4,5-c]pyridine, quinazoline, thieno[2,3-c]pyridine, thieno[3, 2-b]pyridine, thieno[2,3-b]pyridine, indolizine, imidazo[1, 2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo [1,5-a]pyrimidine, imidazo[1,5-c]pyrimidine, pyrrolo[2,3-b] pyridine, pyrrolo[2,3-c]pyridine, pyrrolo[3,2-c]pyridine, pyrrolo[3,2-b]pyridine, pyrrolo[2,3-d]pyrimidine, pyrrolo[3, 2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1, 5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The polycylic heteroaryl ring assembly can be attached to the parent molecule through either the heteroaryl group itself or the aryl, cycloalkyl, cycloalkenyl or heterocycloalkyl group to which it is fused. The heteroaryl groups of this invention can be substituted or unsubstituted.

"Heterobicycloaryl" means bicycloaryl, as defined in this Application, provided that one or more of the atoms within the ring assembly is a heteroatom. For example, hetero $(C_{4-12})$bicycloaryl as used in this Application includes, but is not limited to, indoline, 2-amino-4-oxo-3,4-dihydropteridin-6-yl, tetrahydroisoquinolinyl, and the like.

"Heterocycloalkyl" means cycloalkyl, as defined in this Application, provided that one or more of the atoms forming the ring is a heteroatom. Non-exclusive examples of heterocycloalkyl include piperidyl, 4-morpholyl, 4-piperazinyl, pyrrolidinyl, perhydropyrrolizinyl, 1,3-dioxanyl, 1,4-dioxanyl and the like.

"Heteroatom" refers to an atom that is not a carbon atom. Particular examples of heteroatoms include, but are not limited to nitrogen, oxygen, and sulfur.

"Heteroatom moiety" includes a moiety where the atom by which the moiety is attached is not a carbon. Examples of heteroatom moieties include —N=, —NR—, —N$^+$(O$^-$)=, —O—, —S— or —S(O)$_2$—, wherein R is hydrogen or a non-hydrogen substituent.

"Heterobicycloalkyl" means bicycloalkyl, as defined in this Application, provided that one or more of the atoms within the ring is a heteroatom. For example hetero$(C_{9-12})$ bicycloalkyl as used in this application includes, but is not limited to, 3-aza-bicyclo[4.1.0]hept-3-yl, 2-aza-bicyclo [3.1.0]hex-2-yl, 3-aza-bicyclo[3.1.0]hex-3-yl, and the like.

"Heterocyclyl" refers to a mono- or polycyclic radical, typically a mono-, bi- or tricyclic, unsaturated, partially saturated or saturated ring system with typically 3 to 22, more typically 3 to 14, most typically 3-7, ring atoms, and with one or more, preferably one to four, heteroatoms independently selected from nitrogen, oxygen, sulfur, S(=O)—, —S(=O)$_2$—, and is unsubstituted or substituted by one or more substituents independently selected typically from the substituents defined in this Application.

"Heterocycloalkylene" means cycloalkylene, as defined in this Application, provided that one or more of the ring member carbon atoms is replaced by a heteroatom.

"Hydroxy" means the radical —OH.

"IC$_{50}$" refers to the molar concentration of an inhibitor that produces 50% inhibition of the target enzyme.

"Iminoketone derivative" means a derivative comprising the moiety —C(=NR)—, wherein R is hydrogen or a non-hydrogen substituent attached to the nitrogen.

"Isomers" mean any compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four different substituents (where no two are the same) is termed a "chiral center." A compound with one chiral center has two enantiomeric forms of opposite chirality. A mixture of equal amounts of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-s sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means a moiety that can be displaced by another moiety, such as by nucleophilic attack, during a chemical reaction. Leaving groups are well known in the art and include, for example, halides and OSO$_2$R' where R' is, for example, alkyl, haloalkyl, or aryl optionally substituted by halo, alkyl, alkoxy, amino, and the like. Non-limiting examples of leaving groups include chloro, bromo, iodo, mesylate, tosylate, and other similar groups.

"Moiety" means an interconnected group of atoms, generally referred to by its most characteristic structural component. For example, a "carbonyl moiety" refers to groups that contain a carbonyl group.

"Nitro" means the radical —NO$_2$.

"Oxaalkyl" means an alkyl, as defined above, except where one or more oxygen atoms (—O—) are positioned between carbon atoms of the alkyl. For example, an $(C_{2-6})$oxaalkyl refers to a chain comprising between 2 and 6 carbons wherein one or more oxygen atoms is positioned between two carbon atoms.

"Oxy" typically means the radical —O—. It is noted that the term "oxy" when referring to a monovalent radical can alternatively refer to a substituents oxy group, —OR—, where R is hydrogen or a non-hydrogen substituent on the oxy radical forming oxy-containing groups including hydroxy, alkoxy, aryloxy, heteroaryloxy and carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo [2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Prodrug" means a compound that is convertible in vivo metabolically into an inhibitor according to the present invention. The prodrug itself may or may not also have renin inhibitory activity. For example, an inhibitor comprising a hydroxy group may be administered as an ester that is converted by hydrolysis in vivo to the hydroxy compound. Suitable esters that may be converted in vivo into hydroxy compounds include acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, an inhibitor comprising an amine group may be administered as an amide or as an N-alkyl (particularly N-methyl or N-ethyl) that is converted by hydrolysis or oxidation in vivo to the amine compound.

"Protected derivatives" means derivatives of inhibitors in which a reactive site or sites are blocked with protecting groups. Protected derivatives are useful in the preparation of inhibitors or in themselves may be active as inhibitors. Examples of protected group includes, but are not limited to, acetyl, tetrahydropyran, methoxymethyl ether, β-methoxyethoxymethyl ether, ρ-methoxybenzyl, methylthiomethyl ether, pivaloyl, silyl ether, carbobenzyloxy, benzyl, tert-butoxycarbonyl, ρ-methoxyphenyl, 9-fluorenylmethyloxycarbonyl, acetals, ketals, acylals, dithianes, methylesters, benzyl esters, tert-butyl esters, and silyl esters. A comprehensive list of suitable protecting groups can be found in T. W. Greene, *Protecting Groups in Organic Synthesis,* 3rd edition, John Wiley & Sons, Inc. 1999.

"Ring" means a carbocyclic or a heterocyclic system.

"Substituent convertible to hydrogen in vivo" means any group that is convertible to a hydrogen atom by enzymological or chemical means including, but not limited to, hydrolysis, reduction and oxidation. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl (—(O)CO—C(CH$_3$)$_3$), benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; —C(O)CH (NH2)CH$_3$), Arg (arginine), Asn (asparagine), Asp (aspartic acid), Cys (cysteine), Glu (glutamic acid), H is (histidine), Ile (isoleucine), Leu (leucine; —C(O)CH(NH$_2$)CH$_2$CH(CH$_3$)$_2$), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups (—(O) CO—C(CH$_3$)$_3$), and the like. Suitable peptide residues include peptide residues comprising two to five, and optionally two to three, of the aforesaid amino acid residues. Examples of such peptide residues include, but are not limited to, residues of such peptides as Ala-Ala (—C(O)CH(NH) CH$_3$—C(O)CH(NH$_2$)CH$_3$)), Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups (—(O)CO—C(CH$_3$)$_3$), and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxy-benzyloxycarbonyl); and halogenoethoxycarbonyl groups (such as β,β,β-trichloroethoxycarbonyl and β-iodoethoxycarbonyl). Further examples of substituents "convertible to hydrogen in vivo" include enzymatic oxidizable groups such as N-alkyls, particularly N-methyl and N-ethyl.

"Substituted or unsubstituted" or "optionally substituted" means that a given moiety may consist of only hydrogen atoms bound at available valences (unsubstituted) or may further comprise one or more non-hydrogen atoms bound through available valencies (substituted). The substituents of an "optionally substituted" group may include, without limitation, one or more substituents independently selected from the group or designated subsets thereof, aldehyde, (C$_{1-10}$) alkyl, alkylene, alkylidene, amide, amino, aminoalkyl, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted.

In one particular embodiment, examples of substituents include, but are not limited to, hydrogen, halo, nitro, cyano, thio, oxy, hydroxy, carbonyloxy, (C$_{1-10}$)alkoxy, (C$_{4-14}$)aryloxy, (C$_{1-13}$)heteroaryloxy, carbonyl, oxycarbonyl, aminocarbonyl, amino, (C$_{1-10}$)alkylamino, sulfonamido, imino, sulfonyl, sulfinyl, (C$_{1-10}$)alkyl, (C$_{1-10}$)haloalkyl, hydroxy (C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$)alkyl, (C$_{1-10}$)azaalkyl, imino(C$_{1-10}$)alkyl, (C$_{3-12}$)cycloalkyl(C$_{1-5}$)alkyl, (C$_{3-12}$)heterocycloalkyl(C$_{1-10}$)alkyl, aryl(C$_{1-10}$)alkyl, (C$_{1-10}$)heteroaryl(C$_{1-5}$)alkyl, (C$_{9-12}$)bicycloaryl(C$_{1-5}$)alkyl, (C$_{8-12}$)heterobicycloaryl(C$_{1-5}$)alkyl, (C$_{3-12}$)cycloalkyl, (C$_{3-12}$) heterocycloalkyl, (C$_{9-12}$)bicycloalkyl, (C$_{3-12}$) heterobicycloalkyl, (C$_{4-12}$)aryl, (C$_{1-10}$)heteroaryl, (C$_{9-12}$) bicycloaryl and (C$_{4-12}$)heterobicycloaryl, the substituents are as defined herein. In addition, the substituent is itself optionally substituted by a further substituent. In one particular embodiment, examples of the further substituent include, but are not limited to, hydrogen, halo, nitro, cyano, thio, oxy, hydroxy, carbonyloxy, ($C_{1-10}$)alkoxy, ($C_{4-12}$)aryloxy, ($C_{1-10}$) heteroaryloxy, carbonyl, oxycarbonyl, aminocarbonyl, amino, ($C_{1-10}$)alkylamino, sulfonamido, imino, sulfonyl, sulfinyl, ($C_{1-10}$)alkyl, ($C_{1-10}$)haloalkyl, hydroxy($C_{1-10}$)alkyl, carbonyl($C_{1-10}$)alkyl, thiocarbonyl($C_{1-10}$)alkyl, sulfonyl ($C_{1-10}$)alkyl, sulfinyl($C_{1-10}$)alkyl, ($C_{1-10}$)azaalkyl, imino ($C_{1-10}$)alkyl, ($C_{3-12}$)cycloalkyl($C_{1-5}$)alkyl, ($C_{3-12}$)heterocycloalkyl($C_{1-10}$)alkyl, aryl($C_{1-10}$)alkyl, ($C_{1-10}$)heteroaryl ($C_{1-5}$)alkyl, ($C_{9-12}$)bicycloaryl($C_{1-5}$)alkyl, ($C_{8-12}$)heterobicycloaryl($C_{1-5}$)alkyl, ($C_{3-12}$)cycloalkyl, ($C_{3-12}$)heterocycloalkyl, ($C_{9-12}$)bicycloalkyl, ($C_{3-12}$)heterobicycloalkyl, ($C_{4-12}$)aryl, ($C_{1-10}$)heteroaryl, ($C_{9-12}$)bicycloaryl and ($C_{4-12}$) heterobicycloaryl, the substituents are as defined herein.

"Sulfinyl" means the radical —S(O)—. It is noted that the term "sulfinyl" when referring to a monovalent substituent can alternatively refer to a substituted sulfinyl group, —S(=O)R, where R is hydrogen or a non-hydrogen substituent on the sulfur atom forming different sulfinyl groups including sulfinic acids, sulfinamides, sulfinyl esters, and sulfoxides.

"Sulfonyl" means the radical —S(O)$_2$—. It is noted that the term "sulfonyl" when referring to a monovalent substituent can alternatively refer to a substituted sulfonyl group, —S(=O)$_2$R, where R is hydrogen or a non-hydrogen substituent on the sulfur atom forming different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thiocarbonyl" means the radical —C(S)—. It is noted that the term thiocarbonyl when referring to a monovalent substituent can alternatively refer to a substituted thiocarbonyl group, —C(=S)$_2$R, where R is hydrogen or a non-hydrogen substituent on the carbon atom forming different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is not a hydrogen atom. Hence, —CF$_3$, —CH$_2$OH and —CH$_2$CN, for example, are all $C_1$ alkyls.

It is noted in regard to all of the definitions provided herein that the definitions should be interpreted as being open ended in the sense that further substituents beyond those specified may be included. Hence, a $C_1$ alkyl indicates that there is one carbon atom but does not indicate what are the substituents on the carbon atom. Hence, a $C_1$ alkyl comprises methyl (i.e., —CH$_3$) as well as —CR$_a$R$_b$R$_c$ where R$_a$, R$_b$, and R$_c$ may each independently be hydrogen or any other substituent where the atom attached to the carbon is a heteroatom or cyano. Hence, CF$_3$, CH$_2$OH and CH$_2$CN, for example, are all $C_1$ alkyls.

DETAILED DESCRIPTION OF THE INVENTION

The present invention relates to compounds, pharmaceutical compositions, kits and articles of manufacture that may be used to inhibit renin. The present invention also relates to methods for inhibiting renin and treatment methods using compounds according to the present invention. The present invention further relates to methods for the preparation of the renin inhibitors of the invention, and to compounds that are useful for the preparation of the renin inhibitors of the invention.

It is noted that the compounds of the present invention may also possess inhibitory activity for other aspartyl proteases (e.g., pepsin, gastricsin, napsin, BACE 1 & 2 and cathepsin D and E) and thus may be used to address disease states associated with these other family members. In addition, the compounds of the present invention may be useful as inhibitors of plasmepsins to treat malaria and as inhibitors of *Candida albicans* secreted aspartyl proteases to treat fungal infections.

In one aspect, the invention is directed to compounds that are active against renin.

In one embodiment, compounds of the present invention are of the formula:

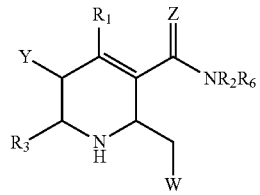

or a hydrate, solvate, tautomer, enantiomer, or pharmaceutically acceptable salt thereof, wherein W is selected from the group consisting of cyano, hydroxy, carbonyloxy, ($C_{1-10}$)alkoxy, ($C_{4-12}$)aryloxy, hetero($C_{1-10}$) aryloxy, carbonyl, oxycarbonyl, aminocarbonyl, amino, ($C_{1-10}$)alkylamino, sulfonamido, imino, ($C_{1-10}$)alkyl, halo ($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl ($C_{1-10}$)alkyl, aza($C_{1-10}$)alkyl, ($C_{1-10}$)oxaalkyl, ($C_{1-10}$) oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero ($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$) bicycloaryl and hetero($C_{4-12}$)bicycloaryl, each unsubstituted or substituted;

Y is selected from the group consisting of hydrogen, cyano, hydroxy, ($C_{1-10}$)alkoxy, ($C_{4-12}$)aryloxy, hetero($C_{1-10}$)aryloxy, aminocarbonyl, amino, ($C_{1-10}$)alkylamino, sulfonamido, imino, ($C_{1-10}$)alkyl, halo($C_{1-10}$)alkyl, hydroxy($C_{1-10}$) alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$) cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

Z is selected from the group consisting of O and S;

$R_1$ is a cyclyl moiety, unsubstituted or substituted;

$R_2$ is selected from the group consisting of hydrogen, ($C_{1-10}$)alkoxy, ($C_{4-12}$)aryloxy, hetero($C_{1-10}$)aryloxy, ($C_{1-10}$)alkyl, hetero($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$R_3$ is selected from the group consisting of hydrogen, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted; and $R_6$ is selected from the group consisting of hydrogen, ($C_{1-10}$)alkoxy, ($C_{4-12}$)aryloxy, hetero($C_{1-10}$)aryloxy, ($C_{1-10}$)alkyl, ($C_{1-10}$)alkenyl, ($C_{1-10}$)alkynyl, halo($C_{1-40}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted.

In another embodiment, the compounds of the present invention are of the formula:

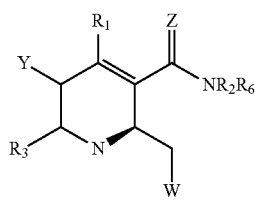

or a hydrate, solvate, tautomer, enantiomer, or pharmaceutically acceptable salt thereof,
wherein
W is selected from the group consisting of cyano, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

Y is selected from the group consisting of hydrogen, cyano, hydroxy, ($C_{1-10}$)alkoxy, ($C_{4-12}$)aryloxy, hetero($C_{1-10}$)aryloxy, aminocarbonyl, amino, ($C_{1-10}$)alkylamino, sulfonamido, imino, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

Z is selected from the group consisting of O and S;

$R_1$ is a cyclyl moiety, unsubstituted or substituted;

$R_2$ is selected from the group consisting of hydrogen, ($C_{1-10}$)alkoxy, ($C_{4-12}$)aryloxy, hetero($C_{1-10}$)aryloxy, ($C_{1-10}$)alkyl, hetero($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$R_3$ is selected from the group consisting of hydrogen, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted; and $R_6$ is selected from the group consisting of hydrogen, ($C_{1-10}$)alkoxy, ($C_{4-12}$)aryloxy, hetero($C_{1-10}$)aryloxy, ($C_{1-10}$)alkyl, ($C_{1-10}$)alkenyl, ($C_{1-10}$)alkynyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted.

In another embodiment, the compounds of the invention are of the formula:

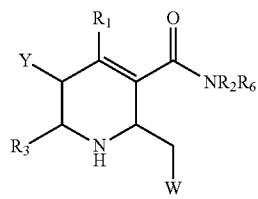

or a hydrate, solvate, tautomer, enantiomer, or pharmaceutically acceptable salt thereof, wherein W is selected from the group consisting of cyano, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

Y is selected from the group consisting of hydrogen, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_1$ is a cyclyl moiety, unsubstituted or substituted;

$R_2$ is selected from the group consisting of hydrogen, $(C_{1-10})$alkoxy, $(C_{4-12})$aryloxy, hetero$(C_{1-10})$aryloxy, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl;

$R_3$ is selected from the group consisting of hydrogen, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted; and $R_6$ is selected from the group consisting of hydrogen, $(C_{1-10})$alkoxy, $(C_{4-12})$aryloxy, hetero$(C_{1-10})$aryloxy, $(C_{1-10})$alkyl, $(C_{1-10})$alkenyl, $(C_{1-10})$alkynyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted.

In other embodiment, the compounds of the present invention are of the formula:

$$\text{structure with } R_1, Y, R_3, N-H, NR_2R_6, O, W$$

or a hydrate, solvate, tautomer, enantiomer, or pharmaceutically acceptable salt thereof, wherein W is selected from the group consisting of cyano, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

Y is selected from the group consisting of hydrogen, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_1$ is a cyclyl moiety, unsubstituted or substituted;

$R_2$ is selected from the group consisting of hydrogen, $(C_{1-10})$alkoxy, $(C_{4-12})$aryloxy, hetero$(C_{1-10})$aryloxy, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl;

$R_3$ is selected from the group consisting of hydrogen, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted; and $R_6$ is selected from the group consisting of hydrogen, $(C_{1-10})$alkoxy, $(C_{4-12})$aryloxy, hetero$(C_{1-10})$aryloxy, $(C_{1-10})$alkyl, $(C_{1-10})$alkenyl, $(C_{1-10})$alkynyl, halo$(C_{1-40})$alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted.

In another embodiment, the compounds of the present invention are of the formula:

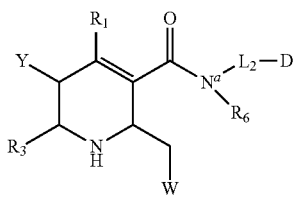

or a hydrate, solvate, tautomer, enantiomer, or pharmaceutically acceptable salt thereof, wherein $N^a$ denotes a nitrogen atom;

D is selected from the group consisting of hydrogen, ($C_{1-10}$)alkoxy, ($C_{4-12}$)aryloxy, hetero($C_{1-10}$)aryloxy, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$L_2$ is absent or is a linker providing 1 or 2 atom separation between D and $N^a$ to which $L_2$ is attached, wherein the atoms of $L_2$ providing the separation are carbon atoms;

W is selected from the group consisting of cyano, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

Y is selected from the group consisting of hydrogen, cyano, hydroxy, ($C_{1-10}$)alkoxy, ($C_{4-12}$)aryloxy, hetero($C_{1-10}$)aryloxy, aminocarbonyl, amino, ($C_{1-10}$)alkylamino, sulfonamido, imino, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$R_1$ is a cyclyl moiety unsubstituted or substituted;

$R_3$ is selected from the group consisting of hydrogen, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, amino($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted; and $R_6$ is selected from the group consisting of hydrogen, ($C_{1-10}$)alkoxy, ($C_{4-12}$)aryloxy, hetero($C_{1-10}$)aryloxy, ($C_{1-10}$)alkyl, ($C_{1-10}$)alkenyl, ($C_{1-10}$)alkynyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted.

In another embodiment, the compounds of the present invention are of the formula:

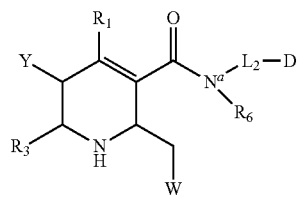

or a hydrate, solvate, tautomer, enantiomer, or pharmaceutically acceptable salt thereof, wherein $N^a$ denotes a nitrogen atom;

D is selected from the group consisting of hydrogen, ($C_{1-10}$)alkoxy, ($C_{4-12}$)aryloxy, hetero($C_{1-10}$)aryloxy, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$L_2$ is absent or is a linker providing 1 or 2 atom separation between D and $N^a$ to which $L_2$ is attached, wherein the atoms of $L_2$ providing the separation are carbon atoms;

W is selected from the group consisting of cyano, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

Y is selected from the group consisting of hydrogen, cyano, hydroxy, ($C_{1-10}$)alkoxy, ($C_{4-12}$)aryloxy, hetero($C_{1-10}$)aryloxy, aminocarbonyl, amino, ($C_{1-10}$)alkylamino, sulfonamido, imino, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

$R_1$ is a cyclyl moiety unsubstituted or substituted;

$R_3$ is selected from the group consisting of hydrogen, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, amino($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted; and $R_6$ is selected from the group consisting of hydrogen, ($C_{1-10}$)alkoxy, ($C_{4-12}$)aryloxy, hetero($C_{1-10}$)aryloxy, ($C_{1-10}$)alkyl, ($C_{1-10}$)alkenyl, ($C_{1-10}$)alkynyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted.

$R_3$

In some variations of the above embodiments of the compounds of the invention, $R_3$ is selected from the group consisting of hydrogen, ($C_{1-10}$)alkyl, ($C_{1-10}$)azaalkyl, ($C_{1-10}$)oxaalkyl, ($C_{1-10}$)oxoalkyl, hetero($C_{1-10}$)alkyl, halo($C_{1-10}$)alkyl, hydroxy($C_{1-10}$)alkyl, and amino($C_{1-10}$)alkyl, each unsubstituted or substituted.

In other variations, $R_3$ is selected from the group consisting of hydrogen, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, hetero($C_{1-10}$)alkyl, ($C_{3-12}$)cycloalkyl, hetero($C_{3-12}$)cycloalkyl, ($C_{4-12}$)aryl, hetero($C_{1-10}$)aryl, each unsubstituted or substituted.

In other variations, $R_3$ is selected from the group consisting of hydrogen, ($C_{1-10}$)alkyl, hetero($C_{1-10}$)alkyl, halo($C_{1-10}$)alkyl, hydroxy($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, and hetero($C_{1-10}$)aryl($C_{1-5}$)alkyl, each unsubstituted or substituted.

In other variations, $R_3$ is selected from the group consisting of hydrogen, unsubstituted ($C_{1-10}$)alkyl, or substituted ($C_{1-10}$)alkyl. In other variations, $R_3$ is unsubstituted ($C_{1-10}$)alkyl. In other variations, $R_3$ is substituted ($C_{1-10}$)alkyl. In other variations, $R_3$ is hydrogen.

$R_6$

In some variations of the above embodiments and variations of the compounds of the invention, $R_6$ is selected from the group consisting of hydrogen, ($C_{1-10}$)alkyl, ($C_{1-10}$)alkenyl, ($C_{1-10}$)alkynyl, ($C_{4-12}$)aryl, hetero($C_{1-10}$)aryl, ($C_{3-12}$)cycloalkyl, hetero($C_{3-12}$)cycloalkyl, aryl($C_{1-10}$)alkyl, hetero($C_{1-10}$)aryl($C_{1-5}$)alkyl, ($C_{3-12}$)cycloalkyl($C_{1-5}$)alkyl, hetero($C_{3-12}$)cycloalkyl($C_{1-10}$)alkyl, each unsubstituted or substituted.

In other variations, $R_6$ is selected from the group consisting of hydrogen, ($C_{1-7}$)alkyl, halo($C_{1-7}$)alkyl, di-phenyl($C_{1-7}$)alkyl, cyclo($C_{3-8}$)alkyl, naphthyl($C_{1-7}$)alkyl, halo substituted-phenyl($C_{1-7}$)alkyl, and phenyl, each unsubstituted or substituted with up to three substituents independently selected from the group consisting of ($C_{1-7}$)alkyl, halo, ($C_{1-7}$)alkoxy, ($C_{1-7}$)alkoxy($C_{1-7}$)alkyloxy.

In other variations, $R_6$ is selected from the group consisting of hydrogen, unsubstituted or substituted ($C_{1-7}$)alkyl, and unsubstituted or substituted ($C_{3-8}$)cycloalkyl. In other variations, $R_6$ is selected from the group consisting of unsubstituted or substituted ($C_{3-8}$)cycloalkyl.

In still other variations, $R_6$ is selected from the group consisting of unsubstituted or substituted ($C_{1-7}$)alkyl. In still other variations, $R_6$ is cyclopropyl, cyclopropylmethyl (cPrCH$_2$—), isopropyl, propyl, isobutyl, methyl, ethyl, butyl, —CH$_2$CH$_2$F, —CH$_2$CHF$_2$ and —CH$_2$CF$_3$. In still other variations, $R_6$ is selected from the group consisting of isopropyl, propyl, isobutyl, cyclopropyl, ethyl, —CH$_2$CH$_2$F, —CH$_2$CHF$_2$ and —CH$_2$CF$_3$. In still other variations, $R_6$ is selected from the group consisting of isopropyl, isobutyl, cyclopropyl, —CH$_2$CH$_2$F, —CH$_2$CHF$_2$ and —CH$_2$CF$_3$. In yet still other variations, when present, $R_6$ is selected from the group consisting of —CH$_2$CH$_2$F, —CH$_2$CHF$_2$ and —CH$_2$CF$_3$. In yet still other variations, $R_6$ is selected from the group consisting of isopropyl, isobutyl and cyclopropyl. In yet still other variations, $R_6$ is cyclopropyl.

Y

In some variations of the above embodiments and variations, when present, Y is selected from the group consisting of hydrogen, hydroxyl, ($C_{1-7}$)alkyloxy, ($C_{1-7}$)alkoxy($C_{1-7}$)alkyloxy, alkoxy($C_{1-7}$)alkyl, ($C_{1-7}$)alkanoylamino, ($C_{1-7}$)alkylsulfonylamino, arylsulfonylamino, hydroxyalkyl, aminoalkyl, ($C_{1-7}$)alkyl, and amino, each unsubstituted or substituted. In other variations, when present, Y is selected from the group consisting of H, —OH, —NH$_2$, —CH$_2$OH, —CH$_2$OCH$_3$, —NHC(O)CH$_3$, —CH$_2$CH(OH)CH$_2$OH, —CH$_2$CH(OH)CH$_2$OCH$_3$, —OCH$_2$CH(OH)CH$_2$OCH$_3$, and —OCH$_2$CH(OH)CH$_2$OH.

In some particular variations of the above embodiment and variations, Y is -L$_1$-R$_5$, where L$_1$ is absent or is a linker providing 1, 2, or 3 atom separation between the ring carbon and R$_5$ to which L$_1$ is attached, wherein the atoms of L$_1$ providing the separation are selected from the group consisting of carbon, oxygen, nitrogen, and sulfur; and R$_5$ is selected from the group consisting of hydrogen, halo, nitro, cyano, thio, oxy, hydroxy, carbonyloxy, ($C_{1-10}$)alkoxy, ($C_{4-12}$)aryloxy, hetero($C_{1-10}$)aryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, hydroxy($C_{1-10}$)alkyl, carbonyl($C_{1-10}$)alkyl, thiocarbonyl($C_{1-10}$)alkyl, sulfonyl($C_{1-10}$)alkyl, sulfinyl($C_{1-10}$)alkyl, aza($C_{1-10}$)alkyl, ($C_{1-10}$)oxaalkyl, ($C_{1-10}$)oxoalkyl, imino($C_{1-10}$)alkyl, ($C_{3-12}$)cycloalkyl($C_{1-5}$)alkyl, hetero($C_{3-12}$)cycloalkyl($C_{1-10}$)alkyl, aryl($C_{1-10}$)alkyl, hetero($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, hetero($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted.

In the variations where Y is -L$_1$-R$_5$, L$_1$ is absent or is selected from the group consisting of (C$_{1-7}$)alkylene, —O—, —S—, —NH—, —N(R$_9$)— and (C$_{1-7}$)alkyleneoxy, where R$_9$ is hydrogen or unsubstituted or substituted alkyl. In other variations L$_1$ is absent or is selected from the group consisting of methylene, —O— and —NH—. In other variations L$_1$ is absent or is methylene. In the variations where Y is -L$_1$-R$_5$, L$_1$ is selected from the group disclosed above, R$_5$ is selected from the group consisting of hydrogen, cyano, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$) alkylamino, sulfonamido, imino, sulfonyl, sulfinyl, (C$_{1-10}$) alkyl, halo(C$_{1-10}$)alkyl, hetero(C$_{1-10}$)alkyl, (C$_{3-12}$) cycloalkyl, hetero(C$_{3-12}$)cycloalkyl, (C$_{4-12}$)aryl, and hetero (C$_{1-10}$)aryl, each unsubstituted or substituted. In other variations R$_5$ is selected from the group consisting of hydrogen, hydroxy, carbonyl, (C$_{1-7}$)alkyl, (C$_{1-7}$)alkoxy(C$_{1-7}$)alkyl, (C$_{1-7}$)alkoxy, (C$_{1-7}$)alkanoyl, (C$_{1-7}$)alkylsulfonyl, arylsulfonyl, and amino, each unsubstituted or substituted. In other variations R$_5$ is selected from the group consisting of hydrogen, hydroxy, methoxy, (C$_{1-7}$)alkyl, hydroxy(C$_{1-7}$)alkyl, amino(C$_{1-7}$)alkyl, alkoxy(C$_{1-3}$)alkyl, and amino, each unsubstituted or substituted. In still other variations R$_5$ is hydrogen.

R$_2$

In some variations of the above embodiments and variations of the compounds of the invention, R$_2$ is selected from the group consisting of hydrogen, cyclylalkyl, heterocyclylalkyl, cyclylcarbonyl, heterocyclylcarbonyl, cyclylsulfonyl, heterocyclylsulfonyl, cyclyloxycarbonyl, heterocyclyloxycarbonyl, cyclyloxysulfonyl, heterocyclyloxysulfonyl wherein each cyclyl moieties is unsubstituted or substituted with one or more substituents each independently selected from the group consisting of halo, nitro, cyano, carboxyl, carboxamido, amido, carboxamidoalkoxy, carbamoyl, (C$_{1-7}$) alkyl, (C$_{1-7}$)alkoxy, —CF$_3$, —OCF$_3$, hydroxy-(C$_{1-7}$)alkyl, alkoxy(C$_{1-7}$)alkyl, alkoxy(C$_{1-7}$)alkoxy, alkoxyalkoxyalkyl, aminoalkyl, alkoxyalkylaminoalkyl, alkanoylaminoalkyl, alkoxycarbonylalkyl, hydroxyalkyloxy, alkoxyalkyloxy, aminoalkoxy, alkanoylaminoalkoxy, carboxyalkyoxy, alkyloxycarbonylalkoxy, carbamoylalkoxy, and alkoxyalkylcarbamoyl.

In other variations, R$_2$ is selected from the group consisting of hydrogen, phenyl(C$_{1-7}$)alkyl, pyridinyl, pyridine-4-yl, di-phenyl(C$_{1-7}$)alkyl, naphthyl(C$_{1-7}$)alkyl, pyridyl(C$_{1-7}$) alkyl, indolyl(C$_{1-7}$)alkyl, 1H-indazolyl(C$_{1-7}$)alkyl, quinolyl (C$_{1-7}$)alkyl, isoquinolyl(C$_{1-7}$)alkyl, 1,2,3,4-tetrahydro-1,4-benzoxazinyl(C$_{1-7}$)alkyl, 2H-1,4-benzoxazin-3(4H)-onyl (C$_{1-7}$)alkyl, 1-benzothiophenyl(C$_{1-7}$)alkyl, phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl, 1-benzothiophenyl, phenylcarbonyl (benzoyl), and naphthylcarbonyl (naphthoyl), where each phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl or 1-benzothiophenyl is unsubstituted or substituted by one or more substituents each independently selected from the group consisting of (C$_{1-7}$)alkyl, hydroxy(C$_{1-7}$)alkyl, (C$_{1-7}$)alkoxy(C$_{1-7}$)alkyl, (C$_{1-7}$)alkoxy(C$_{1-7}$)alkoxy(C$_{1-7}$) alkyl, (C$_{1-7}$)alkanoyloxy(C$_{1-7}$)alkyl, amino(C$_{1-7}$)alkyl, halo (C$_{1-7}$)alkylamino(C$_{1-7}$)alkyl, halo(C$_{1-7}$)alkanoylamino(C$_{1-7}$) alkyl, (C$_{1-7}$)alkoxy(C$_{1-7}$)alkylamino(C$_{1-7}$)alkyl, (C$_{1-7}$) alkanoylamino(C$_{1-7}$)alkyl, (C$_{1-7}$)cycloalkanoylamino(C$_{1-7}$) alkyl, (C$_{1-7}$)alkylsulfonylamino(C$_{1-7}$)alkyl, carboxy(C$_{1-7}$) alkyl, (C$_{1-7}$)alkoxycarbonyl(C$_{1-7}$)alkyl, halo, hydroxy, (C$_{1-7}$) alkoxy, hydroxy(C$_{1-7}$)alkyloxy, (C$_{1-7}$)alkoxy(C$_{1-7}$)alkoxy, (C$_{1-7}$)alkylaminocarbonyl(C$_{1-7}$)alkoxy, amino(C$_{1-7}$)alkoxy, N—(C$_{1-7}$)alkanoylamino(C$_{1-7}$)alkoxy, carboxy(C$_{1-7}$)alkyloxy, (C$_{1-7}$)alkyloxycarbonyl(C$_{1-7}$)alkoxy, carbamoyl(C$_{1-7}$) alkoxy, N-mono-(C$_{1-7}$alkyl)carbamoyl(C$_{1-7}$)alkyl, N-mono-(C$_{1-7}$alkyl)carbamoyl(C$_{1-7}$)alkoxy, N,N-di-((C$_{1-7}$)alkyl) carbamoyl(C$_{1-7}$)alkoxy, morpholino(C$_{1-7}$)alkoxy, pyridyl (C$_{1-7}$)alkoxy, amino, (C$_{1-7}$)alkanoylamino, (C$_{1-7}$)alkanoyl, (C$_{1-7}$)alkyloxy(C$_{1-7}$)alkanoyl, (C$_{1-7}$)alkoxy(C$_{1-7}$)alkanoyl, carboxyl, carbamoyl, N—(C$_{1-7}$)alkoxy(C$_{1-7}$)alkylcarbamoyl, pyrazolyl, pyrazolyl(C$_{1-7}$)alkoxy, 4-(C$_{1-7}$)alkylpiperidin-1-yl, nitro and cyano, each unsubstituted or substituted.

In other variations, R$_2$ is selected from the group consisting of hydrogen, phenyl, pyridinyl, pyridine-4-yl, naphthyl, phenyl(C$_{1-7}$)alkyl, di-(phenyl)(C$_{1-7}$)alkyl, naphthyl(C$_{1-7}$)alkyl, pyridyl(C$_{1-7}$)alkyl, indolyl(C$_{1-7}$)alkyl, 1H-indazolyl(C$_{1-7}$) alkyl, quinolyl(C$_{1-7}$)alkyl, isoquinolyl(C$_{1-7}$)alkyl, 1-benzothiophenyl(C$_{1-7}$)alkyl, phenylcarbonyl (benzoyl), where each phenyl, naphthyl, pyridyl, indolyl, 1H-indazolyl, quinolyl, isoquinolyl or 1-benzothiophenyl is unsubstituted or substituted with one or more substituents each independently selected from the group consisting of (C$_{1-7}$)alkyl, hydroxy(C$_{1-7}$)alkyl, (C$_{1-7}$)alkoxy(C$_{1-7}$)alkyl, (C$_{1-7}$)alkoxy (C$_{1-7}$)alkoxy(C$_{1-7}$)alkyl, (C$_{1-7}$)alkanoyloxy(C$_{1-7}$)alkyl, amino(C$_{1-7}$)alkyl, halo(C$_{1-7}$)alkylamino(C$_{1-7}$)alkyl, halo (C$_{1-7}$)alkanoylamino(C$_{1-7}$)alkyl, (C$_{1-7}$)alkoxy(C$_{1-7}$)alkylamino(C$_{1-7}$)alkyl, (C$_{1-7}$)alkanoylamino(C$_{1-7}$)alkyl, (C$_{1-7}$) cycloalkanoylamino(C$_{1-7}$)alkyl, (C$_{1-7}$)alkylsulfonylamino (C$_{1-7}$)alkyl, carboxy(C$_{1-7}$)alkyl, (C$_{1-7}$)alkoxycarbonyl(C$_{1-7}$) alkyl, halo, hydroxy, (C$_{1-7}$)alkoxy, hydroxy(C$_{1-7}$)alkyloxy, (C$_{1-7}$)alkoxy(C$_{1-7}$)alkoxy, (C$_{1-7}$)alkylaminocarbonyl(C$_{1-7}$) alkoxy, amino(C$_{1-7}$)alkoxy, N—(C$_{1-7}$)alkanoylamino(C$_{1-7}$) alkoxy, carboxy(C$_{1-7}$)alkyloxy, (C$_{1-7}$)alkyloxycarbonyl (C$_{1-7}$)alkoxy, carbamoyl(C$_{1-7}$)alkoxy, N-mono-(C$_{1-7}$alkyl) carbamoyl(C$_{1-7}$)alkyl, N-mono-(C$_{1-7}$alkyl)carbamoyl(C$_{1-7}$) alkoxy, N,N-di-((C$_{1-7}$)alkyl)carbamoyl(C$_{1-7}$)alkoxy, morpholino(C$_{1-7}$)alkoxy, pyridyl(C$_{1-7}$)alkoxy, amino, (C$_{1-7}$) alkanoylamino, (C$_{1-7}$)alkanoyl, (C$_{1-7}$)alkyloxy(C$_{1-7}$) alkanoyl, (C$_{1-7}$)alkoxy(C$_{1-7}$)alkanoyl, carboxyl, carbamoyl, N—(C$_{1-7}$)alkoxy(C$_{1-7}$)alkylcarbamoyl, pyrazolyl, pyrazolyl (C$_{1-7}$)alkoxy, 4-(C$_{1-7}$)alkylpiperidin-1-yl, nitro and cyano, each unsubstituted or substituted.

In some particular embodiments, R$_2$ is -L$_2$-D. In some variations, L$_2$ is absent. In some other variations, L$_2$ is selected from the group consisting of —(CR$_{10}$R$_{10'}$)— and —(CR$_{10}$R$_{10'}$)$_2$, where R$_{10}$ and R$_{10'}$ are each independently selected from the group consisting of hydrogen, alkyl, aryl, heteroaryl, cycloalkyl, heterocycloalkylalkyl, arylalkyl, heteroarylalkyl, cycloalkylalkyl, and heterocycloalkylalkyl, each unsubstituted or substituted. In still other variations, L$_2$ is methylene.

In some variations of the above embodiments and variations, D, when present, is selected from the group consisting of hydrogen, alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero (C$_{4-12}$)bicycloaryl, each unsubstituted or substituted.

In other variations, D is selected from the group consisting of hydrogen, (C$_{4-12}$)aryl and hetero(C$_{1-10}$)aryl, where the (C$_{1-10}$)heteroaryl may contains up to four heteroatoms selected from the group consisting of nitrogen, oxygen and sulfur, and the (C$_{4-12}$)aryl and (C$_{1-10}$)heteroaryl may be unsubstituted or substituted with up to four substituents each independently selected from the group consisting of halo, nitro, cyano, carboxyl, carboxamido, amido, carboxamidoalkoxy, carbamoyl, (C$_{1-7}$)alkyl, (C$_{1-7}$)alkoxy, —CF$_3$, —OCF$_3$, hydroxyl-(C$_{1-7}$)alkyl, alkoxy(C$_{1-7}$)alkyl, alkoxy (C$_{1-7}$)alkoxy, alkoxyalkoxyalkyl, aminoalkyl, alkoxyalkylaminoalkyl, alkanoylaminoalkyl, alkoxycarbonylalkyl, hydroxyalkyloxy, alkoxyalkyloxy, aminoalkoxy, alkanoylaminoalkoxy, carboxyalkyoxy, alkyloxycarbonylalkoxy, carbamoylalkoxy, and alkoxyalkylcarbamoyl.

In yet other variations, D is selected from the group consisting of hydrogen, phenyl, pyridyl, pyranyl, pyridazyinyl, pyrimidinyl, pyrazinyl, indolyl, indazolyl, benzimidazolyl, benzothienyl, benzthiazolyl, benzooxazinyl, purinyl, cinnolinyl, phthalazinyl, pteridinyl, naphthyl, 1H-indazolyl, quinolyl, isoquinolyl, quinoxalinyl, and 1-benzothienyl, each unsubstituted or substituted with up to four substituents each independently selected from the group consisting of halo, $(C_{1-7})$alkyl, $(C_{1-7})$alkoxy, alkanoyl, alkylcarbamoyl, alkoxycarbamoyl, $(C_{1-7})$alkoxy$(C_{1-7})$alkyloxy, $(C_{1-7})$alkoxy$(C_{1-7})$alkyloxyalkyl, $(C_{1-7})$alkoxy$(C_{1-7})$alkyl, halo$(C_{1-7})$alkyl, each further unsubstituted or substituted.

In yet other variations, D when present is unsubstituted or substituted phenyl. In yet other variations, D when present is unsubstituted or substituted pyridyl. In still other variations, D is unsubstituted or substituted pyridin-4-yl.

In some variations, the phenyl, pyridinyl or pyridine-4-yl is substituted with 1-4 substituents, where the substituents are each independently selected from the group consisting of $(C_{1-7})$alkyl, hydroxy$(C_{1-7})$alkyl, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, amino$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$alkoxy$(C_{1-7})$alkylamino$(C_{1-7})$alkyl, $(C_{1-7})$alkanoylamino$(C_{1-7})$alkyl, $(C_{1-7})$cycloalkanoylamino$(C_{1-7})$alkyl, $(C_{1-7})$alkylsulfonylamino$(C_{1-7})$alkyl, carboxy$(C_{1-7})$alkyl, $(C_{1-7})$alkoxycarbonyl$(C_{1-7})$alkyl, halo, hydroxy, $(C_{1-7})$alkoxy, hydroxy$(C_{1-7})$alkyloxy, $(C_{1-7})$alkoxy$(C_{1-7})$alkoxy, $(C_{1-7})$alkylaminocarbonyl$(C_{1-7})$alkoxy, amino$(C_{1-7})$alkoxy, N—$(C_{1-7})$alkanoylamino$(C_{1-7})$alkoxy, carboxy$(C_{1-7})$alkyloxy, $(C_{1-7})$alkyloxycarbonyl$(C_{1-7})$alkoxy, carbamoyl$(C_{1-7})$alkoxy, N-mono-$(C_{1-7}$alkyl$)$carbamoyl$(C_{1-7})$alkyl, N-mono-$(C_{1-7}$alkyl$)$carbamoyl$(C_{1-7})$alkoxy, N,N-di-$((C_{1-7})$alkyl$)$carbamoyl$(C_{1-7})$alkoxy, morpholino$(C_{1-7})$alkoxy, pyridyl$(C_{1-7})$alkoxy, amino, $(C_{1-7})$alkanoylamino, $(C_{1-7})$alkanoyl, $(C_{1-7})$alkyloxy$(C_{1-7})$alkanoyl, $(C_{1-7})$alkoxy$(C_{1-7})$alkanoyl, carboxyl, carbamoyl, N—$(C_{1-7})$alkoxy$(C_{1-7})$alkylcarbamoyl, pyrazolyl, pyrazolyl$(C_{1-7})$alkoxy, 4-$(C_{1-7})$alkylpiperidin-1-yl, nitro and cyano, each unsubstituted or substituted.

In other variations, the substituents on the phenyl, pyridinyl and pyridine-4-yl are selected from the group consisting of halo, $(C_{1-7})$alkyl, $(C_{1-7})$alkoxy, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$cycloalkanoylamino$(C_{1-7})$alkyl, aminoacyl$(C_{1-7})$alkoxy, and N-mono-$(C_{1-7}$alkyl$)$carbamoyl$(C_{1-7})$alkyl.

In still other variations, the substituents on the phenyl, pyridinyl and pyridine-4-yl are selected from the group consisting of chloro, methyl, methoxyethyl, methoxypropyl, —$(CH_2)_2C(O)NHCH_3$, —$(CH_2)_2OC(O)NHCH_3$, —$(CH_2)NHC(O)CH_2CF_3$, —$(CH_2)NHCHF_2$, —$CH_2NHC(O)$-cyclopropyl, methoxyethoxymethyl, and methoxypropyloxy.

In yet other variations, D is selected from the group consisting of

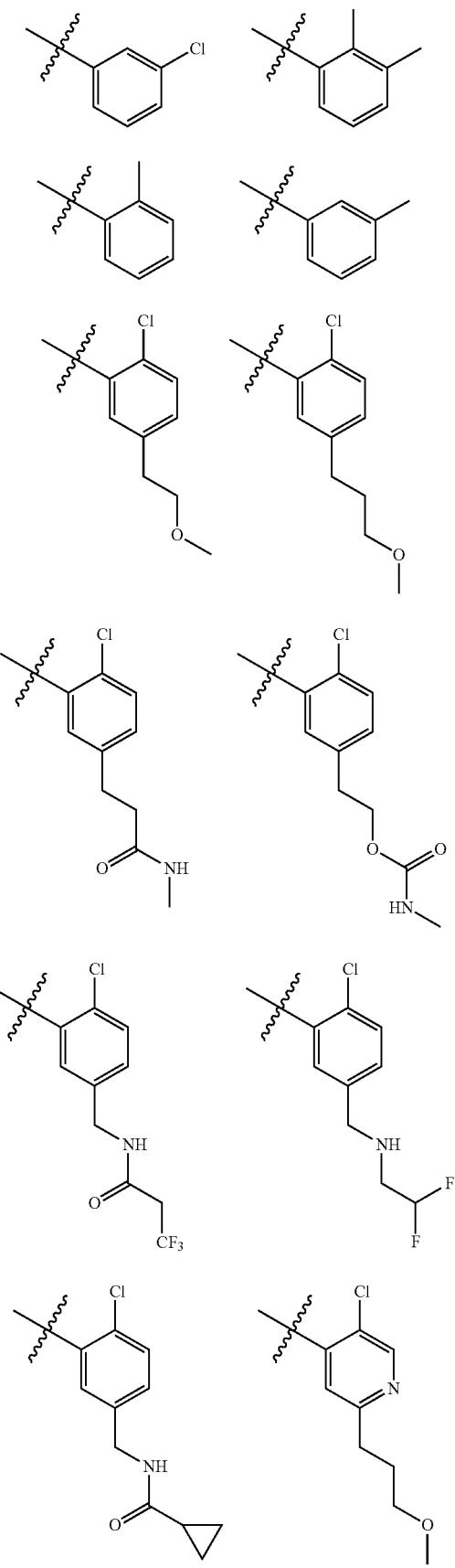

-continued

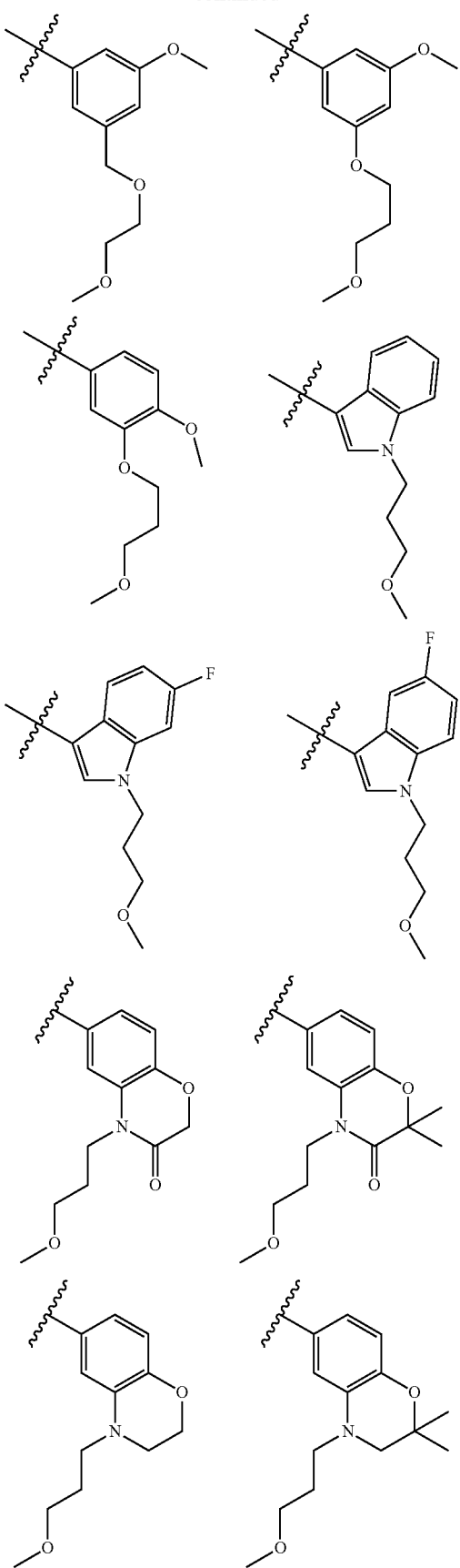

-continued

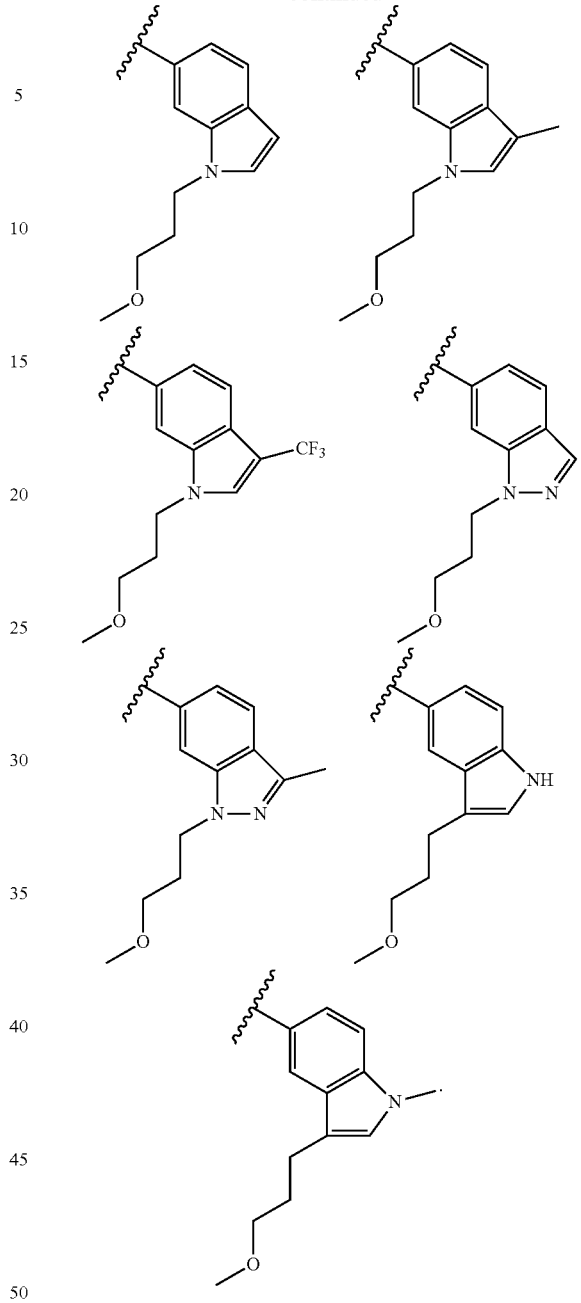

In some variations of the preceding embodiments and variations of the compounds of the invention, $R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

In some particular variations of the preceding embodiments and variations, $R_1$ is -A-$L_3$-B, where A is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

B is absent or is selected from the group consisting of hydrogen, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, ($C_{4-12}$)aryl, hetero($C_{1-10}$)aryl, ($C_{9-12}$)bicycloaryl and hetero ($C_{4-12}$)bicycloaryl, each unsubstituted or substituted; and $L_3$ is absent or is a linker providing 1, 2, 3, 4, 5 or 6 atom separation between A and B to which $L_3$ is attached, wherein the atoms of $L_3$ providing the separation are selected from the group consisting of carbon, oxygen, nitrogen, and sulfur.

In the variations where $R_1$ is -A-$L_3$-B, A is an unsubstituted or substituted five, six or seven membered saturated, unsaturated or aromatic cyclic moiety containing optionally up to four heteroatoms each independently selected from the group consisting of nitrogen, oxygen and sulfur.

In other variations, A is a five-membered heteroaryl containing optionally up to four heteroatoms each independently selected from the group consisting of nitrogen, oxygen and sulfur, where said heteroaryl is unsubstituted or substituted with up to three substituents each independently selected from the group consisting of ($C_{1-7}$)alkyl, ($C_{2-7}$)alkenyl, ($C_{2-7}$)alkynyl, halo, hydroxyl, alkyoxy, mercapto, sulfinyl, sulfonyl, amino, amido, carboxyamido, carboxyl, sulfamoyl, nitro and cyano, each unsubstituted or substituted.

In other variations, A is a five-membered heteroaryl containing optionally up to three heteroatoms that are independently selected from the group consisting of nitrogen, oxygen and sulfur, wherein said heteroaryl is unsubstituted or monosubstituted by ($C_{1-7}$)alkyl.

In yet other variations, A is a thiazolyl, unsubstituted or substituted.

In yet other variations, A is a six-membered aromatic ring containing optionally up to four nitrogen atoms, and said aromatic ring is unsubstituted or substituted with up to four substituents independently selected from the group consisting of ($C_{1-7}$)alkyl, ($C_{2-7}$)alkenyl, ($C_{2-7}$)alkynyl, halo, hydroxyl, alkoxy, mercapto, sulfinyl, sulfonyl, amino, amido, carboxyamido, carboxyl, sulfamoyl, nitro and cyano, each further unsubstituted or substituted.

In yet other particular variations where $R_1$ consists of the formula

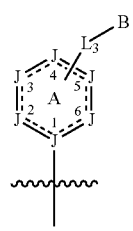

where each J is independently selected from the group consisting of C and N;

A is optionally further substituted with up to two other substituents independently selected from the group consisting of ($C_{1-7}$)alkyl, ($C_{2-7}$)alkenyl, ($C_{2-7}$)alkynyl, halo, hydroxyl, alkoxy, mercapto, sulfinyl, sulfonyl, amino, amido, carboxyamido, carboxyl, sulfamoyl, nitro and cyano, each unsubstituted or substituted;

B is absent or is selected from the group consisting of hydrogen, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero ($C_{4-12}$)bicycloaryl, each unsubstituted or substituted; and $L_3$ is absent or is a linker attaching to a ring atom at the 3-, 4- or 5-position of A and providing 1, 2, 3, 4, 5 or 6 atom separation between A and B to which $L_3$ is attached, wherein the atoms of $L_3$ providing the separation are selected from the group consisting of carbon, oxygen, nitrogen, and sulfur.

In some variations of the preceding variations, the atoms of $L_3$ that provide the separation between A and B are independently selected from the group consisting of carbon and oxygen. In other variations, $L_3$ is selected from the group consisting of —O—, —($CH_2$)$_n$—, —X—($CH_2$)$_n$, —($CH_2$)$_n$—X—, —X—($CH_2$)$_n$—X—, ($CH_2$)$_n$—X—($CH_2$)$_n$—, —X—($CH_2$)$_n$—X—($CH_2$)$_n$— and —($CH_2$)$_n$—X—($CH_2$)$_n$—X—, where X is —O— or —$CH_2$— and n is 0, 1, 2, 3, 4, 5 or 6. In other variations, $L_3$ is selected from the group consisting of —($CH_2$)$_n$— where n is 1, 2, 3, 4, 5 or 6; —$CH_2CH_2$—; —O—($CH_2$); —O—$CH_2CH_2$—; —O—$CH_2CH_2CH_2$—; —$CH_2$—O—, —$CH_2CH_2$—O—; —$CH_2CH_2CH_2$—O—; —O—$CH_2CH_2$—O—; —O—$CH_2CH_2CH_2$—O—; —$CH_2$—O—$CH_2CH_2$—O—; —O—$CH_2CH_2$—O—$CH_2$— and —O—$CH_2CH_2CH_2$—O—$CH_2$—. In other variations, $L_3$ is selected from the group consisting of —O—$CH_2$—, —O—$CH_2CH_2$—, —$CH_2$—O—, —$CH_2CH_2$—O—, —$CH_2CH_2CH_2$—O—, —O—$CH_2CH_2$—O—, and —$CH_2$—O—$CH_2CH_2$—O—. In other variations, $L_3$ is —O—$CH_2CH_2$—O—. In other variations, $L_3$ is —O—. In other variations, $L_3$ is absent.

In some variations of the preceding variations, B is selected from the group consisting of ($C_{1-7}$)alkyl, ($C_{2-7}$)alkenyl, ($C_{2-7}$)alkynyl, aryl, heteroaryl, cycloalkyl, heterocycloalkyl, halo, hydroxyl, alkoxy, mercapto, sulfinyl, sulfonyl, amino, carboxyl, sulfamoyl, nitro and cyano, each unsubstituted or substituted.

In other variations, B is selected from the group consisting of ($C_{1-7}$)alkyl, hetero($C_{1-7}$)alkyl, aryl and heteroaryl, each unsubstituted or substituted where said hetero($C_{1-7}$)alkyl and heteroaryl contain heteroatoms that are independently selected from the group consisting of nitrogen, oxygen and sulfur.

In other variations of the preceding variations, B is a five-membered heteroaryl containing up to four heteroatoms independently selected from the group consisting of nitrogen, oxygen and sulfur, and if substituted, and B is unsubstituted or substituted with one or more substituents are independently selected from the group consisting of ($C_{1-7}$)alkyl, ($C_{1-7}$)alkoxy, —NHC(O)$CH_3$—, —$CF_3$, —$OCF_3$, halogen, and hydroxyl-$C_{1-7}$)alkyl, morpholinyl-alkyloxy; cyano, pyrazolyl, piperazinyl, and aryloxy.

In other variations, B is a six-membered aryl or heteroaryl, wherein said heteroaryl optionally contains up to four nitrogen atoms, and said aryl or heteroaryl is unsubstituted or substituted with up to four substituents each independently selected from the group consisting of ($C_{1-7}$)alkyl, ($C_{1-7}$) alkoxy, —NHC(O)$CH_3$—, —$CF_3$, —$OCF_3$, halogen, hydroxyl-($C_{1-7}$)alkyl, morpholinyl-alkyloxy; cyano, pyrazolyl, piperazinyl, and aryloxy.

In other variations, B is phenyl or pyridyl that is unsubstituted or substituted with up to four substituents each is independently selected from the group consisting of ($C_{1-7}$)alkyl, ($C_{1-7}$)alkoxy, —NHC(O)$CH_3$—, —$CF_3$, —$OCF_3$, halogen, and hydroxyl-$C_{1-7}$)alkyl.

In other variations, B is selected from the group consisting of

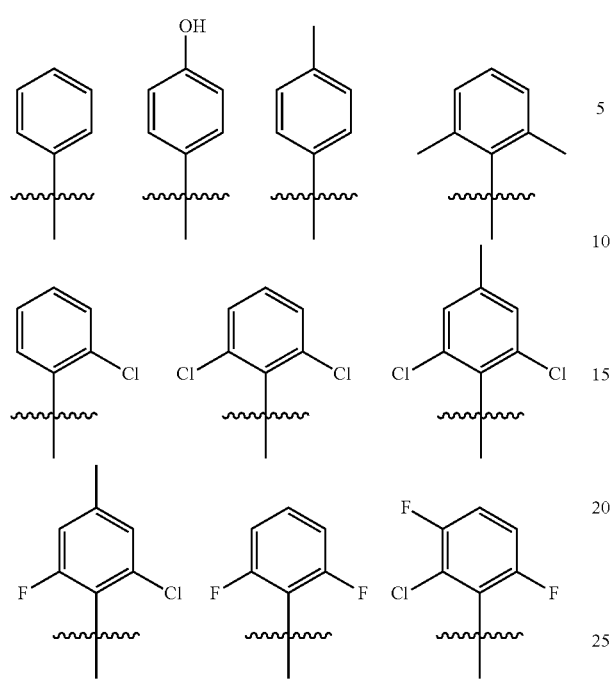
In other variations, B is absent.
In all the above embodiments and variations, in some variations, $R_1$ is selected from the group consisting of
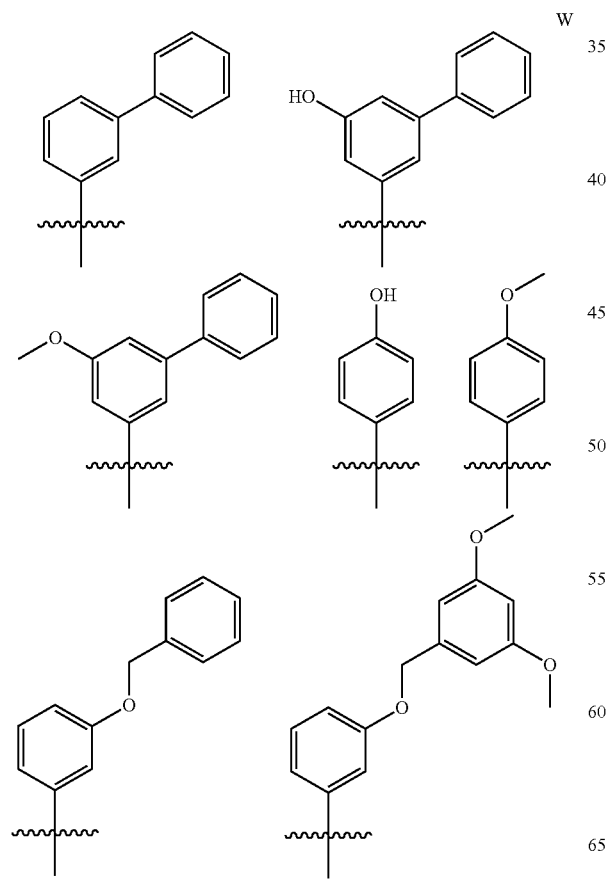
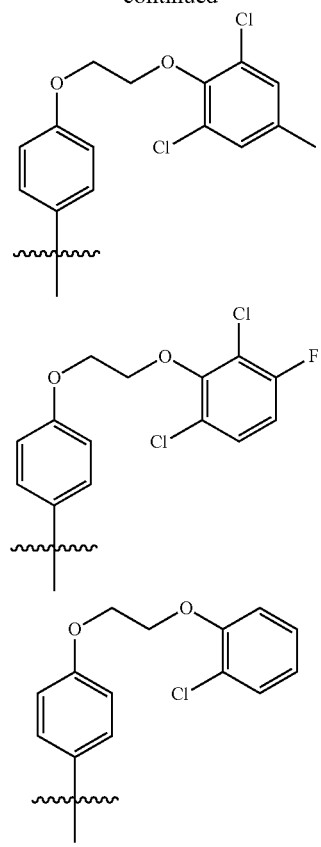

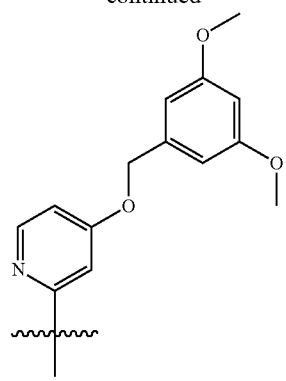

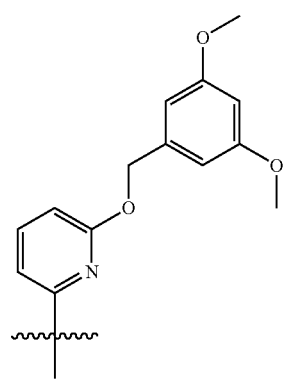

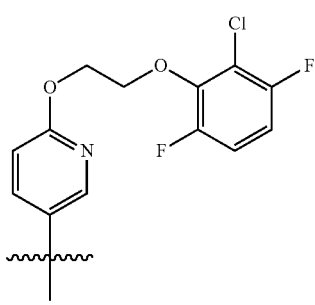

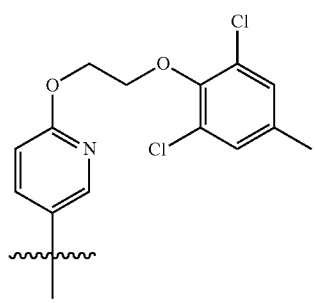

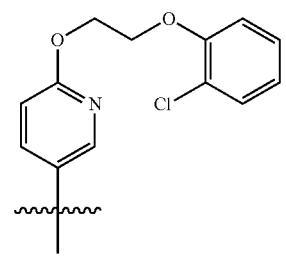

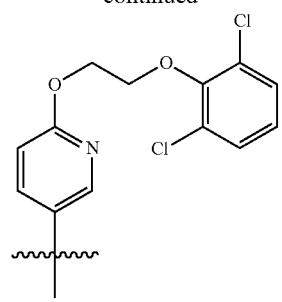

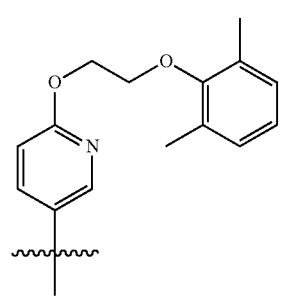

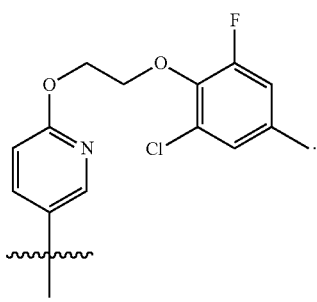

In some variations of the preceding embodiments and variations of the compounds of the invention, W is selected from the group consisting of cyano, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, each unsubstituted or substituted.

In other variations, W is selected from the group consisting of —$OR_7$, —$NR_7R_{7'}$, —$NHC(O)R_7$ and —$O(CH_2)_nOR_7$, wherein $R_7$ and $R_{7'}$ are each independently H or $(C_{1-7})$alkyl, and n is 1 or 2.

In other variations, W is selected from the group consisting of —OH, —$OCH_3$, —$NH_2$, —$NHC(O)CH_3$, —$OCH_2OH$, —$OCH_2OCH_3$, —$OCH_2OCH_2CH_3$, —$O(CH_2)_2OH$, —$O(CH_2)_2OCH_3$, —$O(CH_2)_2OCH_2CH_3$, —$OCH_2CH(OH)CH_2OCH_3$ and —$OCH_2CH(OH)CH_2OH$.

In a particular embodiment, the compound of the invention is of a formula selected from the group consisting of

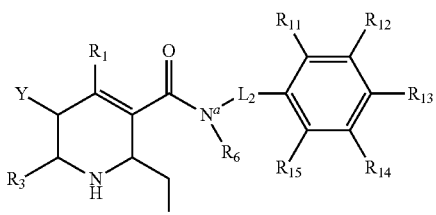

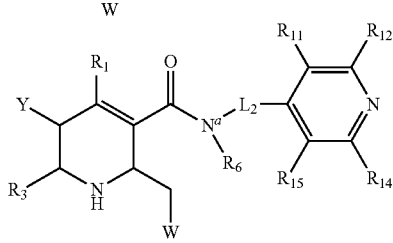

or a hydrate, solvate, tautomer, enantiomer, or pharmaceutically acceptable salt thereof, wherein $N^a$ is a nitrogen atom;

$L_2$ is absent or is selected from the group consisting of —$(CR_{10}R_{10'})$— and —$(CR_{10}R_{10'})_2$, where $R_{10}$ and $R_{10'}$ are each independently selected from the group consisting of hydrogen, alkyl, aryl, heteroaryl, cycloalkyl, heterocycloalkylalkyl, arylalkyl, heteroarylalkyl, cycloalkylalkyl, and heterocycloalkylalkyl, each unsubstituted or substituted;

W is selected from the group consisting of —$OR_7$, —$NR_7R_{7'}$, —$NHC(O)R_7$ and —$O(CH_2)_nOR_7$, where $R_7$ and $R_{7'}$ are each independently H or $(C_{1-7})$alkyl, and n is 1 or 2;

Y is selected from the group consisting of hydrogen, hydroxyl, $(C_{1-7})$alkyloxy, $(C_{1-7})$alkoxy$(C_{1-7})$alkyloxy, alkoxy$(C_{1-7})$alkyl, $(C_{1-7})$alkanoylamino, $(C_{1-7})$alkylsulfonylamino, arylsulfonylamino, hydroxyalkyl, aminoalkyl, $(C_{1-7})$alkyl, and amino, each unsubstituted or substituted;

$R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_3$ is selected from the group consisting of hydrogen, $(C_{1-10})$alkyl, $(C_{1-10})$azaalkyl, $(C_{1-10})$oxaalkyl, $(C_{1-10})$oxoalkyl, hetero$(C_{1-10})$alkyl, halo$(C_{1-10})$alkyl, hydroxy$(C_{1-10})$alkyl, and amino$(C_{1-10})$alkyl, each unsubstituted or substituted;

$R_6$ is selected from the group consisting of hydrogen, $(C_{1-7})$alkyl, and cyclo$(C_{3-8})$alkyl, each unsubstituted or substituted; and $R_{11}$, $R_{12}$, $R_{13}$, $R_{14}$, and $R_{15}$ are each independently selected from the group consisting of hydrogen, hydroxy, halo, nitro, cyano, $(C_{1-7})$alkyl, hydroxy$(C_{1-7})$alkyl, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, amino$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$alkoxy$(C_{1-7})$alkylamino$(C_{1-7})$alkyl, $(C_{1-7})$alkanoylamino$(C_{1-7})$alkyl, $(C_{1-7})$cycloalkanoylamino$(C_{1-7})$alkyl, $(C_{1-7})$alkylsulfonylamino$(C_{1-7})$alkyl, carboxy$(C_{1-7})$alkyl, $(C_{1-7})$alkoxycarbonyl$(C_{1-7})$alkyl, $(C_{1-7})$alkoxy, hydroxy$(C_{1-7})$alkyloxy, $(C_{1-7})$alkoxy$(C_{1-7})$alkoxy, aminoacyl$(C_{1-7})$alkoxy, amino$(C_{1-7})$alkoxy, N—$(C_{1-7})$alkanoylamino$(C_{1-7})$alkoxy, carboxy$(C_{1-7})$alkyloxy, $(C_{1-7})$alkyloxycarbonyl$(C_{1-7})$alkoxy, carbamoyl$(C_{1-7})$alkoxy, N-mono-$(C_{1-7}$alkyl)carbamoyl$(C_{1-7})$alkyl, N-mono-$(C_{1-7}$alkyl)carbamoyl$(C_{1-7})$alkoxy, N,N-di-$((C_{1-7})$alkyl)carbamoyl$(C_{1-7})$alkoxy, morpholino$(C_{1-7})$alkoxy, pyridyl$(C_{1-7})$alkoxy, amino, $(C_{1-7})$alkanoylamino, $(C_{1-7})$alkanoyl, $(C_{1-7})$alkyloxy$(C_{1-7})$alkanoyl, $(C_{1-7})$alkoxy$(C_{1-7})$alkanoyl, carboxyl, carbamoyl, N—$(C_{1-7})$alkoxy$(C_{1-7})$alkylcarbamoyl, pyrazolyl, pyrazolyl$(C_{1-7})$alkoxy, 4-$(C_{1-7})$alkylpiperidin-1-yl, each unsubstituted or substituted.

Another particular embodiment, the compound of invention is of a formula selected from the group consisting of:

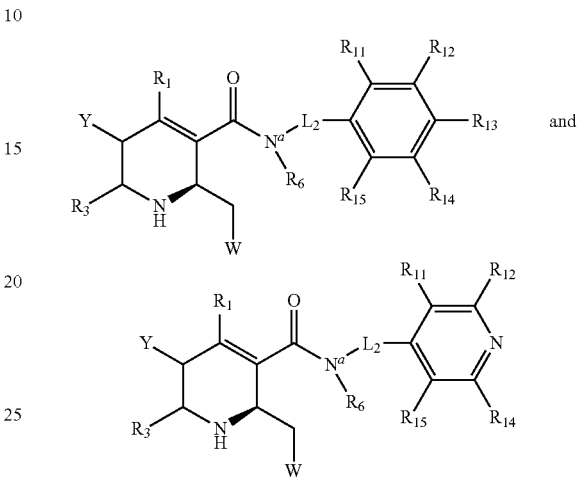

or a hydrate, solvate, tautomer, enantiomer, or pharmaceutically acceptable salt thereof, wherein $N^a$ is a nitrogen atom;

$L_2$ is absent or is selected from the group consisting of —$(CR_{10}R_{10'})$— and —$(CR_{10}R_{10'})_2$, where $R_{10}$ and $R_{10'}$ are each independently selected from the group consisting of hydrogen, alkyl, aryl, heteroaryl, cycloalkyl, heterocycloalkylalkyl, arylalkyl, heteroarylalkyl, cycloalkylalkyl, and heterocycloalkylalkyl, each unsubstituted or substituted;

W is selected from the group consisting of —$OR_7$, —$NR_7R_{7'}$, —$NHC(O)R_7$ and —$O(CH_2)_nOR_7$, where $R_7$ and $R_{7'}$ are each independently H or $(C_{1-7})$alkyl, and n is 1 or 2;

Y is selected from the group consisting of hydrogen, hydroxyl, $(C_{1-7})$alkyloxy, $(C_{1-7})$alkoxy$(C_{1-7})$alkyloxy, alkoxy$(C_{1-7})$alkyl, $(C_{1-7})$alkanoylamino, $(C_{1-7})$alkylsulfonylamino, arylsulfonylamino, hydroxyalkyl, aminoalkyl, $(C_{1-7})$alkyl, and amino, each unsubstituted or substituted;

$R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_3$ is selected from the group consisting of hydrogen, $(C_{1-10})$alkyl, $(C_{1-10})$azaalkyl, $(C_{1-10})$oxaalkyl, $(C_{1-10})$oxoalkyl, hetero$(C_{1-10})$alkyl, halo$(C_{1-10})$alkyl, hydroxy$(C_{1-10})$alkyl, and amino$(C_{1-10})$alkyl, each unsubstituted or substituted;

$R_6$ is selected from the group consisting of hydrogen, $(C_{1-7})$alkyl, and cyclo$(C_{3-8})$alkyl, each unsubstituted or substituted; and $R_{11}$, $R_{12}$, $R_{13}$, $R_{14}$, and $R_{15}$ are each independently selected from the group consisting of hydrogen, hydroxy, halo, nitro, cyano, $(C_{1-7})$alkyl, hydroxy$(C_{1-7})$alkyl, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, amino$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$alkoxy$(C_{1-7})$alkylamino$(C_{1-7})$alkyl, $(C_{1-7})$alkanoylamino ($C_{1-7}$)alkyl, ($C_{1-7}$)cycloalkanoylamino($C_{1-7}$)alkyl, ($C_{1-7}$)alkylsulfonylamino($C_{1-7}$)alkyl, carboxy($C_{1-7}$)alkyl, ($C_{1-7}$)alkoxycarbonyl($C_{1-7}$)alkyl, ($C_{1-7}$)alkoxy, hydroxy($C_{1-7}$)alkyloxy, ($C_{1-7}$)alkoxy($C_{1-7}$)alkoxy, aminoacyl($C_{1-7}$)alkoxy, amino($C_{1-7}$)alkoxy, N—($C_{1-7}$)alkanoylamino($C_{1-7}$)alkoxy, carboxy($C_{1-7}$)alkyloxy, ($C_{1-7}$)alkyloxycarbonyl($C_{1-7}$)alkoxy, carbamoyl($C_{1-7}$)alkoxy, N-mono-($C_{1-7}$alkyl)carbamoyl($C_{1-7}$)alkyl, N-mono-($C_{1-7}$alkyl)carbamoyl($C_{1-7}$)alkoxy, N,N-di-(($C_{1-7}$)alkyl)carbamoyl($C_{1-7}$)alkoxy, morpholino($C_{1-7}$)alkoxy, pyridyl($C_{1-7}$)alkoxy, amino, ($C_{1-7}$)alkanoylamino, ($C_{1-7}$)alkanoyl, ($C_{1-7}$)alkyloxy($C_{1-7}$)alkanoyl, ($C_{1-7}$)alkoxy($C_{1-7}$)alkanoyl, carboxyl, carbamoyl, N—($C_{1-7}$)alkoxy($C_{1-7}$)alkylcarbamoyl, pyrazolyl, pyrazolyl($C_{1-7}$)alkoxy, 4-($C_{1-7}$)alkylpiperidin-1-yl, each unsubstituted or substituted.

In some variations of the preceding two particular embodiments, $R_3$ is selected from the group consisting of hydrogen, unsubstituted alkyl, or substituted alkyl. In other variations, $R_3$ is hydrogen.

In some variations of the preceding two particular embodiments and variations, $R_6$ is isopropyl, propyl, isobutyl, cyclopropyl, ethyl, —$CH_2CH_2F$, —$CH_2CHF_2$ and —$CH_2CF_3$. In other variations, $R_6$ is cyclopropyl.

In some variations of the preceding two particular embodiments and variations, Y is selected from the group consisting of H, —OH, —$NH_2$, —$CH_2OH$, —$CH_2OCH_3$, —NHC(O)$CH_3$, —$CH_2CH(OH)CH_2OH$, —$CH_2CH(OH)CH_2OCH_3$, —$OCH_2CH(OH)CH_2OCH_3$, and —$OCH_2CH(OH)CH_2OH$.

In some variations of the preceding two particular embodiments and variations, W is selected from the group consisting of —OH, —$OCH_3$, —$NH_2$, —NHC(O)$CH_3$, —$OCH_2OH$, —$OCH_2OCH_3$, —$OCH_2OCH_2CH_3$, —O($CH_2$)$_2$OH, —O($CH_2$)$_2$OCH$_3$, —O($CH_2$)$_2$OCH$_2$CH$_3$, —$OCH_2CH(OH)$$CH_2OCH_3$ and —$OCH_2CH(OH)CH_2OH$. In other variations, W is —OH, —$OCH_3$, or —$NH_2$.

In some variations of the preceding two particular embodiments and variations, $R_1$ is -A-$L_3$-B, where A is selected from the group consisting of ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted;

B is absent or is selected from the group consisting of hydrogen, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted; and $L_3$ is absent or is a linker providing 1, 2, 3, 4, 5 or 6 atom separation between A and B to which $L_3$ is attached, wherein the atoms of $L_3$ providing the separation are selected from the group consisting of carbon, oxygen, nitrogen, and sulfur.

In some variations, A is a five-membered heteroaryl containing optionally up to three heteroatoms that are independently selected from the group consisting of nitrogen, oxygen and sulfur, wherein said heteroaryl is unsubstituted or monosubstituted by ($C_{1-7}$)alkyl. In other variations, A is a thiazolyl.

In other variations of the two preceding particular embodiments and variations $R_1$ is of the formula

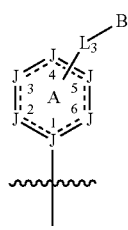

where each J is independently selected from the group consisting of C and N;

$L_3$ is absent or is a linker attaching to a ring atom of A at the 3-, 4- or 5-position and providing 1, 2, 3, 4, 5 or 6 atom separation between A and B to which $L_3$ is also attached, wherein the atoms of $L_3$ providing the separation are independently selected from the group consisting of carbon, oxygen, nitrogen, and sulfur;

A is optionally further substituted with up to two other substituents independently selected from the group consisting of ($C_{1-7}$)alkyl, ($C_{2-7}$)alkenyl, ($C_{2-7}$)alkynyl, halo, hydroxyl, alkoxy, mercapto, sulfinyl, sulfonyl, amino, amido, carboxyamido, carboxyl, sulfamoyl, nitro and cyano, each unsubstituted or substituted; and B is absent or is selected from the group consisting of hydrogen, ($C_{1-10}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each unsubstituted or substituted.

In other variations of the preceding particular embodiments and variations, $R_1$ is selected from the group consisting of

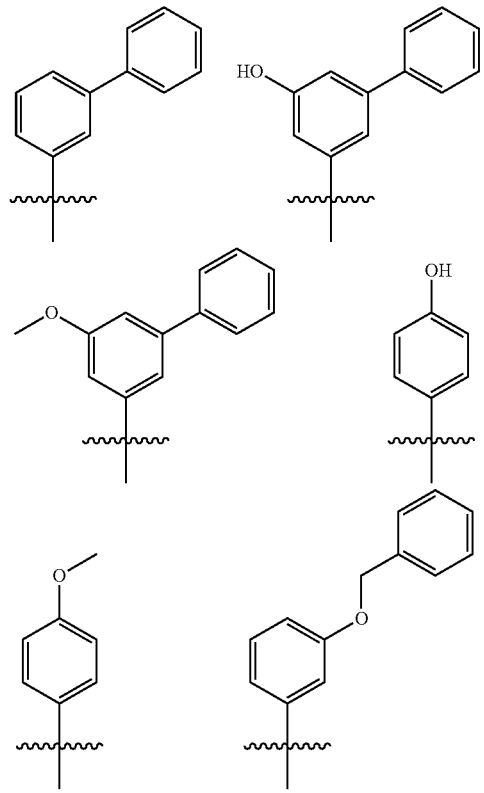

39
-continued
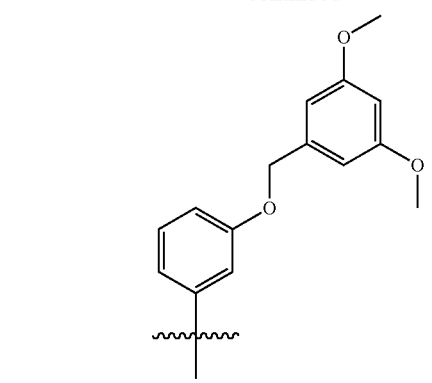
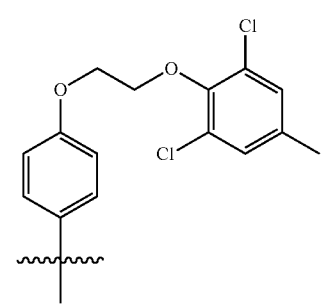
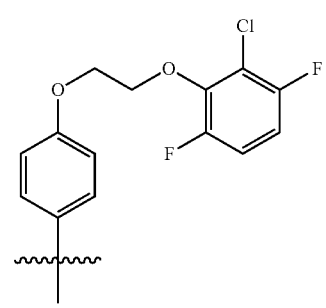
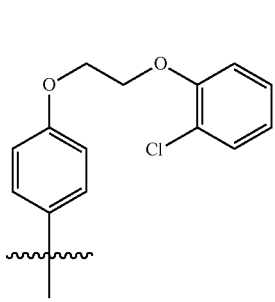 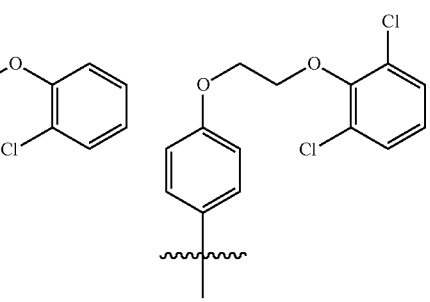
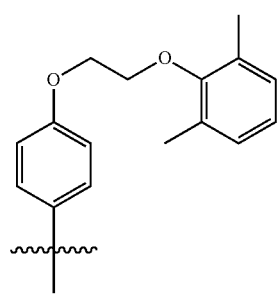
40
-continued
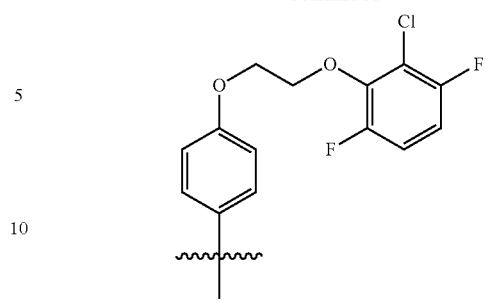
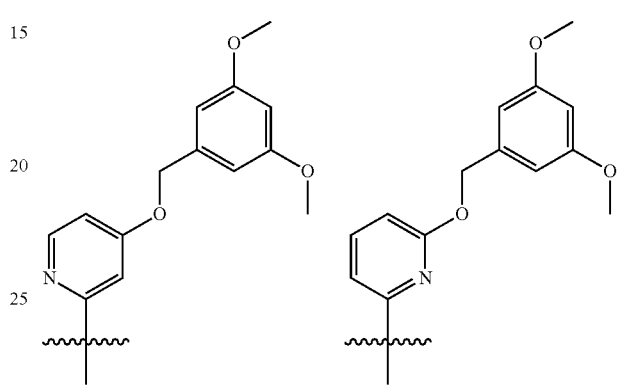
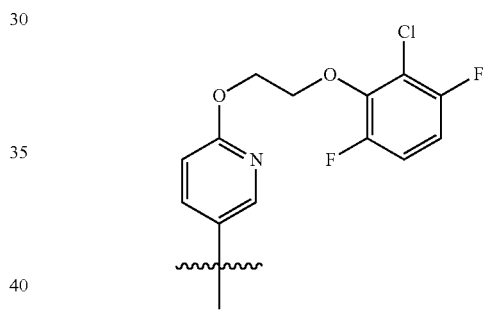
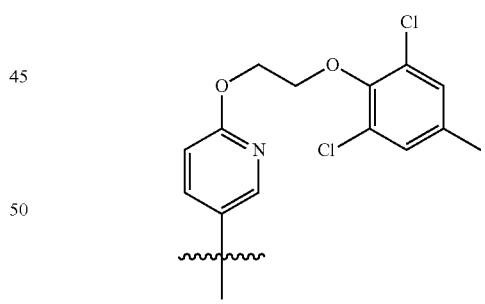
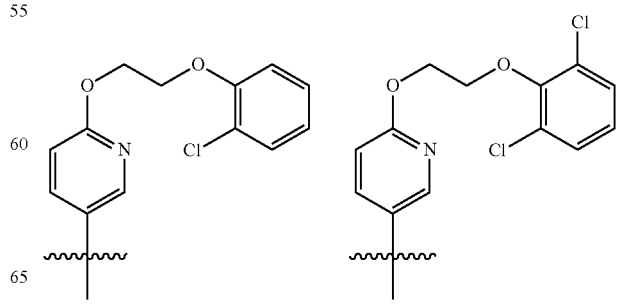

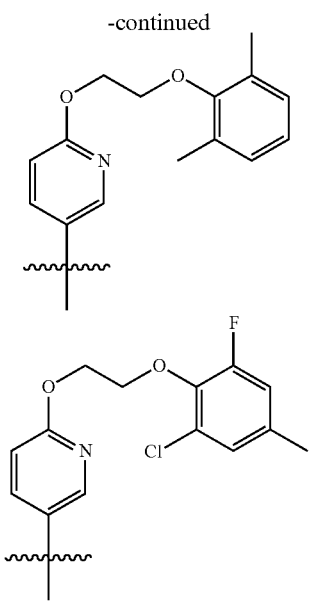

In some variations of the preceding particular embodiments and variations, $L_2$ is methylene.

In some variations of the preceding particular embodiments and variations, $R_{11}$, $R_{12}$, $R_{13}$, $R_{14}$, and $R_{15}$ are each independently selected from the group consisting of hydrogen, halo, nitro, cyano, $(C_{1-7})$alkyl, hydroxy$(C_{1-7})$alkyl, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, amino$(C_{1-7})$alkyl, $(C_{1-7})$alkoxy$(C_{1-7})$alkylamino$(C_{1-7})$alkyl, $(C_{1-7})$alkanoylamino$(C_{1-7})$alkyl, $(C_{1-7})$alkylsulfonylamino$(C_{1-7})$alkyl, carboxy$(C_{1-7})$alkyl, $(C_{1-7})$alkoxycarbonyl$(C_{1-7})$alkyl, halo, hydroxy, $(C_{1-7})$alkoxy, hydroxy$(C_{1-7})$alkyloxy, $(C_{1-7})$alkoxy$(C_{1-7})$alkoxy, acylamino$(C_{1-7})$alkoxy, amino$(C_{1-7})$alkoxy, N—$(C_{1-7})$alkanoylamino$(C_{1-7})$alkoxy, carboxy$(C_{1-7})$alkyloxy, $(C_{1-7})$alkyloxycarbonyl$(C_{1-7})$alkoxy, carbamoyl$(C_{1-7})$alkoxy, N-mono-$(C_{1-7}$alkyl)carbamoyl$(C_{1-7})$alkoxy, N,N-di-(($C_{1-7})$alkyl)carbamoyl$(C_{1-7})$alkoxy, morpholino$(C_{1-7})$alkoxy, pyridyl$(C_{1-7})$alkoxy, amino, $(C_{1-7})$alkanoylamino, $(C_{1-7})$alkanoyl, $(C_{1-7})$alkyloxy$(C_{1-7})$alkanoyl, $(C_{1-7})$alkoxy$(C_{1-7})$alkanoyl, carboxyl, carbamoyl, N—$(C_{1-7})$alkoxy$(C_{1-7})$alkylcarbamoyl, pyrazolyl, pyrazolyl$(C_{1-7})$alkoxy, and 4-$(C_{1-7})$alkylpiperidin-1-yl.

In some variations of the preceding particular embodiments and variations, $R_{11}$, $R_{12}$, $R_{13}$, $R_{14}$, and $R_{15}$ are each independently selected from the group consisting of hydrogen, halo, $(C_{1-7})$alkyl, $(C_{1-7})$alkoxy, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$cycloalkanoylamino$(C_{1-7})$alkyl, aminoacyl$(C_{1-7})$alkoxy, and N-mono-$(C_{1-7}$alkyl)carbamoyl$(C_{1-7})$alkyl.

In other variations, $R_{11}$, $R_{12}$, $R_{13}$, $R_{14}$, and $R_{15}$ are each independently selected from the group consisting of chloro, methyl, methoxyethyl, methoxypropyl, —(CH$_2$)$_2$C(O) NHCH$_3$, —(CH$_2$)$_2$OC(O)NHCH$_3$, —(CH$_2$)NHC(O) CH$_2$CF$_3$, —(CH$_2$)NHCHF$_2$, —CH$_2$NHC(O)-cyclopropyl, methoxyethoxymethyl, and methoxypropyloxy.

In still other variations, $R_{11}$, $R_{12}$, $R_{13}$, $R_{14}$, and $R_{15}$ are each independently selected from the group consisting of hydrogen, halo, unsubstituted or substituted $(C_{1-6})$alkoxy, unsubstituted or substituted $(C_{1-6})$alkyl.

Particular examples of compounds according to the present invention include, but are not limited to:

4-(Biphenyl-3-yl)-N-cyclopropyl-N-(2,3-dichlorobenzyl)-2-(hydroxymethyl)-1,2,5,6-tetrahydropyridine-3-carboxamide;

4-(4-(2-(2-Chlorophenoxy)ethoxy)phenyl)-N-cyclopropyl-N-(2,3-dichlorobenzyl)-2-(hydroxymethyl)-1,2,5,6-tetrahydropyridine-3-carboxamide;

N-(3-Chlorobenzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-4-(Biphenyl-3-yl)-N-cyclopropyl-N-(2,3-dichlorobenzyl)-2-((methoxymethoxy)methyl)-1,2,5,6-tetrahydropyridine-3-carboxamide;

(S)-N-Cyclopropyl-N-(2,3-dichlorobenzyl)-4-(4-(2-(2,6-dichlorophenoxy)ethoxy)phenyl)-2-((methoxymethoxy)methyl)-1,2,5,6-tetrahydropyridine-3-carboxamide;

(S)-N-Cyclopropyl-N-(2,3-dichlorobenzyl)-4-(4-(2-(2,6-dichlorophenoxy)ethoxy)phenyl)-2-(hydroxymethyl)-1,2,5,6-tetrahydropyridine-3-carboxamide;

2-Cyclopropyl-3-(2,3-dichlorophenyl)-1-((S)-4-(4-(2-(2,6-dimethylphenoxy)ethoxy)phenyl)-2-(hydroxymethyl)-1,2,5,6-tetrahydropyridin-3-yl)propan-1-one;

(S)-N-Cyclopropyl-N-(2,3-dichlorobenzyl)-4-(4-(2-(2,6-dimethylphenoxy)ethoxy)phenyl)-2-((methoxymethoxy)methyl)-1,2,5,6-tetrahydropyridine-3-carboxamide;

(S)-N-Cyclopropyl-4-(4-(2-(2,6-dichloro-4-methylphenoxy)ethoxy)phenyl)-N-(2,3-dichlorobenzyl)-2-(hydroxymethyl)-1,2,5,6-tetrahydropyridine-3-carboxamide;

(S)-N-Cyclopropyl-4-(4-(2-(2,6-dichloro-4-methylphenoxy)ethoxy)phenyl)-N-(2,3-dichlorobenzyl)-2-((methoxymethoxy)methyl)-1,2,5,6-tetrahydropyridine-3-carboxamide;

(S)-4-(4-(2-(2-Chloro-3,6-difluorophenoxy)ethoxy)phenyl)-N-cyclopropyl-N-(2,3-dichlorobenzyl)-2-(hydroxymethyl)-1,2,5,6-tetrahydropyridine-3-carboxamide;

(S)-N-Cyclopropyl-N-(2,3-dichlorobenzyl)-2-(hydroxymethyl)-4-(4-hydroxyphenyl)-1,2,5,6-tetrahydropyridine-3-carboxamide;

(S)-N-Cyclopropyl-N-(2,3-dichlorobenzyl)-2-(hydroxymethyl)-4-(4-methoxyphenyl)-1,2,5,6-tetrahydropyridine-3-carboxamide;

(S)-2-(Aminomethyl)-N-cyclopropyl-N-(2,3-dichlorobenzyl)-4-(4-(2-(2,6-dichlorophenoxy)ethoxy)phenyl)-1,2,5,6-tetrahydropyridine-3-carboxamide;

(S)-N-((5-chloro-2-(3-methoxypropyl)pyridin-4-yl)methyl)-N-cyclopropyl-4-(4-(2-(2,6-dimethylphenoxy)ethoxy)phenyl)-2-(hydroxymethyl)-1,2,5,6-tetrahydropyridine-3-carboxamide;

(S)-N-((5-chloro-2-(3-methoxypropyl)pyridin-4-yl)methyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;

(S)-N-((5-chloro-2-(3-methoxypropyl)pyridin-4-yl)methyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-((5-chloro-2-(3-methoxypropyl)pyridin-4-yl)methyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-((5-chloro-2-(3-methoxypropyl)pyridin-4-yl)methyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-((5-chloro-2-(3-methoxypropyl)pyridin-4-yl)methyl)-N-cyclopropyl-4-(4-(2-(2,6-dichloro-4-methylphenoxy)ethoxy)phenyl)-2-((methoxymethoxy)methyl)-1,2, 5,6-tetrahydropyridine-3-carboxamide;
(S)-N-(2-chloro-5-(3-methoxypropyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-(2-chloro-5-(3-methoxypropyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;
(S)-N-(2-chloro-5-(3-methoxypropyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;
(S)-N-(2-chloro-5-(3-methoxypropyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;
(S)-N-(2-chloro-5-(3-methoxypropyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;
(S)-N-(2-chloro-5-(3-methoxypropyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;
(S)-N-(2-chloro-5-(2-methoxyethyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-(2-chloro-5-(2-methoxyethyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;
(S)-N-(2-chloro-5-(2-methoxyethyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;
(S)-N-(2-chloro-5-(2-methoxyethyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;
(S)-N-(2-chloro-5-(2-methoxyethyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;
(S)-N-(2-chloro-5-(2-methoxyethyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;
(S)-N-(2-chloro-5-(cyclopropanecarboxamidomethyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-(2-chloro-5-(cyclopropanecarboxamidomethyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;
(S)-N-(2-chloro-5-(cyclopropanecarboxamidomethyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;
(S)-N-(2-chloro-5-(cyclopropanecarboxamidomethyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;
(S)-N-(2-chloro-5-(cyclopropanecarboxamidomethyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;
(S)-N-(2-chloro-5-(cyclopropanecarboxamidomethyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;
(S)-N-(2-chloro-5-((3,3,3-trifluoropropanamido)methyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-(2-chloro-5-((3,3,3-trifluoropropanamido)methyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;
(S)-N-(2-chloro-5-((3,3,3-trifluoropropanamido)methyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;
(S)-N-(2-chloro-5-((3,3,3-trifluoropropanamido)methyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;
(S)-N-(2-chloro-5-((3,3,3-trifluoropropanamido)methyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;
(S)-N-(2-chloro-5-((3,3,3-trifluoropropanamido)methyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;
(S)-N-(2-chloro-5-((2,2-difluoroethylamino)methyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-(2-chloro-5-((2,2-difluoroethylamino)methyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;
(S)-N-(2-chloro-5-((2,2-difluoroethylamino)methyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;
(S)-N-(2-chloro-5-((2,2-difluoroethylamino)methyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;
(S)-N-(2-chloro-5-((2,2-difluoroethylamino)methyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;
(S)-N-(2-chloro-5-((2,2-difluoroethylamino)methyl)benzyl)-N-cyclopropyl-4-(4-(2-(2,6-dichloro-4-methylphenoxy)ethoxy)phenyl)-2-((methoxymethoxy)methyl)-1,2, 5,6-tetrahydropyridine-3-carboxamide;
(S)-N-(2-chloro-5-(3-(methylamino)-3-oxopropyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-(2-chloro-5-(3-(methylamino)-3-oxopropyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;
(S)-N-(2-chloro-5-(3-(methylamino)-3-oxopropyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;

(S)-4-chloro-3-((N-cyclopropyl-4-(4-(2-(2,6-dimethylphenoxy)ethoxy)phenyl)-2-(hydroxymethyl)-1,2,5,6-tetrahydropyridine-3-carboxamido)methyl)phenethyl methylcarbamate;

(S)-4-chloro-3-((N-cyclopropyl-4-(4-(2-(2,6-dimethylphenoxy)ethoxy)phenyl)-2-((methoxymethoxy)methyl)-1,2,5,6-tetrahydropyridine-3-carboxamido)methyl)phenethyl methylcarbamate;

(S)-4-chloro-3-((N-cyclopropyl-4-(4-(2-(2,6-dichlorophenoxy)ethoxy)phenyl)-2-(hydroxymethyl)-1,2,5,6-tetrahydropyridine-3-carboxamido)methyl)phenethyl methylcarbamate;

(S)-4-chloro-3-((N-cyclopropyl-4-(4-(2-(2,6-dichlorophenoxy)ethoxy)phenyl)-2-((methoxymethoxy)methyl)-1,2,5,6-tetrahydropyridine-3-carboxamido)methyl)phenethyl methylcarbamate;

(S)-4-chloro-3-((N-cyclopropyl-4-(4-(2-(2,6-dichloro-4-methylphenoxy)ethoxy)phenyl)-2-(hydroxymethyl)-1,2,5,6-tetrahydropyridine-3-carboxamido)methyl)phenethyl methylcarbamate; and (S)-4-chloro-3-((N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamido)methyl)phenethyl methylcarbamate.

It is noted that the compounds of the present invention may be in the form of a pharmaceutically acceptable salt. It is further note that the compounds of the present invention may be in a mixture of stereoisomers, or the compound may comprise a single stereoisomer.

In another aspect, the present invention is related to a pharmaceutical composition comprising as an active ingredient a compound according to any one of the above embodiments and variations. In one embodiment, the composition is a solid formulation adapted for oral administration. In another embodiment, the composition is a liquid formulation adapted for oral administration. In yet another embodiment, the composition is a tablet. In still another embodiment, the composition is a liquid formulation adapted for parenteral administration.

In another embodiment, the pharmaceutical composition comprises a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In another aspect, the invention is related to a kit which comprises a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another aspect, the invention is related to an article of manufacture comprising a compound of any one of the above embodiments and variations and packaging materials. In one embodiment, the packaging material comprises a container for housing the compound. In another embodiment, the container comprises a label indicating one or more members of the group consisting of a disease state for which the compound is to be administered, storage information, dosing information and/or instructions regarding how to administer the compound. In another embodiment, the article of manufacture comprises the compound in a multiple dose form.

In a further aspect, the invention is related to a therapeutic method comprising administering a compound to a subject.

In one embodiment, the method comprises contacting renin with a compound of any one of the above embodiments and variations.

In yet another embodiment is a method of inhibiting renin which comprises causing a compound of any one of the above embodiments and variations to be present in a subject in order to inhibit renin in vivo.

A further embodiment is a method of inhibiting renin which comprises administering a first compound to a subject that is converted in vivo to a second compound wherein the second compound inhibits renin in vivo, the second compound being a compound according to any one of the above embodiments and variations.

Another further embodiment is a method of treating a disease state for which renin possesses activity contributes to the pathology and/or symptomology of the disease state. In one variation, the method comprises causing a compound of any one of the above embodiments and variations to be present in a subject in a therapeutically effective amount for the disease state. In another variation, the method comprises administering a compound of any one of the above embodiments and variations to a subject, wherein the compound is present in the subject in a therapeutically effective amount for the disease state. In a further variation, the method comprises administering a first compound to a subject that is converted in vivo to a second compound wherein the second compound inhibits renin in vivo, the second compound being a compound according to any one of the above embodiments and variations.

In one variation of the above embodiments and variations, the disease state is selected from the group consisting of cardiovascular disease, hypertension, congestive heart failure, myocardial infarction, renal protection, inflammation, neurological disease and cancer.

Another aspect of the invention is directed to method of preparing the compounds of the invention.

In one embodiment, the method comprising
coupling a compound 2I¹ of the formula

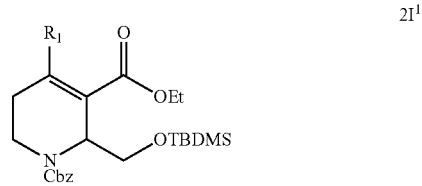

to a compound of the formula HNR$_2$R$_6$, under conditions that form a reaction product $2K^1$ of the formula

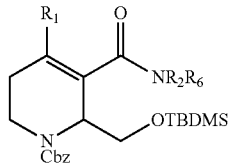

2K$^1$ wherein
Cbz is benzyloxycarbonyl;
OTBDMS is tert-butyldimethylsilyloxy;
$R_1$ is a cyclyl moiety, unsubstituted or substituted;
$R_2$ is selected from the group consisting of hydrogen, $(C_{1-10})$alkoxy, $(C_{4-12})$aryloxy, hetero$(C_{1-10})$aryloxy, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and
$R_6$ is selected from the group consisting of hydrogen, $(C_{1-10})$alkoxy, $(C_{4-12})$aryloxy, hetero$(C_{1-10})$aryloxy, $(C_{1-10})$alkyl, $(C_{1-10})$alkenyl, $(C_{1-10})$alkynyl, halo$(C_{1-40})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted.

In some variations of the preceding embodiment, the method further comprises
deprotecting the reaction product $2K^1$ of the formula

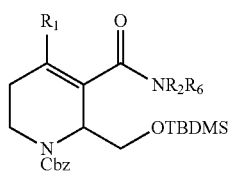

2K$^1$ under conditions that form compound $2L^1$ of the formula

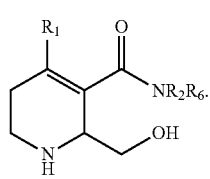

2L$^1$

In other variations of the preceding embodiment and variations, the method further comprises coupling a compound $2F^1$ of the formula

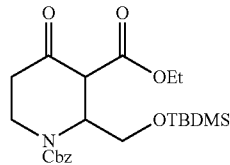

2F$^1$ to a compound of the formula $R_1$—$B(OH)_2$, under conditions that form a reaction product of the formula

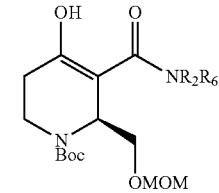

2I$^1$

In other variations of the preceding embodiment and variations, the method further comprises
coupling (E)-ethyl 4-(tert-butyldimethylsilyloxy)but-2-enoate to ethyl 3-aminopropanoate (EtOC(O)(CH$_2$)$_2$NH$_2$), under conditions that form a reaction product $2F^1$ of the formula

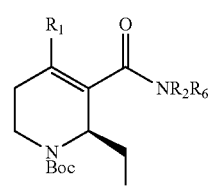

2F$^1$

In another embodiment of the method of preparing compounds of the invention, the method comprises coupling a compound 5I of the formula

5I

OH O
NR$_2$R$_6$
N
Boc
OMOM to a compound of the formula $R_1$—$B(OH)_2$, under conditions that form a reaction product 5L of the formula

5L

R$_1$ O
NR$_2$R$_6$
N
Boc
OMOM wherein

Boc is tert-butyloxycarbonyl;

OMOM is methoxymethoxy;

$R_1$ is a cyclyl moiety, unsubstituted or substituted;

$R_2$ is selected from the group consisting of hydrogen, $(C_{1-10})$alkoxy, $(C_{4-12})$aryloxy, hetero$(C_{1-10})$aryloxy, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and $R_6$ is selected from the group consisting of hydrogen, $(C_{1-10})$alkoxy, $(C_{4-12})$aryloxy, hetero$(C_{1-10})$aryloxy, $(C_{1-10})$alkyl, $(C_{1-10})$alkenyl, $(C_{1-10})$alkynyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, hetero$(C_{1-10})$aryl, each unsubstituted or substituted.

In some variations of the preceding embodiment, the method further comprises deprotecting the reaction product 5L of the formula

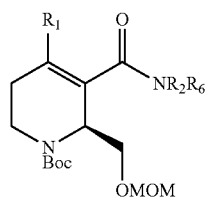

5L under conditions that form a compound selected from the group consisting of

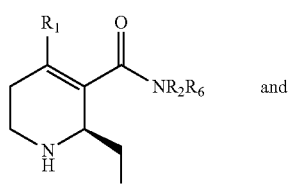

5M and

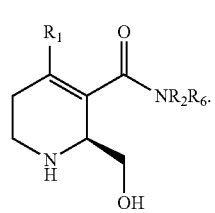

5N

In other variations of the preceding embodiment and variations, the method further comprises coupling

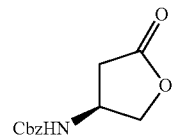

((S)-benzyl 5-oxotetrahydrofuran-3-ylcarbamate), to a compound of the formula $HNR_2R_6$, under conditions that form a reaction product 5E of the formula

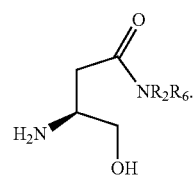

5E

In other variations of the preceding embodiment and variations, the method further comprises coupling compound 5E of the formula

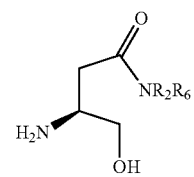

5E to methyl acrylate, under conditions that form a reaction product 5I of the formula

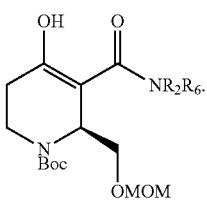

5I

Salts, Hydrates, and Prodrugs of Renin Inhibitors

It should be recognized that the compounds of the present invention may be present and optionally administered in the form of salts, hydrates and prodrugs that are converted in vivo into the compounds of the present invention.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

It is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as $(C_{1-4})$ alkyl halides, e.g., methyl, ethyl, iso-propyl and tert-butyl chlorides, bromides and iodides; di $(C_{1-4})$ alkyl sulfates, e.g., dimethyl, diethyl and diamyl sulfates; $(C_{10-18})$ alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water-soluble and oil-soluble compounds of the present invention.

Compounds of the invention further include prodrug derivatives of the compounds. It is noted that in many instances, the prodrugs themselves also fall within the scope of the range of compounds according to the present invention.

Various forms of prodrugs are well known in the art. For examples of such prodrug derivatives, see, e.g., a) Design of Prodrugs, Bundgaard, A. Ed., Elsevier, 1985 and Method in Enzymology, Widder, K. et al., Ed.; Academic, 1985, vol. 42, p. 309-396;

b) Bundgaard, H. "Design and Application of Prodrugs" in A Textbook of Drug Design and Development, Krosgaard-Larsen and H. Bundgaard, Ed., 1991, Chapter 5, p. 113-191; and c) Bundgaard, H., Advanced Drug Delivery Review, 1992, 8, 1-38.

Each of which is incorporated herein by reference.

Pharmaceutically acceptable prodrugs of the compounds of this invention include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Indications for Use of Renin Inhibitors

Renin inhibitors of the present invention may be used to treat and/or prevent high blood pressure, cardiovascular diseases, congestive heart failure, myocardial infarction, renal protection, inflammation, neurological disease and cancer.

Renin is a proteolytic enzyme synthesized and stored principally in the juxtaglomerular apparatus. When renin is released into the blood from the kidney, the renin-angiotensin-aldosterone system ("RAAS") is activated. Renin acts on the alpha-2 globulin angiotensinogen (synthesized in the liver) to generate angiotensin I. This non-pressor decapeptide is converted to angiotensin II by angiotensin-converting enzyme (ACE). The major pharmacological effects of angiotensin II are vasoconstriction and stimulation of the adrenal cortex to release aldosterone, a hormone which causes sodium retention. Vasoconstriction and conservation of sodium both contribute to increased blood pressure. Angiotensin II also produces other physiological effects such as inhibiting renin secretion, increasing sympathetic nervous system activity, stimulating vasopressin secretion, causing a positive cardiac inotropic effect and modulating other hormonal systems. Thus, the renin-angiotensin system plays an important role in normal cardiovascular homeostasis and in some forms of elevated blood pressure (hypertension).

The reduction of the activity of renin in a subject through inhibition may therefore be used to therapeutically address the diseases and conditions caused by the overactivation of RAAS.

Thus, renin inhibiting compounds of the present invention may be used as agents for control of hypertension, may also be used to treat and/or prevent congestive heart failure and hyperaldosteronism, vascular diseases related to diabetes, and renal diseases such as acute or chronic renal failure. In addition, the renin inhibiting compounds may also be used as diagnostic agents for identification of cases of hypertension due to renin excess.

It is noted that the compounds of the present invention may also possess inhibitory activity for other aspartyl proteases (e.g., pepsin, gastricsin, napsin, BACE 1 & 2 and cathepsin D and E) and thus may be used to address disease states associated with these other family members.

In addition, the compounds of the present invention may be useful as inhibitors of plasmepsins to treat malaria and as inhibitors of *Candida albicans* secreted aspartyl proteases to treat fungal infections.

It is further noted that additional diseases beyond those disclosed herein may also be identified as the biological roles that renin and the RAAS system play in various pathways become more fully understood.

Combination Therapy

A wide variety of therapeutic agents may have a therapeutic additive or synergistic effect when used in combination with renin inhibitors according to the present invention. Such therapeutic agents may additively or synergistically combine with the renin inhibitors to reduce or alleviate the effects and symptoms of cardiovascular disease.

The compounds according to the present invention may be used in combination with other therapeutic agents, wherein the cells are treated with a compound according to the present invention before, at the same time, and/or after the cells are treated with the one or more additional cardiovascular therapeutics; these treatments are referred to herein as combination therapy. It is noted that administration of one agent before another is referred to herein as sequential therapy, even if the agents are also administered together. It is noted that combination therapy is intended to cover methods where agents are administered before or after each other (sequential therapy) as well as when the agents are administered at the same time.

Representative classes of cardiovascular agents that may be used with the renin inhibitors of the present invention include, but are not limited to, diuretics, adrenergic blocking agents, vasodilators, calcium channel blockers, angiotensin converting enzyme (ACE) inhibitors, potassium channel activators, antiserotoninergic agents, thromboxane synthetase inhibitors, angiotensin II antagonists, angiotensin II receptor blockers, and other agents useful for treating (in a human or other mammal) hypertension, congestive heart failure, or vascular diseases related to diabetes, or for treating renal diseases such as acute or chronic renal failure.

Representative diuretics include hydrochlorothiazide, polythiazide, piretanide, torasemide, bumetanide, amiloride, chlorothiazide, indapamide, acetazolamide, amiloride, bumetanide, benzthiazide, ethacrynic acid, furosemide, indacrinone, metolazone, spironolactone, triamterene, chlorthalidone and the like or a pharmaceutically acceptable salt thereof.

Representative adrenergic blocking agents include phentolamine, phenoxybenzamine, prazosin, terazosin, tolazine, atenolol, metoprolol, albuterol, nadolol, propranolol, timolol, carteolol and the like or a pharmaceutically acceptable salt thereof.

Representative vasodilators include hydralazine, minoxidil, diazoxide, nitroprusside, flos equinan and the like or a pharmaceutically acceptable salt thereof.

Representative calcium channel blockers include aminone, bencyclane, diltiazem, fendiline, flunarizine, nicardipine, nimodipine, perhexylene, verapamil, gallopamil, nifedipine and the like or a pharmaceutically acceptable salt thereof.

Representative ACE inhibitors include ramipril, aptopril, enalapril, lisinopril, fosinopril, captopril and the like or a pharmaceutically acceptable salt thereof.

Representative potassium channel activators include pinacidil, glibenclamide, glimepiride, diaoxide, cromocalim, and the like or a pharmaceutically acceptable salt thereof.

Representative antiserotoninergic agents include ketanserin and the like or a pharmaceutically acceptable salt thereof.

Representative angiotensin II antagonists include DUP527 and the like or a pharmaceutically acceptable salt thereof.

Representative angiotensin II receptor blockers (angiotensin II receptor antagonists (ARBs)) include losartan, irbesartan, valsartan, omapatrilat, gemopatrilat and the like or a pharmaceutically acceptable salt thereof.

Other representative cardiovascular agents include sympatholytic agents such as methyldopa, clonidine, guanabenz, reserpine and the like or a pharmaceutically acceptable salt thereof.

Dosage, Host and Safety

The compounds of the present invention are stable and can be used safely. In particular, the compounds of the present invention are useful as renin inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Compositions Comprising Renin Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The renin inhibitors and compositions comprising them may be administered or coadministered in any conventional dosage form. Co-administration in the context of this invention is intended to mean the administration of more than one therapeutic agent, one of which includes a renin inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerin, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acacia gelatin, glucose, molasses, polyvinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of an inhibitor of the present invention to reduce renin activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more renin inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

A. Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain variation of the above embodiments and variations, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, *lycopodium* and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof; and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and sucrose. Sweetening agents include sucrose, syrups, glycerin and artificial sweetening agents such as sodium cyclamate and saccharin.

Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

B. Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is known and practiced in the art.

Injectables may be designed for local and systemic administration. Typically a therapeutically effective dosage is formulated to contain a concentration of at least about 0.1% w/w up to about 90% w/w or more, preferably more than 1% w/w of the renin inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The renin inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

C. Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral Ph. Then, a renin inhibitor is added to the resulting mixture, preferably above room temperature, more preferably at about 30-35 Oc, and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

D. Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The renin inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the renin inhibitor alone or in combination with other pharmaceutically acceptable excipients can also be administered.

E. Formulations for Other Routes of Administrations

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

F. Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |

| INTRAVENOUS FORMULATION | |
|---|---|
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |

| TABLET FORMULATION | |
|---|---|
| Compound of the Present Invention | 1% |
| Microcrystalline Cellulose | 73% |
| Stearic Acid | 25% |
| Colloidal Silica | 1%. |

Kits Comprising Renin Inhibitors

The invention is also directed to kits and other articles of manufacture for treating diseases associated with renin. It is noted that diseases are intended to cover all conditions for which the renin possess activity that contributes to the pathology and/or symptomology of the condition.

In one variation of the above embodiments and variations, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another variation of the above embodiments and variations, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific variation of the above embodiments and variations of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered microchip memory coupled with a liquid crystal readout, or audible reminder signal which, for example, reads out the date that the last daily dose has been taken and/or reminds one when the next dose is to be taken.

Preparation and Assaying of Renin Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet and Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art. For example, appropriate prodrugs can be prepared by reacting a non-derivatized compound with a suitable carbamylating agent (e.g., 1,1-acyloxyalkylcarbonochloridate, para-nitrophenyl carbonate, or the like) or an acylating agent. Further examples of methods of making prodrugs are described in Saulnier et al. Bioorganic and Medicinal Chemistry Letters, 1994, Vol. 4, p. 1985. Those of ordinary skill in the art have the knowledge and means to accomplish this without undue experimentation.

Protected derivatives of the compounds can be made by methods known to those of ordinary skill in the art. A detailed description of the techniques applicable to the creation of protecting groups and their removal can be found in T. W. Greene, Protecting Groups in Organic Synthesis, 3rd edition, John Wiley & Sons, Inc. 1999.

Compounds according to the present invention may be conveniently prepared or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet and Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| Ac | (acetyl) |
| atm | (atmosphere) |
| ATP | (Adenosine Triphophatase) |
| Boc | (tert-butyloxycarbonyl) |
| BOP | (bis(2-oxo-3-oxazolidinyl)phosphinic chloride) |
| Brij35 | (polyoxyethyleneglycol dodecyl ether) |
| BSA | (Bovine Serum Albumin) |
| CBZ | (benzyloxycarbonyl) |
| CDI | (1,1-carbonyldiimidazole) |
| DCC | (dicyclohexylcarbodiimide) |
| DCE | (dichloroethane) |
| DCM | (dichloromethane) |
| DIEA | (di-isopropylethylamine) |
| DMAP | (4-dimethylaminopyridine) |
| DME | (1,2-dimethoxyethane) |
| DMF | (N,N-dimethylformamide) |
| DMPU | (N,N'-dimethylpropyleneurea) |

| | -continued |
|---|---|
| DMSO | (dimethylsulfoxide) |
| DTT | (dithiothreitol) |
| EDCI | (ethylcarbodiimide hydrochloride) |
| EDTA | (Ethylenediaminetetraacetic acid) |
| Et | (ethyl) |
| Et$_2$O | (diethyl ether) |
| EtOAc | (ethyl acetate) |
| FMOC | (9-fluorenylmethoxycarbonyl) |
| g | (grams) |
| h | (hours) |
| HOAc or AcOH | (acetic acid) |
| HOBT | (1-hydroxybenzotriazole) |
| HOSu | (N-hydroxysuccinimide) |
| HPLC | (high pressure liquid chromatography) |
| Hz | (Hertz) |
| IBCF | (isobutyl chloroformate) |
| i.v. | (intravenous) |
| i-PrOH | (isopropanol) |
| L | (liters) |
| LAH | (lithium aluminium hydride) |
| M | (molar) |
| mCPBA | (meta-chloroperbenzoic acid) |
| Me | (methyl) |
| MeOH | (methanol) |
| mg | (milligrams) |
| MHz | (megahertz) |
| μL | (microliters) |
| mL | (milliliters) |
| mM | (millimolar) |
| min | (minutes) |
| mmol | (millimoles) |
| mol | (moles) |
| MOMCl | (methoxymethyl chloride) |
| MOPS | (morpholinepropanesulfonic acid) |
| mp | (melting point) |
| NaOAc | (sodium acetate) |
| NEt$_3$ | (triethylamine) |
| OMe | (methoxy) |
| OTf | (O-triflate) |
| OMs | (O-mesylate) |
| Pd(dppf)Cl$_2$ | (bis(diphenyl phosphino)ferrocene dichloro palladium (II) |
| psi | (pounds per square inch) |
| RP | (reverse phase) |
| RT | (ambient temperature) |
| SPA | (Scintillation Proximity Assay) |
| TBAF | (tetra-n-butylammonium fluoride) |
| TBDMS | (tert-butyldimethylsilyl) |
| TBS | (t-butyldimethylsilyl) |
| tBu | (tert-butyl) |
| TEA | (triethylamine) |
| TFA | (trifluoroacetic acid) |
| TFAA | (trifluoroacetic anhydride) |
| THF | (tetrahydrofuran) |
| TIPS | (triisopropylsilyl) |
| TLC | (thin layer chromatography) |
| TMS | (trimethylsilyl) |
| TMSE | (2-(trimethylsilyl)ethyl) |
| TMSI | (trimethylsilyliodide) |
| Tr | (retention time) |

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad). When two rotomers are observed, the combined NMR spectra are presented.

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60° F.-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in *Protective Groups in Organic Chemistry*, John Wiley and Sons, 1991.

General synthetic routes for producing compounds of the present invention are shown in the schemes below. The various substituents may be selected from among the various substituents otherwise taught herein.

Scheme 1. Preparation of Racemic Tetrahydropyridines

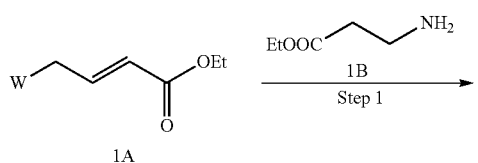

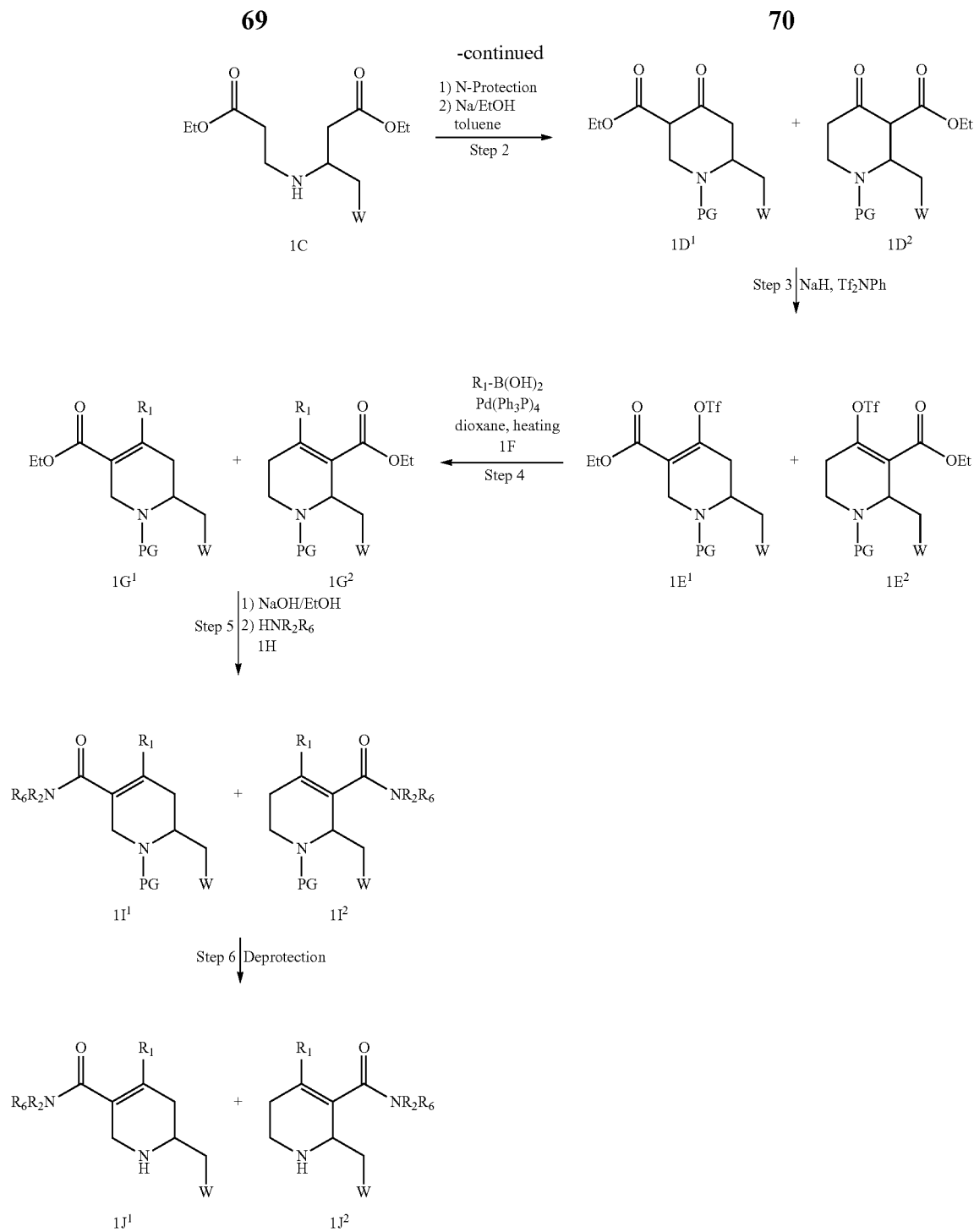

PG is a protecting group
$R_1$, $R_2$, $R_3$, and $R_6$ are as defined in the application The Michael addition reaction of 3-substituted acrylate 1A with beta-amino ester, e.g. ethyl 3-aminopropanoate (1B), gives the diester 1C (Step 1). Protection of the amino group followed by Dieckmann condensation, mediated by sodium/ethanol or methanol, affords the piperidine-4-one 1D as two regioisomers $1D^1$ and $1D^2$ (Step 2) Compound 1D may be transformed into the enol triflate 1E by reacting with a triflating reagent such as 1,1,1-trifluoro-N-phenyl-N-(trifluoromethylsulfonyl)methanesulfonamide in the presence of base such as NaH (Step 3). The enol triflate 1E can then be coupled to an $R_1$-derivative 1F using either a boronic acid derivative ($R_1$—$B(OH)_2$) (1F) under Suzuki conditions or an organozinc reagent ($R_1$—ZnX) under Negishi conditions giving the 4-$R_1$-substituted tetrahydropyridine 1G. Ester hydrolysis of 1G followed by amide coupling with amine 1H forms amide 1I (Step 5). Deprotection of the amino group affords the product 1J (Step 6).

Scheme 2. Preparation of Racemic Hydroxymethyl Analogs

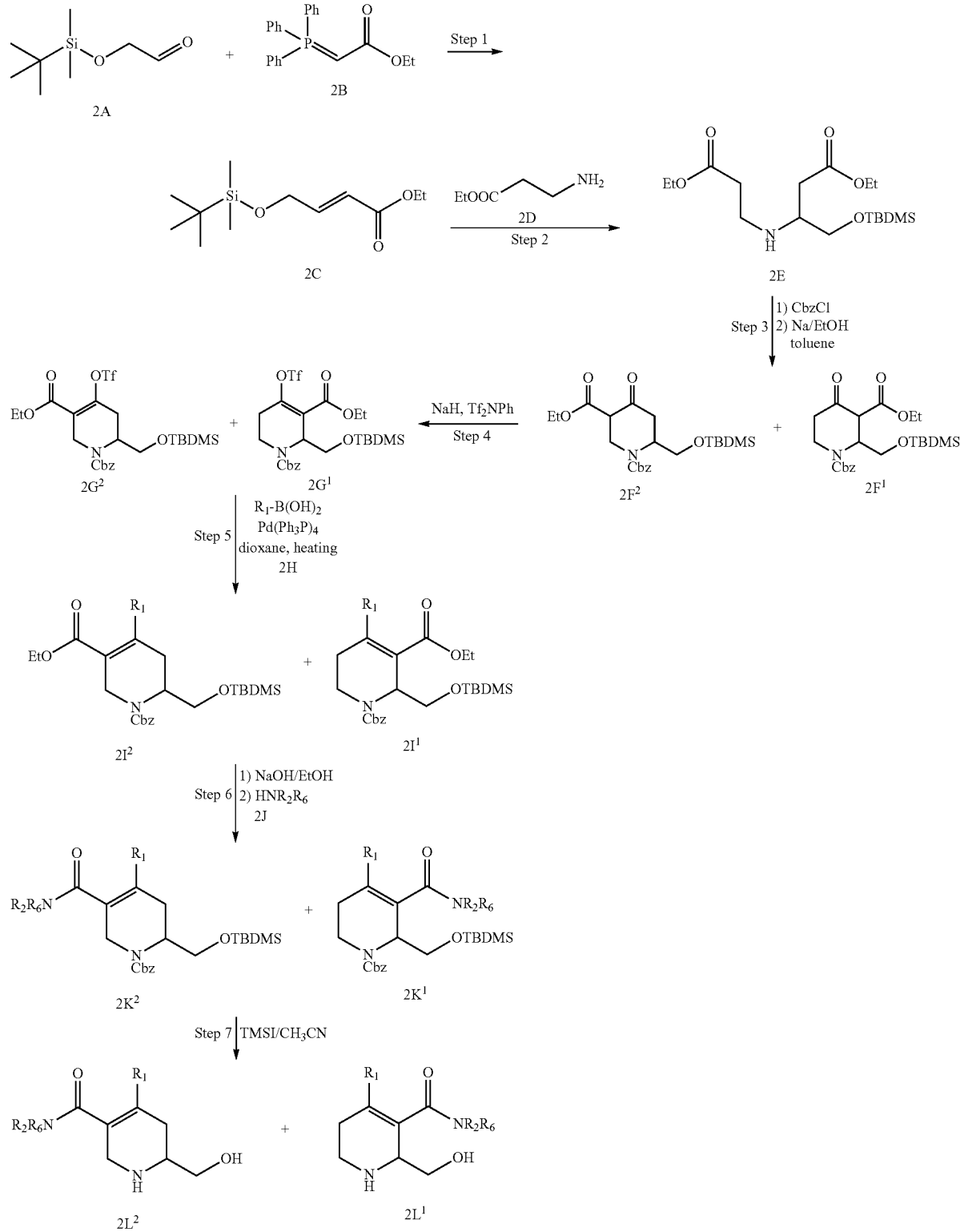

Condensation of the aldehyde 2A with the stable ylide 2B gives the siloxy alpha, beta-unsaturated ester 2C. Michael addition of 2C with beta-aminoalanine ester 2D gives 2E, which may be transformed to the hydroxymethyl racemate analogs 2L (a mixture of regioisomers $2L^1$ and $2L^2$) following procedures described earlier in Scheme 1, Steps 2-6.

Scheme 3. Preparation of Racemic Thioamide Analogs

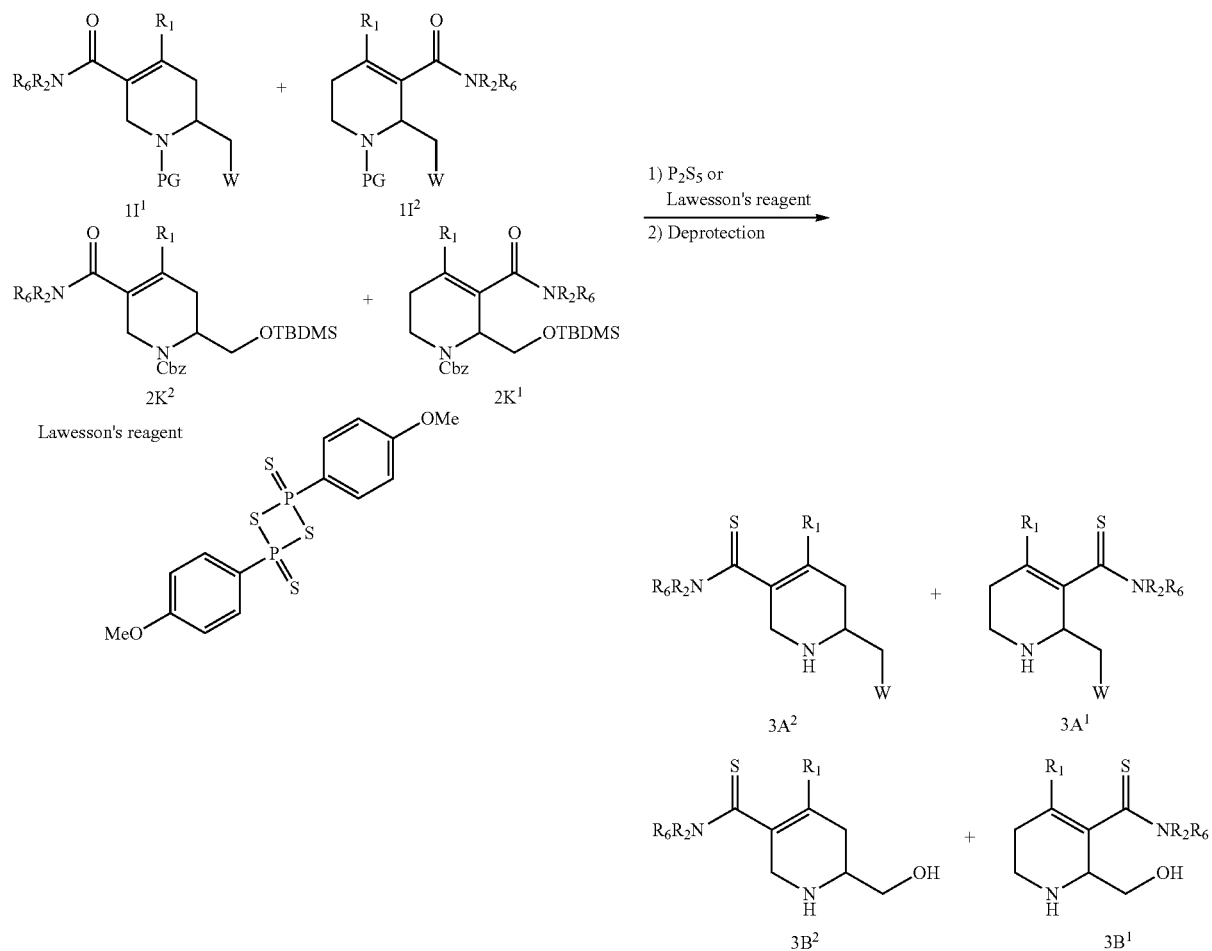

PG is a protecting group
$R_1$, $R_2$, $R_3$, and $R_6$ are as defined in the application.

Amide 1I (Scheme 1) or 2K (Scheme 2) may be converted to thioamides when it reacts with Lawesson's reagent or $P_2S_5$. Lawesson's reagent or $P_{255}$ may be added to a solution of amide 1I or 2K in toluene (or dioxane); the resulting mixture may be stirred at room temperature or heated (up to reflux) for 2 hr to 48 hrs. After removal of solvent under reduced pressure, the crude product may be purified by RP-HPLC to give the N-protected tetrahydropyridinyl thioamides, which upon deprotection with acid (e.g., TFA) to give the desired thioamide 3A or 3B.

Scheme 4. Preparation of Enantiopure Analogs

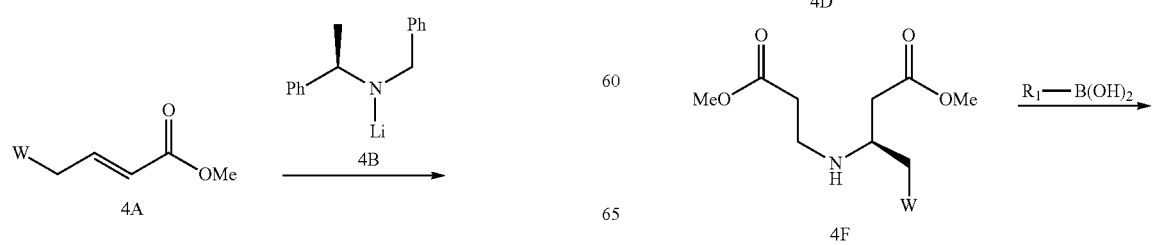

-continued

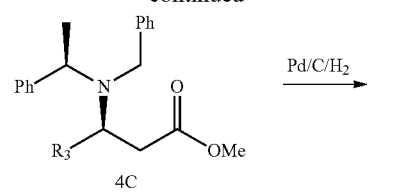

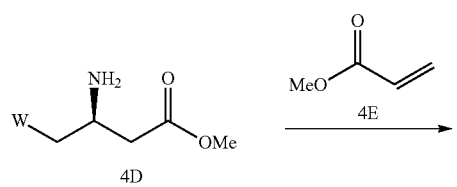

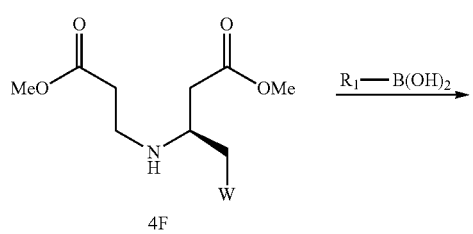

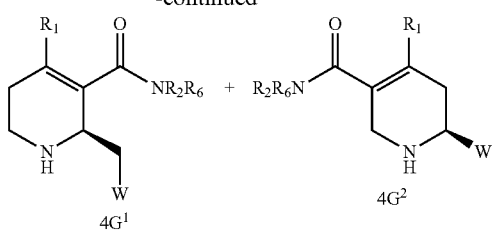

Using a procedure originally reported by Davies and Ichihara, the highly diastereoselective Michael addition reaction of a suitable unsaturated ester 4A with a lithium amide 4B, the N,N-disubstituted beta-amino ester 4C can be synthesized. Removal of the N-benzyl protecting group by palladium catalyzed hydrogenation reaction, the un-substituted beta aminoacid ester 4D is obtained with high enantiomeric purity. Michael addition reaction of 4D to methyl acrylate (4E) gives bis-ester 4F. Subsequent reactions following a similar reaction sequence as shown in Scheme 1, Steps 2-6 gives the final enantiopure renin inhibitor 4G. Additionally, the thioamides may be obtained via the reactions described in Scheme 3.

Scheme 5. Preparation of Enantiopure Hydroxymethyl Analogs - Method 1

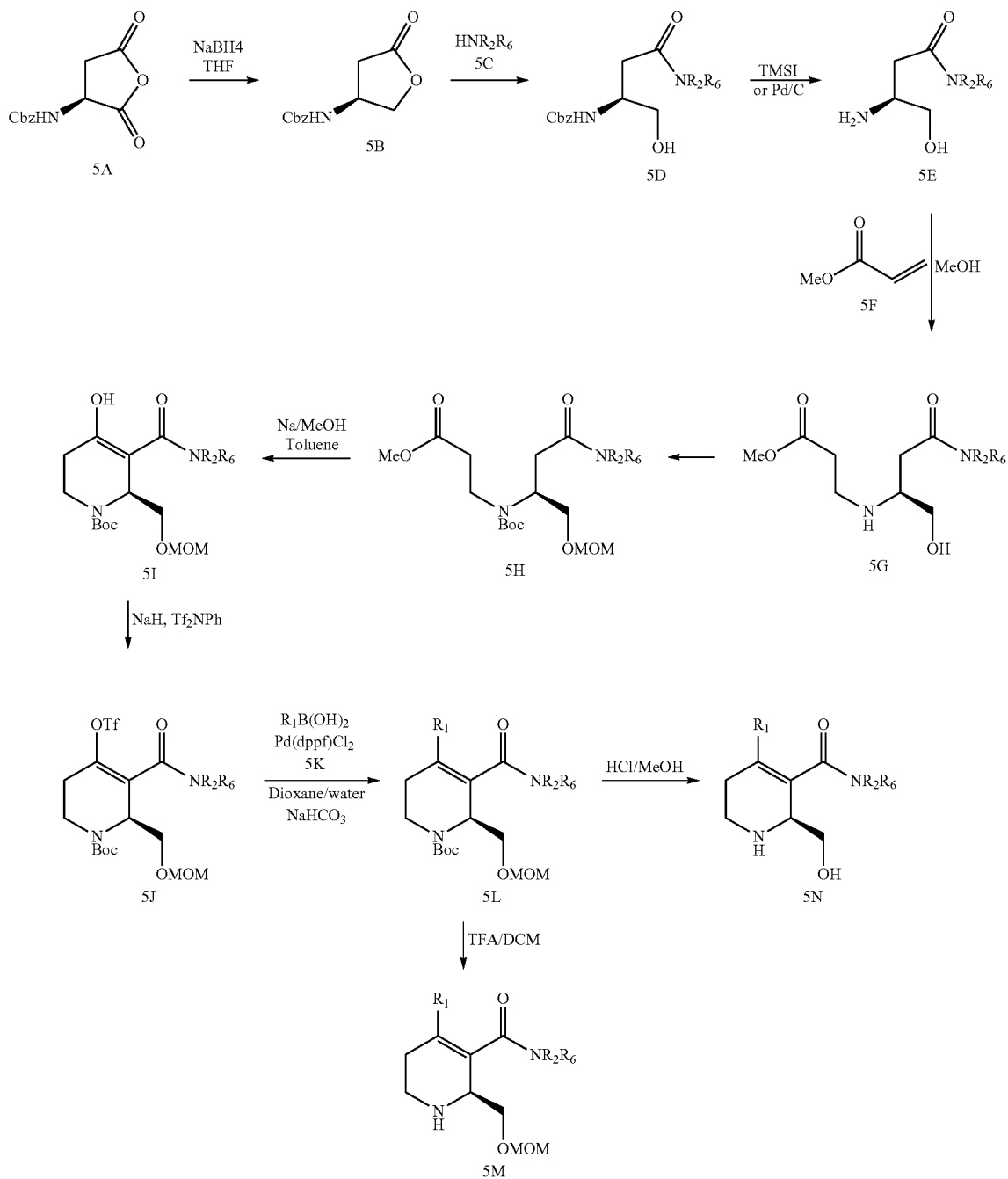

N-carbobenzyloxy(Cbz)-L-aspartic anhydride 5A, may be first partially reduced to cyclic lactone 5B with sodium borohydride in THF. Lactone ring opening was achieved with an amine 5C to give hydroxyl-amide analog 5D. The Cbz protecting group is then removed with trimethylsilyl iodide (TMSI) to yield the hydroxyl-amine 5E. Michael addition with 5F yield 5G, and followed by, N— and O— protection to give the chirally pure di-ester 5H, which is then subjected to Dieckmann condensation in the presence of Na and MeOH to give the ring closure product tetrahydropyrdine 5I. Following a similar reaction sequence as those shown in Scheme 2 (Steps 4-5), reaction with boronic acid derivative of $R_1$, 5K, compound 5L can be obtained. The Boc protecting can be selectively removed in the presence of MOM ether with TFA in DCM to give 5M; or a more drastic acidic condition can be used to deprotect both MOM and Boc groups at the same time to give the free hydroxyl analog 5N.

Scheme 6. Preparation of Enantiopure Hydroxymethyl Analogs - Method 2

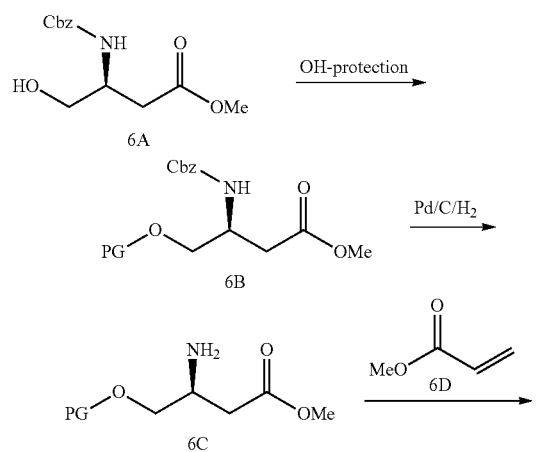

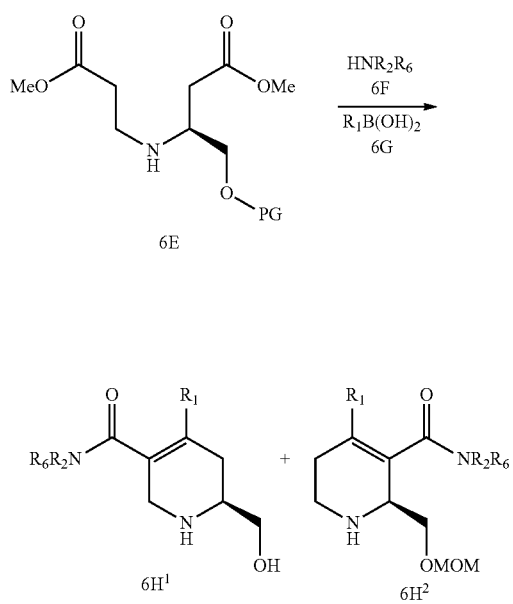

PG is a protecting group, e.g., TBDMS or MOM etc

Alternatively, O-protection of the commercial chiral amino acid derivative 6A by groups such as methoxymethyl (MOM) ether or tert-butyldimethylsilyl (TBDMS) ether give 6B, which is then converted to the free amine 6C by hydrogenation reaction. Michael addition with methyl acrylate 6D gives di-ester 6E. Compound 6E is then transformed to the amides $6H^1$ and $6H^2$ by using similar reaction procedures as outlined in Scheme 2, Steps 3-7.

Scheme 7. Preparation of Aminomethyl Analogs

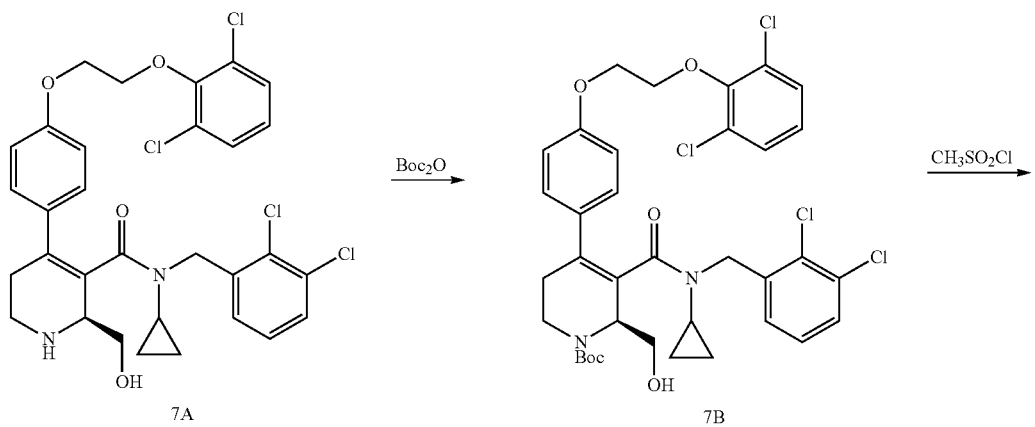

-continued
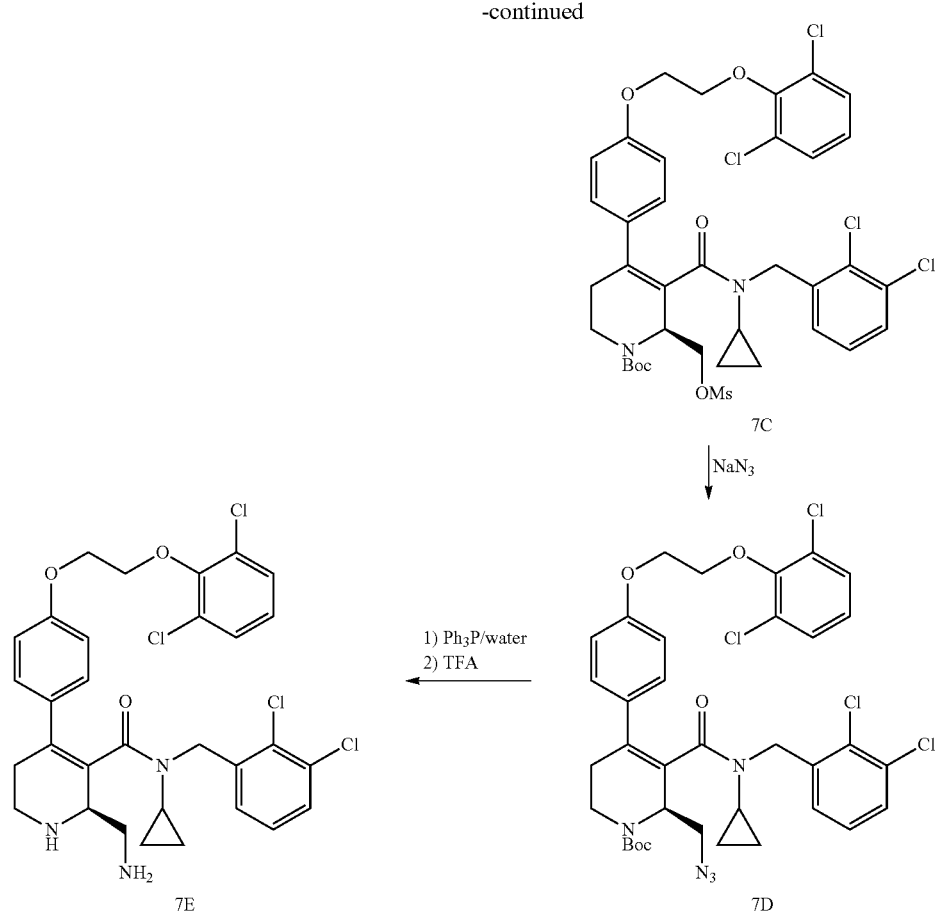
Boc protection of the ring nitrogen of 7A gives 7B. Mesylation of 7B followed with azide displacement of the mesylate gives the azido analogs 7D. Finally, reduction of the azide 7D with triphenylphosphine-water yields the amine 7E.
Scheme 8. Substitution ($NH_2$, OH) at C-5 Position
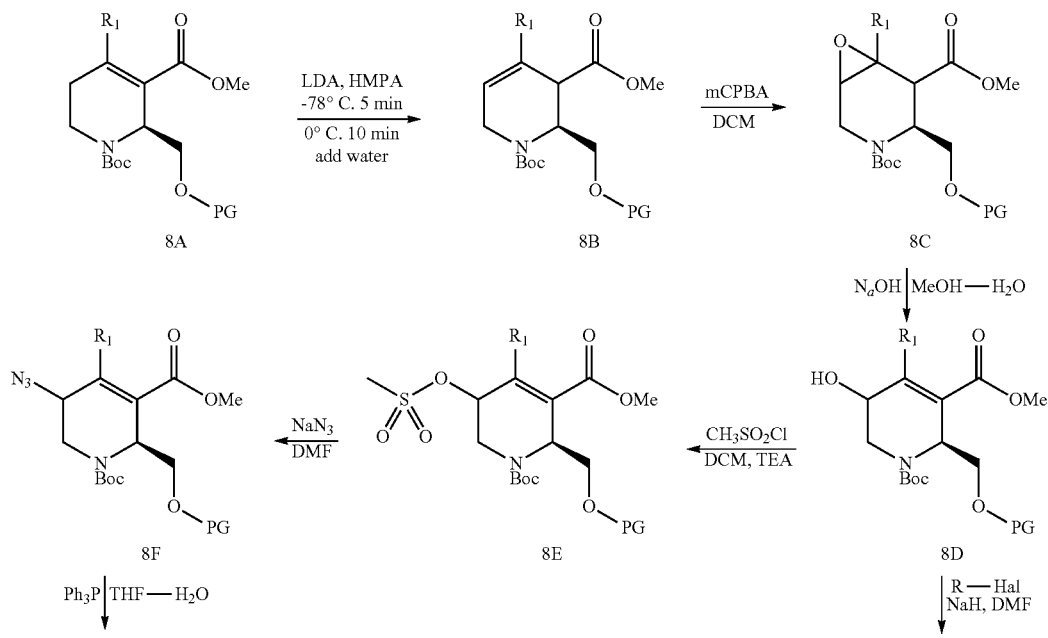

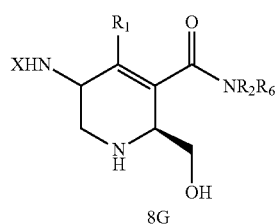

8G

R is H, alkyl, aryl
Hal is Cl or Br

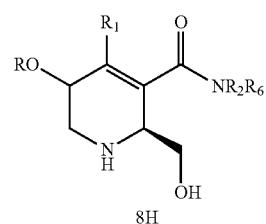

8H

Deprotonation of 8A with a base such as LDA isomerizes the double bond to compound 8B. Epoxidation with reagent such as 3-chloroperbenzoic acid (mCPBA) in dichloromethane or chloroform followed by ring opening with hydroxide (NaOH/MeOH—H$_2$O) gives hydroxyl analog 8D, which can be O-alkylated (NaH/R—X, DMF) to 8H or transformed into mesylate 8E (CH$_3$SO$_2$Cl/DCM, triethylamine), then azide 8F (NaN$_3$/DMF) and amine analog 8G (Ph$_3$P/THF—H$_2$O, then TFA/DCM).

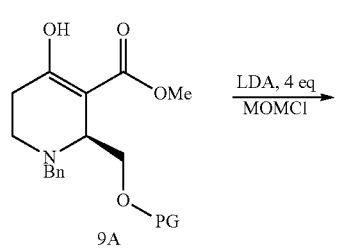

9A

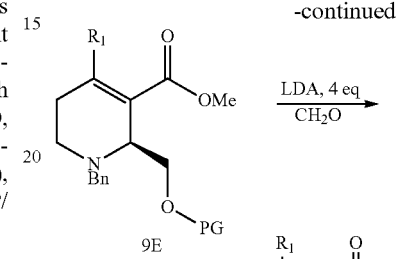

9E

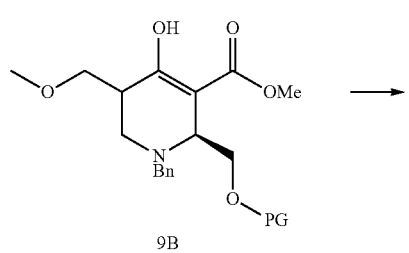

9B

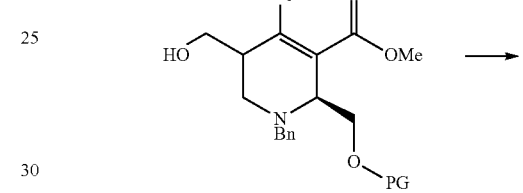

9F

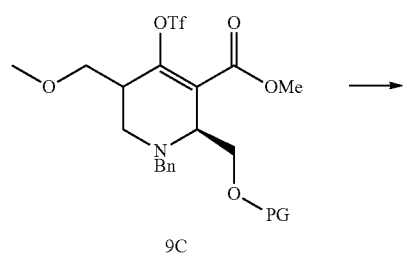

9C

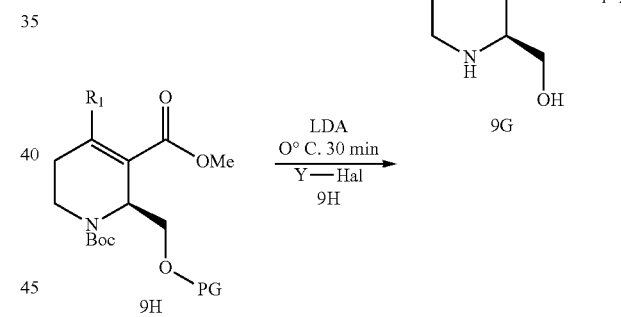

9G

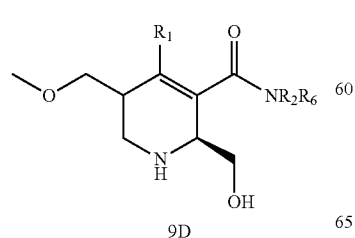

9D

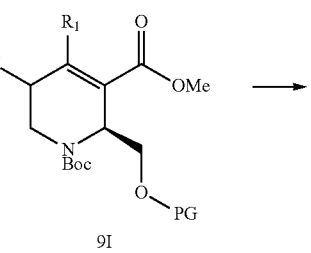

9H

9I

9J

Hal is Cl, Br, or F
PG is a protecting group

C-Alkylated products 9D, 9G and 9J can also be made according to the routes shown above.

In each of the above reaction procedures or schemes, the various substituents may be selected from among the various substituents otherwise taught herein.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5 μL, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10 g). In particular variations, the flow rate for separation can be 70 mL/min, the injection volume up to 2 mL, and the inlet pressure set at 130 bar. Stacked injections can be applied to increase the efficiency.

Description of the syntheses of particular compounds according to the present invention based on the above reaction schemes as set forth herein.

The present invention is further exemplified, but not limited, by examples provided below that describe the synthesis of particular compounds according to the invention.

Biological Testing

The activity of compounds as renin inhibitors may be assayed in vitro, in vivo or in a cell line. Example D below provides an in vitro enzymatic activity assay for activity against renin.

Test compounds in varying concentrations may be reacted with recombinant human renin in the presence of substrate, e.g., QXL520-γ-Abu-Ile-His-Pro-Phe-His-Leu-Val-Ile-His-Thr-Lys (HiLyteFluo488)-Arg-OH (Anaspec, San Jose, Calif.). The reaction can be followed kinetically using fluorescence (excitation λ=485 nm; emission λ=538 nm) Inhibition constants ($IC_{50}$) may be calculated by non-linear curve fitting of the compound concentrations and fluorescence intensities to the standard $IC_{50}$ equation. $IC_{50}$ values for selected compounds of the present invention are given in Table 1.

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

EXAMPLE

The present invention is further exemplified, but not limited by, the following examples that described the synthesis of particular compounds according to the invention.

HPLC Conditions:

The following HPLC conditions are used through out the examples. The HPLC is an Agilent 1100 system equipped with a MSD mass detector. For condition 1-3 (FAST method) a Phenomenex Luna 110A C18 3.5 μm 4.6×30 mm column is used. For condition 4-6 (analytical method) a Waters SunFire C18 5 μm 4.6×50 mm column is used. Solvent A 0.05% TFA in $H_2O$; Solvent B: 0.035% TFA in Acetonitrile.

| Condition 1-3: | | | | |
|---|---|---|---|---|
| Time (min) | Flow Rate (mL/min) | Fast-2 (B %) | Fast-3 (B %) | Fast-4 (B %) |
| 0.00 | 3.5 | 5 | 10 | 25 |
| 0.10 | 3.5 | 5 | 10 | 25 |
| 0.50 | 3.5 | 5 | 10 | 25 |
| 2.50 | 3.5 | 95 | 95 | 95 |
| 2.60 | 3.5 | 95 | 95 | 95 |
| 2.70 | 3.5 | 5 | 5 | 5 |
| 2.90 | 3.5 | 5 | 5 | 5 |
| 3.00 | 0.2 | 5 | 5 | 5 |

| Condition 4-6: | | | | |
|---|---|---|---|---|
| Time (min) | Flow Rate (mL/min) | Analytical-2 (B %) | Analytical-3 (B %) | Analytical-4 (B %) |
| 0.00 | 3.5 | 5 | 10 | 25 |
| 0.50 | 3.5 | 5 | 10 | 25 |
| 3.75 | 3.5 | 95 | 95 | 95 |
| 4.45 | 3.5 | 95 | 95 | 95 |
| 4.50 | 3.5 | 5 | 10 | 25 |
| 5.00 | 3.5 | 5 | 10 | 25 |
| 5.95 | 3.5 | 5 | 5 | 5 |
| 6.00 | 0.2 | 5 | 5 | 5 |

Example 1

Preparation of Reagents

1A. N-(2,3-dichlorobenzyl)cyclopropanamine (1A)

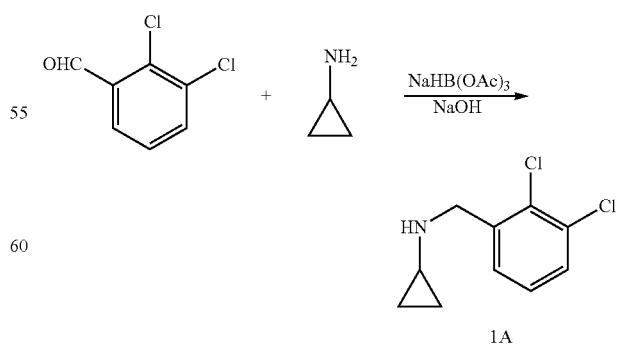

1A

To a mixture of the aldehyde (8.75 g, 50.0 mmol) and cyclopropylamine (3.43 g, 60.0 mmol) in 100 mL of dichloromethane was added 1 mL of AcOH at 0° C. Then NaBH(OAC)₃ (11.65 g, 55.0 mmol) was added in portions over 20 mins at 0° C. The mixture was stirred at 0° C. for 4 hrs. A solution of NaOH (4 g in 4 mL of water) was added, and the mixture was stirred for 30 min, filtered through a pad of SiO₂. The filtrate was concentrated to give the clean product 1A (10.7 g) as colorless liquid. ESI-MS:m/z 216.3 (M+H)⁺ and 218.2 (M+2H)⁺, HPLC retention time: T=1.377 min (FAST-2).

1B. N-(2,3-dimethylbenzyl)cyclopropanamine (1B)

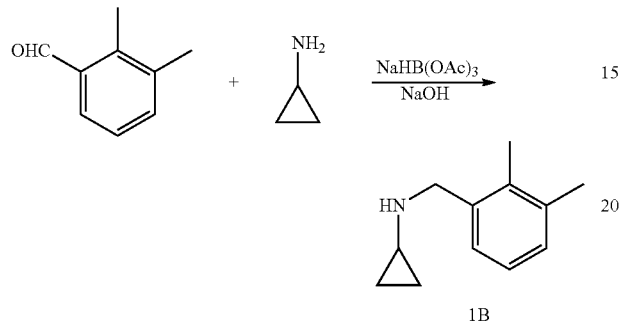

1B was synthesized from 2,3-dimethylbenzaldehyde (5.0 g, 37.3 mmol) using the procedure described for 1A. Yield: 6.0 g (92%) as light yellow oil. ESI-MS:m/z 176.3 (M+H)⁺, HPLC retention time: T=1.340 min (FAST-2).

1C. N-(3-chlorobenzyl)cyclopropanamine (1C)

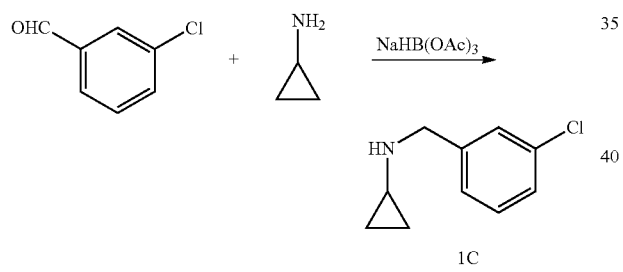

1C was synthesized from 3-chlorobenzaldehyde (20.0 g, 142.3 mmol) using the procedure described for 1A as clear liquid. ESI-MS:m/z 182.08 (M+H)⁺.

Example 2

Preparation of Reagents 2A. 2-(2-Bromoethoxy)-1,3-dichlorobenzene (2A)

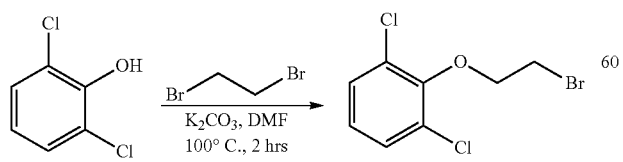

Into a 10 mL round bottom flask was added 2,6-dichlorophenol (326 mg, 2 mmol) and DMF (2 mL). Potassium carbonate (276 mg, 2 mmol, 10 eq) and 1,2-dibromoethane (3.76 g, 20 mmol, 10 eq) was added. The flask was fitted with a reflux condenser and nitrogen inlet and the reaction heated to 100° C. for 2 hours. The mixture was partitioned between water (20 mL) and chloroform (20 mL). The organic layer was separated and the aqueous layer was further extracted with chloroform (3×20 mL). The organic layers were combined, washed twice with 10% sodium carbonate (20 mL) and once with brine (20 mL). The combined organic phase was dried over sodium sulfate and filtered. Solvent was removed under vacuum to leave a brown oil of 2A (264 mg, 49%) which was analytically pure.

2B. 2-(2-Bromoethoxy)-1,3-dichloro-5-methylbenzene (2B)

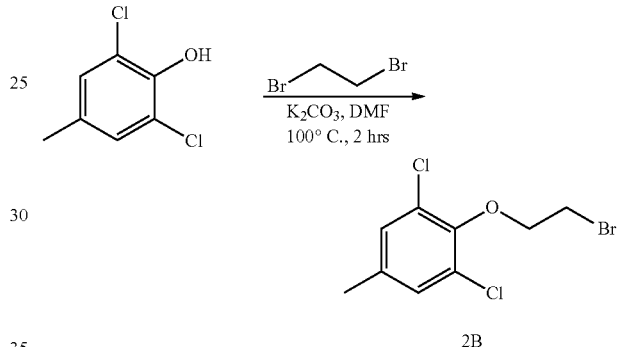

4-Methyl-2,6-dichlorophenol was reacted with 1,2-dibromoethane according to the procedure described in Step 2A to yield the titled compound (4.66 g, 61%). ¹H NMR (400 MHz, CHLOROFORM-d) δ ppm 2.29 (s, 3H) 3.70 (d, J=7.20 Hz, 2H) 4.29 (d, J=7.20 Hz, 2H) 7.11 (s, 2H).

2C. 2-(2-Bromoethoxy)-3-chloro-1,4-difluorobenzene (2C)

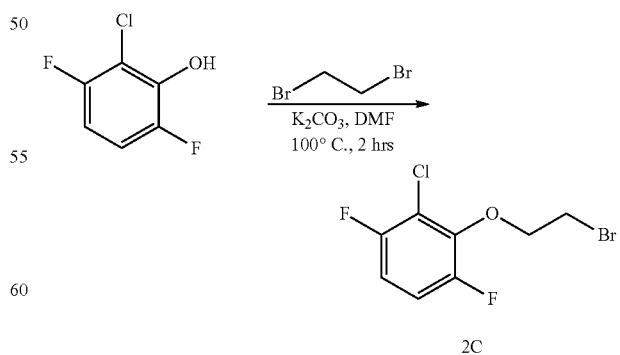

2-Chloro-3,6-difluorophenol was reacted with 1,2-dibromoethane according to the procedure described in Step 2A to yield 2C (2.1 g, 31%). ¹H NMR (400 MHz, CHLORO- FORM-d) δ ppm 3.65 (t, J=6.57 Hz, 2H), 4.43 (t, J=6.57 Hz, 2H) 6.89 (m, 1H) 7.01 (m, 1H).

2D. 2-(2-Bromoethoxy)-1,3-dimethylbenzene (2D)

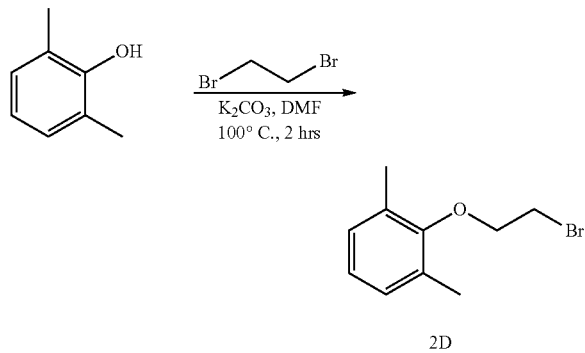

2,6 Dimethylphenol (2 mmol) was reacted with 1,2-dibromoethane (10 eq) as described in Step 2A to yield the titled compound.

2E. 1-(2-Bromoethoxy)-2-chlorobenzene (2E)

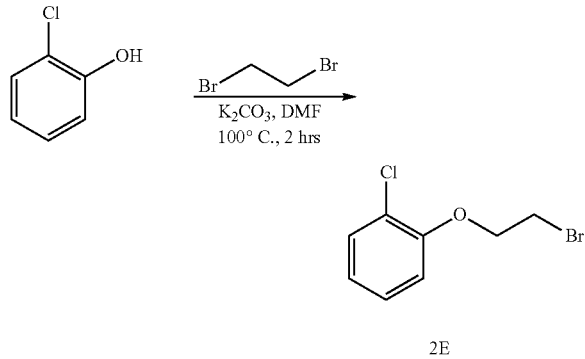

2-Chlorophenol was reacted with 1,2-dibromoethane according to the procedure described in Step 2A to yield the titled compound.

Example 3

Preparation of the Racemate Triflate Regioisomers 3E[1] and 3E[2]

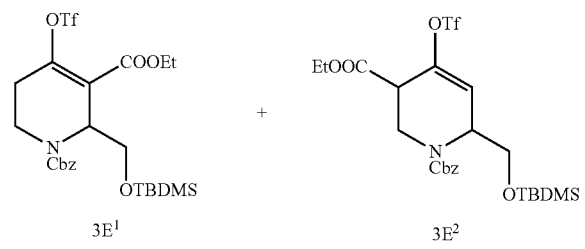

3A. (E)-Ethyl 4-(tert-butyldimethylsilyloxy)but-2-enoate (3A)

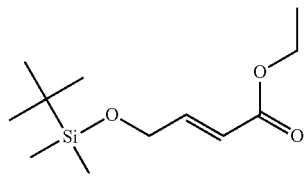

2-(Tert-butyldimethylsilyloxy)acetaldehyde (10.0 g, 57.3 mmol) was added to a solution of (2-ethoxy-2-oxoethyl)triphenylphosphorane (20.0 g, 57.4 mmol) in 150 mL toluene, the mixture was stirred at RT overnight and then heated to 50° C. for 5 hrs. Solvents were removed and the residue was suspended in 400 mL of hexane. The solution was filtered, the filtrate was concentrated to give the product 3A as a colorless liquid 13.7 g (98%). $^1$H NMR (400 MHz, CDCl$_3$) δ ppm 0.08 (s, 6H), 0.92 (s, 9H), 1.30 (t, 3H, 6 Hz), 4.21 (q, 2H, 6 Hz), 4.34 (dt, 2H), 6.09 (dt, 1H), 7.00 (dt, 1H); ESI-MS:m/z 245.3 (M+H)$^+$, HPLC retention time: T=2.737 min (analytical-3).

3B. Ethyl 4-(tert-butyldimethylsilyloxy)-3-(3-ethoxy-3-oxopropylamino)butanoate (3B)

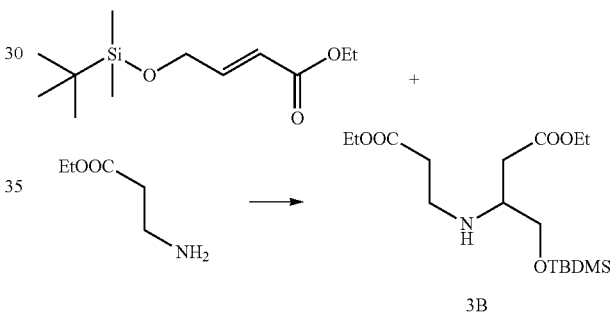

Ethyl 3-aminopropanoate HCl salt (4.6 g, 39.2 mmol, 1.4 eq) was added to a solution of (E)-ethyl 4-(tert-butyldimethylsilyloxy)but-2-enoate in 50 mL of ethanol. The mixture was stirred at RT overnight and then heated to reflux overnight. Another 9.2 g of 3-aminopropanoate HCl salt was added. The reaction was continued to heat at reflux for 2 hr. Solvents were removed; the yellow oily residue was dissolved in DCM, filtered through a pad of SiO$_2$ (~80 g), and washed with 800 mL EtOAc. The filtrate was concentrated to give the product 7.8 g (76%) as a light yellow liquid. HPLC retention time: T=1.844 min (analytical-3); ESI-MS:m/z 362.3 (M+H)$^+$.

3C. Ethyl 3-((benzyloxycarbonyl)(3-ethoxy-3-oxopropyl)amino)-4-(tert-butyldimethylsilyloxy)butanoate (3C)

-continued

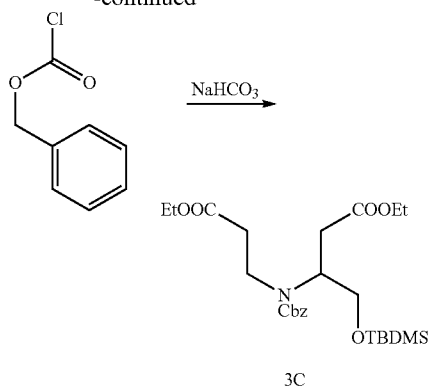

To the amine 3B (7.80 g, 21.6 mmol) and NaHCO$_3$ (2.82 g, 33.6 mmol, 1.55 eq) in 40 mL anhydrous dioxane was added benzyl chloroformate (4.80 g, 28.1 mmol, 1.3 eq) at 0° C. over 5 mins. The ice bath was removed, and the mixture was allowed to warm to RT overnight. Solvents were removed in vacuo; the residue was diluted with 50 mL of water and 100 mL of EtOAc. The organic phase was separated, and the aqueous phase was further extracted with ethyl acetate (3×50 mL). The combined organic phase was dried over Na$_2$SO$_4$, and concentrated. The residue was chromatographed on SiO$_2$ to afford 7.8 g (73%) of product 3C as a colorless liquid along with the recovery of 1.02 g starting material. ESI-MS:m/z 496.5 (M+H)$^+$.

3D. 1-Benzyl 3-ethyl 2-((tert-butyldimethylsilyloxy) methyl)-4-oxopiperidine-1,3-dicarboxylate (3D$^1$); and 1-Benzyl 3-ethyl 6-((tert-butyldimethylsilyloxy) methyl)-4-oxopiperidine-1,3-dicarboxylate (3D$^2$)

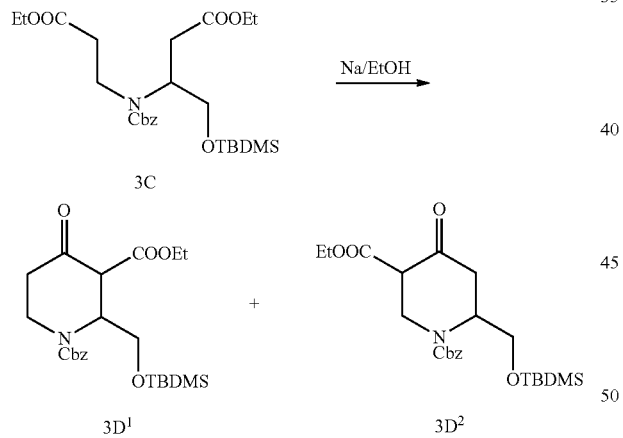

Sodium metal in small pieces (470 mg, 20.4 mmol, 1.3 eq) was added to the di-ester 3C (7.8 g, 15.7 mmol) in anhydrous toluene 50 mL over 15 mins. This was followed by the addition of anhydrous EtOH (275 μL, 217 mg, 4.71 mmol, 0.3 eq). The mixture was stirred at RT for 48 hrs, and then poured onto a cold mixture of saturated of NH$_4$Cl (20 mL) and saturated NaCl (30 mL) solution. The solution was extracted with EtOAc (3×100 mL); the organic phase was dried over Na$_2$SO$_4$ and concentrated to give 5.80 g of crude product as a yellow liquid which was purified chromatographically on a 120 g SiO$_2$ column (5% EtOAc then 20% EtOAC/hexanes) to give a mixture of two the regioisomers 3D$^1$ and 3D$^2$, as a colorless liquid. 5.1 g (72%); ESI-MS:m/z 450.4 (M+H)$^+$; HPLC retention time: T=3.142 min and 3.12 min (analytical-3).

3E. 1-Benzyl 3-ethyl 2-((tert-butyldimethylsilyloxy) methyl)-4-(trifluoromethylsulfonyloxy)-5,6-dihydro-pyridine-1,3(2H)-dicarboxylate (1E$^1$) and 1-benzyl 3-ethyl 6-((tert-butyldimethylsilyloxy)methyl)-4-(trifluoromethylsulfonyloxy)-5,6-dihydropyridine-1,3(2H)-dicarboxylate (1E$^2$)

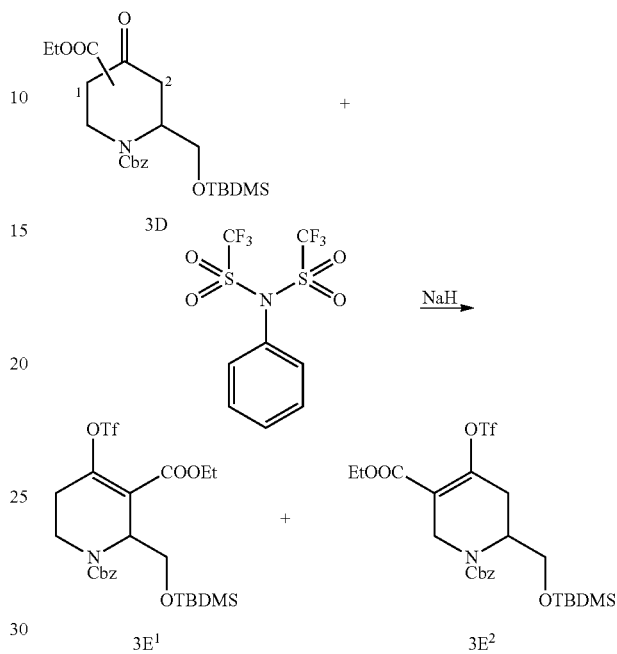

NaH (535 mg, 60%, 13.4 mmol, 1.25 eq) was added to a solution of the beta-ketone esters 3D (4.8 g, 10.7 mmol) in 50 mL THF at 0° C. in portions over 10 mins. After addition, the reaction mixture was stirred for additional 20 mins; Tf$_2$NPh (4.58 g, 12.8 mmol, 1.2 eq) was then added. The mixture was stirred at RT for 3 days. It was then poured onto ice, extracted with EtOAc (3×50 mL). The combined organic phase was dried over Na$_2$SO$_4$ and concentrated to give 10.1 g yellow liquid, which was purified by flash chromatography on a 120 g SiO$_2$ column using 5% EtOAc/hexanes and then 25% EtOAC as eluants. Two triflate regioisomers, 3E$^1$ and 3E$^2$ were obtained as a colorless liquid (6.74 g, 100%). ESI-MS: m/z 582.4 (M+H)$^+$. HPLC retention time: T=2.687 min (analytical-3).

Example 4

Preparation of (S)-tert-butyl 3-(cyclopropyl(2,3-dichlorobenzyl)carbamoyl)-4-(4-hydroxyphenyl)-2-((methoxymethoxy)methyl)-5,6-dihydropyridine-1(2H)-carboxylate (4H)

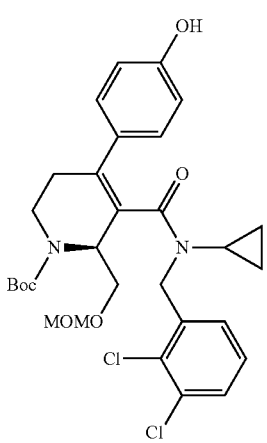

4A (S)-Benzyl-4-(cyclopropyl(2,3-dichlorobenzyl)amino)-1-hydroxy-4-oxobutan-2-ylcarbamate (4A)

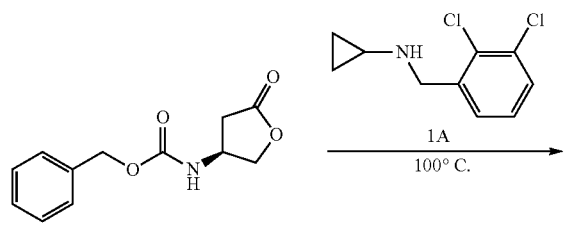

Into a 100 mL round bottom flask fitted with a reflux condenser and a nitrogen inlet, N-(2,3-dichlorobenzyl)cyclopropanamine (30.3 g, 140.3 mmol) (Example 1A) and (S)-benzyl 5-oxotetrahydrofuran-3-ylcarbamate (22.0 g, 93.5 mmol) were added. The mixture was heated without solvent at 100° C. for 24 hours. Purification by column chromatography (5%->10% MeOH/dichloromethane) gave 22.0 g (52%) of 4A. ESI-MS:m/z 451.3 (M+H)$^+$.

4B. (S)-3-Amino-N-cyclopropyl-N-(2,3-dichlorobenzyl)-4-hydroxybutanamide (4B)

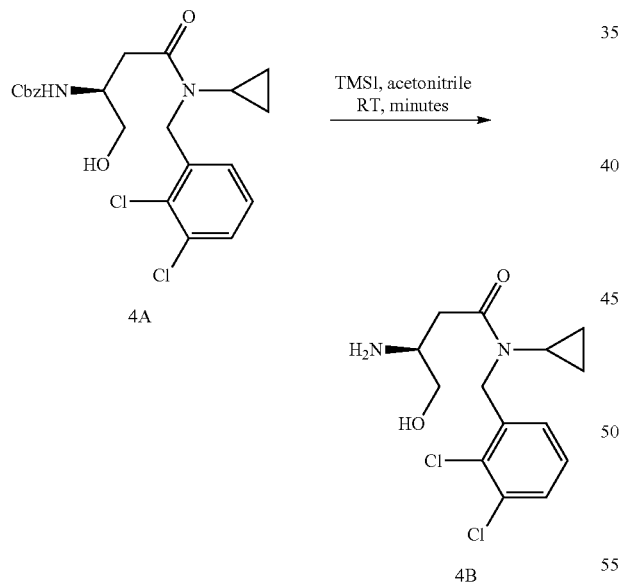

Into a 1L round bottom flask fitted with a nitrogen inlet was added 4A (18.3 g, 40.6 mmol) and acetonitrile (450 mL). Trimethylsilyliodide (TMSI) (17.4 mL, 121.7 mmol, 3 eq) was added quickly at room temperature. After stirring for 15 minutes, the reaction was quenched with 50 mL of methanol. The solvent was removed under vacuum. The residue was partitioned between ethyl acetate (100 mL) and saturated sodium bicarbonate (50 mL). The organic layer was separated and the aqueous layer was extracted further with ethyl acetate (2×50 mL). The organic layers were combined and washed once with brine (50 mL). The organic phase was dried over sodium sulfate and filtered. Solvent was removed under vacuum and the residue was purified by column chromatography (5% methanol/1% triethylamine/DCM) to give 10.6 g of 4B (69%). ESI-MS:m/z 317.3 (M+H)$^+$.

4C. (S)-Methyl 3-(4-(cyclopropyl(2,3-dichlorobenzyl)amino)-1-hydroxy-4-oxobutan-2-ylamino)propanoate (4C)

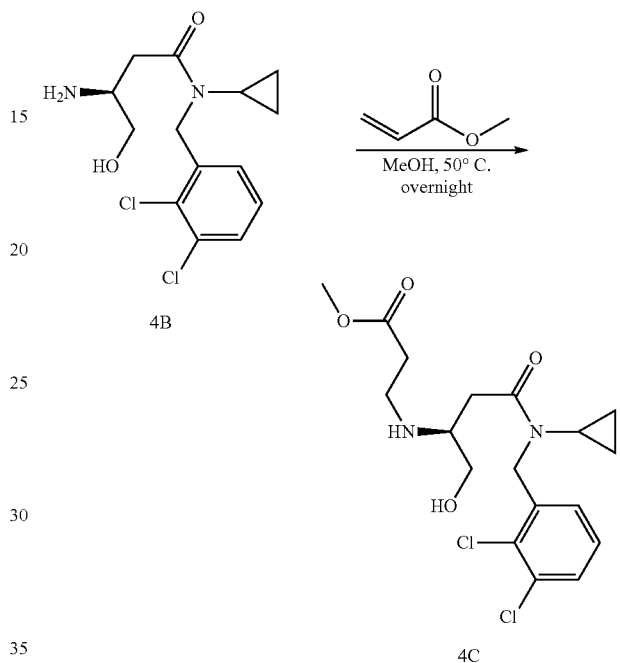

Into a 250 mL round bottom was 4B (10.6 g, 33.4 mmol) and methanol (90 mL). Methyl acrylate (3.16 g, 36.8 mmol, 1.1 eq) was added and the reaction was heated to 50° C. overnight. Solvent was removed under vacuum. The residue was used in the next step without further purification. ESI-MS:m/z 403.3 (M+H)$^+$.

4D. (S)-Methyl 3-(tert-butoxycarbonyl(4-(cyclopropyl(2,3-dichlorobenzyl)amino)-1-hydroxy-4-oxobutan-2-yl)amino)propanoate (4D)

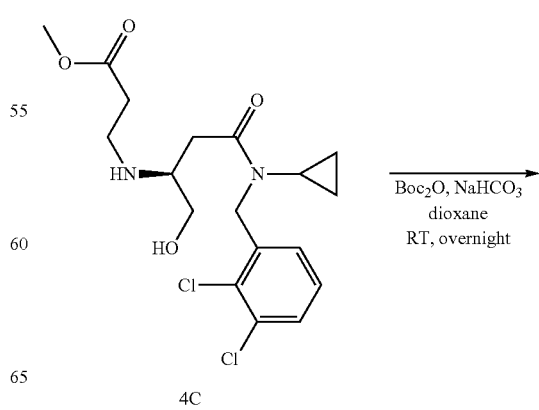

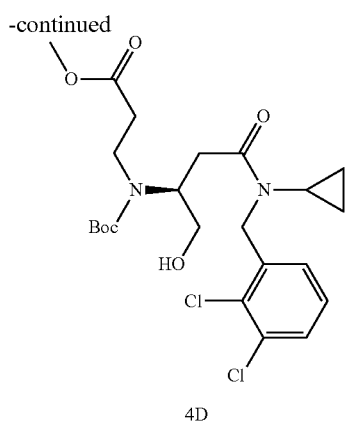

4D 4C from the previous step was dissolved in 1,4-dioxane (65 mL). Sodium bicarbonate (3.59 g, 42.7 mmol, 1.5 eq) and di-tert-butyl dicarbonate (13.12 g, 60.1 mmol, 1.8 eq) were added and stirred at room temperature overnight. Solvent was removed under vacuum and the residue was partitioned between water (50 mL) and ethyl acetate (50 mL). The organic layer was separated and the aqueous layer was further extracted with ethyl acetate (2×50 mL). The organic layers were combined and washed with brine. The organic phase was dried over sodium sulfate and filtered. Solvent was removed under vacuum. The residue was purified by column chromatography (2% MeOH/dichloromethane) to give 12.4 g of 4D (74% over two steps). ESI-MS:m/z 503.3 (M+H)$^+$.

4E. (S)-Methyl 3-(tert-butoxycarbonyl(4-(cyclopropyl(2,3-dichlorobenzyl)amino)-1-(methoxymethoxy)-4-oxobutan-2-yl)amino)propanoate (4E)

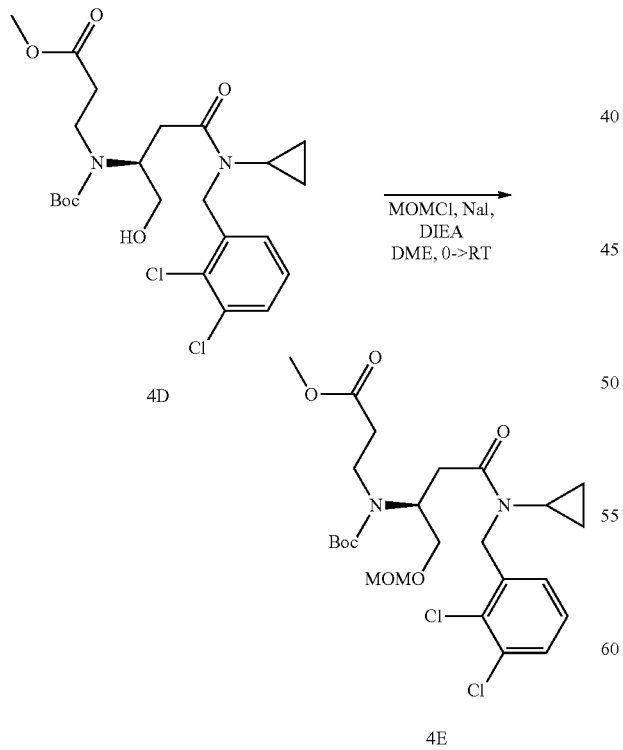

Into a 250 mL round bottom flask was added 4D (12.42 g, 24.7 mmol) and DME (137 mL). Di-isopropylethylamine (DIEA) or Hunig's base (23.6 mL, 135.7 mmol, 5.5 eq) and sodium iodide (14.79 g, 98.7 mmol, 4.0 eq) was added to the solution and cooled with an ice bath. Methoxymethyl chloride (MOMCl) (10.7 mL, 127.1 mmol, 5.15 eq) was added slowly at 0° C. The reaction was allowed to warm to room temperature overnight. Solvent was removed under vacuum and the residue was portioned between water (150 mL) and ethyl acetate (100 mL). The organic layer was separated and the aqueous layer was extracted with ethyl acetate (2×100 mL). The organic layers were combined and washed once with brine (100 mL). The organic phase was dried over sodium sulfate and filtered. Solvent was removed under vacuum and the residue was purified by column chromatography (30% ethyl acetate/hexanes) to give 4E (7.18 g, 53%) as a viscous oil. $^1$H NMR (400 MHz, CHLOROFORM-d) δ ppm 0.87 (m, 4H) 1.46 (br. s., 9H) 2.63 (br. s., 4H) 3.36 (s, 3H) 3.66 (s, 8H) 4.06-4.30 (m, 1H) 4.62 (m, 3H) 4.79 (m, 1H) 6.94 (d, J=7.83 Hz, 1H) 7.11-7.17 (m, 1H) 7.36 (dd, J=8.08, 1.26 Hz, 1H). ESI-MS:m/z 547.4 (M+H)$^+$.

4F. (2S)-tert-butyl 3-(cyclopropyl(2,3-dichlorobenzyl)carbamoyl)-2-((methoxymethoxy)methyl)-4-oxopiperidine-1-carboxylate (4F)

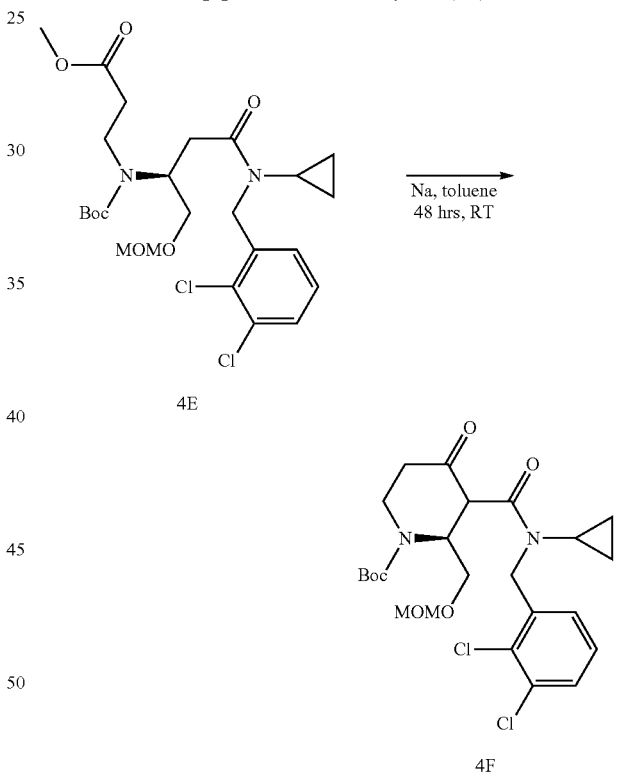

Into a 100 mL round bottom flask was added 4E and toluene (42 mL) under nitrogen. Sodium metal (392 mg, 17.1 mmol, 1.3 eq) was added at once followed by methanol (160 μL, 3.9 mmol, 0.3 eq). The reaction was allowed to stir under nitrogen over 48 hours. After sodium metal had dissolved, saturated ammonium chloride (50 mL) was added to quench the reaction. Ethyl acetate (50 mL) was added and the mixture was transferred to a separatory funnel. The organic layer was separated and the aqueous layer was further extracted with ethyl acetate (2×50 mL). The organic layers were combined and dried over sodium sulfate and filtered. Solvent was removed under vacuum to leave a residue which was purified by column chromatography (20% ethyl acetate/hexanes) to give 4F (4.17 g, 62%). ESI-MS:m/z 459.3 (M+H)+.

4G. (S)-Tert-butyl 3-(cyclopropyl(2,3-dichlorobenzyl)carbamoyl)-2-((methoxymethoxy)methyl)-4-(trifluoromethylsulfonyloxy)-5,6-dihydropyridine-1(2H)-carboxylate (4G)

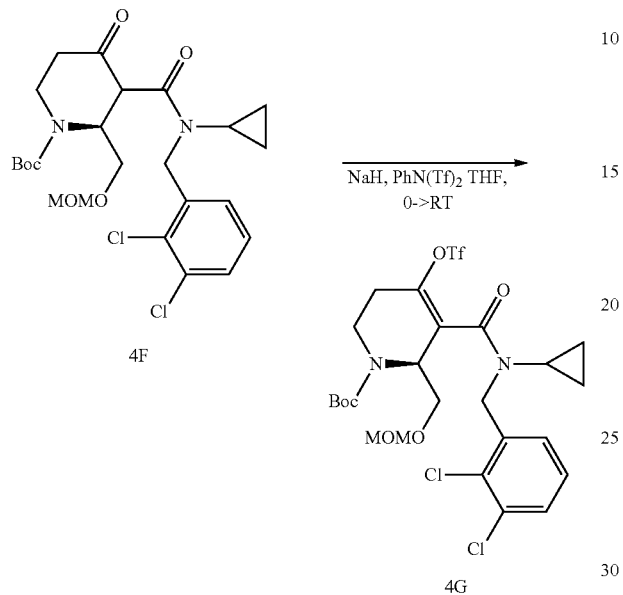

Into a 100 mL round bottom flask was added 4F and THF (37 mL). The flask was cooled with an ice bath and sodium hydride (410 mg, 60% disp., 10.2 mmol, 1.3 eq) was added in portions. After addition, the reaction was stirred for 20 minutes. PhN(Tf)$_2$ (3.94 g, 11.0 mmol, 1.4 eq) was added at once and the reaction stirred overnight at room temperature. The reaction was poured onto ice water (100 mL) and transferred to a separatory funnel. Ethyl acetate (50 mL) was added and the organic was separated. The aqueous was extracted with ethyl acetate (2×50 mL). The organics were combined and dried over sodium sulfate. Solution was filtered and solvent was removed under vacuum. The residue was purified by column chromatography (25% ethyl acetate/hexanes) to give 4G (2.86 g, 56%). ESI-MS:m/z 647.3 (M+H)+.

4H. (S)-Tert-butyl 3-(cyclopropyl(2,3-dichlorobenzyl)carbamoyl)-4-(4-hydroxyphenyl)-2-((methoxymethoxy)methyl)-5,6-dihydropyridine-1(2H)-carboxylate (4H)

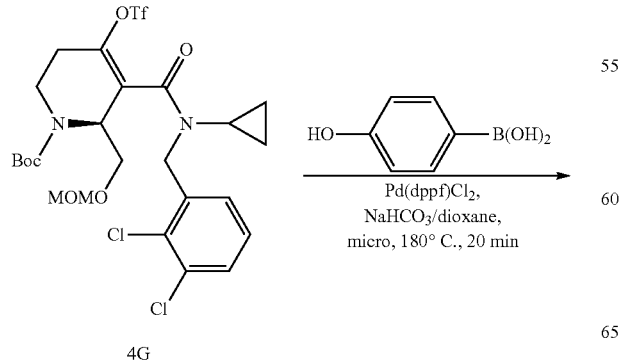

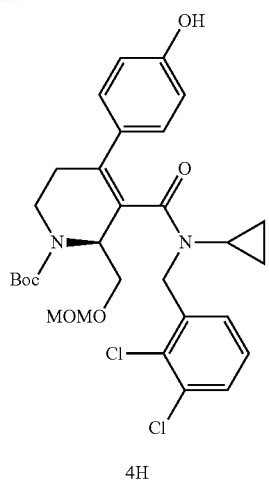

4H

Into a 20 mL microwave vial was added 4G (1.33 g, 2.05 mmol) and 4-hydroxyphenyl boronic acid (425 mg, 3.1 mmol, 1.5 eq). Dioxane (12 mL) and saturated sodium bicarbonate (4 mL) was added and the mixture was degassed by bubbling N$_2$ through the solution for 10 minutes. After degassing, 1,1'-bis-diphenyl phosphinoferrocene dichloro palladium (II) (Pd(dppf)Cl$_2$) (150 mg, 206 µmol, 0.05 eq) was added and the reaction was capped. The reaction was microwaved at 150° C. for 20 minutes, and the reaction was transferred to a round bottom and the solvent was removed under vacuum. Saturated ammonium chloride (25 mL) and ethyl acetate (25 mL) was added to the residue and transferred to a separatory funnel. The organic layer was separated and the aqueous layer was further extracted with ethyl acetate (2×25 mL). The organic layers were combined and dried over sodium sulfate. Solution was filtered and the solvent was removed under vacuum. The residue was purified by column chromatography (40% ethyl acetate/hexanes) to give 4H (948 mg, 37%). ESI-MS:m/z 591.3 (M+H)+.

Example 5

Preparation of 4-(biphenyl-3-yl)-N-cyclopropyl-N-(2,3-dichlorobenzyl)-2-(hydroxymethyl)-1,2,5,6-tetrahydropyridine-3-carboxamide (Compound 1)

Compound 1

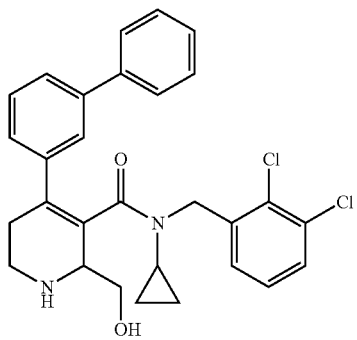

5A. 1-Benzyl 3-ethyl 4-(biphenyl-3-yl)-2-((tert-butyldimethylsilyloxy)methyl)-5,6-dihydropyridine-1,3(2H)-dicarboxylate (5A¹) and 1-benzyl 3-ethyl 4-(biphenyl-3-yl)-6-((tert-butyldimethylsilyloxy)methyl)-5,6-dihydropyridine-1,3(2H)-dicarboxylate (5A²)

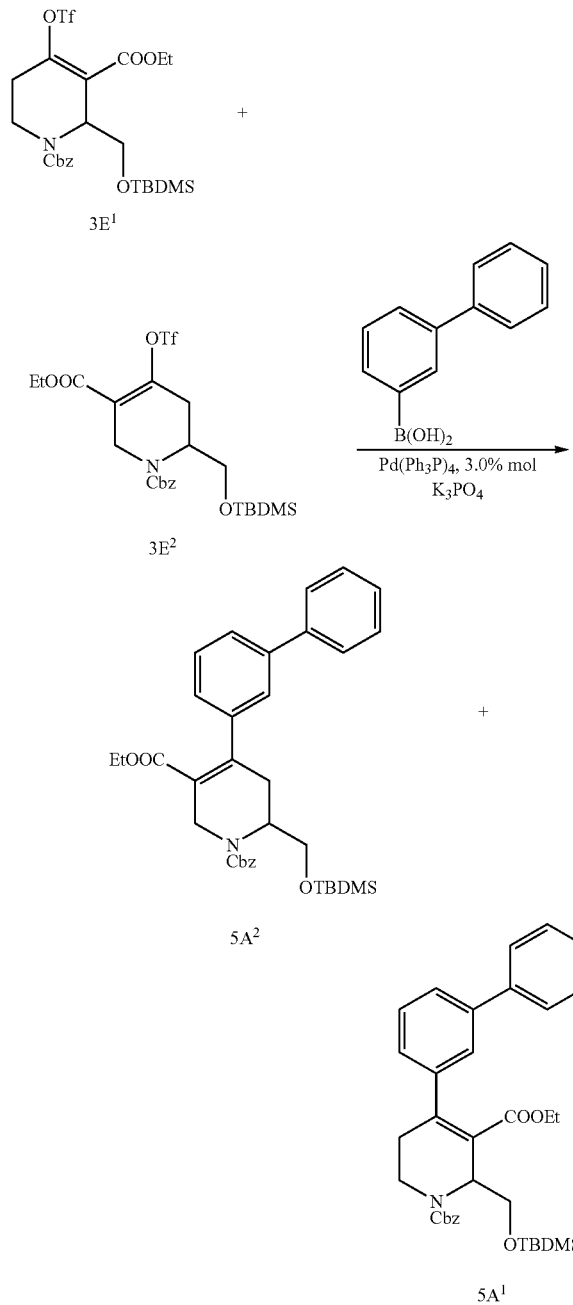

5B. 1-(Benzyloxycarbonyl)-4-(biphenyl-3-yl)-2-((tert-butyldimethylsilyloxy)methyl)-1,2,5,6-tetrahydropyridine-3-carboxylic acid (1G¹) and 1-(benzyloxycarbonyl)-4-(biphenyl-3-yl)-6-((tert-butyldimethylsilyloxy)methyl)-1,2,5,6-tetrahydropyridine-3-carboxylic acid (1G²)

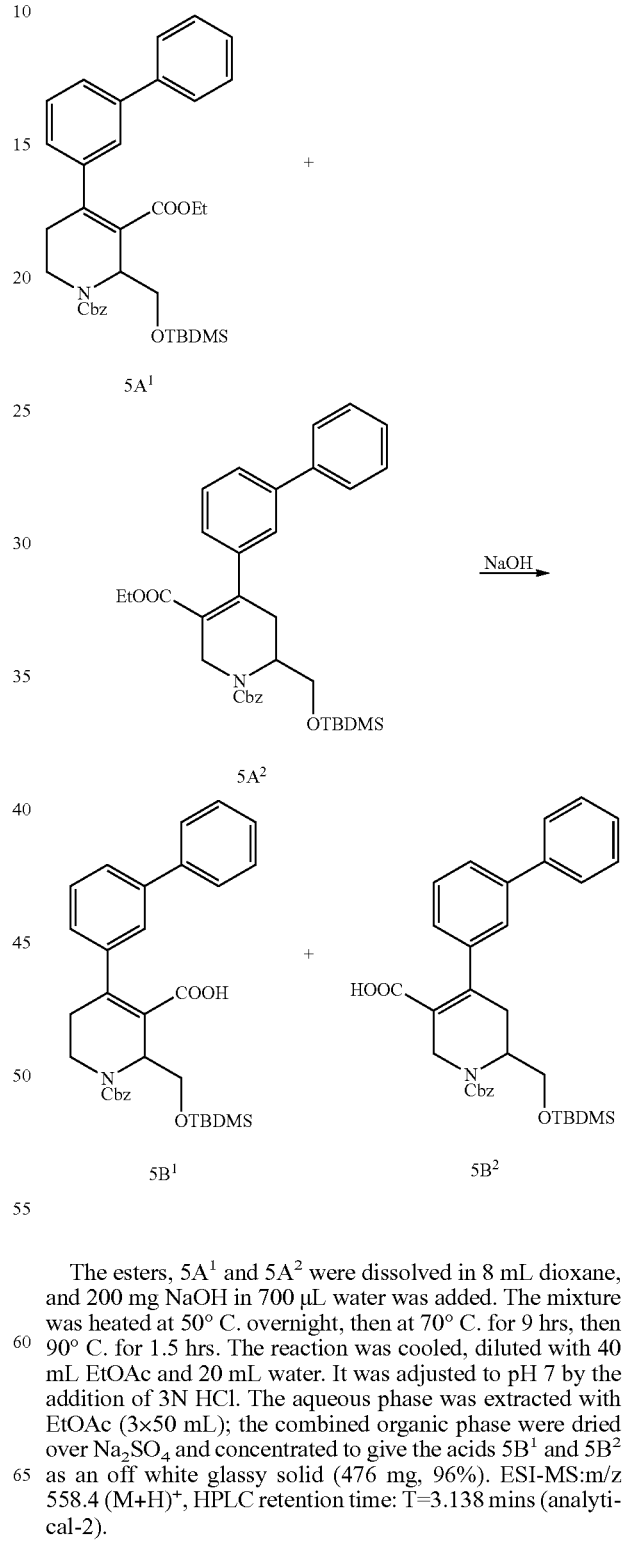

The triflates 3E¹ and 3E² were prepared as described in Example 3, Step 3A-3E. To a mixture of the triflates (582 mg, 1.00 mmol), biphenylboronic acid (257 mg, 1.3 mmol, 1.3 eq) and potassium phosphate (424 mg, 2.00 mmol, 2 eq) in 10 mL dioxane was added palladium (0) tetrakistriphenylphosphine (35 mg, 3% mol). The mixture was de-oxygenated for 5 cycles (vacuo/flash with nitrogen) and was then heated at 150° C. for 20 mins in a microwave reactor. The mixture was filtered through a pad of $SiO_2$ and celite, washed with EtOAc. The filtrate was concentrated to give a yellow oil, which was purified on a 40 g $SiO_2$ column using a gradient of 5% EtOAc/hexanes to 100% EtOAc/hexanes. The products 5A¹ and 5A² were isolated as a clear oil (518 mg, 76%). ESI-MS:m/z 586.5 $(M+H)^+$, HPLC retention time: T=3.509 min (analytical-2).

The esters, 5A¹ and 5A² were dissolved in 8 mL dioxane, and 200 mg NaOH in 700 μL water was added. The mixture was heated at 50° C. overnight, then at 70° C. for 9 hrs, then 90° C. for 1.5 hrs. The reaction was cooled, diluted with 40 mL EtOAc and 20 mL water. It was adjusted to pH 7 by the addition of 3N HCl. The aqueous phase was extracted with EtOAc (3×50 mL); the combined organic phase were dried over $Na_2SO_4$ and concentrated to give the acids 5B¹ and 5B² as an off white glassy solid (476 mg, 96%). ESI-MS:m/z 558.4 $(M+H)^+$, HPLC retention time: T=3.138 mins (analytical-2).

5C. Benzyl 4-(biphenyl-3-yl)-6-((tert-butyldimethyl-silyloxy)methyl)-3-(cyclopropyl(2,3-dichlorobenzyl)carbamoyl)-5,6-dihydropyridine-1(2H)-carboxylate (5C$^1$) and benzyl 4-(biphenyl-3-yl)-2-((tert-butyldimethylsilyloxy)methyl)-3-(cyclopropyl(2,3-dichlorobenzyl)carbamoyl)-5,6-dihydropyridine-1(2H)-carboxylate (5C$^2$) and

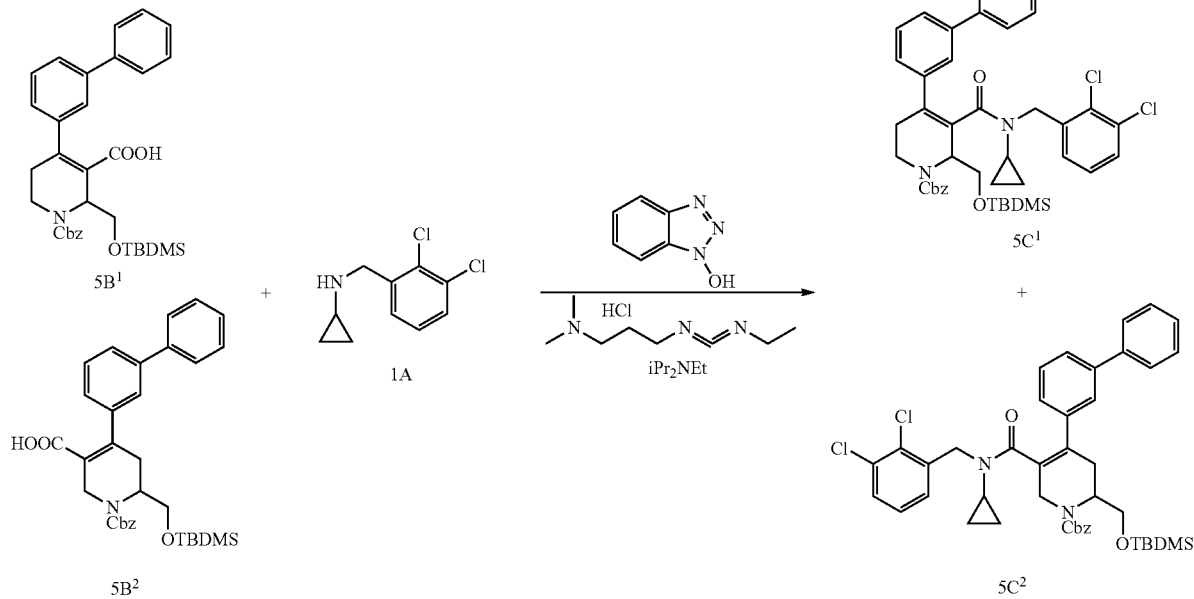

To a solution of the acids 5B$^1$ and 5B$^2$ (476 mg, 0.853 mmol), N-(2,3-dichlorobenzyl)cyclopropanamine (211 mg, 1.2 eq), HOBt (144 mg, 1.06 mmol, 1.25 eq) and Hunig's base (297 µL, 221 mg, 2 eq) in 4 mL DMF 0° C. was added EDCI (204 mg, 1.07 mmol, 1.25 eq). Ice batch was removed, the reaction was continued for 3 days at RT. The solution was then diluted with DCM (100 mL), and washed with 2N HCl (50 mL). The organic phase was separated and dried over Na$_2$SO$_4$, and was concentrated to give 910 mg of a brown oil which was purified on SiO$_2$ (40 g column) using a gradient of 5% EtOAc/hexanes to 100% EtOAc/hexanes. The products 5C$^1$ and 5C$^2$ were isolated as a yellow oil (401 mg, 62%). ESI-MS:m/z 755.4 (M+H)$^+$, HPLC retention time: T=3.929 min (FAST-2).

5D. 4-(Biphenyl-3-yl)-N-cyclopropyl-N-(2,3-dichlorobenzyl)-2-(hydroxymethyl)-1,2,5,6-tetrahydropyridine-3-carboxamide (5D$^1$) and 4-(biphenyl-3-yl)-N-cyclopropyl-N-(2,3-dichlorobenzyl)-6-(hydroxymethyl)-1,2,5,6-tetrahydropyridine-3-carboxamide (5D$^2$)

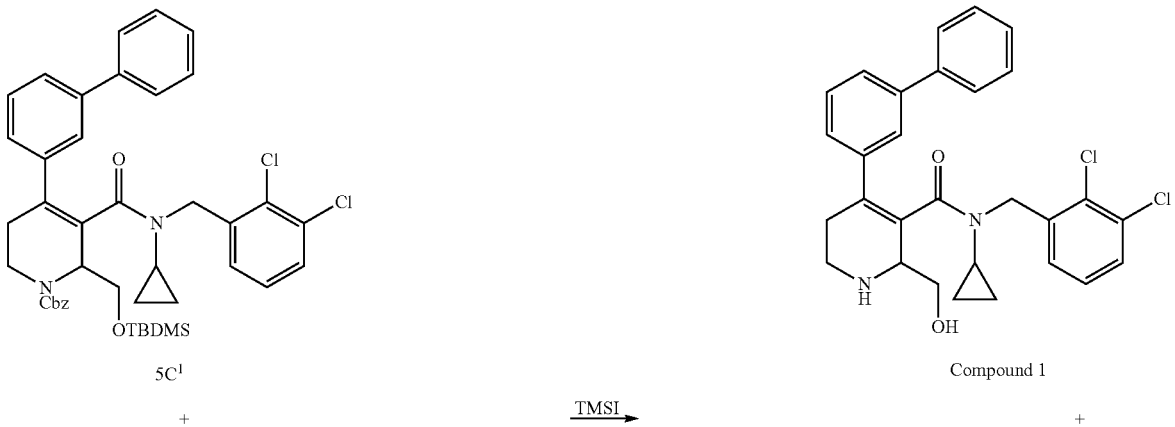

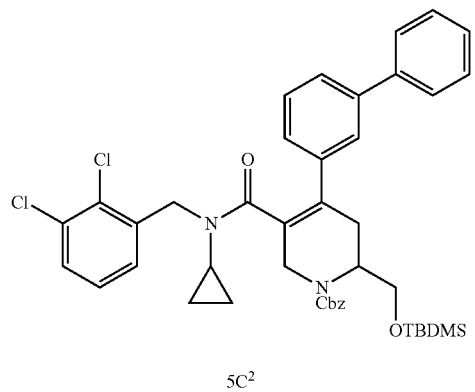

5C²

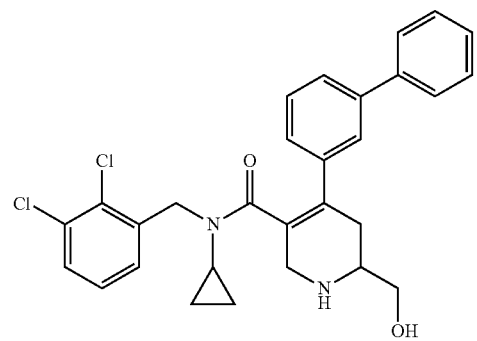

5D²

To a solution of 5C¹ and 5C² (115 mg, 0.152 mmol) in CH₃CN was added trimethylsilyl iodide (TMSI) (44 μL, 61 mg, 2 eq) at 0° C.; the mixture turned dark brown immediately. The mixture was stirred at RT for 40 min; then MeOH (200 μL) was added. The solvents were removed and the residue was purified on preparative silica gel TLC plate using EtOAc/MeOH/DCM/NH4OH(3/1/3/0.05) solvent system. The SiO₂ bands correspond to Compound 1 and 5D² were cut off from the TLC plate. The SiO₂ bands were separately suspended in 1% MeOH/EtOAc and then the mixture was stirred for 10 mins and then filtered; it was washed several times with 1% MeOH/EtOAc. The filtrate was then concentrated to give pure Compound 1 and 5D². When higher purity was desired, the filtrates were purified repeatedly with the same preparatory TLC procedure until pure samples were isolated. The products were isolated as yellow films:

Compound 1: 8.6 mg, Rf=(bottom) (592-77 and 82), ESI-MS:m/z 507.3 (M+H)⁺, HPLC retention time: T=2.637 min (FAST-2); and 5D²: 4.9 mg, Rf=(top), ESI-MS:m/z 507.3 (M+H)⁺, HPLC retention time: T=2.708 min (FAST-2).

Example 6

Preparation of 1-benzyl 3-ethyl 2-((tert-butyldimethylsilyloxy)methyl)-4-(4-hydroxyphenyl)-5,6-dihydropyridine-1,3(2H)-dicarboxylate (6A¹); and 1-benzyl 3-ethyl 6-((tert-butyldimethylsilyloxy)methyl)-4-(4-hydroxyphenyl)-5,6-dihydropyridine-1,3(2H)-dicarboxylate (6A²)

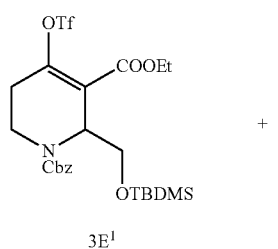

3E¹

+

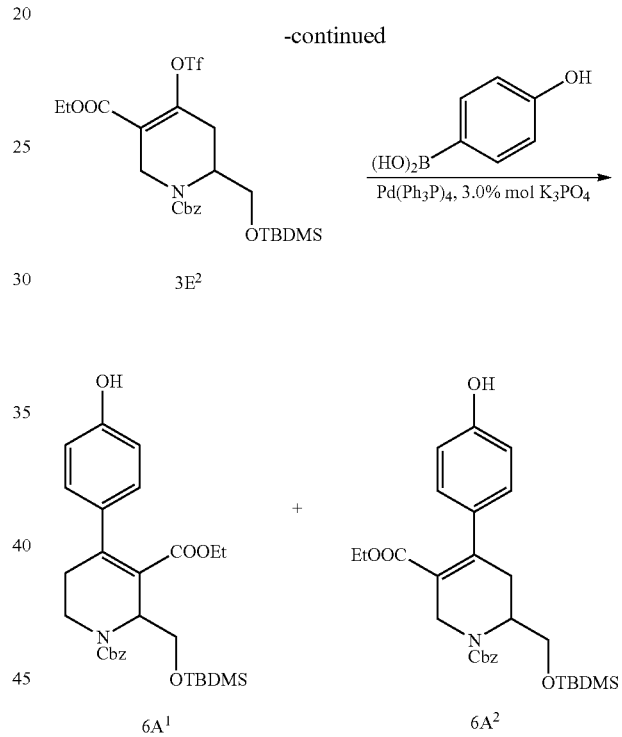

The triflates mixture, 3E¹ and 3E², was prepared according to Example 3, Steps 3A-3E. To the mixture of the triflates (1.454 g, 2.50 mmol), 4-hydroxyphenylboronic acid (448 mg, 3.25 mmol, 1.3 eq) and potassium phosphate (1.06 mg, 5.00 mmol, 2 eq) in 20 mL dioxane was added palladium(0) tetrakistriphenylphosphine (87 mg, 3% mol). The mixture was de-oxygenated for 5 cycles (vacuo/flash with nitrogen) and was then heated at 150° C. for 20 mins in a microwave reactor. The mixture was filtered through a pad of SiO₂ and celite, washed with EtOAc, and was concentrated to give a yellow oil (2.1 g), which was purified on a 120 g SiO₂ column using a gradient of 10% EtOAc/hexanes to 100% EtOAc/hexanes. The titled compounds were isolated as a clear oil (772 mg, 59%). ESI-MS:m/z 526.4 (M+H)⁺, HPLC retention time: T=2.922 min (FAST-2) and T=3.274 min (analytical-2).

Example 7

Preparation of 4-(4-(2-(2-chlorophenoxy)ethoxy)phenyl)-N-cyclopropyl-N-(2,3-dichlorobenzyl)-2-(hydroxymethyl)-1,2,5,6-tetrahydropyridine-3-carboxamide (Compound 2)

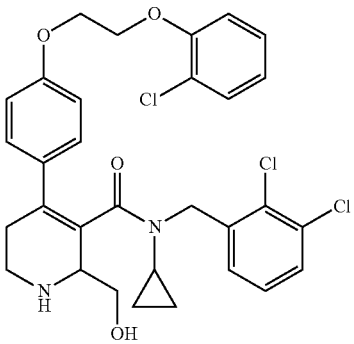

7A. 1-Benzyl 3-ethyl 2-((tert-butyldimethylsilyloxy)methyl)-4-(4-(2-(2-chlorophenoxy)ethoxy)phenyl)-5,6-dihydropyridine-1,3(2H)-dicarboxylate (7A¹) and 1-benzyl 3-ethyl 6-((tert-butyldimethylsilyloxy)methyl)-4-(4-(2-(2-chlorophenoxy)ethoxy)phenyl)-5,6-dihydropyridine-1,3(2H)-dicarboxylate (7A²)

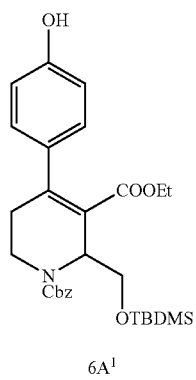

6A¹

+

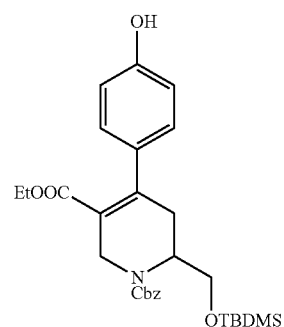 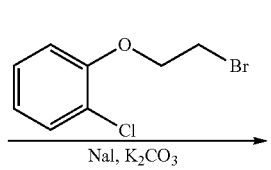

6A²

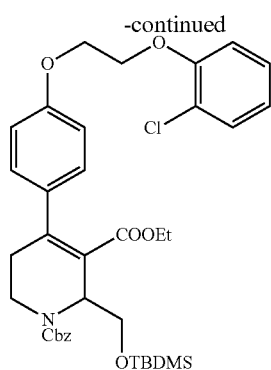

7A¹

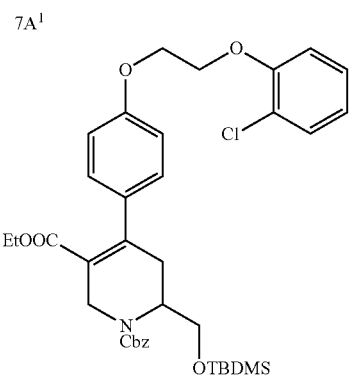

7A²

The phenols 6A¹ and 6A² were prepared as described in Example 6. To the mixture of the phenols (195 mg, 0.371 mmol), 2-(2-bromoethoxy)-2-chlorobenzene (104 mg, 0.445 mmol, 1.2 eq) and NaI (72 mg, 0.48 mmol, 1.3 eq) K₂CO₃ (62 mg, 0.448 mmol, 1.2 eq) in 2 mL acetone was added and the mixture heated to 75° C. for 7 days. Solvents were removed, the brown residue (630 mg) was about 80% pure O-alkylated product 7A¹ and 7A² with some inorganic salt. ESI-MS:m/z 680.4 (M+H)⁺, HPLC retention time: T=4.204 min (analytical-4).

7B. Preparation of 1-(benzyloxycarbonyl)-2-((tert-butyldimethylsilyloxy)methyl)-4-(4-(2-(2-chlorophenoxy)ethoxy)phenyl)-1,2,5,6-tetrahydropyridine-3-carboxylic acid (7C¹) and 1-(benzyloxycarbonyl)-6-((tert-butyldimethylsilyloxy)methyl)-4-(4-(2-(2-chlorophenoxy)ethoxy)phenyl)-1,2,5,6-tetrahydropyridine-3-carboxylic acid (7C²)

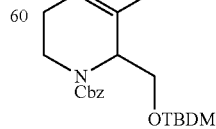

7A¹

+

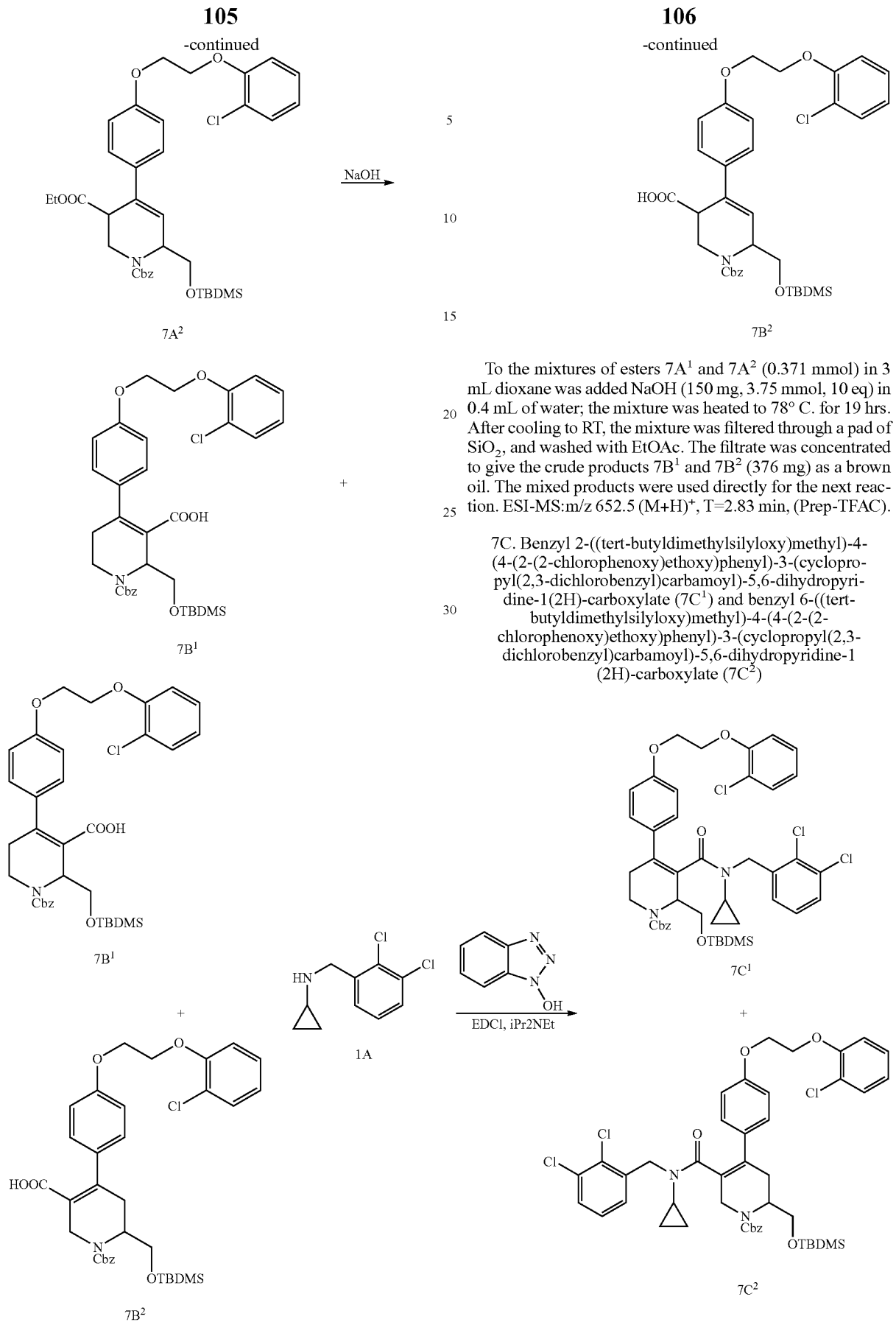

To the mixtures of esters 7A$^1$ and 7A$^2$ (0.371 mmol) in 3 mL dioxane was added NaOH (150 mg, 3.75 mmol, 10 eq) in 0.4 mL of water; the mixture was heated to 78° C. for 19 hrs. After cooling to RT, the mixture was filtered through a pad of SiO$_2$, and washed with EtOAc. The filtrate was concentrated to give the crude products 7B$^1$ and 7B$^2$ (376 mg) as a brown oil. The mixed products were used directly for the next reaction. ESI-MS:m/z 652.5 (M+H)$^+$, T=2.83 min, (Prep-TFAC).

7C. Benzyl 2-(((tert-butyldimethylsilyloxy)methyl)-4-(4-(2-(2-chlorophenoxy)ethoxy)phenyl)-3-(cyclopropyl(2,3-dichlorobenzyl)carbamoyl)-5,6-dihydropyridine-1(2H)-carboxylate (7C$^1$) and benzyl 6-((tert-butyldimethylsilyloxy)methyl)-4-(4-(2-(2-chlorophenoxy)ethoxy)phenyl)-3-(cyclopropyl(2,3-dichlorobenzyl)carbamoyl)-5,6-dihydropyridine-1(2H)-carboxylate (7C$^2$)

To a mixture of the crude acids 7B[1] and 7B[2] (~0.371 mmol), HOBT (60 mg, 0.44 mmol, 1.2 eq) and amine (95 mg, 1.2 eq) in 1.5 mL DMF was added EDCI (85 mg, 44 mmol, 1.2 eq) and Hunig's base (130 μL, 2 eq). The mixture was stirred at RT for 3 days, then diluted with DCM (100 mL), washed with 2 NHCl (50 mL). The organic phase was separated, dried over $Na_2SO_4$, and then concentrated to give 470 mg crude product as a brown oil. The crude was purified on $SiO_2$ (12 g column, 5% EtOAc/hexanes to 100% EtOAc/hexanes) to give a partially purified products 7C[1] and 7C[2] (140 mg) as a yellow solid. No MH+ peak for the products were found.

7D. Preparation of 4-(4-(2-(2-chlorophenoxy)ethoxy)phenyl)-N-cyclopropyl-N-(2,3-dichlorobenzyl)-2-(hydroxymethyl)-1,2,5,6-tetrahydropyridine-3-carboxamide (Compound 2) and 4-(4-(2-(2-chlorophenoxy)ethoxy)phenyl)-N-cyclopropyl-N-(2,3-dichlorobenzyl)-6-(hydroxymethyl)-1,2,5,6-tetrahydropyridine-3-carboxamide (7D[2])

To the N-Cbz and O-TBDMS mixture 7C[1] and 7C[2] (140 mg, 0.23 mmol), in 1 mL acetonitrile was added TMSI (71 μL, 99 mg, 0.49 mmol); the mixture turned to dark brown color. The colored mixture was stirred at RT for 15 mins; MeOH (100 μL) was added to quench the reaction. After removing solvents, the brown residue (200 mg) was purified on preparative silica gel TLC plate using EtOAc/MeOH/DCM/NH4OH(3/1/3/0.05) solvent system. The products Compound 2 and 7D[2] were isolated as a yellow film using similar procedures as described for Compound 1 and 5D[2] (Example 5, Step 5D). Compound 2 (bottom band): 0.8 mg, ESI-MS:m/z 601.2 (M+H)+ and 603.2 (M+2H)+; HPLC retention time: T=2.674 min (analytical-2). 7D[2] (top band): 1.3 mg, ESI-MS:m/z 601.2 (M+H)+ and 603.2 (M+2H)+; HPLC retention time: T=2.678 min (analytical-2).

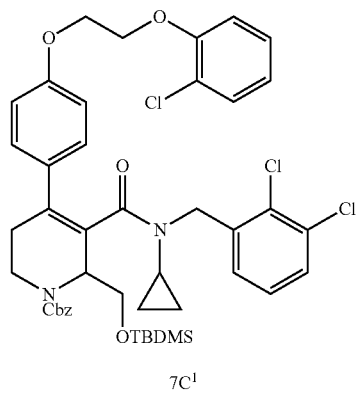

7C[1]

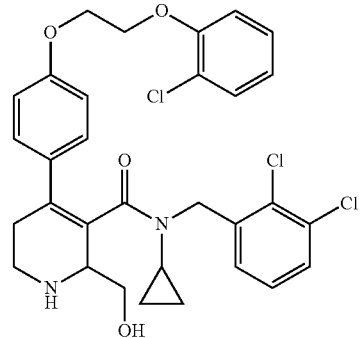

Compound 2

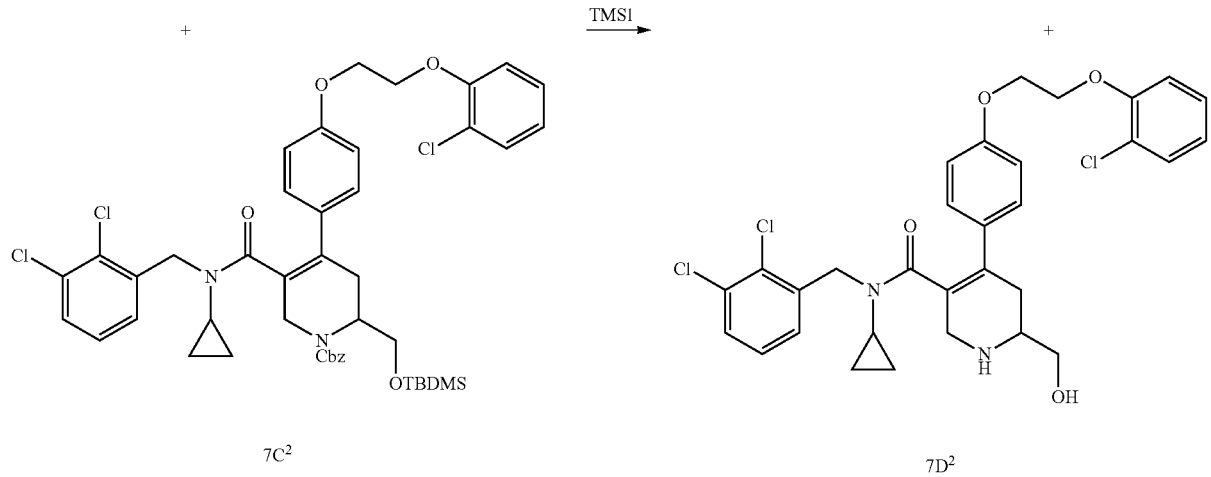

7C[2]                                      7D[2]

Example 8

Preparation of 4-(4-(2-(2,6-dichlorophenoxy)ethoxy)phenyl)-N-cyclopropyl-N-(2,3-dichlorobenzyl)-2-(hydroxymethyl)-1,2,5,6-tetrahydropyridine-3-carboxamide (Compound 3)

Compound 3

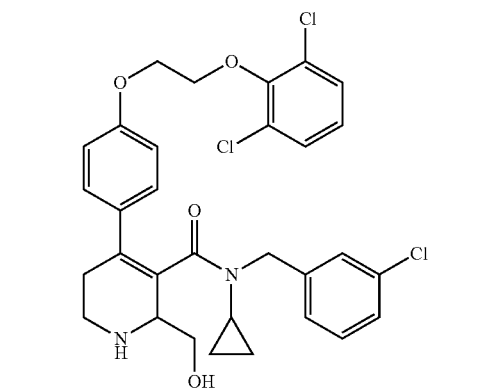

8A. 1-Benzyl 3-ethyl 2-((tert-butyldimethylsilyloxy)methyl)-4-(4-(2-(2,6-dichlorophenoxy)ethoxy)phenyl)-5,6-dihydropyridine-1,3(2H)-dicarboxylate (8A¹) and 1-benzyl 3-ethyl 6-((tert-butyldimethylsilyloxy)methyl)-4-(4-(2-(2,6-dichlorophenoxy)ethoxy)phenyl)-5,6-dihydropyridine-1,3(2H)-dicarboxylate (8A²)

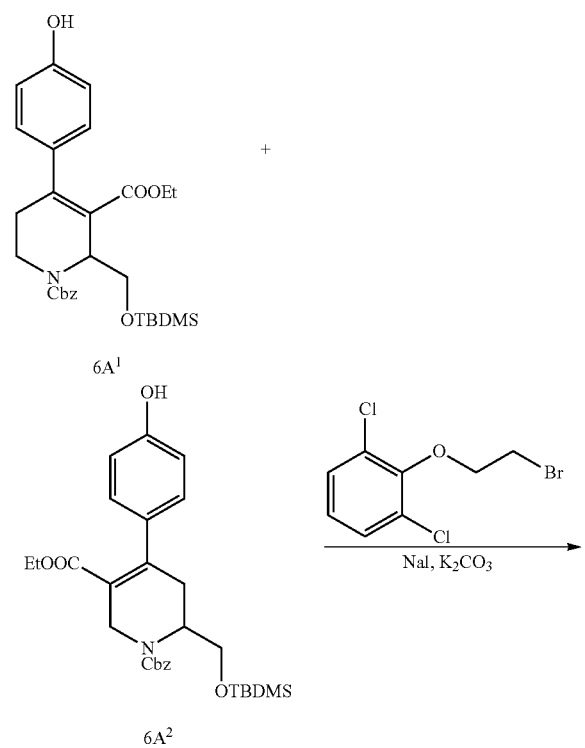

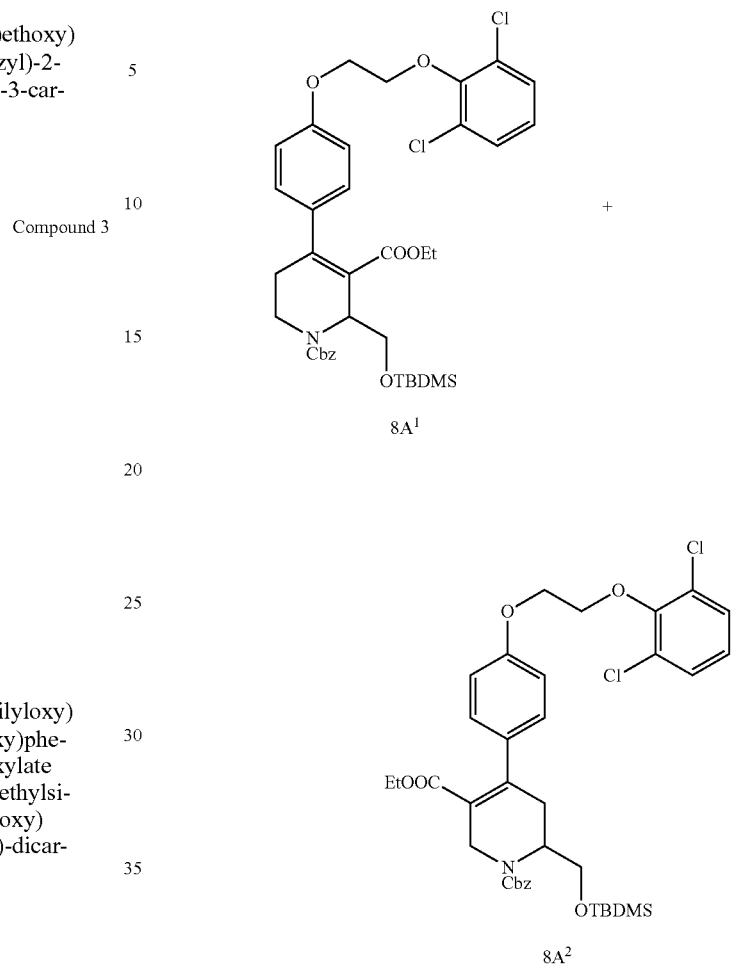

The phenols 6A¹ and 6A² were prepared as described in Example 6. To the mixture of the phenols (314 mg, 0.597 mmol), 2-(2-bromoethoxy)-1,3-dichlorobenzene (241 mg, 0.892 mmol, 1.5 eq) and NaI (135 mg, 0.90 mmol, 1.5 eq) and $K_2CO_3$ (125 mg, 0.90 mmol, 1.5 eq) in 2 mL acetone were added and the mixture was heated to 75° C. for 3 days. Solvents were removed in vacuo, and the residue was redissolved in 1.5 mL DMF, heated at 90° C. for 2 days and then at 130° C. for 8 hrs. Solvents were removed, the brown residue was purified on a 12 g $SiO_2$ column to give the O-alkylated product 8A¹ and 8A² (351 mg, 74%) as a light yellow oil. ESI-MS:m/z 714 (M+H)⁺.

Alternatively, the carboxylates 8A¹ and 8A² were also prepared by adding to a mixture of the phenols (890 mg, 1.69 mmol) and NaI (305 mg, 2.03 mmol, 1.2 eq) in 2 mL dry DMF, NaH (60%, 82 mg, 2.05 mmol, 1.2 eq) at 0° C. The mixture was stirred at RT for 15 mins and then 2-(2-bromoethoxy)-1,3-dichlorobenzene (548 mg, 2.03 mmol, 1.2 eq) in 1 mL DMF was added. The reaction was heated to 50° C. for 3 hrs, and precipitation was observed. The suspension was poured into an ice-brine solution containing 500 mg of $NH_4Cl$. The organic layer was separated and the aqueous phase was extracted with EtOAc (200 mL), then DCM (200 mL). The organic layers were combined and dried over $Na_2SO_4$, concentrated to give 2.1 g brown oil, which was purified on a 40 g $SiO_2$ column using a gradient of 10% EtOAc/hexanes to 100% EtOAc/hexanes. The products $8A^1$ and $8A^2$ were isolated as a light brown oil (981 mg, 81%); Rf=0.46 (25% EtOAc/hexanes). ESI-MS:m/z 714.4 $(M+H)^+$ and 716.3 $(M+2H)^+$, HPLC retention time: T=4.128 min (analytical-5).

8B. Preparation of 1-(benzyloxycarbonyl)-2-((tert-butyldimethylsilyloxy)methyl)-4-(4-(2-(2,6-dichlorophenoxy)ethoxy)phenyl)-1,2,5,6-tetrahydropyridine-3-carboxylic acid ($8B^1$) and 1-(benzyloxycarbonyl)-6-((tert-butyldimethylsilyloxy)methyl)-4-(4-(2-(2,6-dichlorophenoxy)ethoxy)phenyl)-1,2,5,6-tetrahydropyridine-3-carboxylic acid ($8B^2$)

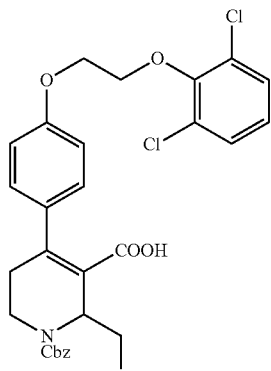

$8B^1$

+

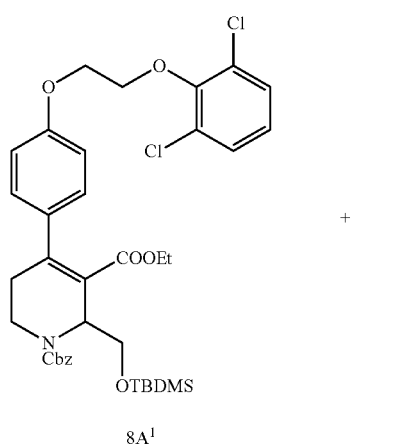

$8A^1$

+

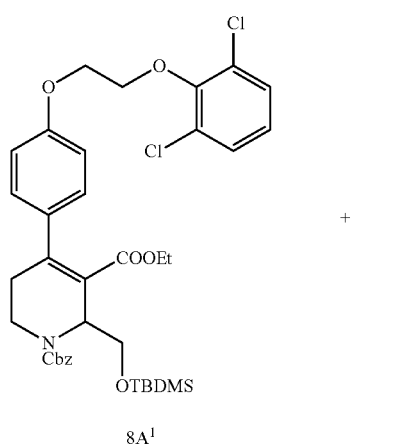

$8A^2$

NaOH →

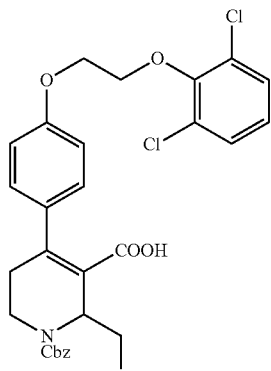

$8B^2$

To a solution of the esters $8A^1$ and $8A^2$ (351 mg, 0.49 mmol) in 3 mL dioxane was added aqueous NaOH (196 mg, 4.9 mmol, 10 eq) in 0.4 mL of water. The mixture was heated to 78° C. for 19 hrs, then cooled. $NH_4Cl$ (300 mg) was added, the mixture was filtered through a pad of $SiO_2$, washed with EtOAc. The filtrate was then concentrated to give the crude products (231 mg) as brown oil, which was purified on a 4 g $SiO_2$ column at a gradient of 10% EtOAc/hexanes to 100% EtOAc/hexanes. The products $8B^1$ and $8B^2$ were isolated as a yellow oil (89 mg, 27%); Rf=<0.1 in 25% EtOAc/hexanes; ESI-MS: m/z 686.3 $(M+H)^+$ and 688.3 $(M+2H)^+$, HPLC retention time: T=3.953 min (FAST-2), T=3.682 min (analytical-5) and T=3.944 min (analytical-4).

In a separate experiment, the acids $8B^1$ and $8B^2$ were synthesized by the hydrolysis of the esters $8A^1$ and $8A^2$ (891 mg) as described above. The products were isolated as a yellow oil (756 mg, 88%), ESI-MS:m/z 686.3 $(M+H)^+$ and 688.3 $(M+2H)^+$, HPLC retention time: T=3.888 min (analytical-2).

8C. Preparation of 4-(4-(2-(2,6-dichlorophenoxy)ethoxy)phenyl)-N-cyclopropyl-N-(2,3-dichlorobenzyl)-2-(hydroxymethyl)-1,2,5,6-tetrahydropyridine-3-carboxamide (Compound 3) and N-(3-chlorobenzyl)-4-(4-(2-(2,6-dichlorophenoxy)ethoxy)phenyl)-N-cyclopropyl-6-(hydroxymethyl)-1,2,5,6-tetrahydropyridine-3-carboxamide (8C²)

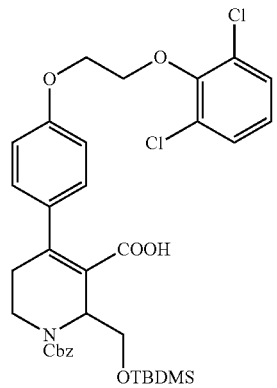

8B¹

+

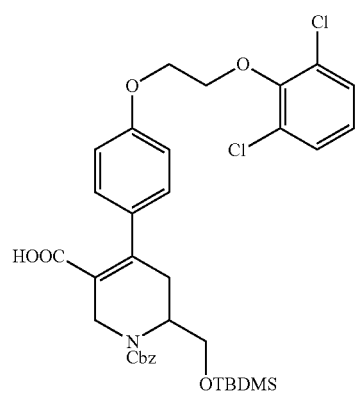

8B²

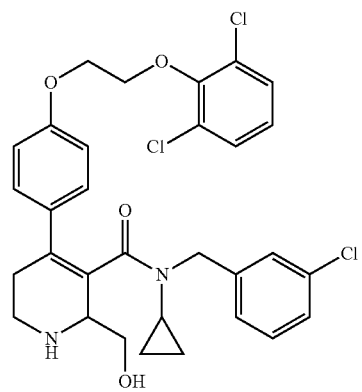

Compound 3

+

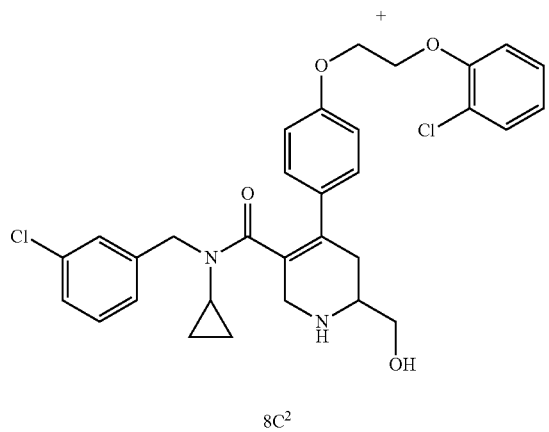

8C²

The acids 8B¹ and 8B² were coupled with N-(3-chlorobenzyl)cyclopropanamine (1C) follow by deprotection according to the procedure described in Example 7, Steps 7C and 7D to yield Compound 3 and 8C².

The products Compound 3 and 8C² were isolated as a yellow film using similar procedures as described for Compound 1 and 5D² (Example 5, Step 5D). Compound 3 (bottom band): 2.6 mg, ESI-MS: m/z 601.2 (M+H)⁺; HPLC retention time: T=2.357 min (analytical-2). 8C² (top band): 6.7 mg, ESI-MS:m/z 601.2 (M+H); HPLC retention time: T=2.451 min (analytical-2).

Example 9

Preparation of (S)-N-cyclopropyl-N-(2,3-dichlorobenzyl)-4-(4-(2-(2,6-dichlorophenoxy)ethoxy)phenyl)-2-((methoxymethoxy)methyl)-1,2,5,6-tetrahydropyridine-3-carboxamide (Compound 5)

Compound 5

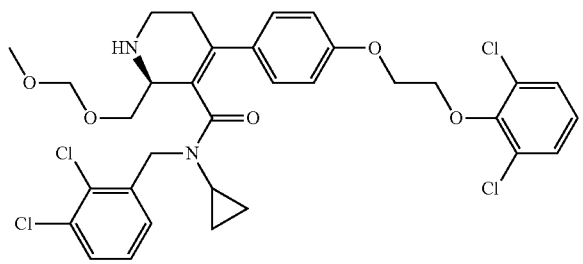

9A. (S)-Tert-butyl 3-(cyclopropyl(2,3-dichlorobenzyl)carbamoyl)-4-(4-(2-(2,6-dichlorophenoxy)ethoxy)phenyl)-2-((methoxymethoxy)methyl)-5,6-dihydropyridine-1(2H)-carboxylate (9A)

9B. (S)-N-Cyclopropyl-N-(2,3-dichlorobenzyl)-4-(4-(2-(2,6-dichlorophenoxy)ethoxy)phenyl)-2-((methoxymethoxy)methyl)-1,2,5,6-tetrahydropyridine-3-carboxamide (Compound 5)

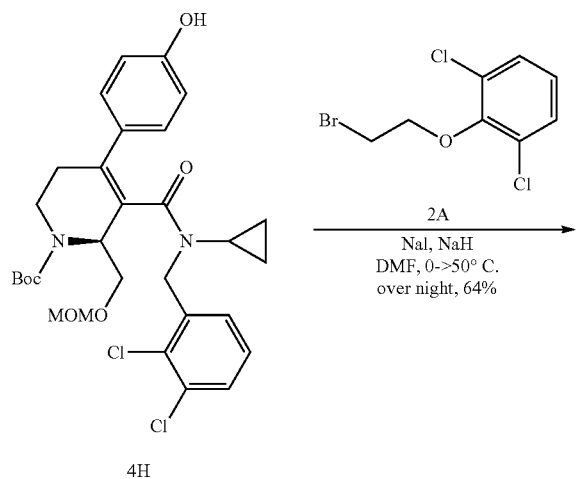

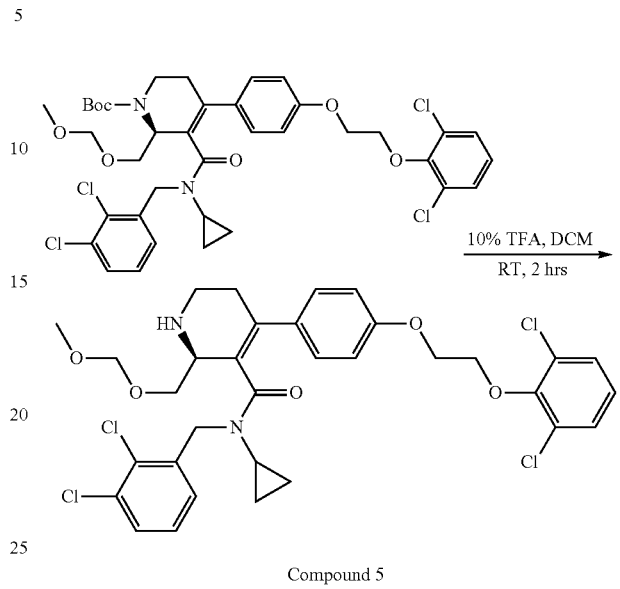

Compound 5

9A (50 mg, 64 μmol) was dissolved in 10% trifluoroacetic acid in dichloromethane. The mixture was stirred at room temperature for 2 hours. Solvent was removed under vacuum. The residue was purified by preparatory LCMS (water:acetonitrile, 40-65%) to give Compound 5 (15 mg, 33%). ESI-MS: m/z 679.3 (M+H)⁺.

Example 10

Preparation of (S)-N-cyclopropyl-N-(2,3-dichlorobenzyl)-4-(4-(2-(2,6-dichlorophenoxy)ethoxy)phenyl)-2-(hydroxymethyl)-1,2,5,6-tetrahydropyridine-3-carboxamide (Compound 6)

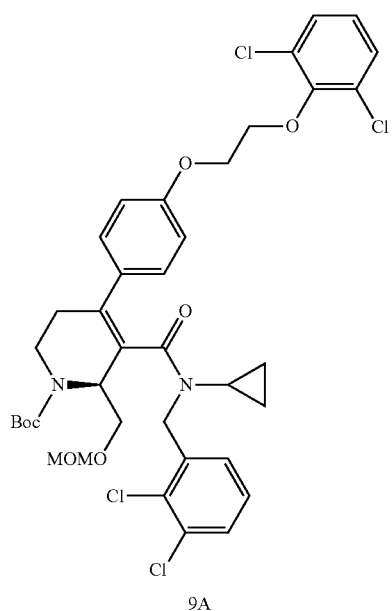

9A

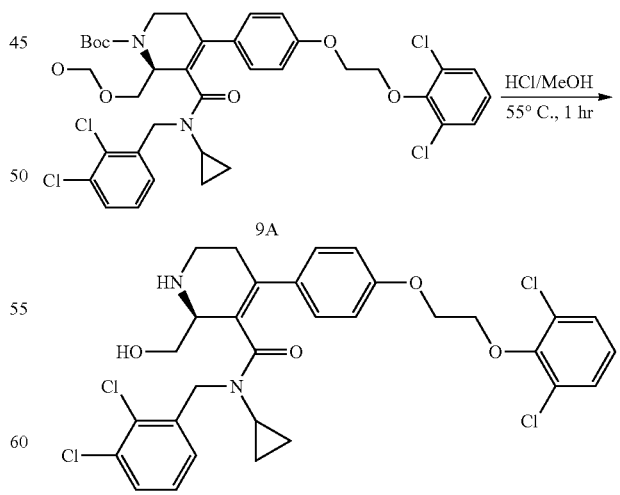

Compound 6

4H was prepared as described in Example 4, Steps 4A-4H. Into a 25 mL round bottom flask, 4H (1.31 g, 2.2 mmol) and DMF (6.5 mL) were added. NaI (397 mg, 2.7 mmol, 1.2 eq) was added followed by sodium hydride (106 mg, 60% disp., 1.2 eq). The reaction was allowed to stir at room temperature for 20 minutes, then 2-(2-bromoethoxy)-1,3-dichlorobenzene (2A) (716 mg, 2.7 mmol, 1.2 eq) in DMF (1.3 mL) was added. The reaction was heated at 55° C. for 2.5 hours under $N_2$. Water (1 mL) was added to quench the reaction and all solvent was removed under vacuum. The residue was purified by column chromatography (35% ethyl acetate/hexanes) to give 9A (1.1 g, 64%). ESI-MS:m/z 779.3 (M+H)⁺.

9A (52 mg, 65 μmol) as prepared in Example 9, Step A, was dissolved in 1.25 M HCl in methanol and stirred at 55° C. for 1 hour. Solvent was removed under vacuum. The residue was purified by preparatory LCMS (water:acetonitrile, 45-60%) to give Compound 6 (25 mg, 61%). ESI-MS:m/z 635.2 (M+H)$^+$.

Example 11

Preparation of (S)-4-(biphenyl-3-yl)-N-cyclopropyl-N-(2,3-dichlorobenzyl)-2-((methoxymethoxy)methyl)-1,2,5,6-tetrahydropyridine-3-carboxamide (Compound 4)

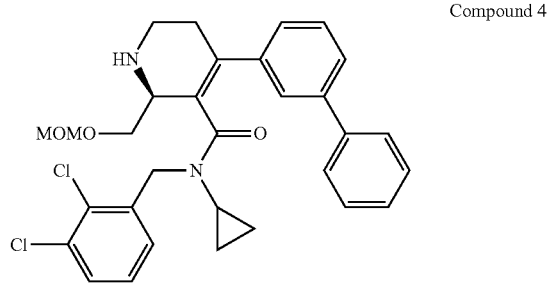

Compound 4

11A. (S)-Tert-butyl 4-(biphenyl-3-yl)-3-(cyclopropyl(2,3-dichlorobenzyl)carbamoyl)-2-((methoxymethoxy)methyl)-5,6-dihydropyridine-1(2H)-carboxylate (11A)

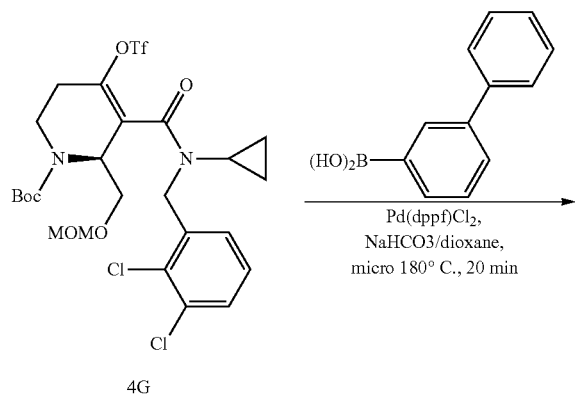

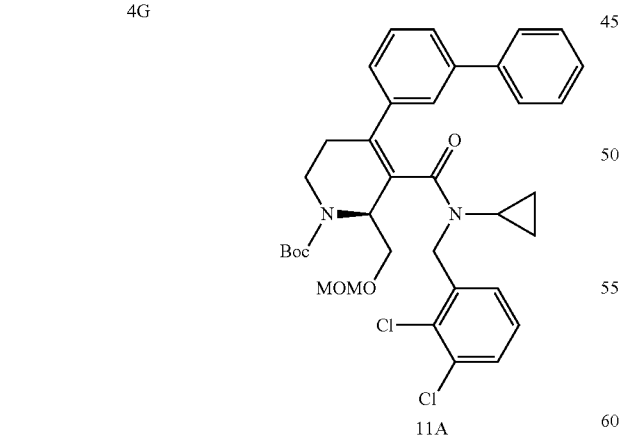

11A 4G was prepared as described in Example 4, Steps 4A-4G. 4G (50 mg, 77 μmol), (3-phenyl)-phenyl boronic acid (23 mg, 116 μmol) and Pd(dppf)Cl$_2$ were added into a microwave tube. The mixture was suspended in dioxane (600 μL) and saturated sodium bicarbonate (300 μL) and was degassed by bubbling nitrogen for 10 minutes. The vial was capped and microwaved at 150° C. for 15 minutes. The mixture was filtered thought a silica gel plug and carried to the next step without further purification. ESI-MS:m/z 651.4 (M+H)$^+$.

11B. (S)-4-(Biphenyl-3-yl)-N-cyclopropyl-N-(2,3-dichlorobenzyl)-2-((methoxymethoxy)methyl)-1,2,5,6-tetrahydropyridine-3-carboxamide (Compound 4)

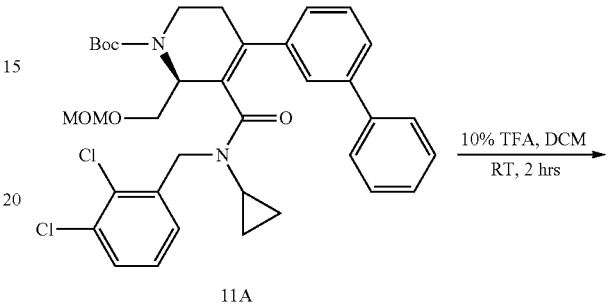

11A

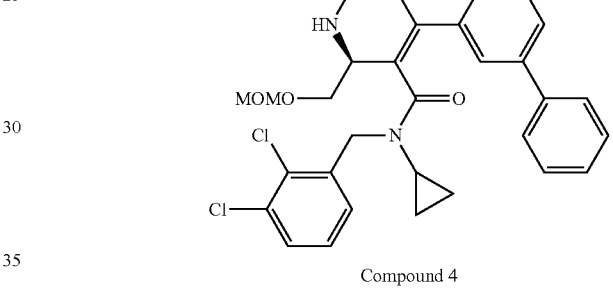

Compound 4

11A was deprotected according to the procedure described in Example 9, Step B to yield Compound 4 which was purified by preparatory LCMS (water/acetonitrile, 35-75%). ESI-MS: m/z 551.4 (M+H)$^+$.

Example 12

Preparation of (S)-N-cyclopropyl-N-(2,3-dichlorobenzyl)-4-(4-(2-(2,6-dimethylphenoxy)ethoxy)phenyl)-2-(hydroxymethyl)-1,2,5,6-tetrahydropyridine-3-carboxamide (Compound 7)

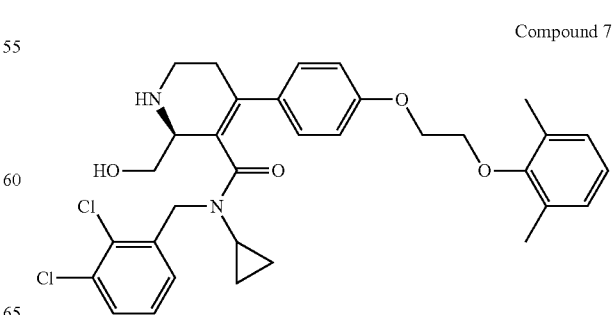

Compound 7

12A. (S)-Tert-butyl-3-(cyclopropyl(2,3-dichlorobenzyl)carbamoyl)-4-(4-(2-(2,6-dimethylphenoxy)ethoxy)phenyl)-2-((methoxymethoxy)methyl)-5,6-dihydropyridine-1(2H)-carboxylate (12A)

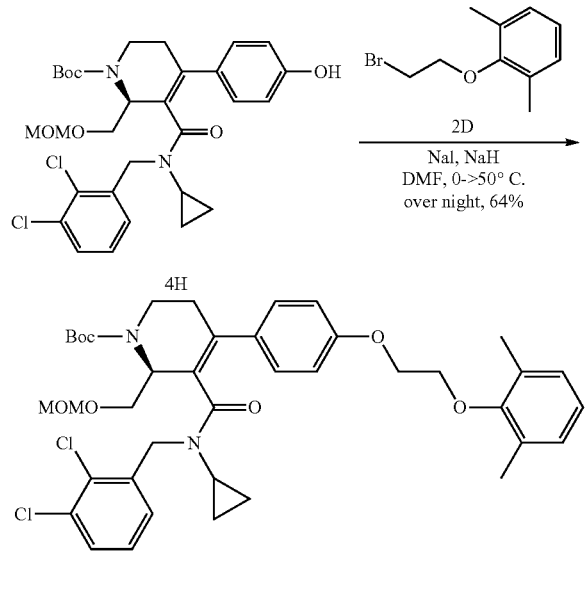

4H was prepared as described in Example 4, Steps 4A-4H. 4H was reacted with 2D (Example 2, Step 2D) as described in Example 9, Step 9A and yielded 12A which was then purified by preparatory LCMS (water/acetonitrile 90->95%). ESI-MS:m/z 739.4 (M+H)+.

12B. (S)-N-cyclopropyl-N-(2,3-dichlorobenzyl)-4-(4-(2-(2,6-dimethylphenoxy)ethoxy)phenyl)-2-(hydroxymethyl)-1,2,5,6-tetrahydropyridine-3-carboxamide (Compound 7)

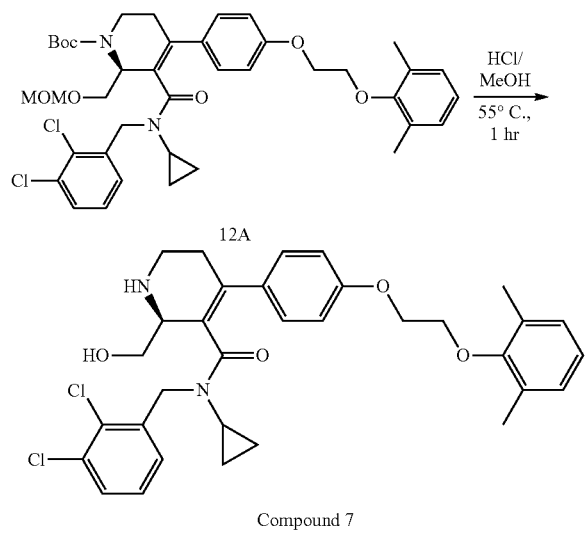

12A was deprotected according to the procedure described in Example 10 to yield Compound 7 which was then purified by preparatory LCMS (water:acetonitrile, 50-55%). ESI-MS: m/z 595.5 (M+H)+.

Example 13

Preparation of (S)-N-cyclopropyl-N-(2,3-dichlorobenzyl)-4-(4-(2-(2,6-dimethylphenoxy)ethoxy)phenyl)-2-((methoxymethoxy)methyl)-1,2,5,6-tetrahydropyridine-3-carboxamide (Compound 8)

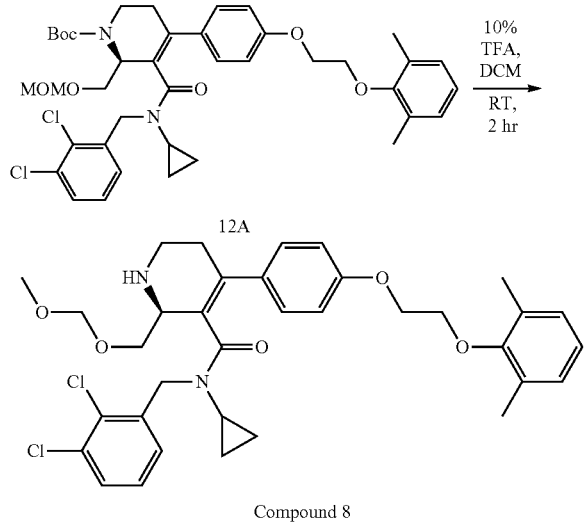

Compound 8

12A was prepared as described in Example 12, Step 12A. 12A was deprotected according to the procedure in Example 9, Step 9B to yield Compound 8 which was purified by preparatory LCMS (water:acetonitrile, 50-55%). 1H NMR (400 MHz, DMSO-d6) δ ppm 0.13-0.88 (m, 4H) 2.25 (m, 6H) 2.39 (m, 1H) 2.91-3.12 (m, 1H) 3.33 (m, 3H) 3.41-3.53 (m, 1H) 3.64-4.72 (m, 13H) 6.83-7.06 (m, 6H) 7.15-7.31 (m, 3H) 7.37-7.58 (m, 1H). ESI-MS:m/z 639.4 (M+H)+.

Example 14

Preparation of (S)-N-cyclopropyl-4-(4-(2-(2,6-dichloro-4-methylphenoxy)ethoxy)phenyl)-N-(2,3-dichlorobenzyl)-2-(hydroxymethyl)-1,2,5,6-tetrahydropyridine-3-carboxamide (Compound 9)

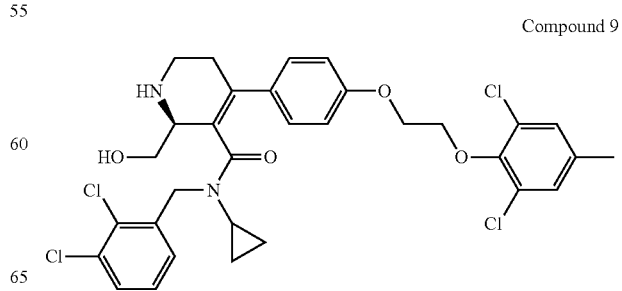

Compound 9

14A. Preparation of (S)-tert-butyl 3-(cyclopropyl(2,3-dichlorobenzyl)carbamoyl)-4-(4-(2-(2,6-dichloro-4-methylphenoxy)ethoxy)phenyl)-2-((methoxymethoxy)methyl)-5,6-dihydropyridine-1(2H)-carboxylate (14A)

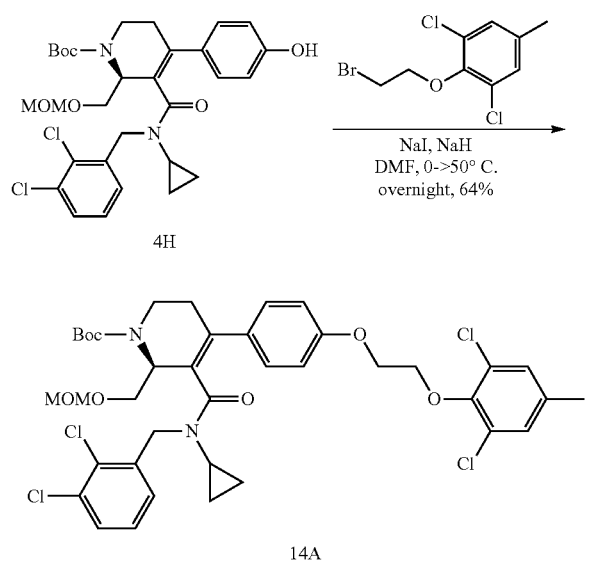

4H (Example 4, Steps 5A-5H) was alkylated with 2B (Example 2, Step 2B) as described in Example 9, Step 9A to yield 14A which was then purified by preparatory LCMS (water/acetonitrile 90->95%). ESI-MS:m/z 793.3 (M+H)⁺.

14B. (S)-N-cyclopropyl-4-(4-(2-(2,6-dichloro-4-methylphenoxy)ethoxy)phenyl)-N-(2,3-dichlorobenzyl)-2-(hydroxymethyl)-1,2,5,6-tetrahydropyridine-3-carboxamide (Compound 9)

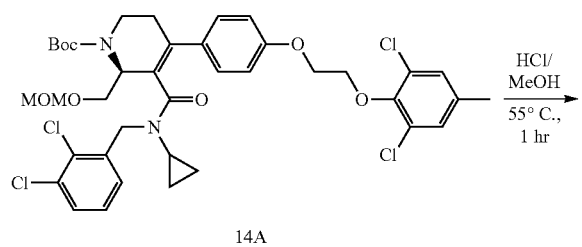

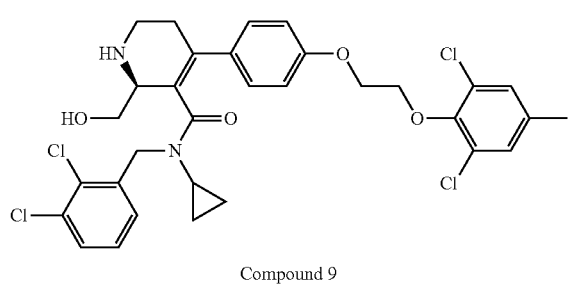

Compound 9

14A was deprotected according to the procedure in Example 10 to yield Compound 9 which was then purified by preparatory LCMS (water:acetonitrile, 50-55%). ESI-MS: m/z 649.3 (M+H)⁺.

Example 15

(S)-N-cyclopropyl-4-(4-(2-(2,6-dichloro-4-methylphenoxy)ethoxy)phenyl)-N-(2,3-dichlorobenzyl)-2-((methoxymethoxy)methyl)-1,2,5,6-tetrahydropyridine-3-carboxamide (Compound 10)

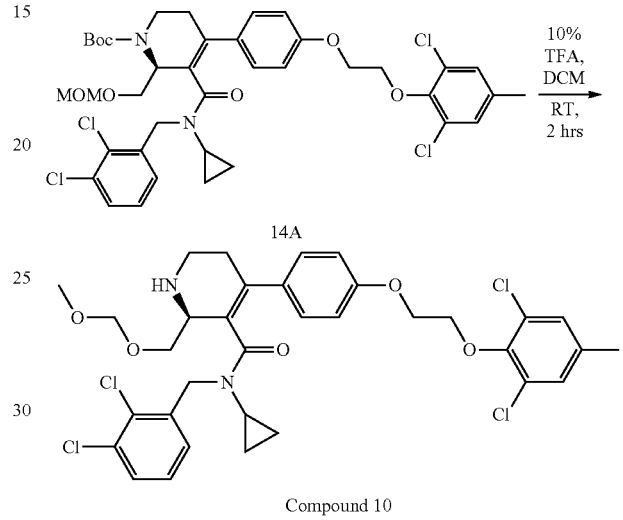

Compound 10

14A was prepared as described in Example 14, Step 14A. 14A was deprotected according to the procedure in Example 9, Step 9B to yield Compound 10 which was purified by preparatory LCMS (water:acetonitrile, 50-55%). ¹H NMR (400 MHz, DMSO-d₆) δ ppm 0.12-0.88 (m, 4H) 2.27 (s, 3H) 2.31-2.46 (m, 1H) 2.91-3.12 (m, 1H) 3.30-3.36 (m, 3H) 3.40-4.72 (m, 14H) 6.73-7.05 (m, 3H) 7.14-7.35 (m, 5H) 7.39-7.58 (m, 1H). ESI-MS:m/z 693.3 (M+H)⁺.

Example 16

Preparation of (S)-4-(4-(2-(2-chloro-3,6-difluorophenoxy)ethoxy)phenyl)-N-cyclopropyl-N-(2,3-dichlorobenzyl)-2-(hydroxymethyl)-1,2,5,6-tetrahydropyridine-3-carboxamide (Compound 11)

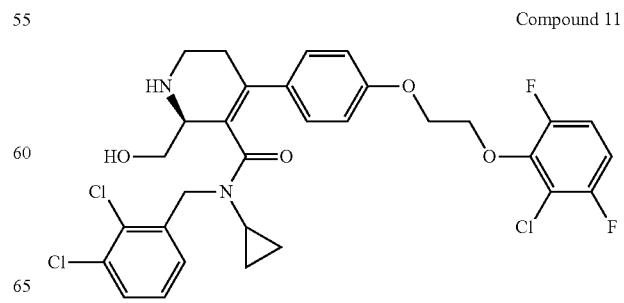

Compound 11

16A. (S)-tert-butyl 4-(4-(2-(2-chloro-3,6-difluorophenoxy)ethoxy)phenyl)-3-(cyclopropyl(2,3-dichlorobenzyl)carbamoyl)-2-((methoxymethoxy)methyl)-5,6-dihydropyridine-1(2H)-carboxylate (16A)

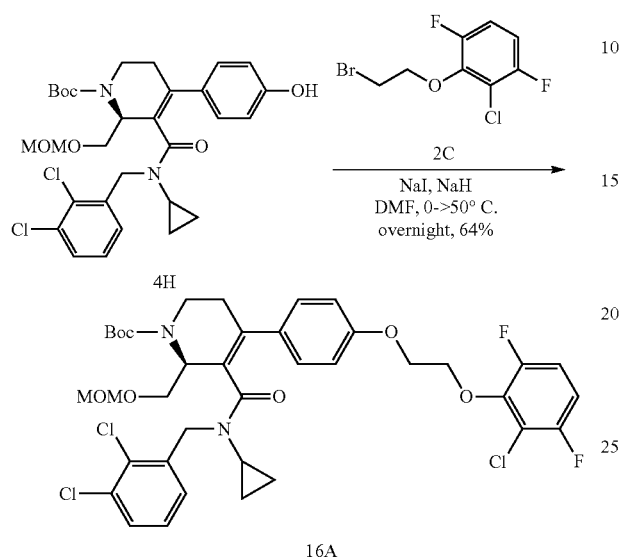

4H (Example 4, Step 4H) was alkylated to 2C (Example 2, Step 2C) as described in Example 9, Step 9A to yield 16A which was then purified by preparatory LCMS (water/acetonitrile 90->95%). ESI-MS:m/z 781.3 (M+H)$^+$.

16B. (S)-4-(4-(2-(2-chloro-3,6-difluorophenoxy)ethoxy)phenyl)-N-cyclopropyl-N-(2,3-dichlorobenzyl)-2-(hydroxymethyl)-1,2,5,6-tetrahydropyridine-3-carboxamide (Compound 11)

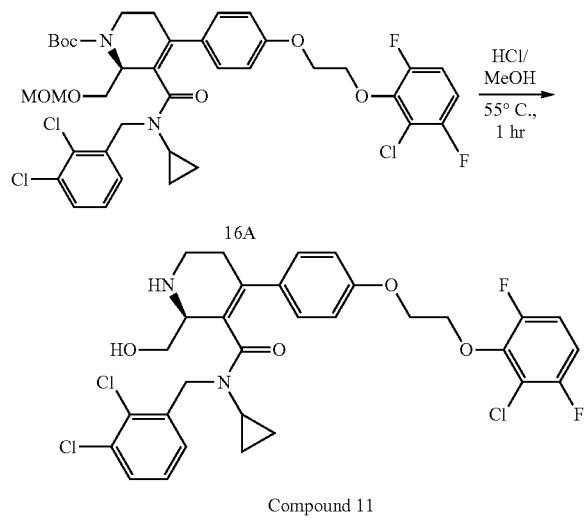

Compound 11

16A was deprotected according to the procedure described in Example 10 to yield Compound 11 which was then purified by preparatory LCMS (water:acetonitrile 40-55%). $^1$H NMR (400 MHz, DMSO-d$_6$) δ ppm 0.11-0.83 (m, 4H) 2.31-2.44 (m, 1H) 2.89-3.09 (m, 1 H) 3.22-3.52 (m, 3H) 3.61-3.94 (m, 3H) 4.16 (d, J=16.67 Hz, 1H) 4.37 (m, 3H) 4.58 (d, J=16.67 Hz, 2H) 6.80-7.03 (m, 3H) 7.12-7.29 (m, 4H) 7.34-7.57 (m, 2H). ESI-MS:m/z 637.3 (M+H)$^+$.

Example 17

Preparation of (S)-N-cyclopropyl-N-(2,3-dichlorobenzyl)-2-(hydroxymethyl)-4-(4-methoxyphenyl)-1,2,5,6-tetrahydropyridine-3-carboxamide (Compound 13)

17A. (S)-tert-butyl 3-(cyclopropyl(2,3-dichlorobenzyl)carbamoyl)-2-((methoxymethoxy)methyl)-4-(4-methoxyphenyl)-5,6-dihydropyridine-1(2H)-carboxylate (17A)

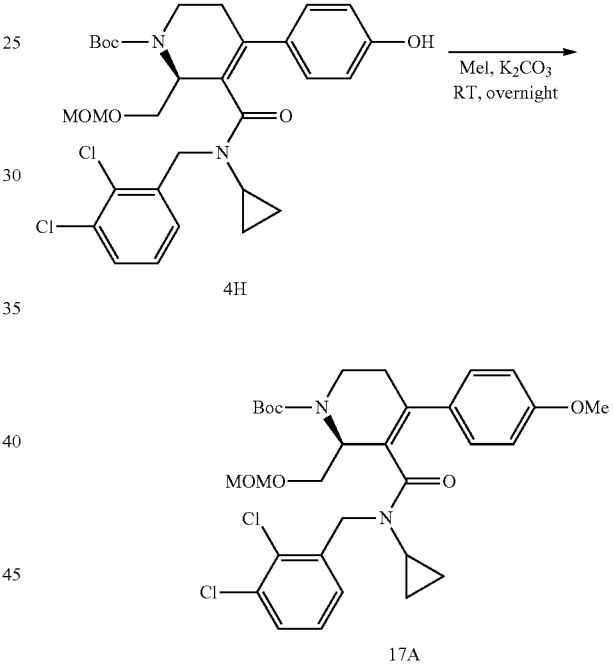

4H was prepared as described in Example 4, Steps 4A-4H. Into a 10 mL round bottom flask was added 4H (197 mg, 333 μmol) and DMF (1.3 mL). To this solution was added K$_2$CO$_3$ (92 mg, 666 μmol) and methyl iodide (95 mg, 666 μmol). The round bottom was fitted with a nitrogen balloon and stirred overnight at room temperature. Solvent was removed under vacuum and the residue was partitioned between water (10 mL) and ethyl acetate (10 mL). The organic layer was separated and the aqueous layer was extracted further with ethyl acetate (2×20 mL). The organic layers were combined and washed once with saturated sodium bicarbonate (15 mL) and once with brine (15 mL). The organic phase was dried over sodium sulfate and filtered and the solvent was removed under vacuum. The residue was used in the next step without further purification. ESI-MS:m/z 605.3 (M+H)$^+$

17B. (S)-N-cyclopropyl-N-(2,3-dichlorobenzyl)-2-(hydroxymethyl)-4-(4-methoxyphenyl)-1,2,5,6-tetrahydropyridine-3-carboxamide (Compound 13)

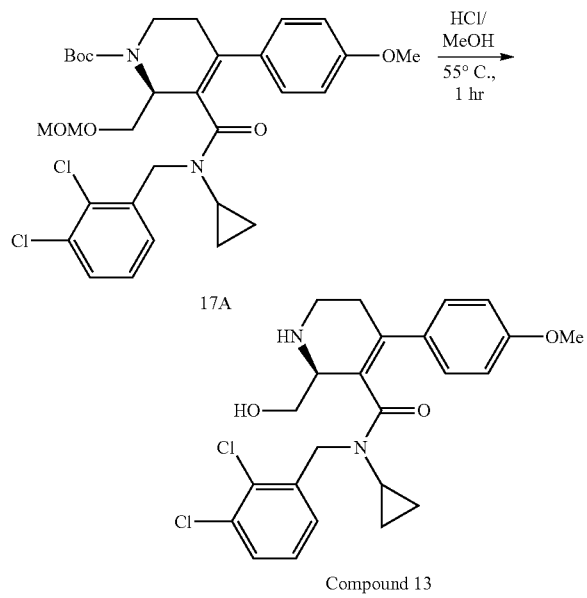

Compound 13

17A was deprotected according to the procedure described in Example 10 to yield Compound 13 which was then purified by preparatory LCMS (water:acetonitrile, 40-60%). $^1$H NMR (400 MHz, DMSO-d$_6$) δ ppm 0.16-1.11 (m, 4H) 2.38 (m, 1H) 2.86-3.08 (m, 1H) 3.40 (br. s, 2H) 3.62-3.95 (m, 7H) 4.09-4.83 (m, 4H) 6.81-7.00 (m, 3H) 7.13-7.29 (m, 3H) 7.49 (m, 1H). ESI-MS:m/z 461.3 (M+H)$^+$.

Example 18

Preparation of (S)-N-cyclopropyl-N-(2,3-dichlorobenzyl)-2-(hydroxymethyl)-4-(4-hydroxyphenyl)-1,2,5,6-tetrahydropyridine-3-carboxamide (Compound 12)

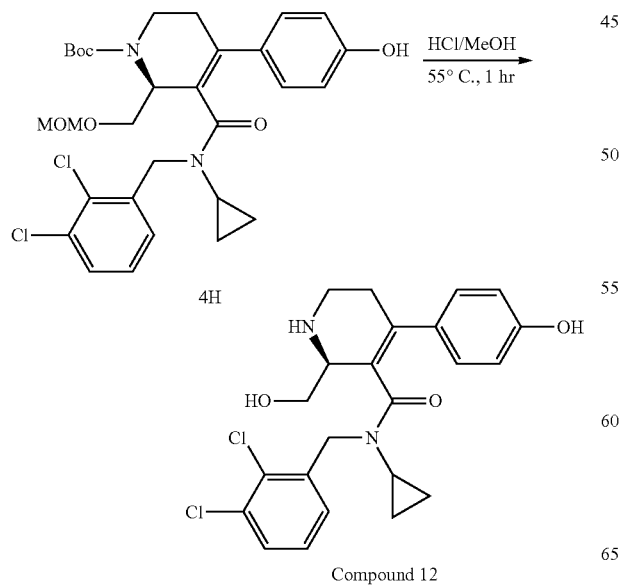

Compound 12

4H was prepared as described in Example 4, Steps 4A-4H. 4H was deprotected according to the procedure described in Example 10 to yield Compound 12 which was then purified by preparatory LCMS (water:acetonitrile, 20-40%). $^1$H NMR (400 MHz, DMSO-d$_6$) δ ppm 0.10-0.83 (m, 4H) 2.40 (m, 1H) 2.83-3.05 (m, 1H) 3.41 (m, 3H) 3.60-4.67 (m, 5H) 6.74 (m, 2H) 6.99-7.12 (m, 2H) 7.14-7.28 (m, 2H) 7.48-7.56 (m, 1H). ESI-MS:m/z 447.3 (M+H)$^+$.

Example 19

Preparation of (S)-2-(aminomethyl)-N-cyclopropyl-N-(2,3-dichlorobenzyl)-4-(4-(2-(2,6-dichlorophenoxy)ethoxy)phenyl)-1,2,5,6-tetrahydropyridine-3-carboxamide (Compound 14)

Compound 14

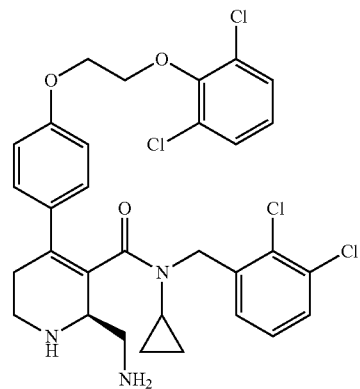

19A. (S)-Tert-butyl 3-(cyclopropyl(2,3-dichlorobenzyl)carbamoyl)-4-(4-(2-(2,6-dichlorophenoxy)ethoxy)phenyl)-2-(hydroxymethyl)-5,6-dihydropyridine-1(2H)-carboxylate (19A)

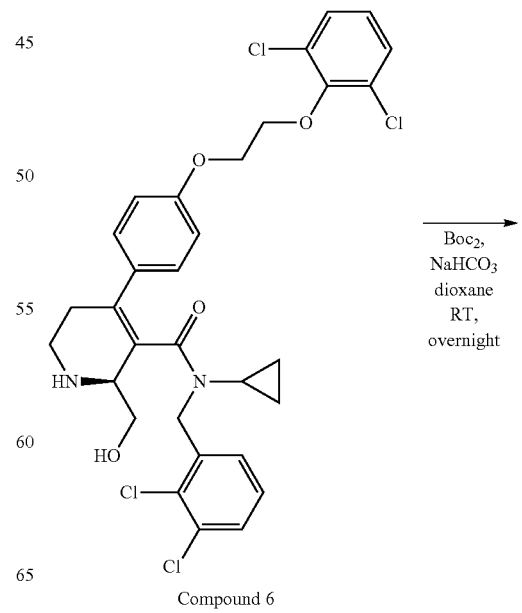

Compound 6

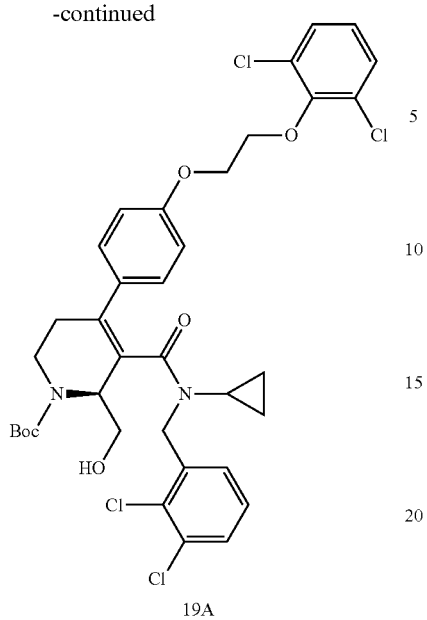

19A

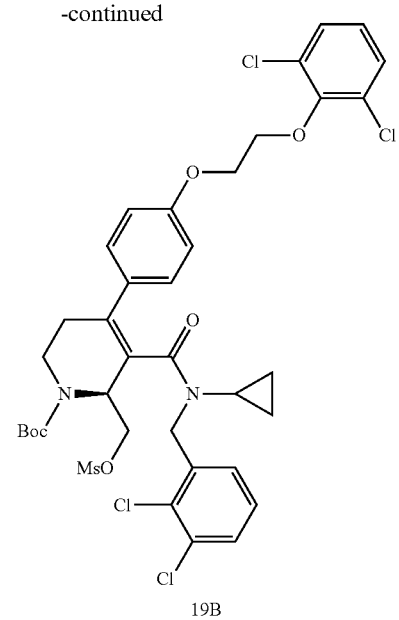

19B

Compound 6 was prepared as described in Example 10. Into a 10 mL round bottom flask was added Compound 6 (546 mg, 858 µmol) and dioxane (1.9 mL). The reaction was added sodium bicarbonate (180 mg, 2.15 mmol) and di-tert-butyl carbonate (337 mg, 1.54 mmol). The reaction was stirred overnight at room temperature. Solvent was removed under vacuum and the residue partitioned between water (10 mL) and ethyl acetate (10 mL). The organic layer was separated and the aqueous layer was extracted further with ethyl acetate (2×10 mL). The organic layers were combined and dried over sodium sulfate. The solution was filtered and solvent removed under vacuum. The residue was purified by column chromatography (0->2% MeOH/DCM) to give 19A (465 mg, 74%). ESI-MS:m/z 735.3 (M+H)$^+$ Into a 10 mL round bottom flask was added 19A (325 mg, 441 µmol) and dichloromethane (3.5 mL). The reaction was cooled with an ice bath. Triethylamine (90 mg, 882 µmol) was added followed by slow addition of methanesulfonyl chloride (61 mg, 530 µmol). The reaction stirred for 4 hours and poured into brine (20 mL). The organic layer was separated and the aqueous layer was extracted with dichloromethane (2×10 mL). The organic layers were combined and dried over sodium sulfate. The solution was filtered and solvent removed under vacuum. The residue was purified by column chromatography (2% MeOH/DCM) to give (29) (331 mg, 92%). ESI-MS:m/z 407.4 (M+H)$^+$.

19B. (S)-tert-butyl 3-(cyclopropyl(2,3-dichlorobenzyl)carbamoyl)-4-(4-(2-(2,6-dichlorophenoxy)ethoxy)phenyl)-2-((methylsulfonyloxy)methyl)-5,6-dihydropyridine-1(2H)-carboxylate (19B)

19C. (S)-tert-butyl 2-(azidomethyl)-3-(cyclopropyl (2,3-dichlorobenzyl)carbamoyl)-4-(4-(2-(2,6-dichlorophenoxy)ethoxy)phenyl)-5,6-dihydropyridine-1(2H)-carboxylate (19C)

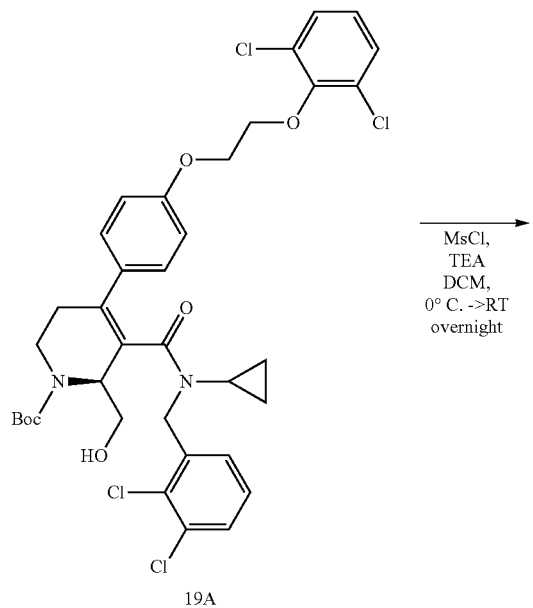

19A

MsCl, TEA DCM, 0° C. ->RT overnight

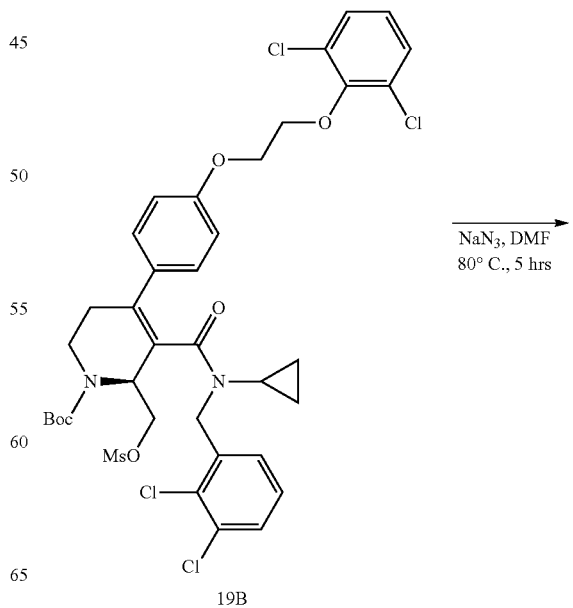

19B

NaN$_3$, DMF 80° C., 5 hrs

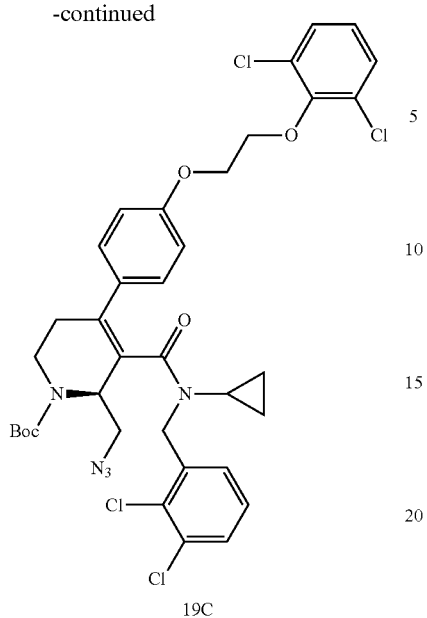

19C

Into a 10 mL round bottom flask was added 19B (324 mg, 398 μmol) and DMF (1.3 mL). Sodium azide (129 mg, 1.99 mmol) was added and the flask was fitted with a condenser and nitrogen inlet. The reaction was heated to 80° C. for 5 hours. Solvent was removed under vacuum and residue was partitioned between water (10 mL) an ethyl acetate (10 mL). The organic layer was separated and the aqueous layer was extracted with ethyl acetate (2×10 mL). The organic layers were combined and dried over sodium sulfate. The solution was filtered and solvent removed under vacuum. The residue was filtered through a silica gel plug with 10% ethyl acetate/ hexanes (150 mL). The solvent was removed to leave a residue (300 mg) which contained the mesylate and the azide 19C. The residue was used without further purification. ESI-MS:m/z 661.2 (M+H)+.

19D. (S)-tert-butyl 2-(aminomethyl)-3-(cyclopropyl (2,3-dichlorobenzyl)carbamoyl)-4-(4-(2-(2,6-dichlo- rophenoxy)ethoxy)phenyl)-5,6-dihydropyridine-1 (2H)-carboxylate (19D)

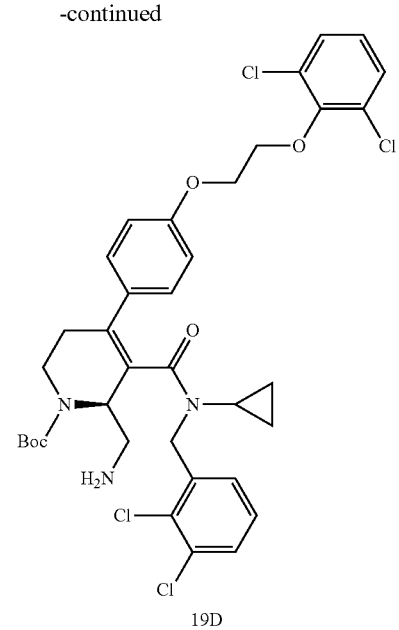

19D

Into a 10 mL round bottom flask was added 19C (200 mg, 302 μmol) and THF (3 mL). Triphenylphosphine (166 mg, 634 μmol) and water (112 mg, 6.22 mmol) was added and the flask was fitted with a reflux condenser and nitrogen inlet. The mixture was refluxed for three hours. Solvent was removed under vacuum and the residue was purified by preparatory LCMS to give 19D (40 mg, 21%). ESI-MS:m/z 734.2 (M+H)+.

19E. (S)-2-(aminomethyl)-N-cyclopropyl-N-(2,3- dichlorobenzyl)-4-(4-(2-(2,6-dichlorophenoxy) ethoxy)phenyl)-1,2,5,6-tetrahydropyridine-3-car- boxamide (Compound 14)

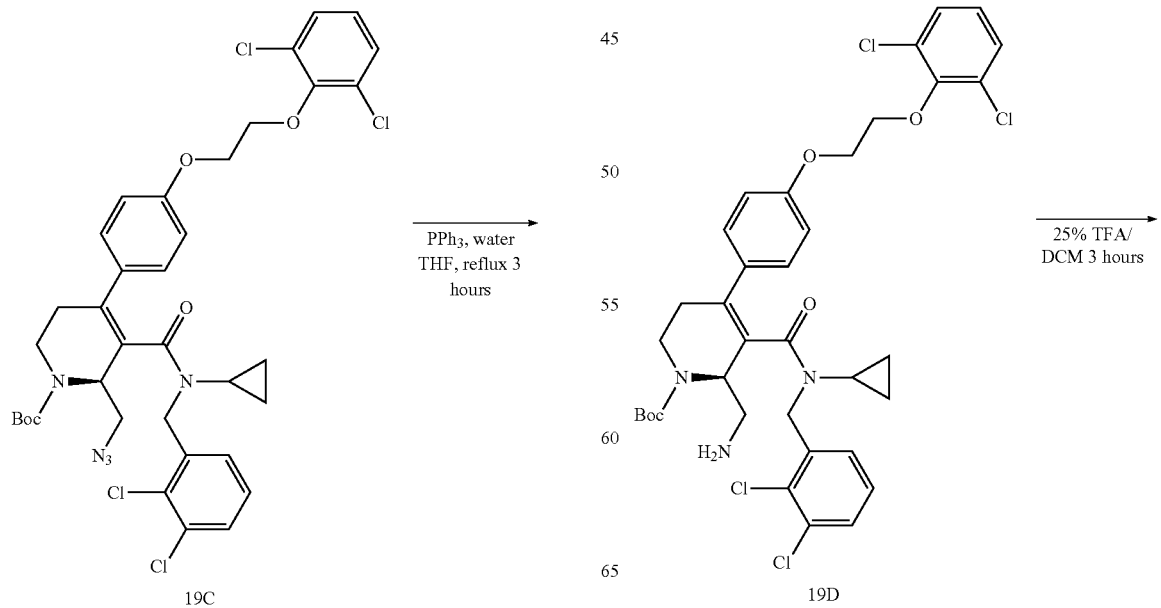

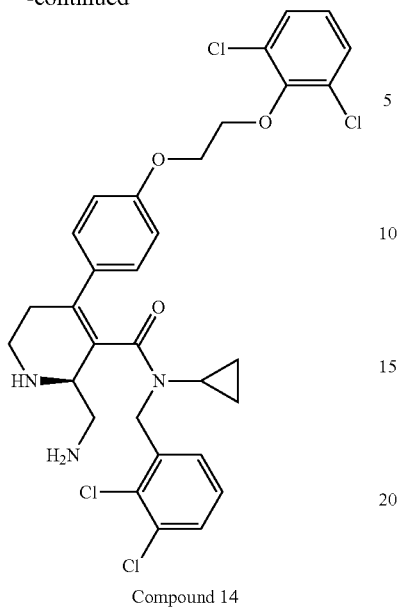

Compound 14

Into a 10 mL round bottom flask was added 19D (50 mg, 79 μmol) and 25% TFA/DCM (5 mL). The mixture was stirred at room temperature for 3 hours. Solvent was removed under vacuum and the residue was purified by preparatory LCMS to yield Compound 14 (25-80%). $^1$H NMR (400 MHz, DMSO-$d_6$) δ ppm 0.23-0.91 (m, 4H) 2.33 (m, 2H) 2.99 (br. s., 1H) 3.30-3.59 (m, 4H) 4.07-4.68 (m, 7H) 6.85-7.07 (m, 2H) 7.14-7.31 (m, 4H) 7.40-7.59 (m, 4H). ESI-MS:m/z 636.2 (M+H)$^+$.

In addition, the above reaction schemes and variations thereof can be used to prepare the following compounds. It is understood that recitation of a compound is intended to encompass all of the different possible stereoisomers.

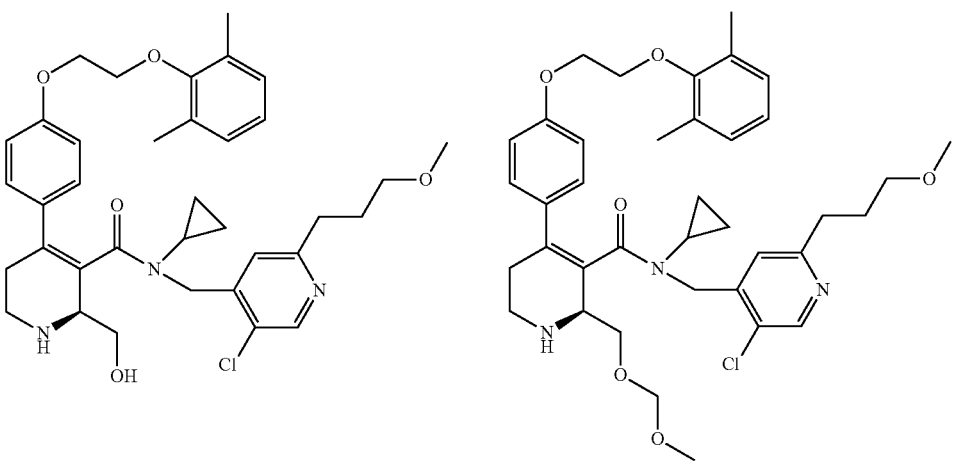

(S)-N-((5-chloro-2-(3-methoxypropyl)pyridin-4-yl)methyl)-N-cyclopropyl-4-(4-(2-(2,6-dimethylphenoxy)ethoxy)phenyl)-2-(hydroxymethyl)-1,2,5,6-tetrahydropyridine-3-carboxamide (S)-N-((5-chloro-2-(3-methoxypropyl)pyridin-4-yl)methyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide

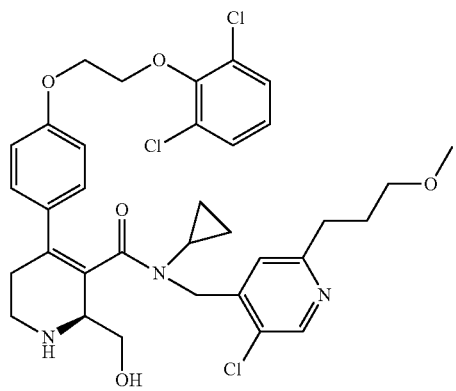

(S)-N-((5-chloro-2-(3-methoxypropyl)pyridin-4-yl)methyl)-N-cyclopropyl-4-(4-(2-(2,6-dichlorophenoxy)ethoxy)phenyl)-2-(hydroxymethyl)-1,2,5,6-tetrahydropyridine-3-carboxamide

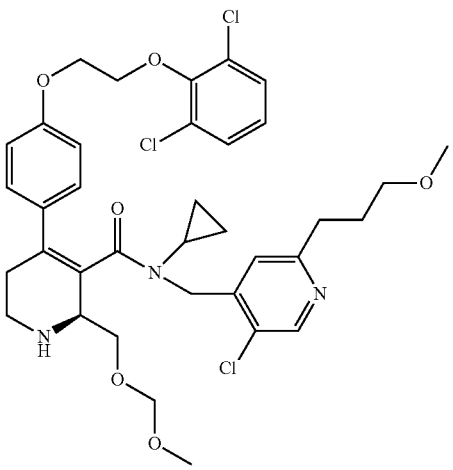

(S)-N-((5-chloro-2-(3-methoxypropyl)pyridin-4-yl)methyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide

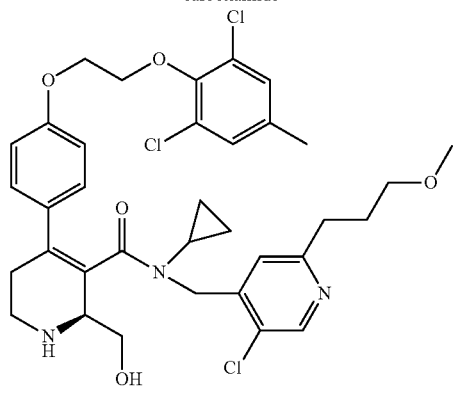

(S)-N-((5-chloro-2-(3-methoxypropyl)pyridin-4-yl)methyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide

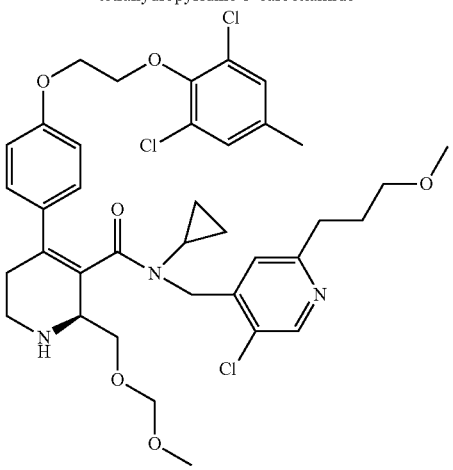

(S)-N-((5-chloro-2-(3-methoxypropyl)pyridin-4-yl)methyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide

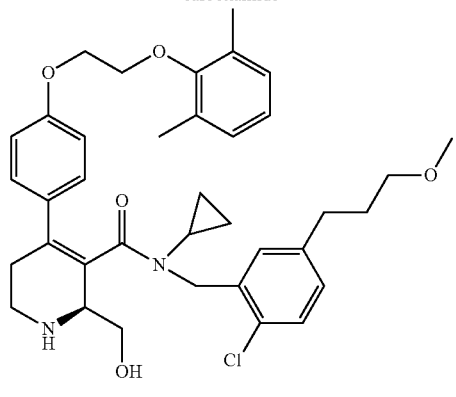

(S)-N-(2-chloro-5-(3-methoxypropyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide

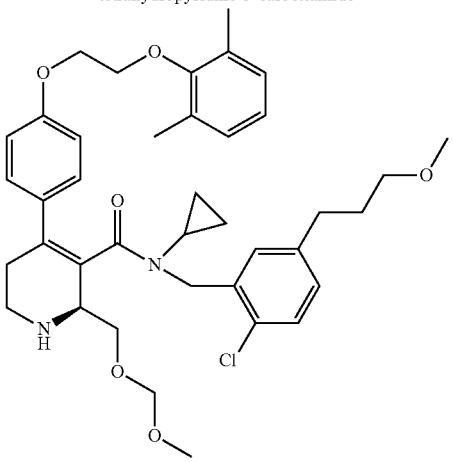

(S)-N-(2-chloro-5-(3-methoxypropyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide

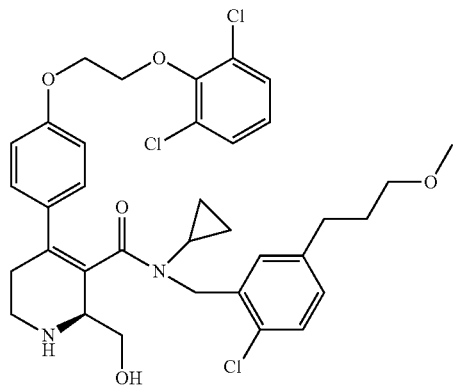

(S)-N-(2-chloro-5-(3-methoxypropyl)benzyl)-
N-cyclopropyl-4-(4-(2-(2,6-
dichlorophenoxy)ethoxy)phenyl)-2-
(hydroxymethyl)-1,2,5,6-tetrahydropyridine-3-
carboxamide

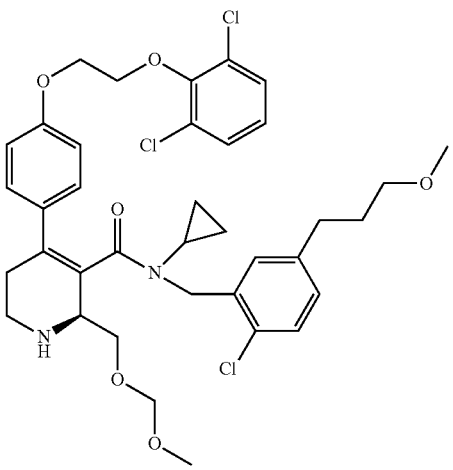

(S)-N-(2-chloro-5-(3-methoxypropyl)benzyl)-
N-cyclopropyl-4-(4-(2-(2,6-
dichlorophenoxy)ethoxy)phenyl)-2-
((methoxymethoxy)methyl)-1,2,5,6-
tetrahydropyridine-3-carboxamide

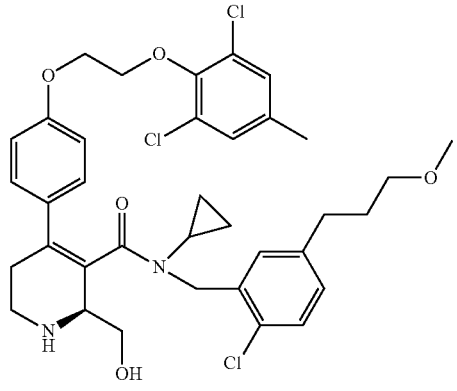

(S)-N-(2-chloro-5-(3-methoxypropyl)benzyl)-
N-cyclopropyl-4-(4-(2-(2,6-dichloro-4-
methylphenoxy)ethoxy)phenyl)-2-
(hydroxymethyl)-1,2,5,6-tetrahydropyridine-3-
carboxamide

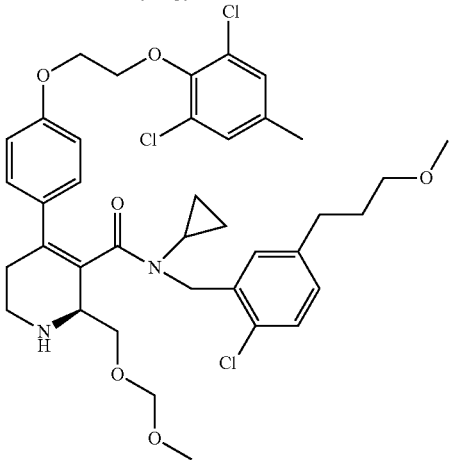

(S)-N-(2-chloro-5-(3-methoxypropyl)benzyl)-
N-cyclopropyl-4-(4-(2-(2,6-dichloro-4-
methylphenoxy)ethoxy)phenyl)-2-
((methoxymethoxy)methyl)-1,2,5,6-
tetrahydropyridine-3-carboxamide

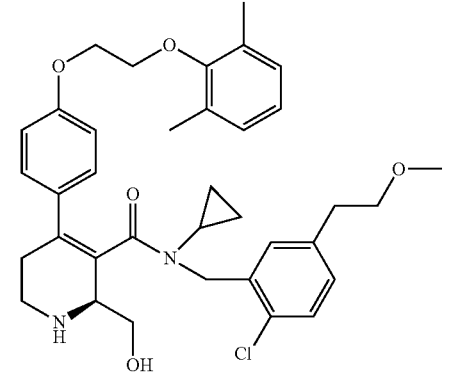

(S)-N-(2-chloro-5-(2-methoxyethyl)benzyl)-N-
cyclopropyl-4-(4-(2-(2,6-
dimethylphenoxy)ethoxy)phenyl)-2-
(hydroxymethyl)-1,2,5,6-tetrahydropyridine-3-
carboxamide

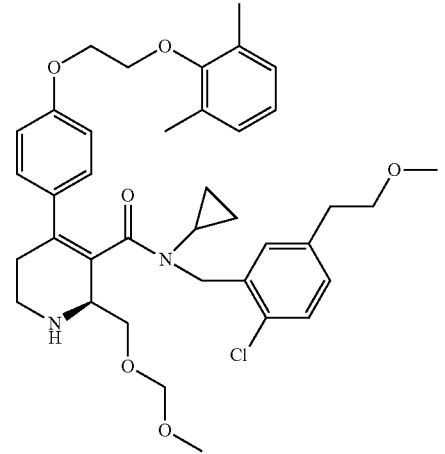

(S)-N-(2-chloro-5-(2-methoxyethyl)benzyl)-N-
cyclopropyl-4-(4-(2-(2,6-
dimethylphenoxy)ethoxy)phenyl)-2-
((methoxymethoxy)methyl)-1,2,5,6-
tetrahydropyridine-3-carboxamide

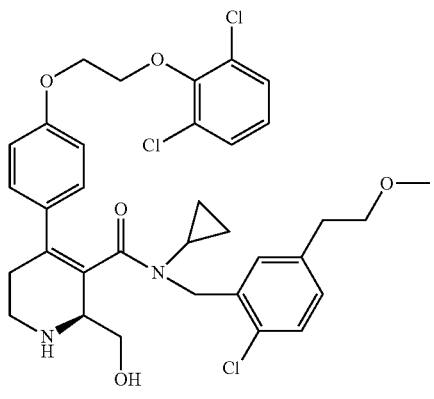

(S)-N-(2-chloro-5-(2-methoxyethyl)benzyl)-N-
cyclopropyl-4-(4-(2-(2,6-
dichlorophenoxy)ethoxy)phenyl)-2-
(hydroxymethyl)-1,2,5,6-tetrahydropyridine-3-
carboxamide

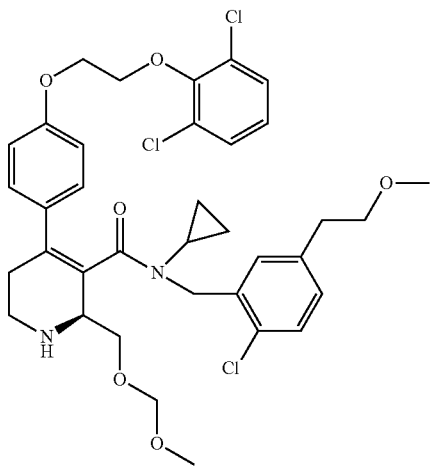

(S)-N-(2-chloro-5-(2-methoxyethyl)benzyl)-N-
cyclopropyl-4-(4-(2-(2,6-
dichlorophenoxy)ethoxy)phenyl)-2-
((methoxymethoxy)methyl)-1,2,5,6-
tetrahydropyridine-3-carboxamide

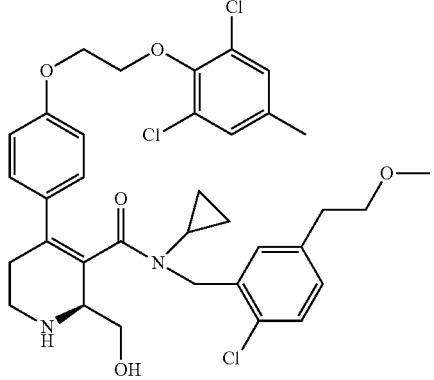

(S)-N-(2-chloro-5-(2-methoxyethyl)benzyl)-N-
cyclopropyl-4-(4-(2-(2,6-dichloro-4-
methylphenoxy)ethoxy)phenyl)-2-
(hydroxymethyl)-1,2,5,6-tetrahydropyridine-3-
carboxamide

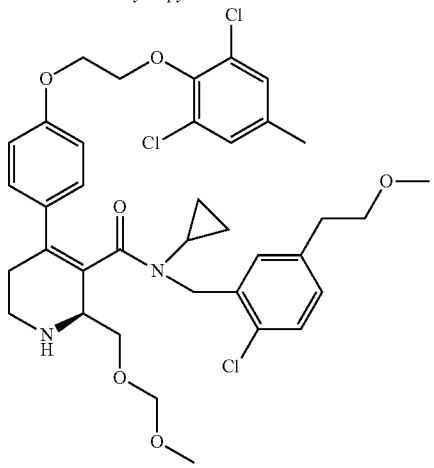

(S)-N-(2-chloro-5-(2-methoxyethyl)benzyl)-N-
cyclopropyl-4-(4-(2-(2,6-dichloro-4-
methylphenoxy)ethoxy)phenyl)-2-
((methoxymethoxy)methyl)-1,2,5,6-
tetrahydropyridine-3-carboxamide

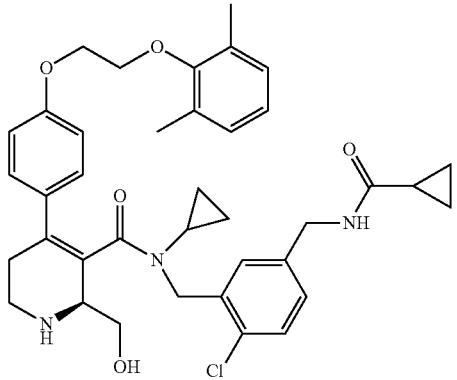

(S)-N-(2-chloro-5-
(cyclopropanecarboxamidomethyl)benzyl)-N-
cyclopropyl-4-(4-(2-(2,6-
dimethylphenoxy)ethoxy)phenyl)-2-
(hydroxymethyl)-1,2,5,6-tetrahydropyridine-3-
carboxamide

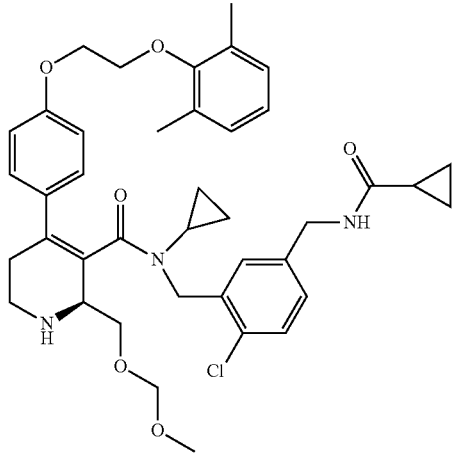

(S)-N-(2-chloro-5-
(cyclopropanecarboxamidomethyl)benzyl)-N-
cyclopropyl-4-(4-(2-(2,6-
dimethylphenoxy)ethoxy)phenyl)-2-
((methoxymethoxy)methyl)-1,2,5,6-
tetrahydropyridine-3-carboxamide

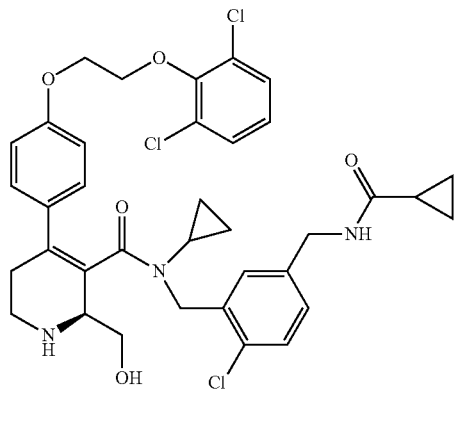

(S)-N-(2-chloro-5-
(cyclopropanecarboxamidomethyl)benzyl)-N-
cyclopropyl-4-(4-(2-(2,6-
dichlorophenoxy)ethoxy)phenyl)-2-
(hydroxymethyl)-1,2,5,6-tetrahydropyridine-3-
carboxamide

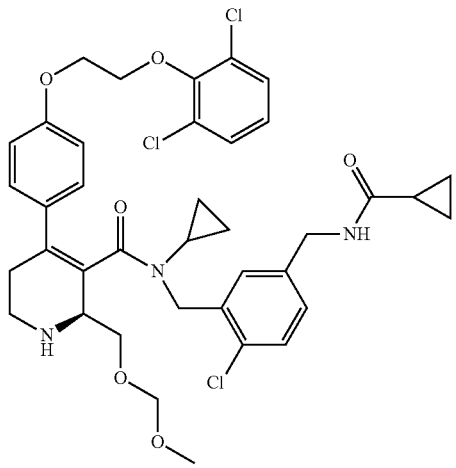

(S)-N-(2-chloro-5-
(cyclopropanecarboxamidomethyl)benzyl)-N-
cyclopropyl-4-(4-(2-(2,6-
dichlorophenoxy)ethoxy)phenyl)-2-
((methoxymethoxy)methyl)-1,2,5,6-
tetrahydropyridine-3-carboxamide

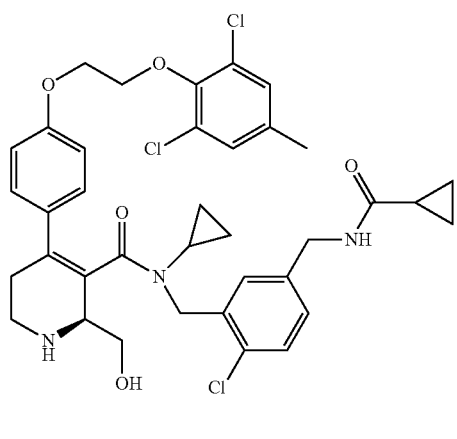

(S)-N-(2-chloro-5-
(cyclopropanecarboxamidomethyl)benzyl)-N-
cyclopropyl-4-(4-(2-(2,6-dichloro-4-
methylphenoxy)ethoxy)phenyl)-2-
(hydroxymethyl)-1,2,5,6-tetrahydropyridine-3-
carboxamide

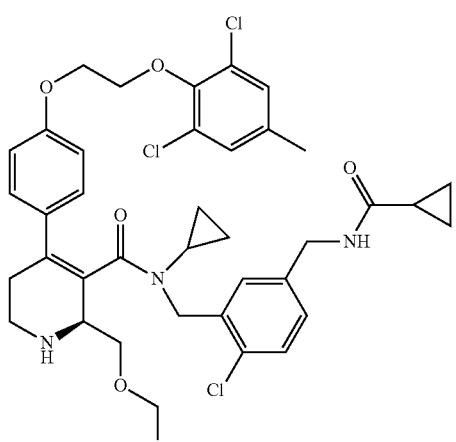

(S)-N-(2-chloro-5-
(cyclopropanecarboxamidomethyl)benzyl)-N-
cyclopropyl-4-(4-(2-(2,6-dichloro-4-
methylphenoxy)ethoxy)phenyl)-2-
((methoxymethoxy)methyl)-1,2,5,6-
tetrahydropyridine-3-carboxamide

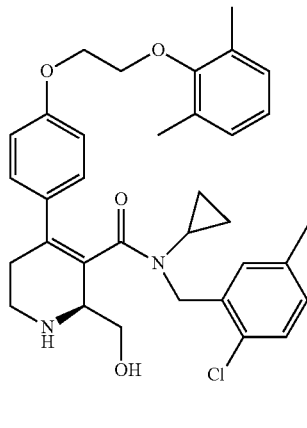

(S)-N-(2-chloro-5-((3,3,3-trifluoropropanamido)methyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide

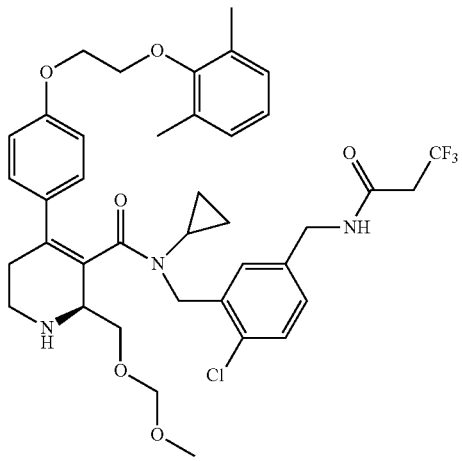

(S)-N-(2-chloro-5-((3,3,3-trifluoropropanamido)methyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide

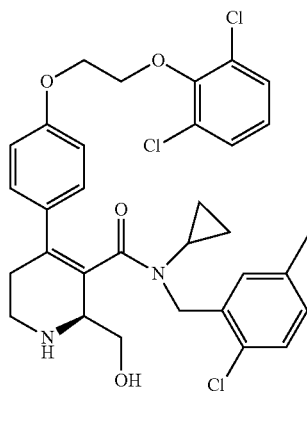

(S)-N-(2-chloro-5-((3,3,3-trifluoropropanamido)methyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide

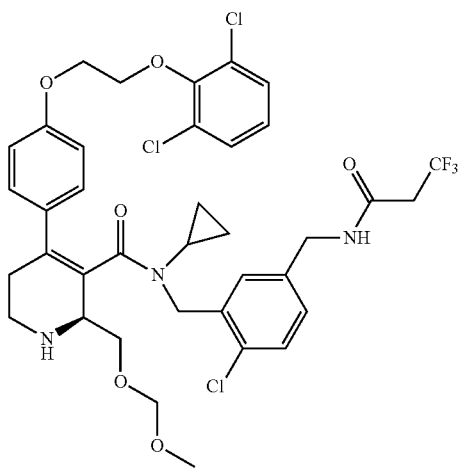

(S)-N-(2-chloro-5-((3,3,3-trifluoropropanamido)methyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide

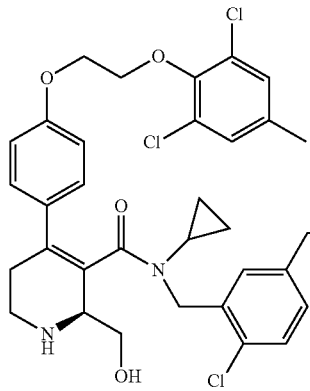
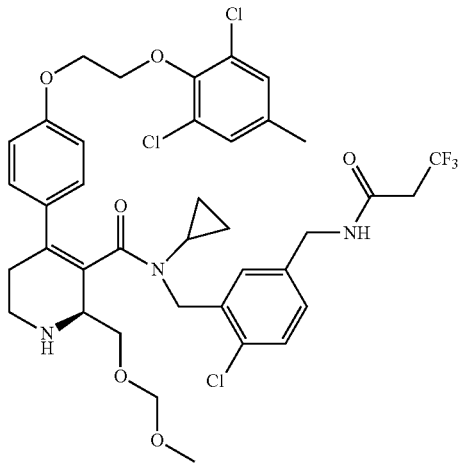

(S)-N-(2-chloro-5-((3,3,3-trifluoropropanamido)methyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide (S)-N-(2-chloro-5-((3,3,3-trifluoropropanamido)methyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide

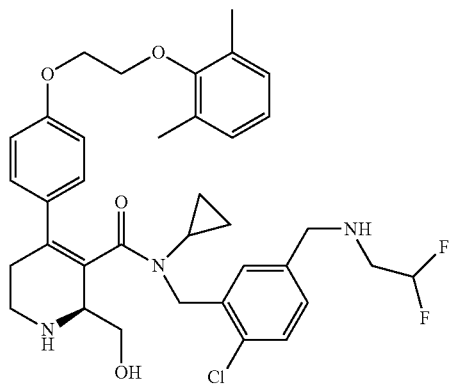
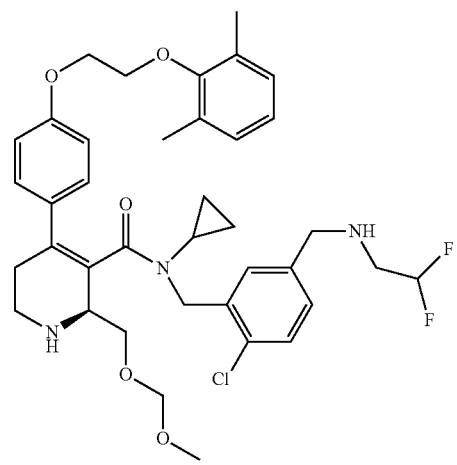

(S)-N-(2-chloro-5-((2,2-difluoroethylamino)methyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide (S)-N-(2-chloro-5-((2,2-difluoroethylamino)methyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide

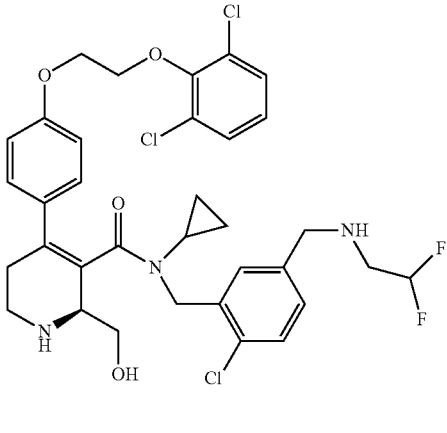

(S)-N-(2-chloro-5-((2,2-difluoroethylamino)methyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide

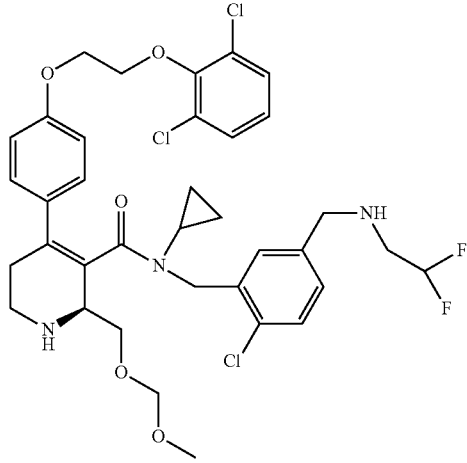

(S)-N-(2-chloro-5-((2,2-difluoroethylamino)methyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide

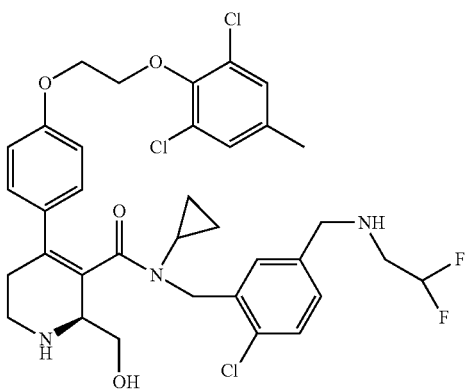

(S)-N-(2-chloro-5-((2,2-difluoroethylamino)methyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide

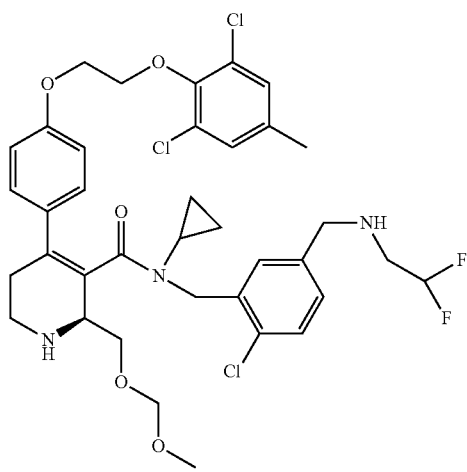

(S)-N-(2-chloro-5-((2,2-difluoroethylamino)methyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide -continued

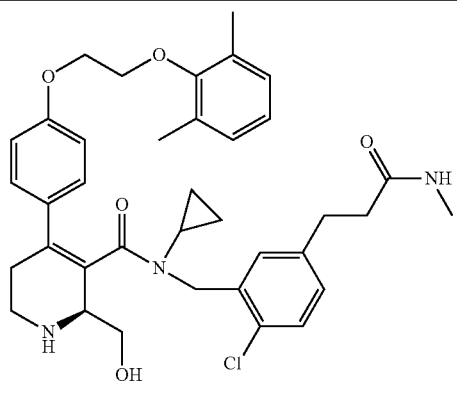

(S)-N-(2-chloro-5-(3-(methylamino)-3-
oxopropyl)benzyl)-N-cyclopropyl-4-(4-(2-(2,6-
dimethylphenoxy)ethoxy)phenyl)-2-
(hydroxymethyl)-1,2,5,6-tetrahydropyridine-3-
carboxamide

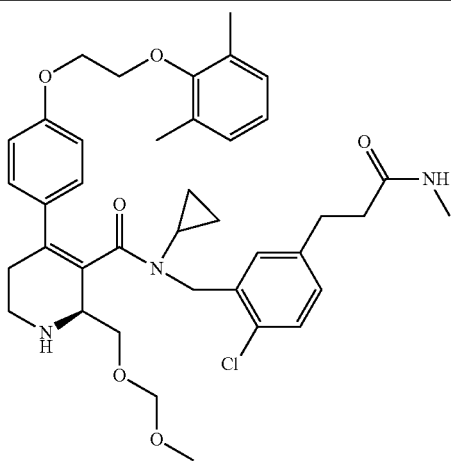

(S)-N-(2-chloro-5-(3-(methylamino)-3-
oxopropyl)benzyl)-N-cyclopropyl-4-(4-(2-(2,6-
dimethylphenoxy)ethoxy)phenyl)-2-
((methoxymethoxy)methyl)-1,2,5,6-
tetrahydropyridine-3-carboxamide

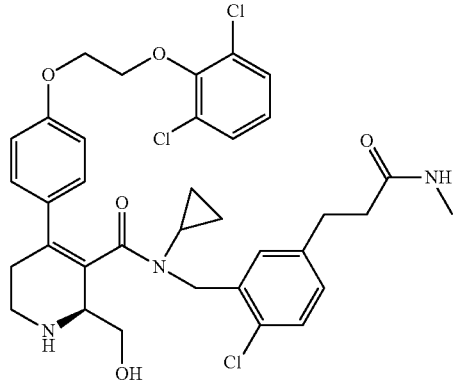

(S)-N-(2-chloro-5-(3-(methylamino)-3-
oxopropyl)benzyl)-N-cyclopropyl-4-(4-(2-(2,6-
dichlorophenoxy)ethoxy)phenyl)-2-
(hydroxymethyl)-1,2,5,6-tetrahydropyridine-3-
carboxamide

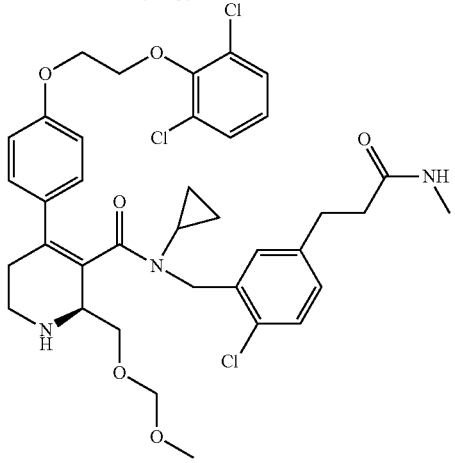

(S)-N-(2-chloro-5-(3-(methylamino)-3-
oxopropyl)benzyl)-N-cyclopropyl-4-(4-(2-(2,6-
dichlorophenoxy)ethoxy)phenyl)-2-
((methoxymethoxy)methyl)-1,2,5,6-
tetrahydropyridine-3-carboxamide

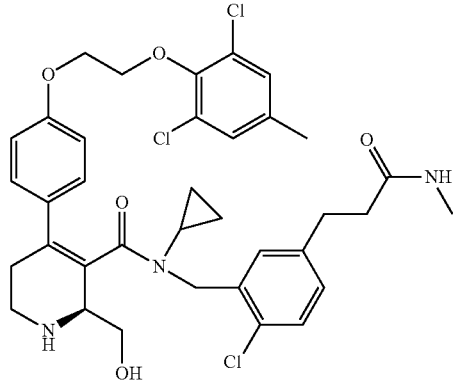

(S)-N-(2-chloro-5-(3-(methylamino)-3-
oxopropyl)benzyl)-N-cyclopropyl-4-(4-(2-(2,6-
dichloro-4-methylphenoxy)ethoxy)phenyl)-2-
(hydroxymethyl)-1,2,5,6-tetrahydropyridine-3-
carboxamide

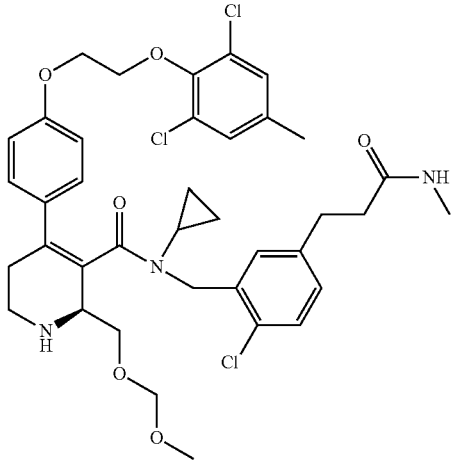

(S)-N-(2-chloro-5-(3-(methylamino)-3-
oxopropyl)benzyl)-N-cyclopropyl-4-(4-(2-(2,6-
dichloro-4-methylphenoxy)ethoxy)phenyl)-2-
((methoxymethoxy)methyl)-1,2,5,6-
tetrahydropyridine-3-carboxamide

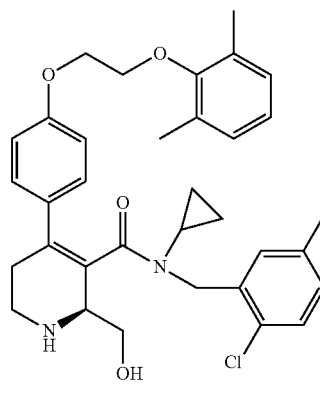

(S)-4-chloro-3-((N-cyclopropyl-4-(4-(2-(2,6-dimethylphenoxy)ethoxy)phenyl)-2-(hydroxymethyl)-1,2,5,6-tetrahydropyridine-3-carboxamido)methyl)phenethyl methylcarbamate

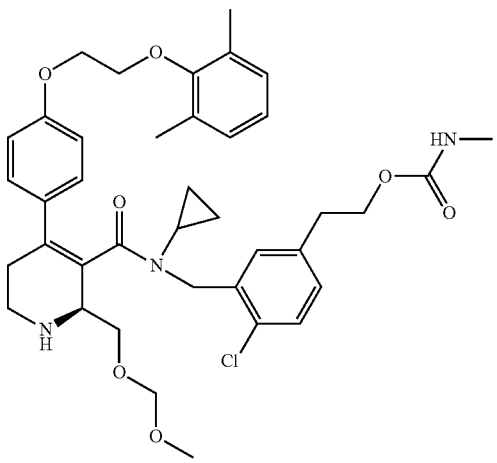

(S)-4-chloro-3-((N-cyclopropyl-4-(4-(2-(2,6-dimethylphenoxy)ethoxy)phenyl)-2-((methoxymethoxy)methyl)-1,2,5,6-tetrahydropyridine-3-carboxamido)methyl)phenethyl methylcarbamate

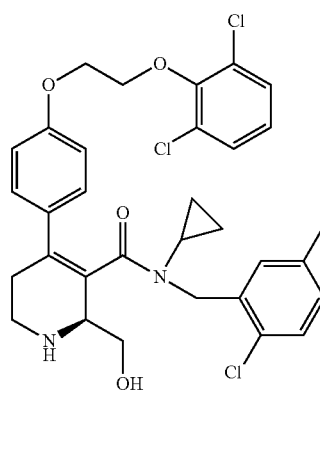

(S)-4-chloro-3-((N-cyclopropyl-4-(4-(2-(2,6-dichlorophenoxy)ethoxy)phenyl)-2-(hydroxymethyl)-1,2,5,6-tetrahydropyridine-3-carboxamido)methyl)phenethyl methylcarbamate

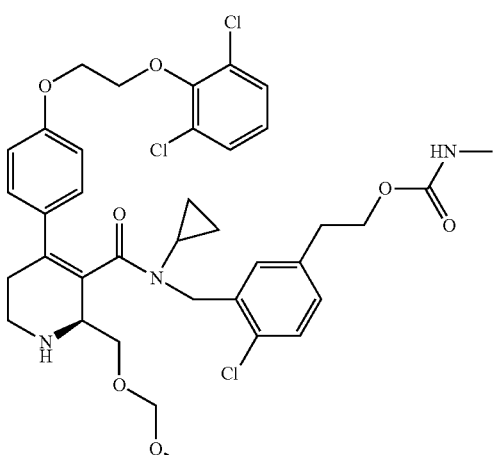

(S)-4-chloro-3-((N-cyclopropyl-4-(4-(2-(2,6-dichlorophenoxy)ethoxy)phenyl)-2-((methoxymethoxy)methyl)-1,2,5,6-tetrahydropyridine-3-carboxamido)methyl)phenethyl methylcarbamate

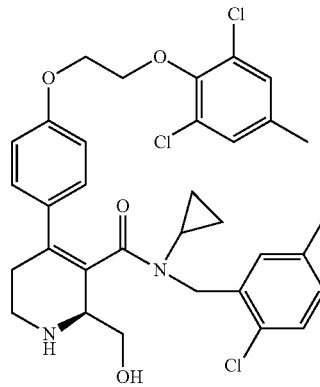

(S)-4-chloro-3-((N-cyclopropyl-4-(4-(2-(2,6-dichloro-4-methylphenoxy)ethoxy)phenyl)-2-(hydroxymethyl)-1,2,5,6-tetrahydropyridine-3-carboxamido)methyl)phenethyl methylcarbamate

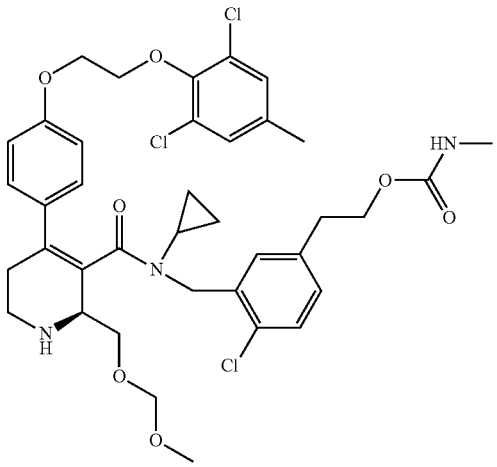

(S)-4-chloro-3-((N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamido)methyl)phenethyl methylcarbamate

Example A

Expression of Preprorenin and Purification of Prorenin

The sequence of human wild-type renin is known in the art; see, Imai, T. et al., Proc. Natl. Acad. Sci. USA 1983, 80, 7105-7409. It is noted that the fragment of the renin protein useful for the assay comprises amino acid residues 67-406 of human renin (active renin). To prepare active renin, a fragment longer than active renin, a preprorenin (e.g., comprising residues 1-406), may be expressed and from which a prorenin (e.g., comprising residues 23-406) may be recovered. The prorenin may later be cleaved to obtain active renin.

Expression of human preprorenin (residues 1-406) can be conducted using a FreeStyle 293 Expression System (Invitrogen Corp.), wherein the plasmid DNA for human prorenin expression (pcDNA3.1(+)/hREN) is used to conduct transient expression in FreeStyle 293-F cells. After transfection of the plasmid DNA, the cells are subjected to shaking at 37° C., 8% $CO_2$ and 125 rpm for 3 days.

The prorenin protein is then accumulated and purified by salting out. Powdered ammonium sulfate is added to the culture medium and dissolved to make a 40% saturation of the salt. The resulting precipitate can be collected by centrifugation and discarded. Ammonium sulfate is added to the remaining solution and dissolved to make an 80% saturation of salt. The resulting precipitate can be collected by, for example, centrifugation. The prorenin protein is recovered by dissolving the precipitate in buffer.

The concentrated liquid is subjected to gel filtration chromatography using, for example, HiLoad 16/60 Superdex 200 pg (Amersham Biosciences, Inc.) equilibrated with 20 mM Tris-hydrochloric acid (pH 8.0) containing 0.15 M sodium chloride, at a flow rate of 1.4 mL/min, to obtain 3.6 mg of purified prorenin (residues 24-406).

Example B

Purification of Active Renin

To 3.6 mg of prorenin (residues 24-406, as prepared in Example A) dissolved in 5.2 mL of 0.1 M Tris-hydrochloric acid (pH 8.0), is added 12 μg of trypsin (Roche Diagnostics Corp.), and the mixture is allowed to react at 28° C. for 55 minutes to carry out activation of renin. After the reaction, 0.4 mL of immobilized trypsin inhibitor (Pierce Biotechnology, Inc.) is added to remove the trypsin used in the activation, by adsorption. The reaction liquid containing the active renin is concentrated using Vivaspin 20 (molecular weight of the fraction 10,000; Vivascience, Inc.), and diluted with 20 mM Tris-hydrochloric acid (pH 8.0). The diluted liquid is fed to a TSKgel DEAE-5 PW column (7.5 mm I.D.×75 mm, Tosoh Corp.) equilibrated with 20 mM Tris-hydrochloric acid (pH 8.0) at a flow rate of 1 mL/min to adsorb the active renin (residues 67-406). The column is washed with the buffer solution used for the equilibration, and then elution is carried out by means of a linear concentration gradient of sodium chloride from 0 M to 0.3 M, to obtain 1.5 mg of purified active renin (residues 67-406).

Example C

Establishment of Renin Expressing Vector

A plasmid DNA to express human renin in HEK293 cells can be prepared as follows. PCR is carried out using human renal cDNA (Clontech Laboratories, Inc., Marathon Ready cDNA) as the template and using two synthetic DNAs (5'-AAGCTTATGGATGGATGGAGA-3' (SEQ ID NO: 1) and 5'-GGATCCTCAGCGGGCCAAGGC-3' (SEQ ID NO: 2)), and the obtained fragment is cloned using TOPO TA Cloning Kit (Invitrogen Corp.). The obtained fragment is subcloned into pcDNA3.1(+) that has been cleaved by HindIII and BamHI, to obtain a plasmid DNA for human preprorenin expression (pcDNA3.1(+)/hREN).

Example D

Assaying the In Vitro Enzymatic Activity of Renin Inhibitors

Solutions of test compounds in varying concentrations (≦2 mM final concentration) are prepared in dimethyl sulfoxide (DMSO) and then diluted into assay buffer comprising 50 mM Hepes, 1 mM EDTA, 1 mM DTT, 0.1 mg/mL BSA, 0.01% Brij35, pH 7.4. Alternatively, the assay can be performed with a high BSA concentration, wherein the buffer contains an additional 2% BSA.

Recombinant human renin (3 nM final concentration) is added to the dilutions and pre-incubated with the compounds for 10 minutes at 37° C. As described in Examples A-C above, human renin can be obtained by expressing preprorenin (residue 1-406) in mammalian cells, treating the prorenin (residues 24-406) contained in the culture supernatant with trypsin, and isolate the active form (residues 67-406). After pre-incubation, the reaction is initiated with 1 µM of substrate QXL520-γ-Abu-Ile-His-Pro-Phe-His-Leu-Val-Ile-His-Thr-Lys (HiLyteFluo488)-Arg-OH (Anaspec, San Jose, Calif.). The final DMSO in the assay is 5%. The total volume of the reaction mixture is 20 µL, which can be placed on Greiner 384-well small volume plates.

Renin activity may be determined via fluorescence (excitation λ=485 nm; emission λ=538 nm), e.g., on a Molecular Devices SPECTROmax GEMINI XPS. The fluorescence intensity is determined upon the addition of substrate and determined again after incubation at 37° C. for one hour. The fluorescence intensity of a blank (no inhibition) using vehicle alone is also determined. Renin activity is linearly proportional to the change in fluorescence observed (final-initial).

The percent inhibition of renin at a given compound concentration is defined as:

$$100\% \times [1-(F_{compound}/F_{blank})]$$

where $F_{compound}$ is the observed fluorescence at a given concentration of test compound and $F_{blank}$ is the observed fluorescence in the presence of vehicle alone.

The pIC50 value (negative log of the molar concentration of the compound that produces 50% inhibition) of a test compound is calculated by non-linear least squares curve fitting of the equation:

$$\text{Percent Inhibition} = 100\%/(1+(10-\text{pIC}50/10 \log [I]))$$

to percent inhibition versus compound concentration. The 50% inhibitory concentration ($IC_{50}$) of a test compound is calculated by raising 10 to the negative $pIC_{50}$ ($10\text{-}pIC_{50}$).

$IC_{50}$ values for selected compounds of the present invention are given in Table 1.

TABLE 1

| IC$_{50}$ of Exemplified Compounds Against Renin ||
| --- | --- |
| COMPOUND | IC$_{50}$ (nM) |
| 1 | >1000 |
| 2 | >1000 |
| 3 | 100-1000 |
| 4 | 100-1000 |
| 5 | <100 |
| 6 | <100 |
| 7 | <100 |
| 8 | <100 |
| 9 | <100 |
| 10 | <100 |
| 11 | <100 |
| 12 | >1000 |
| 13 | >1000 |
| 14 | 100-1000 |

What is claimed is:

1. A compound of the formula:

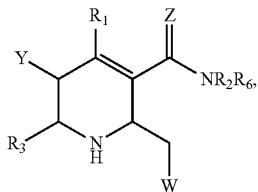

a tautomer or stereoisomer thereof or a pharmaceutically acceptable salt of the compound, tautomer or stereoisomer, wherein Z is selected from the group consisting of O and S;

W is selected from the group consisting of cyano, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl $(C_{1-10})$alkyl, aryl$(C_{1-10})$alkyl, hetero$(C_{1-10})$aryl $(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

Y is selected from the group consisting of hydrogen, cyano, hydroxy, $(C_{1-10})$alkoxy, $(C_{4-12})$aryloxy, hetero$(C_{1-10})$aryloxy, aminocarbonyl, amino, $(C_{1-10})$alkylamino, sulfonamido, imino, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, hetero$(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_1$ is a cyclyl moiety, unsubstituted or substituted;

$R_2$ is selected from the group consisting of hydrogen, $(C_{1-10})$alkoxy, $(C_{4-12})$aryloxy, hetero$(C_{1-10})$aryloxy, $(C_{1-10})$alkyl, hetero$(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

$R_3$ is selected from the group consisting of hydrogen, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, aza$(C_{1-10})$alkyl, $(C_{1-10})$oxaalkyl, $(C_{1-10})$oxoalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, hetero$(C_{1-10})$alkyl, $(C_{3-12})$cycloalkyl, hetero$(C_{3-12})$cycloalkyl, $(C_{4-12})$aryl, and hetero$(C_{1-10})$aryl, each unsubstituted or substituted; and $R_6$ is selected from the group consisting of hydrogen, $(C_{1-10})$alkoxy, $(C_{4-12})$aryloxy, hetero$(C_{1-10})$aryloxy, $(C_{1-10})$alkyl, $(C_{1-10})$alkenyl, $(C_{1-10})$alkynyl, halo$(C_{1-10})$alkyl, hydroxy$(C_{1-10})$alkyl, carbonyl $(C_{1-10})$alkyl, thiocarbonyl$(C_{1-10})$alkyl, sulfonyl $(C_{1-10})$alkyl, sulfinyl$(C_{1-10})$alkyl, aza$(C_{1-10})$alkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$ alkyl, hetero$(C_{1-10})$aryl$(C_{1-5})$alkyl, hetero$(C_{1-10})$ alkyl, $(C_{3-12})$cycloalkyl, hetero$(C_{3-12})$cycloalkyl, $(C_{4-12})$aryl, and hetero$(C_{1-10})$aryl, each unsubstituted or substituted.

2. The compound, tautomer or pharmaceutically acceptable salt according to claim 1, the compound having the formula:

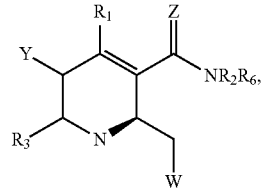

wherein $R_1$, $R_2$, $R_3$, $R_6$, W, Y, and Z are as defined in claim 1.

3. The compound, tautomer or pharmaceutically acceptable salt according to claim 1, the compound having the formula:

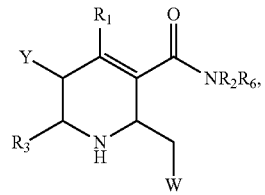

wherein $R_1$, $R_2$, $R_3$, $R_6$, W, and Y are as defined in claim 1.

4. The compound, tautomer or pharmaceutically acceptable salt according to claim 3, the compound having the formula:

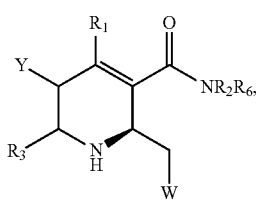

wherein $R_1$, $R_2$, $R_3$, $R_6$, W, and Y are as defined in claim 1.

5. The compound, tautomer or pharmaceutically acceptable salt according to claim 3, the compound having the formula:

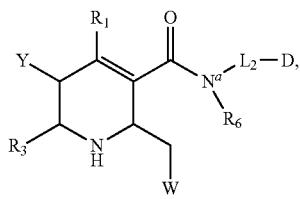

wherein
$R_1$, $R_3$, $R_6$, W, and Y are as defined in claim 1;
$N^a$ denotes a nitrogen atom;
D is selected from the group consisting of hydrogen, $(C_{3-12})$cycloalkyl, hetero$(C_{3-12})$cycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and
$L_2$ is absent or is a linker providing 1 or 2 atom separation between D and $N^a$ to which $L_2$ is attached, wherein the atoms of $L_2$ providing the separation are carbon atoms.

6. The compound, tautomer or pharmaceutically acceptable salt according to claim 5, the compound having the formula:

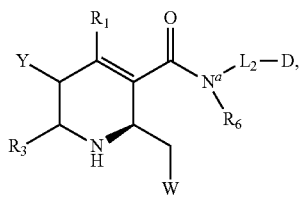

wherein $R_1$, $R_3$, $R_6$, W, and Y are as defined in claim 1, and $N^a$, $L_2$, and D are as defined in claim 5.

7. The compound, tautomer or pharmaceutically acceptable salt according to claim 1, wherein $R_3$ is selected from the group consisting of hydrogen, $(C_{1-10})$alkyl, $(C_{1-10})$azaalkyl, $(C_{1-10})$oxaalkyl, $(C_{1-10})$oxoalkyl, hetero$(C_{1-10})$alkyl, halo$(C_{1-10})$alkyl, hydroxy$(C_{1-10})$alkyl, and amino$(C_{1-10})$alkyl, each unsubstituted or substituted.

8. The compound, tautomer or pharmaceutically acceptable salt according to claim 1, wherein $R_3$ is selected from the group consisting of hydrogen, unsubstituted $(C_{1-10})$alkyl, or substituted $(C_{1-10})$alkyl.

9. The compound, tautomer or pharmaceutically acceptable salt according to claim 1, wherein $R_3$ is hydrogen.

10. The compound, tautomer or pharmaceutically acceptable salt according to claim 1, wherein $R_6$ is selected from the group consisting of hydrogen, $(C_{1-10})$alkyl, $(C_{1-10})$alkenyl, $(C_{1-10})$alkynyl, $(C_{4-12})$aryl, hetero$(C_{1-10})$aryl, $(C_{3-12})$cycloalkyl, hetero$(C_{3-12})$cycloalkyl, aryl$(C_{1-10})$alkyl, hetero$(C_{1-10})$aryl$(C_{1-5})$alkyl, $(C_{3-12})$cycloalkyl$(C_{1-5})$alkyl, and hetero$(C_{3-12})$cycloalkyl$(C_{1-10})$alkyl, each unsubstituted or substituted.

11. The compound, tautomer or pharmaceutically acceptable salt according to claim 1, wherein $R_6$ is selected from the group consisting of hydrogen, $(C_{1-7})$alkyl, halo$(C_{1-7})$alkyl, di-phenyl$(C_{1-7})$alkyl, cyclo$(C_{3-8})$alkyl, naphthyl$(C_{1-7})$alkyl, halo substituted-phenyl$(C_{1-7})$alkyl, and phenyl, each unsubstituted or substituted with up to three substituents independently selected from the group consisting of $(C_{1-7})$alkyl, halo, $(C_{1-7})$alkoxy, $(C_{1-7})$alkoxy$(C_{1-7})$alkyloxy.

12. The compound, tautomer or pharmaceutically acceptable salt according to claim 1, wherein $R_6$ is selected from the group consisting of hydrogen, unsubstituted or substituted $(C_{1-7})$alkyl, and unsubstituted or substituted $(C_{3-8})$cycloalkyl.

13. The compound, tautomer or pharmaceutically acceptable salt according to claim 1, wherein $R_6$ when present is isopropyl, propyl, isobutyl, cyclopropyl, ethyl, —$CH_2CH_2F$, —$CH_2CHF_2$ and —$CH_2CF_3$.

14. The compound, tautomer or pharmaceutically acceptable salt according to claim 1, wherein $R_6$ is cyclopropyl.

15. The compound, tautomer or pharmaceutically acceptable salt according to claim 1, wherein Y is selected from the group consisting of hydrogen, hydroxyl, $(C_{1-7})$alkyloxy, $(C_{1-7})$alkoxy$(C_{1-7})$alkyloxy, alkoxy$(C_{1-7})$alkyl, $(C_{1-7})$alkanoylamino, $(C_{1-7})$alkylsulfonylamino, arylsulfonylamino, hydroxyalkyl, aminoalkyl, $(C_{1-7})$alkyl, and amino, each unsubstituted or substituted.

16. The compound, tautomer or pharmaceutically acceptable salt according to claim 1, wherein Y is selected from the group consisting of H, —OH, —$NH_2$, —$CH_2OH$, —$CH_2OCH_3$, —$NHC(O)CH_3$, —$CH_2CH(OH)CH_2OH$, —$CH_2CH(OH)CH_2OCH_3$, —$OCH_2CH(OH)CH_2OCH_3$, and —$OCH_2CH(OH)CH_2OH$.

17. The compound, tautomer or pharmaceutically acceptable salt according to claim 1, wherein Y is H.

18. The compound, tautomer or pharmaceutically acceptable salt according to claim 1, wherein $R_2$ is selected from the group consisting of hydrogen, cyclylalkyl, heterocyclylalkyl, cyclylcarbonyl, heterocyclylcarbonyl, cyclylsulfonyl, heterocyclylsulfonyl, cyclyloxycarbonyl, heterocyclyloxycarbonyl, cyclyloxysulfonyl, and heterocyclyloxysulfonyl wherein each cyclyl moieties is unsubstituted or substituted with one or more substituents each independently selected from the group consisting of halo, nitro, cyano, carboxyl, carboxamido, amido, carboxamidoalkoxy, carbamoyl, $(C_{1-7})$alkyl, $(C_{1-7})$alkoxy, —$CF_3$, —$OCF_3$, hydroxy-$(C_{1-7})$alkyl, alkoxy$(C_{1-7})$alkyl, alkoxy$(C_{1-7})$alkoxy, alkoxyalkoxyalkyl, aminoalkyl, alkoxyalkylaminoalkyl, alkanoylaminoalkyl, alkoxycarbonylalkyl, hydroxyalkyloxy, alkoxyalkyloxy, aminoalkoxy, alkanoylaminoalkoxy, carboxyalkyoxy, alkyloxycarbonylalkoxy, carbamoylalkoxy, and alkoxyalkylcarbamoyl.

19. The compound, tautomer or pharmaceutically acceptable salt according to claim 1, wherein $R_2$ is selected from the group consisting of hydrogen, phenyl$(C_{1-7})$alkyl, pyridinyl, pyridine-4-yl, di-phenyl$(C_{1-7})$alkyl, naphthyl$(C_{1-7})$alkyl, pyridyl$(C_{1-7})$alkyl, indolyl$(C_{1-7})$alkyl, 1H-indazolyl$(C_{1-7})$alkyl, quinolyl$(C_{1-7})$alkyl, isoquinolyl$(C_{1-7})$alkyl, 1,2,3,4-tetrahydro-1,4-benzoxazinyl$(C_{1-7})$alkyl, 2H-1,4-benzoxazin-3(4H)-onyl$(C_{1-7})$alkyl, 1-benzothiophenyl$(C_{1-7})$alkyl, phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl, 1-benzothiophenyl, phenylcarbonyl (benzoyl), and naphthylcarbonyl (naphthoyl), wherein each phenyl, naphthyl, pyridyl, indolyl, 1H-indazolyl, quinolyl, isoquinolyl, 1,2,3,4-tetrahydro-1,4-benzoxazinyl, 2H-1,4-benzoxazin-3(4H)-onyl or 1-benzothiophenyl is unsubstituted or substituted by one or more substituents each independently selected from the group consisting of $(C_{1-7})$alkyl, hydroxy$(C_{1-7})$alkyl, $(C_{1-7})$alkoxy$(C_{1-7})$alkyl, $(C_{1-7})$alkoxy $(C_{1-7})$alkoxy$(C_{1-7})$alkyl, $(C_{1-7})$alkanoyloxy$(C_{1-7})$alkyl, amino$(C_{1-7})$alkyl, halo$(C_{1-7})$alkylamino$(C_{1-7})$alkyl, halo $(C_{1-7})$alkanoylamino$(C_{1-7})$alkyl, $(C_{1-7})$alkoxy$(C_{1-7})$alkylamino$(C_{1-7})$alkyl, $(C_{1-7})$alkanoylamino$(C_{1-7})$alkyl, $(C_{1-7})$cycloalkanoylamino$(C_{1-7})$alkyl, $(C_{1-7})$alkylsulfonylamino $(C_{1-7})$alkyl, carboxy$(C_{1-7})$alkyl, $(C_{1-7})$alkoxycarbonyl$(C_{1-7})$alkyl, halo, hydroxy, $(C_{1-7})$alkoxy, hydroxy$(C_{1-7})$alkyloxy, $(C_{1-7})$alkoxy$(C_{1-7})$alkoxy, $(C_{1-7})$alkylaminocarbonyl$(C_{1-7})$alkoxy, amino$(C_{1-7})$alkoxy, N—$(C_{1-7})$alkanoylamino$(C_{1-7})$alkoxy, carboxy$(C_{1-7})$alkyloxy, $(C_{1-7})$alkyloxycarbonyl $(C_{1-7})$alkoxy, carbamoyl$(C_{1-7})$alkoxy, N-mono-$(C_{1-7}$alkyl) carbamoyl$(C_{1-7})$alkyl, N-mono-$(C_{1-7}$alkyl)carbamoyl$(C_{1-7})$alkoxy, N,N-di-$((C_{1-7})$alkyl)carbamoyl$(C_{1-7})$alkoxy, morpholino$(C_{1-7})$alkoxy, pyridyl$(C_{1-7})$alkoxy, amino, $(C_{1-7})$alkanoylamino, $(C_{1-7})$alkanoyl, $(C_{1-7})$alkyloxy$(C_{1-7})$alkanoyl, $(C_{1-7})$alkoxy$(C_{1-7})$alkanoyl, carboxyl, carbamoyl, N—$(C_{1-7})$alkoxy$(C_{1-7})$alkylcarbamoyl, pyrazolyl, pyrazolyl $(C_{1-7})$alkoxy, 4-$(C_{1-7})$alkylpiperidin-1-yl, nitro and cyano, each unsubstituted or substituted.

20. The compound, tautomer or pharmaceutically acceptable salt according to claim 1, wherein $R_2$ is selected from the group consisting of hydrogen, phenyl, pyridinyl, pyridine-4-yl, naphthyl, phenyl$(C_{1-7})$alkyl, di-(phenyl)$(C_{1-7})$alkyl, naphthyl$(C_{1-7})$alkyl, pyridyl$(C_{1-7})$alkyl, indolyl$(C_{1-7})$alkyl, 1H-indazolyl$(C_{1-7})$alkyl, quinolyl$(C_{1-7})$alkyl, isoquinolyl $(C_{1-7})$alkyl, 1-benzothiophenyl$(C_{1-7})$alkyl, and phenylcarbonyl (benzoyl), wherein each phenyl, naphthyl, pyridyl, indolyl, 1H-indazolyl, quinolyl, isoquinolyl or 1-benzothiophenyl is unsubstituted or substituted with one or more substituents each independently selected from the group consisting of $(C_{1-7})$alkyl, hydroxy$(C_{1-7})$alkyl, $(C_{1-7})$alkoxy $(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, amino$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$alkoxy$(C_{1-7})$alkylamino$(C_{1-7})$alkyl, $(C_{1-7})$alkanoylamino$(C_{1-7})$alkyl, $(C_{1-7})$cycloalkanoylamino$(C_{1-7})$alkyl, $(C_{1-7})$alkylsulfonylamino$(C_{1-7})$alkyl, carboxy$(C_{1-7})$alkyl, $(C_{1-7})$alkoxycarbonyl$(C_{1-7})$alkyl, halo, hydroxy, $(C_{1-7})$alkoxy, hydroxy$(C_{1-7})$alkyloxy, $(C_{1-7})$alkoxy$(C_{1-7})$alkoxy, $(C_{1-7})$alkylaminocarbonyl$(C_{1-7})$alkoxy, amino$(C_{1-7})$alkoxy, N—$(C_{1-7})$alkanoylamino$(C_{1-7})$alkoxy, carboxy$(C_{1-7})$alkyloxy, $(C_{1-7})$alkyloxycarbonyl$(C_{1-7})$alkoxy, carbamoyl$(C_{1-7})$alkoxy, N-mono-$(C_{1-7}$alkyl)carbamoyl$(C_{1-7})$alkyl, N-mono-$(C_{1-7}$alkyl)carbamoyl$(C_{1-7})$alkoxy, N,N-di-$((C_{1-7})$alkyl) carbamoyl$(C_{1-7})$alkoxy, morpholino$(C_{1-7})$alkoxy, pyridyl $(C_{1-7})$alkoxy, amino, $(C_{1-7})$alkanoylamino, $(C_{1-7})$alkanoyl, $(C_{1-7})$alkyloxy$(C_{1-7})$alkanoyl, $(C_{1-7})$alkoxy$(C_{1-7})$alkanoyl, carboxyl, carbamoyl, N—$(C_{1-7})$alkoxy$(C_{1-7})$alkylcarbamoyl, pyrazolyl, pyrazolyl$(C_{1-7})$alkoxy, 4-$(C_{1-7})$alkylpiperidin-1-yl, nitro and cyano, each unsubstituted or substituted.

21. The compound, tautomer or pharmaceutically acceptable salt according to claim 5, wherein $L_2$ is absent or is selected from the group consisting of —$(CR_{10}R_{10'})$— and —$(CR_{10}R_{10'})_2$—, wherein $R_{10}$ and $R_{10'}$ are each independently selected from the group consisting of hydrogen, alkyl, aryl, heteroaryl, cycloalkyl, heterocycloalkylalkyl, arylalkyl, heteroarylalkyl, cycloalkylalkyl, and heterocycloalkylalkyl, each unsubstituted or substituted.

22. The compound, tautomer or pharmaceutically acceptable salt according to claim 5, wherein $L_2$ is methylene.

23. The compound, tautomer or pharmaceutically acceptable salt according to claim 5, wherein D is selected from the group consisting of hydrogen, $(C_{4-12})$aryl and hetero$(C_{1-10})$aryl,
wherein
the $(C_{1-10})$heteroaryl contains up to four heteroatoms selected from the group consisting of nitrogen, oxygen and sulfur, and
the $(C_{4-12})$aryl and $(C_{1-10})$heteroaryl may be unsubstituted or substituted with up to four substituents each independently selected from the group consisting of halo, nitro, cyano, carboxyl, carboxamido, amido, carboxamidoalkoxy, carbamoyl, $(C_{1-7})$alkyl, $(C_{1-7})$alkoxy, —$CF_3$, —$OCF_3$, hydroxy-$(C_{1-7})$alkyl, alkoxy $(C_{1-7})$alkyl, alkoxy$(C_{1-7})$alkoxy, alkoxyalkoxyalkyl, aminoalkyl, alkoxyalkylaminoalkyl, alkanoylaminoalkyl, alkoxycarbonylalkyl, hydroxyalkyloxy, alkoxyalkyloxy, aminoalkoxy, alkanoylaminoalkoxy, carboxyalkyoxy, alkyloxycarbonylalkoxy, carbamoylalkoxy, and alkoxyalkylcarbamoyl.

24. The compound, tautomer or pharmaceutically acceptable salt according to claim 5, wherein D is selected from the group consisting of hydrogen, phenyl, pyridyl, pyranyl, pyridazyinyl, pyrimidinyl, pyrazinyl, indolyl, indazolyl, benzimidazolyl, benzothienyl, benzthiazolyl, benzooxazinyl, purinyl, cinnolinyl, phthalazinyl, pteridinyl, naphthyl, 1H-indazolyl, quinolyl, isoquinolyl, quinoxalinyl, and 1-benzothienyl, each unsubstituted or substituted with up to four substituents each independently selected from the group consisting of halo, $(C_{1-7})$alkyl, $(C_{1-7})$alkoxy, alkanoyl, alkylcarbamoyl, alkoxycarbamoyl, $(C_{1-7})$alkoxy$(C_{1-7})$alkyloxy, $(C_{1-7})$alkoxy$(C_{1-7})$alkyloxyalkyl, $(C_{1-7})$alkoxy$(C_{1-7})$alkyl, and halo$(C_{1-7})$alkyl, each further unsubstituted or substituted.

25. The compound, tautomer or pharmaceutically acceptable salt according to claim 5, wherein D is phenyl or pyridyl, unsubstituted or substituted.

26. The compound, tautomer or pharmaceutically acceptable salt according to claim 5, wherein D is phenyl, unsubstituted or substituted.

27. The compound, tautomer or pharmaceutically acceptable salt according to claim 5, wherein D is substituted pyridin-4-yl.

28. The compound, tautomer or pharmaceutically acceptable salt according to claim 25 wherein D is phenyl or pyridinyl, each substituted with 1-4 substituents independently selected from the group consisting of $(C_{1-7})$alkyl, hydroxy $(C_{1-7})$alkyl, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, amino $(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$alkoxy$(C_{1-7})$alkylamino $(C_{1-7})$alkyl, $(C_{1-7})$alkanoylamino$(C_{1-7})$alkyl, $(C_{1-7})$cycloalkanoylamino$(C_{1-7})$alkyl, $(C_{1-7})$alkylsulfonylamino$(C_{1-7})$alkyl, carboxy$(C_{1-7})$alkyl, $(C_{1-7})$alkoxycarbonyl$(C_{1-7})$alkyl, halo, hydroxy, $(C_{1-7})$alkoxy, hydroxy$(C_{1-7})$alkyloxy, $(C_{1-7})$alkoxy$(C_{1-7})$alkoxy, $(C_{1-7})$alkylaminocarbonyl$(C_{1-7})$alkoxy, amino$(C_{1-7})$alkoxy, N—$(C_{1-7})$alkanoylamino$(C_{1-7})$alkoxy, carboxy$(C_{1-7})$alkyloxy, $(C_{1-7})$alkyloxycarbonyl$(C_{1-7})$alkoxy, carbamoyl$(C_{1-7})$alkoxy, N-mono-$(C_{1-7}$alkyl)carbamoyl$(C_{1-7})$alkyl, N-mono-$(C_{1-7}$alkyl)carbamoyl$(C_{1-7})$alkoxy, N,N-di-$((C_{1-7})$alkyl)carbamoyl$(C_{1-7})$alkoxy, morpholino $(C_{1-7})$alkoxy, pyridyl$(C_{1-7})$alkoxy, amino, $(C_{1-7})$alkanoylamino, $(C_{1-7})$alkanoyl, $(C_{1-7})$alkyloxy$(C_{1-7})$alkanoyl, $(C_{1-7})$alkoxy$(C_{1-7})$alkanoyl, carboxyl, carbamoyl, N—$(C_{1-7})$alkoxy$(C_{1-7})$alkylcarbamoyl, pyrazolyl, pyrazolyl$(C_{1-7})$alkoxy, 4-$(C_{1-7})$alkylpiperidin-1-yl, nitro and cyano, each unsubstituted or substituted.

29. The compound, tautomer or pharmaceutically acceptable salt according to claim 25, wherein D is phenyl or pyridinyl, each substituted with 1-4 substituents independently selected from the group consisting of halo, $(C_{1-7})$alkyl, $(C_{1-7})$alkoxy, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$cycloalkanoylamino$(C_{1-7})$alkyl, aminoacyl$(C_{1-7})$alkoxy, and N-mono-$(C_{1-7}$alkyl)carbamoyl$(C_{1-7})$alkyl.

30. The compound, tautomer or pharmaceutically acceptable salt according to claim 25, wherein D is phenyl or pyridinyl, each substituted with 1-4 substituents independently selected from the group consisting of chloro, methyl, methoxyethyl, methoxypropyl, —$(CH_2)_2C(O)NHCH_3$, —$(CH_2)_2OC(O)NHCH_3$, —$(CH_2)NHC(O)CH_2CF_3$, —$(CH_2)NHCHF_2$, —$CH_2NHC(O)$-cyclopropyl, methoxyethoxymethyl, and methoxypropyloxy.

31. The compound, tautomer or pharmaceutically acceptable salt according to claim 5, wherein D is selected from the group consisting of

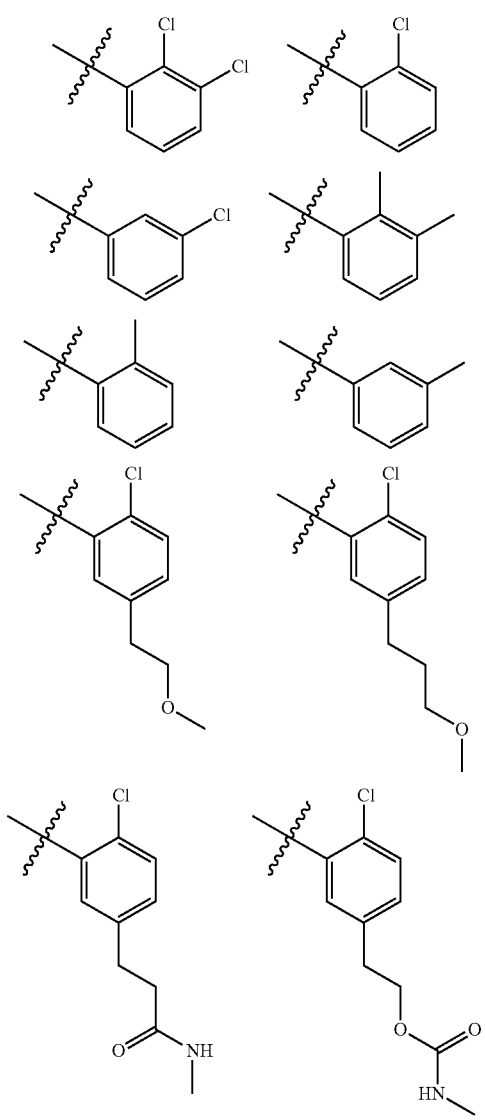

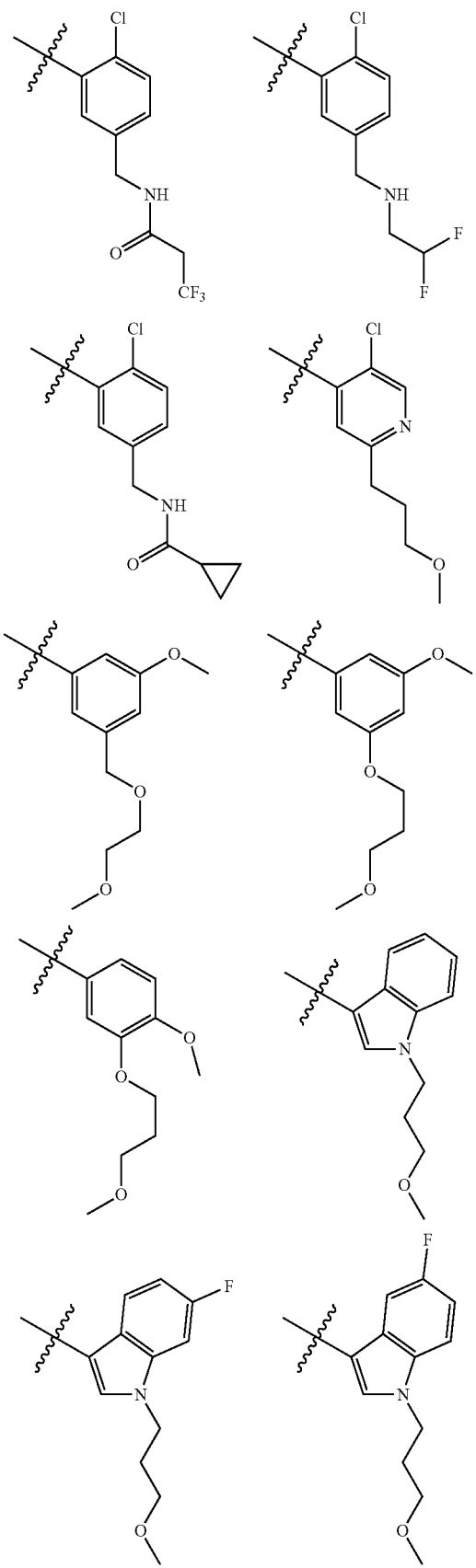

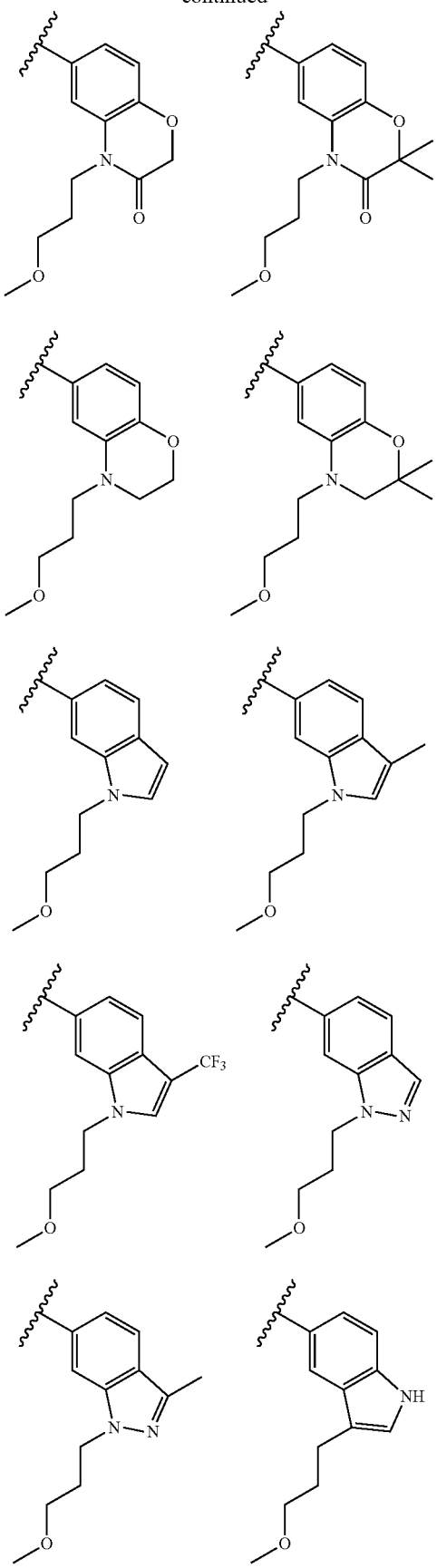

-continued

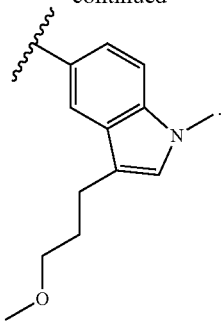

32. The compound, tautomer or pharmaceutically acceptable salt according to claim 1, wherein $R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted.

33. The compound, tautomer or pharmaceutically acceptable salt according to claim 1, wherein $R_1$ is -A-$L_3$-B, wherein A is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted;

B is absent or is selected from the group consisting of hydrogen, $(C_{1-10})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each unsubstituted or substituted; and $L_3$ is absent or is a linker providing 1, 2, 3, 4, 5 or 6 atom separation between A and B to which $L_3$ is attached, wherein the atoms of $L_3$ providing the separation are selected from the group consisting of carbon, oxygen, nitrogen, and sulfur.

34. The compound, tautomer or pharmaceutically acceptable salt according to claim 33, wherein A is an unsubstituted or substituted five, six or seven membered saturated, unsaturated or aromatic cyclic moiety containing optionally up to four heteroatoms each independently selected from the group consisting of nitrogen, oxygen and sulfur.

35. The compound, tautomer or pharmaceutically acceptable salt according to claim 33, wherein A is a five-membered heteroaryl containing optionally up to four heteroatoms each independently selected from the group consisting of nitrogen, oxygen and sulfur, wherein said heteroaryl is unsubstituted or substituted with up to three substituents each independently selected from the group consisting of $(C_{1-7})$alkyl, $(C_{2-7})$alkenyl, $(C_{2-7})$alkynyl, halo, hydroxyl, alkyoxy, mercapto, sulfinyl, sulfonyl, amino, amido, carboxyamido, carboxyl, sulfamoyl, nitro and cyano, each unsubstituted or substituted.

36. The compound, tautomer or pharmaceutically acceptable salt according to claim 33, wherein A is a five-membered heteroaryl containing optionally up to three heteroatoms that are independently selected from the group consisting of nitrogen, oxygen and sulfur, wherein said heteroaryl is unsubstituted or mono-substituted by $(C_{1-7})$alkyl.

37. The compound, tautomer or pharmaceutically acceptable salt according to claim 33, wherein A is a thiazolyl, unsubstituted or substituted.

38. The compound, tautomer or pharmaceutically acceptable salt according to claim 33, wherein A is a six-membered aromatic ring containing optionally up to four nitrogen atoms, and said aromatic ring is unsubstituted or substituted with up to four substituents independently selected from the group consisting of $(C_{1-7})$alkyl, $(C_{2-7})$alkenyl, $(C_{2-7})$alkynyl, halo, hydroxyl, alkoxy, mercapto, sulfinyl, sulfonyl, amino, amido, carboxyamido, carboxyl, sulfamoyl, nitro and cyano, each further unsubstituted or substituted.

39. The compound, tautomer or pharmaceutically acceptable salt according to claim 33, wherein $R_1$ is of the formula

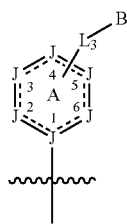

wherein
each J is independently selected from the group consisting of C and N;
$L_3$ is attached to a ring atom at the 3-, 4- or 5-position; and
A is optionally further substituted with up to two other substituents independently selected from the group consisting of $(C_{1-7})$alkyl, $(C_{2-7})$alkenyl, $(C_{2-7})$alkynyl, halo, hydroxyl, alkoxy, mercapto, sulfinyl, sulfonyl, amino, amido, carboxyamido, carboxyl, sulfamoyl, nitro and cyano, each unsubstituted or substituted.

40. The compound, tautomer or pharmaceutically acceptable salt according to claim 39, wherein the atoms of $L_3$ that provide the separation are independently selected from the group consisting of carbon and oxygen.

41. The compound, tautomer or pharmaceutically acceptable salt according to claim 39, wherein $L_3$ is selected from the group consisting of —O—, —$(CH_2)_n$—, —X—$(CH_2)_n$—, —$(CH_2)_n$—X—, —X—$(CH_2)_n$—X—, —$(CH_2)_n$—X—$(CH_2)_n$—, —X—$(CH_2)_n$—X—$(CH_2)_n$— and —$(CH_2)_n$—X—$(CH_2)_n$—X—; X is —O— or —$CH_2$—; and n is 0, 1, 2, 3, 4, 5 or 6.

42. The compound, tautomer or pharmaceutically acceptable salt according to claim 39, wherein $L_3$ is selected from the group consisting of —$(CH_2)_n$—, when n is 1, 2, 3, 4, 5 or 6; —$CH_2CH_2$—; —O—$(CH_2)$; —O—$CH_2CH_2$—; —O—$CH_2CH_2CH_2$—; —$CH_2$—O—; —$CH_2CH_2$—O—; —$CH_2CH_2CH_2$—O—; —O—$CH_2CH_2$—O—; —O—$CH_2CH_2CH_2$—O—; —$CH_2$—O—$CH_2CH_2$—O—; —O—$CH_2CH_2$—O—$CH_2$—; and —O—$CH_2CH_2CH_2$—O—$CH_2$—.

43. The compound, tautomer or pharmaceutically acceptable salt according to claim 39, wherein $L_3$ is selected from the group consisting of —O—$CH_2$—, —O—$CH_2CH_2$—, —$CH_2$—O—, —$CH_2CH_2$—O—, —$CH_2CH_2CH2$-O—, —O—$CH_2CH_2$—O—, and —$CH_2$—O—$CH_2CH_2$—O—.

44. The compound, tautomer or pharmaceutically acceptable salt according to claim 39, wherein $L_3$ is —O—$CH_2CH_2$—O—.

45. The compound, tautomer or pharmaceutically acceptable salt according to claim 39, wherein $L_3$ is —O—.

46. The compound, tautomer or pharmaceutically acceptable salt according to claim 39, wherein $L_3$ is absent.

47. The compound, tautomer or pharmaceutically acceptable salt according to claim 39, wherein B is selected from the group consisting of $(C_{1-7})$alkyl, $(C_{2-7})$alkenyl, $(C_{2-7})$alkynyl, aryl, heteroaryl, cycloalkyl, heterocycloalkyl, halo, hydroxyl, alkoxy, mercapto, sulfinyl, sulfonyl, amino, carboxyl, sulfamoyl, nitro and cyano, each unsubstituted or substituted.

48. The compound, tautomer or pharmaceutically acceptable salt according to claim 39, wherein B is selected from the group consisting of $(C_{1-7})$alkyl, hetero$(C_{1-7})$alkyl, aryl and heteroaryl, each unsubstituted or substituted, wherein said hetero$(C_{1-7})$alkyl and heteroaryl contain heteroatoms that are independently selected from the group consisting of nitrogen, oxygen and sulfur.

49. The compound, tautomer or pharmaceutically acceptable salt according to claim 39, wherein B is a five-membered heteroaryl containing up to four heteroatoms independently selected from the group consisting of nitrogen, oxygen and sulfur, and is unsubstituted or substituted with one or more substituents are independently selected from the group consisting of $(C_{1-7})$alkyl, $(C_{1-7})$alkoxy, —NHC(O)$CH_3$—, —$CF_3$, —$OCF_3$, halogen, and hydroxyl-$(C_{1-7})$alkyl, morpholinyl-alkyloxy, cyano, pyrazolyl, piperazinyl, and aryloxy.

50. The compound, tautomer or pharmaceutically acceptable salt according to claim 39, wherein B is a six-membered aryl or heteroaryl, wherein said heteroaryl optionally contains up to four nitrogen atoms, and said aryl or heteroaryl is unsubstituted or substituted with up to four substituents each independently selected from the group consisting of $(C_{1-7})$alkyl, $(C_{1-7})$alkoxy, —NHC(O)$CH_3$—, —$CF_3$, —$OCF_3$, halogen, hydroxyl-$(C_{1-7})$alkyl, morpholinyl-alkyloxy, cyano, pyrazolyl, piperazinyl, and aryloxy.

51. The compound, tautomer or pharmaceutically acceptable salt according to claim 39, wherein B is phenyl or pyridyl, each unsubstituted or substituted with up to four substituents independently selected from the group consisting of $(C_{1-7})$alkyl, $(C_{1-7})$alkoxy, —NHC(O)$CH_3$—, —$CF_3$, —$OCF_3$, halogen, and hydroxyl-$(C_{1-7})$alkyl.

52. The compound, tautomer or pharmaceutically acceptable salt according to claim 39, wherein B is selected from the group consisting of

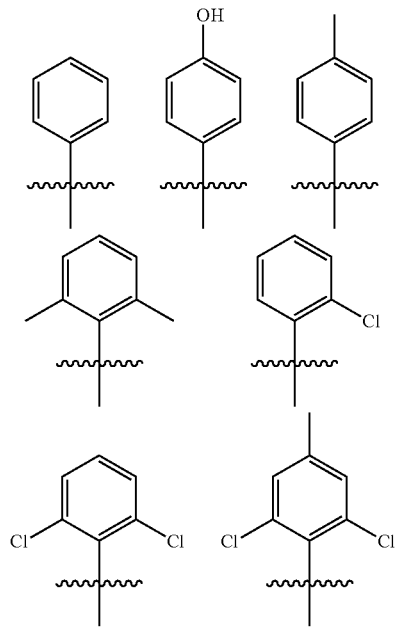

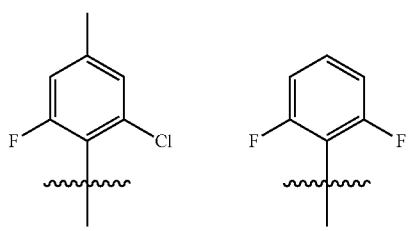
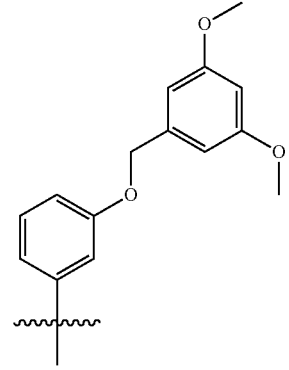
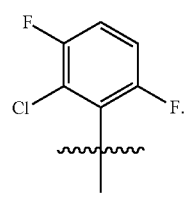
53. The compound, tautomer or pharmaceutically acceptable salt according to claim 39, wherein B is absent.
54. The compound, tautomer or pharmaceutically acceptable salt according to claim 1, wherein $R_1$ is selected from the group consisting of
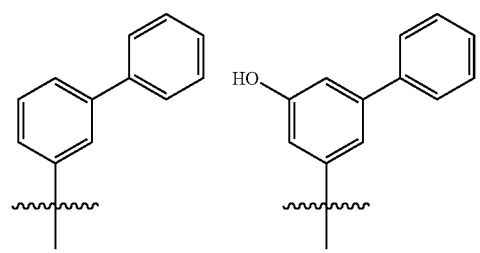
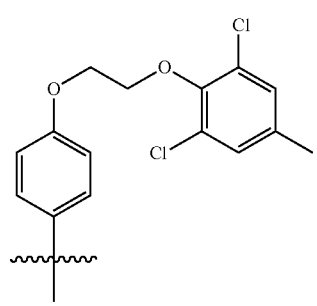
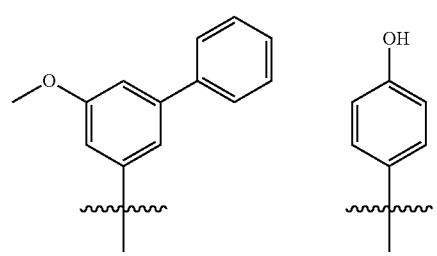
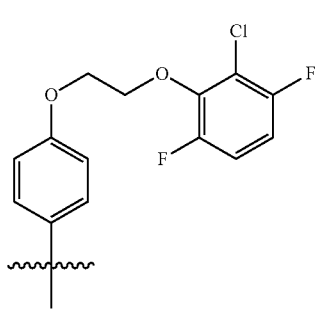
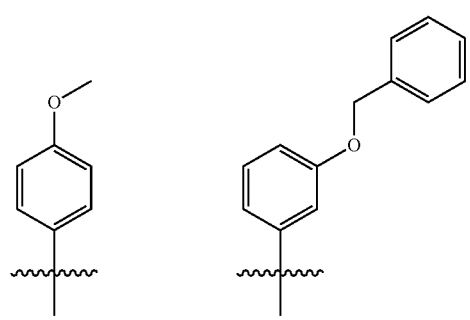
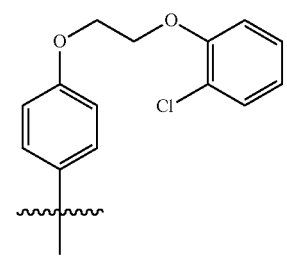
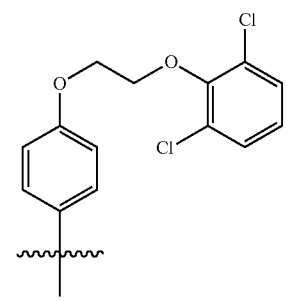

169
-continued

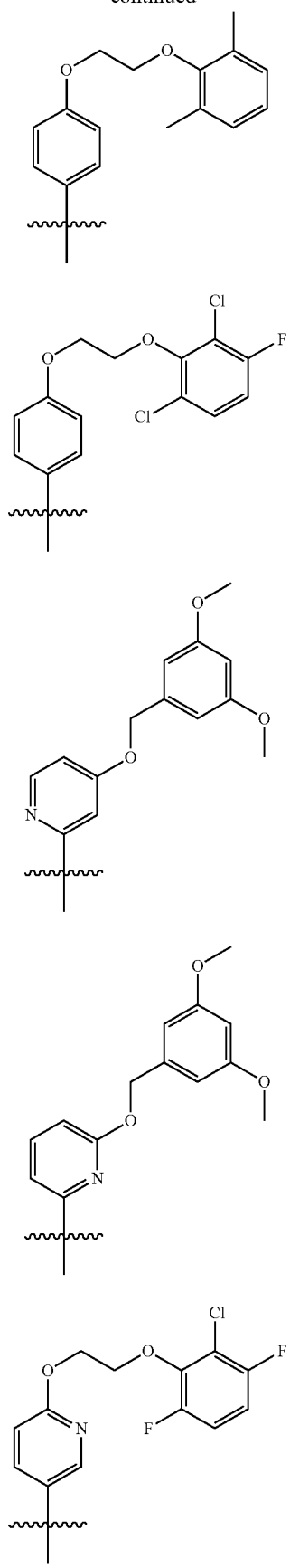

170
-continued

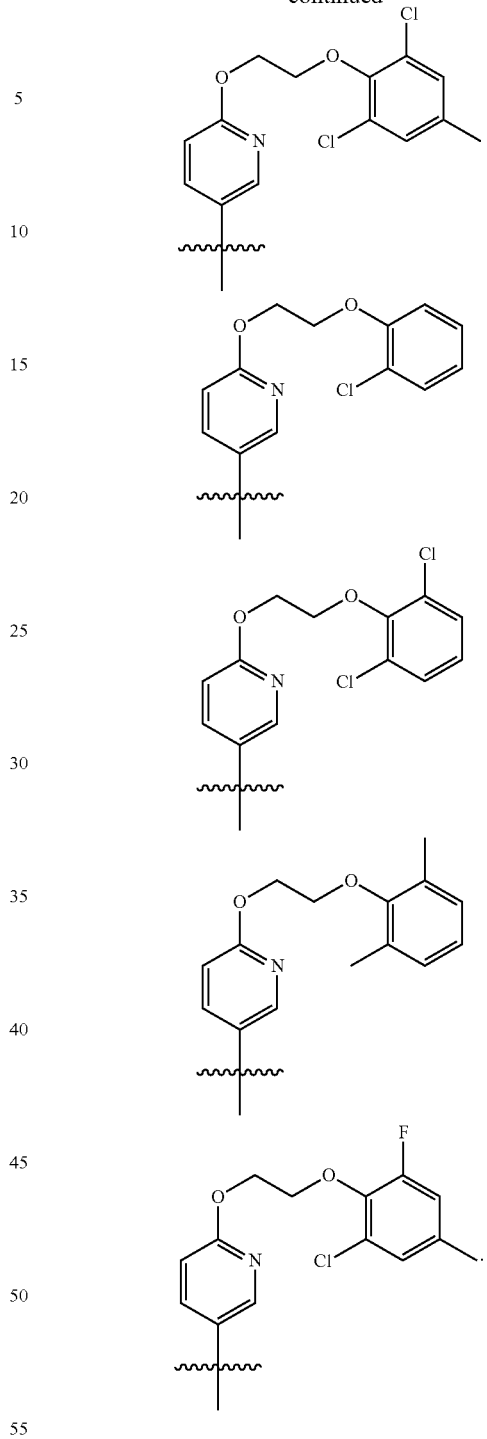

55. The compound, tautomer or pharmaceutically acceptable salt according to claim 1, wherein W is selected from the group consisting of cyano, hydroxy, carbonyloxy, $(C_{1-10})$ alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl $(C_{1-10})$alkyl, aza$(C_{1-10})$alkyl, $(C_{1-10})$oxaalkyl, $(C_{1-10})$ oxoalkyl, and imino$(C_{1-10})$alkyl, each unsubstituted or substituted.

56. The compound, tautomer or pharmaceutically acceptable salt according to claim 1, wherein W is selected from the group consisting of —OR$_7$, —NR$_7$R$_{7'}$, —NHC(O)R$_7$ and —O(CH$_2$)$_n$OR$_7$, wherein R$_7$ and R$_{7'}$ are each independently H or (C$_{1-7}$)alkyl, and n is 1 or 2.

57. The compound, tautomer or pharmaceutically acceptable salt according to claim 1, wherein W is selected from the group consisting of —OH, —OCH$_3$, —NH$_2$, —NHC(O)CH$_3$, —OCH$_2$OH, —OCH$_2$OCH$_3$, —OCH$_2$OCH$_2$CH$_3$, —O(CH$_2$)$_2$OH, —O(CH$_2$)$_2$OCH$_3$, —O(CH$_2$)$_2$OCH$_2$CH$_3$, —OCH$_2$CH(OH)CH$_2$OCH$_3$ and —OCH$_2$CH(OH)CH$_2$OH.

58. A compound having a formula selected from the group consisting of

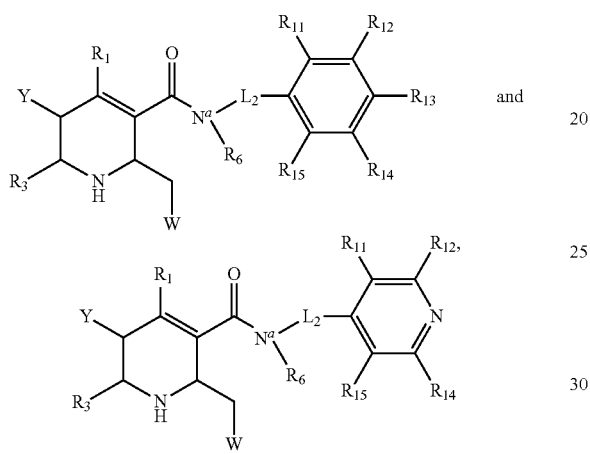

a tautomer thereof or a pharmaceutically acceptable salt of the compound or tautomer,
wherein
N$^a$ is a nitrogen atom;
L$_2$ is absent or is selected from the group consisting of —(CR$_{10}$R$_{10'}$)— and —(CR$_{10}$R$_{10'}$)$_2$—, wherein R$_{10}$ and R$_{10'}$ are each independently selected from the group consisting of hydrogen, alkyl, aryl, heteroaryl, cycloalkyl, heterocycloalkylalkyl, arylalkyl, heteroarylalkyl, cycloalkylalkyl, and heterocycloalkylalkyl, each unsubstituted or substituted;
W is selected from the group consisting of —OR$_7$, —NR$_7$R$_{7'}$, —NHC(O)R$_7$ and —O(CH$_2$)$_n$OR$_7$, wherein R$_7$ and R$_{7'}$ are each independently H or (C$_{1-7}$)alkyl, and n is 1 or 2;
Y is selected from the group consisting of hydrogen, hydroxyl, (C$_{1-7}$)alkyloxy, (C$_{1-7}$)alkoxy(C$_{1-7}$)alkyloxy, alkoxy(C$_{1-7}$)alkyl, (C$_{1-7}$)alkanoylamino, (C$_{1-7}$)alkylsulfonylamino, arylsulfonylamino, hydroxyalkyl, aminoalkyl, (C$_{1-7}$)alkyl, and amino, each unsubstituted or substituted;
R$_1$ is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted;
R$_3$ is selected from the group consisting of hydrogen, (C$_{1-10}$)alkyl, (C$_{1-10}$)azaalkyl, (C$_{1-10}$)oxaalkyl, (C$_{1-10}$)oxoalkyl, hetero(C$_{1-10}$)alkyl, halo(C$_{1-10}$)alkyl, hydroxy(C$_{1-10}$)alkyl, and amino(C$_{1-10}$)alkyl, each unsubstituted or substituted;

R$_6$ is selected from the group consisting of hydrogen, (C$_{1-7}$)alkyl, and cyclo(C$_{3-8}$)alkyl, each unsubstituted or substituted; and
R$_{11}$, R$_{12}$, R$_{13}$, R$_{14}$, and R$_{15}$ are each independently selected from the group consisting of hydrogen, hydroxy, halo, nitro, cyano, (C$_{1-7}$)alkyl, hydroxy(C$_{1-7}$)alkyl, (C$_{1-7}$)alkoxy(C$_{1-7}$)alkyl, (C$_{1-7}$)alkoxy(C$_{1-7}$)alkoxy(C$_{1-7}$)alkyl, (C$_{1-7}$)alkanoyloxy(C$_{1-7}$)alkyl, amino(C$_{1-7}$)alkyl, halo(C$_{1-7}$)alkylamino(C$_{1-7}$)alkyl, halo(C$_{1-7}$)alkanoylamino(C$_{1-7}$)alkyl, (C$_{1-7}$)alkoxy(C$_{1-7}$)alkylamino(C$_{1-7}$)alkyl, (C$_{1-7}$)alkanoylamino(C$_{1-7}$)alkyl, (C$_{1-7}$)cycloalkanoylamino(C$_{1-7}$)alkyl, (C$_{1-7}$)alkylsulfonylamino(C$_{1-7}$)alkyl, carboxy(C$_{1-7}$)alkyl, (C$_{1-7}$)alkoxycarbonyl(C$_{1-7}$)alkyl, (C$_{1-7}$)alkoxy, hydroxy(C$_{1-7}$)alkyloxy, (C$_{1-7}$)alkoxy(C$_{1-7}$)alkoxy, aminoacyl(C$_{1-7}$)alkoxy, amino(C$_{1-7}$)alkoxy, N—(C$_{1-7}$)alkanoylamino(C$_{1-7}$)alkoxy, carboxy(C$_{1-7}$)alkyloxy, (C$_{1-7}$)alkyloxycarbonyl(C$_{1-7}$)alkoxy, carbamoyl(C$_{1-7}$)alkoxy, N-mono-(C$_{1-7}$alkyl)carbamoyl(C$_{1-7}$)alkyl, N-mono-(C$_{1-7}$alkyl)carbamoyl(C$_{1-7}$)alkoxy, N,N-di-((C$_{1-7}$)alkyl)carbamoyl(C$_{1-7}$)alkoxy, morpholino(C$_{1-7}$)alkoxy, pyridyl(C$_{1-7}$)alkoxy, amino, (C$_{1-7}$)alkanoylamino, (C$_{1-7}$)alkanoyl, (C$_{1-7}$)alkyloxy(C$_{1-7}$)alkanoyl, (C$_{1-7}$)alkoxy(C$_{1-7}$)alkanoyl, carboxyl, carbamoyl, N—(C$_{1-7}$)alkoxy(C$_{1-7}$)alkylcarbamoyl, pyrazolyl, pyrazolyl(C$_{1-7}$)alkoxy, and 4-(C$_{1-7}$)alkylpiperidin-1-yl, each unsubstituted or substituted.

59. The compound, tautomer or pharmaceutically acceptable salt according to claim 58, having a formula selected from the group consisting of:

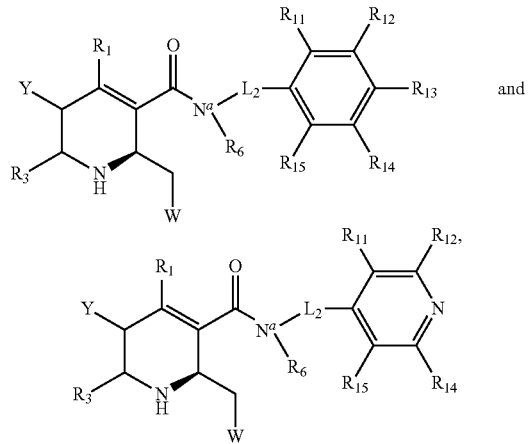

wherein R$_1$, R$_3$, R$_6$, R$_{11}$, R$_{12}$, R$_{13}$, R$_{14}$, R$_{15}$, L$_2$, N$^a$, W, and Y are as defined in claim 58.

60. The compound, tautomer or pharmaceutically acceptable salt according to claim 58, wherein R$_3$ is selected from the group consisting of hydrogen, unsubstituted alkyl, and substituted alkyl.

61. The compound, tautomer or pharmaceutically acceptable salt according to claim 58, wherein R$_3$ is hydrogen.

62. The compound, tautomer or pharmaceutically acceptable salt according to claim 58, wherein R$_6$ when present is isopropyl, propyl, isobutyl, cyclopropyl, ethyl, —CH$_2$CH$_2$F, —CH$_2$CHF$_2$ and —CH$_2$CF$_3$.

63. The compound, tautomer or pharmaceutically acceptable salt according to claim 58, wherein R$_6$ is cyclopropyl.

64. The compound, tautomer or pharmaceutically acceptable salt according to claim 58, wherein Y is selected from the group consisting of H, —OH, —NH$_2$, —CH$_2$OH, —CH$_2$OCH$_3$, —NHC(O)CH$_3$, —CH$_2$CH(OH)CH$_2$OH, —CH$_2$CH(OH)CH$_2$OCH$_3$, —OCH$_2$CH(OH)CH$_2$OCH$_3$, and —OCH$_2$CH(OH)CH$_2$OH.

65. The compound, tautomer or pharmaceutically acceptable salt according to claim 58, wherein W is selected from the group consisting of —OH, —OCH$_3$, —NH$_2$, —NHC(O)CH$_3$, —OCH$_2$OH, —OCH$_2$OCH$_3$, —OCH$_2$OCH$_2$CH$_3$, —O(CH$_2$)$_2$OH, —O(CH$_2$)$_2$OCH$_3$, —O(CH$_2$)$_2$OCH$_2$CH$_3$, —OCH$_2$CH(OH)CH$_2$OCH$_3$ and —OCH$_2$CH(OH)CH$_2$OH.

66. The compound, tautomer or pharmaceutically acceptable salt according to claim 58, wherein W is —OH, —OCH$_3$, or —NH$_2$.

67. The compound, tautomer or pharmaceutically acceptable salt according to claim 58, wherein R$_1$ is -A-L$_3$-B, wherein
- A is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted;
- B is absent or is selected from the group consisting of hydrogen, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted; and
- L$_3$ is absent or is a linker providing 1, 2, 3, 4, 5 or 6 atom separation between A and B to which L$_3$ is attached, wherein the atoms of L$_3$ providing the separation are selected from the group consisting of carbon, oxygen, nitrogen, and sulfur.

68. The compound, tautomer or pharmaceutically acceptable salt according to claim 67, wherein A is a five-membered heteroaryl containing up to three heteroatoms that are independently selected from the group consisting of nitrogen, oxygen and sulfur, wherein said heteroaryl is unsubstituted or mono-substituted by (C$_{1-7}$)alkyl.

69. The compound, tautomer or pharmaceutically acceptable salt according to claim 67, wherein A is a thiazolyl.

70. The compound, tautomer or pharmaceutically acceptable salt according to claim 58, wherein R$_1$ is of the formula

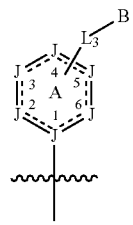

wherein
- each J is independently selected from the group consisting of C and N;
- L$_3$ is absent or is a linker attached to a ring atom of A at the 3-, 4- or 5-position and providing 1, 2, 3, 4, 5 or 6 atom separation between A and B to which L$_3$ is also attached, wherein the atoms of L$_3$ providing the separation are independently selected from the group consisting of carbon, oxygen, nitrogen, and sulfur;
- A is optionally further substituted with up to two other substituents independently selected from the group consisting of (C$_{1-7}$)alkyl, (C$_{2-7}$)alkenyl, (C$_{2-7}$)alkynyl, halo, hydroxyl, alkoxy, mercapto, sulfinyl, sulfonyl, amino, amido, carboxyamido, carboxyl, sulfamoyl, nitro and cyano, each unsubstituted or substituted; and
- B is absent or is selected from the group consisting of hydrogen, (C$_{1-10}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each unsubstituted or substituted.

71. The compound, tautomer or pharmaceutically acceptable salt according to claim 58, wherein R$_1$ is selected from the group consisting of

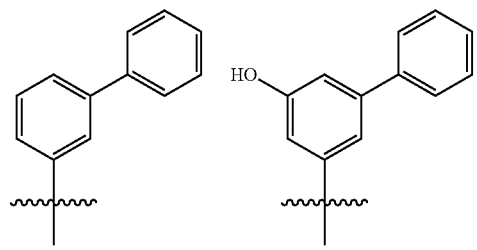

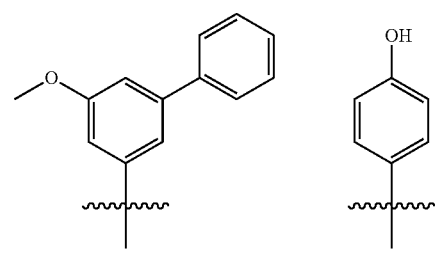

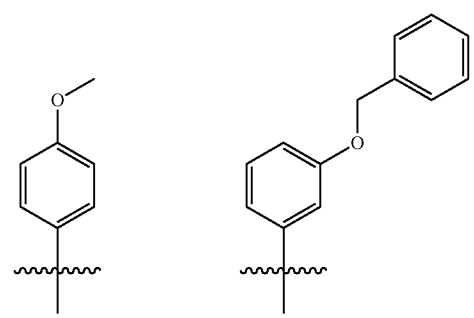

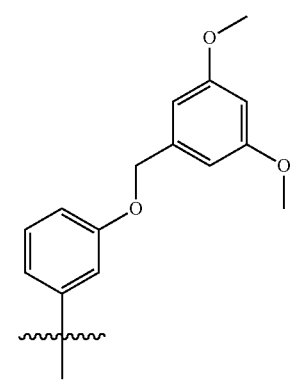

175
-continued
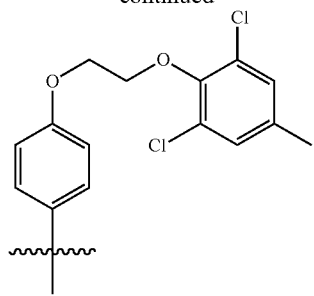
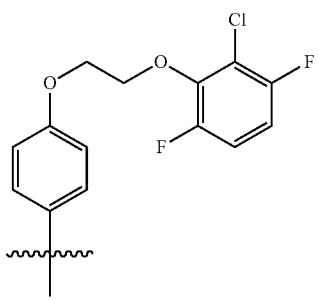
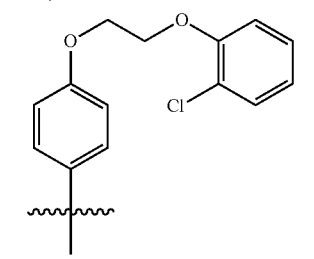
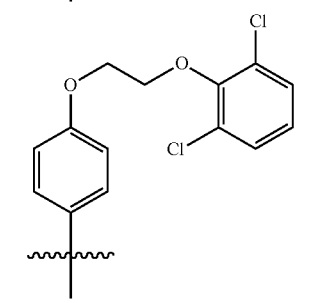
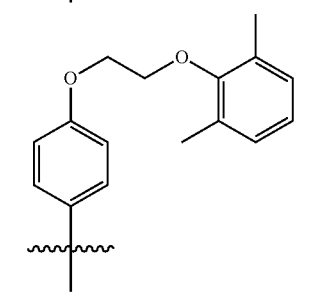
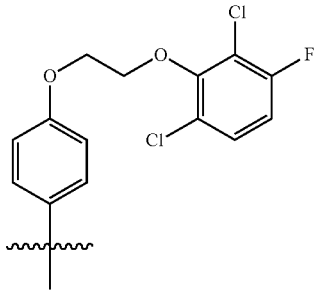
176
-continued
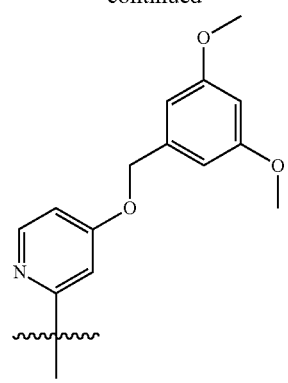
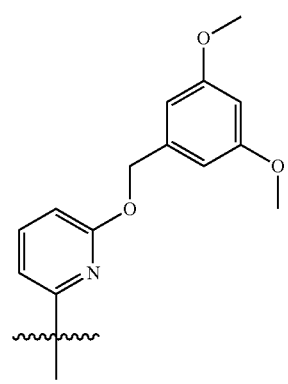
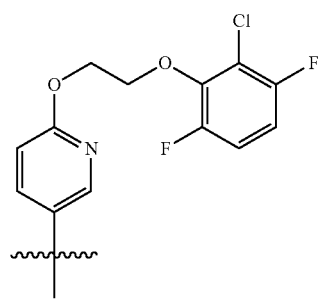
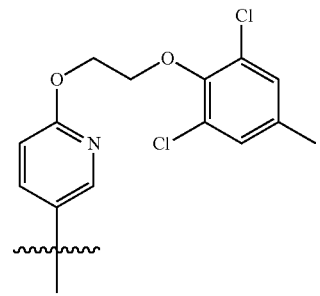
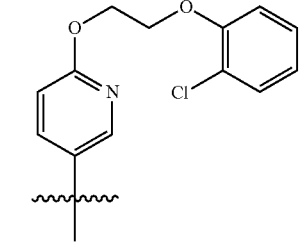

-continued

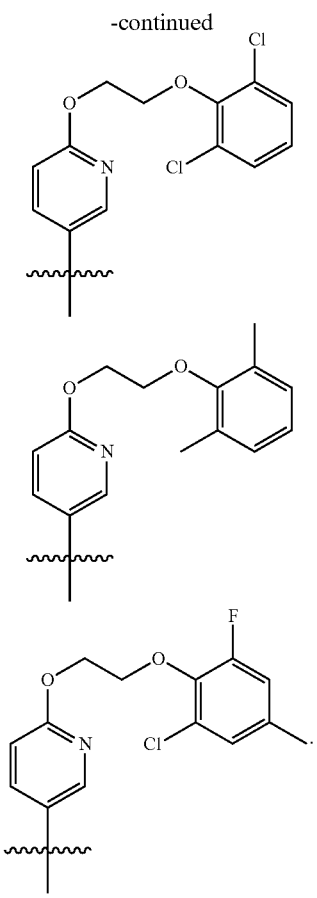

72. The compound, tautomer or pharmaceutically acceptable salt according to claim 58, wherein $L_2$ is methylene.

73. The compound, tautomer or pharmaceutically acceptable salt according to claim 58, wherein $R_{11}$, $R_{12}$, $R_{13}$, $R_{14}$, and $R_{15}$ are each independently selected from the group consisting of hydrogen, halo, $(C_{1-7})$alkyl, $(C_{1-7})$alkoxy, $(C_{1-7})$alkoxy$(C_{1-7})$alkyl, $(C_{1-7})$alkoxy$(C_{1-7})$alkoxy$(C_{1-7})$alkyl, $(C_{1-7})$alkanoyloxy$(C_{1-7})$alkyl, halo$(C_{1-7})$alkylamino$(C_{1-7})$alkyl, halo$(C_{1-7})$alkanoylamino$(C_{1-7})$alkyl, $(C_{1-7})$cycloalkanoylamino$(C_{1-7})$alkyl, aminoacyl$(C_{1-7})$alkoxy, and N-mono-$(C_{1-7}$alkyl)carbamoyl$(C_{1-7})$alkyl.

74. The compound, tautomer or pharmaceutically acceptable salt according to claim 58, wherein $R_{11}$, $R_{12}$, $R_{13}$, $R_{14}$, and $R_{15}$ are each independently selected from the group consisting of chloro, methyl, methoxyethyl, methoxypropyl, —$(CH_2)_2C(O)NHCH_3$, —$(CH_2)_2OC(O)NHCH_3$, —$(CH_2)NHC(O)CH_2CF_3$, —$(CH_2)NHCHF_2$, —$CH_2NHC(O)$-cyclopropyl, methoxyethoxymethyl, and methoxypropyloxy.

75. A compound selected from the group consisting of:
4-(Biphenyl-3-yl)-N-cyclopropyl-N-(2,3-dichlorobenzyl)-2-(hydroxymethyl)-1,2,5,6-tetrahydropyridine-3-carboxamide;
4-(4-(2-(2-Chlorophenoxy)ethoxy)phenyl)-N-cyclopropyl-N-(2,3-dichlorobenzyl)-2-(hydroxymethyl)-1,2,5,6-tetrahydropyridine-3-carboxamide;
N-(3-Chlorobenzyl)-N-cyclopropyl-4-(4-(2-(2,6-dichlorophenoxy)ethoxy)phenyl)-2-(hydroxymethyl)-1,2,5,6-tetrahydropyridine-3-carboxamide;
(S)-4-(Biphenyl-3-yl)-N-cyclopropyl-N-(2,3-dichlorobenzyl)-2-((methoxymethoxy)methyl)-1,2,5,6-tetrahydropyridine-3-carboxamide;
(S)-N-Cyclopropyl-N-(2,3-dichlorobenzyl)-4-(4-(2-(2,6-dichlorophenoxy)ethoxy)phenyl)-2-((methoxymethoxy)methyl)-1,2,5,6-tetrahydropyridine-3-carboxamide;
(S)-N-Cyclopropyl-N-(2,3-dichlorobenzyl)-4-(4-(2-(2,6-dichlorophenoxy)ethoxy)phenyl)-2-(hydroxymethyl)-1,2,5,6-tetrahydropyridine-3-carboxamide;
2-Cyclopropyl-3-(2,3-dichlorophenyl)-1-((S)-4-(4-(2-(2,6-dimethylphenoxy)ethoxy)phenyl)-2-(hydroxymethyl)-1,2,5,6-tetrahydropyridin-3-yl)propan-1-one;
(S)-N-Cyclopropyl-N-(2,3-dichlorobenzyl)-4-(4-(2-(2,6-dimethylphenoxy)ethoxy)phenyl)-2-((methoxymethoxy)methyl)-1,2,5,6-tetrahydropyridine-3-carboxamide;
(S)-N-Cyclopropyl-4-(4-(2-(2,6-dichloro-4-methylphenoxy)ethoxy)phenyl)-N-(2,3-dichlorobenzyl)-2-(hydroxymethyl)-1,2,5,6-tetrahydropyridine-3-carboxamide;
(S)-N-Cyclopropyl-4-(4-(2-(2,6-dichloro-4-methylphenoxy)ethoxy)phenyl)-N-(2,3-dichlorobenzyl)-2-((methoxymethoxy)methyl)-1,2,5,6-tetrahydropyridine-3-carboxamide;
(S)-4-(4-(2-(2-Chloro-3,6-difluorophenoxy)ethoxy)phenyl)-N-cyclopropyl-N-(2,3-dichlorobenzyl)-2-(hydroxymethyl)-1,2,5,6-tetrahydropyridine-3-carboxamide;
(S)-N-Cyclopropyl-N-(2,3-dichlorobenzyl)-2-(hydroxymethyl)-4-(4-hydroxyphenyl)-1,2,5,6-tetrahydropyridine-3-carboxamide;
(S)-N-Cyclopropyl-N-(2,3-dichlorobenzyl)-2-(hydroxymethyl)-4-(4-methoxyphenyl)-1,2,5,6-tetrahydropyridine-3-carboxamide;
(S)-2-(Aminomethyl)-N-cyclopropyl-N-(2,3-dichlorobenzyl)-4-(4-(2-(2,6-dichlorophenoxy)ethoxy)phenyl)-1,2,5,6-tetrahydropyridine-3-carboxamide; and
(S)-N-((5-chloro-2-(3-methoxypropyl)pyridin-4-yl)methyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-((5-chloro-2-(3-methoxypropyl)pyridin-4-yl)methyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;
(S)-N-((5-chloro-2-(3-methoxypropyl)pyridin-4-yl)methyl)-N-cyclopropyl-4-(4-(2-(2,6-dichlorophenoxy)ethoxy)phenyl)-2-(hydroxymethyl)-1,2,5,6-tetrahydropyridine-3-carboxamide;
(S)-N-((5-chloro-2-(3-methoxypropyl)pyridin-4-yl)methyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;
(S)-N-((5-chloro-2-(3-methoxypropyl)pyridin-4-yl)methyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;
(S)-N-((5-chloro-2-(3-methoxypropyl)pyridin-4-yl)methyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;
(S)-N-(2-chloro-5-(3-methoxypropyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;
(S)-N-(2-chloro-5-(3-methoxypropyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;

(S)-N-(2-chloro-5-(3-methoxypropyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-(2-chloro-5-(3-methoxypropyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-(2-chloro-5-(3-methoxypropyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-(2-chloro-5-(3-methoxypropyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;

(S)-N-(2-chloro-5-(2-methoxyethyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;

(S)-N-(2-chloro-5-(2-methoxyethyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;

(S)-N-(2-chloro-5-(2-methoxyethyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-(2-chloro-5-(2-methoxyethyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-(2-chloro-5-(2-methoxyethyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-(2-chloro-5-(2-methoxyethyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;

(S)-N-(2-chloro-5-(cyclopropanecarboxamidomethyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;

(S)-N-(2-chloro-5-(cyclopropanecarboxamidomethyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;

(S)-N-(2-chloro-5-(cyclopropanecarboxamidomethyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-(2-chloro-5-(cyclopropanecarboxamidomethyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-(2-chloro-5-(cyclopropanecarboxamidomethyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-(2-chloro-5-(cyclopropanecarboxamidomethyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;

(S)-N-(2-chloro-5-((3,3,3-trifluoropropanamido)methyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;

(S)-N-(2-chloro-5-((3,3,3-trifluoropropanamido)methyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;

(S)-N-(2-chloro-5-((3,3,3-trifluoropropanamido)methyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-(2-chloro-5-((3,3,3-trifluoropropanamido)methyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-(2-chloro-5-((3,3,3-trifluoropropanamido)methyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-(2-chloro-5-((3,3,3-trifluoropropanamido)methyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;

(S)-N-(2-chloro-5-((2,2-difluoroethylamino)methyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;

(S)-N-(2-chloro-5-((2,2-difluoroethylamino)methyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;

(S)-N-(2-chloro-5-((2,2-difluoroethylamino)methyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-(2-chloro-5-((2,2-difluoroethylamino)methyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-(2-chloro-5-((2,2-difluoroethylamino)methyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-(2-chloro-5-((2,2-difluoroethylamino)methyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dimethylphenoxy)ethoxy)phenyl)-2-(hydroxymethyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dimethylphenoxy)ethoxy)phenyl)-2-((methoxymethoxy)methyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dichlorophenoxy)ethoxy)phenyl)-2-(hydroxymethyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dichlorophenoxy)ethoxy)phenyl)-2-((methoxymethoxy)methyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dichloro-4-methylphenoxy)ethoxy)phenyl)-2-(hydroxymethyl)-1,2,5,6-tetrahydropyridine-3-carboxamide;

(S)-N-(2-chloro-5-(3-(methylamino)-3-oxopropyl)benzyl)-N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamide;

(S)-4-chloro-3-((N-cyclopropyl-4-(4-(2-(2,6-dimethylphenoxy)ethoxy)phenyl)-2-(hydroxymethyl)-1,2,5,6-tetrahydropyridine-3-carboxamido)methyl)phenethyl methylcarbamate;

(S)-4-chloro-3-((N-cyclopropyl-4-(4-(2-(2,6-dimethylphenoxy)ethoxy)phenyl)-2-((methoxymethoxy)methyl)-1,2,5,6-tetrahydropyridine-3-carboxamido)methyl)phenethyl methylcarbamate;

(S)-4-chloro-3-((N-cyclopropyl-4-(4-(2-(2,6-dichlorophenoxy)ethoxy)phenyl)-2-(hydroxymethyl)-1,2,5,6-tetrahydropyridine-3-carboxamido)methyl)phenethyl methylcarbamate;

(S)-4-chloro-3-((N-cyclopropyl-4-(4-(2-(2,6-dichlorophenoxy)ethoxy)phenyl)-2-((methoxymethoxy)methyl)-1,2,5,6-tetrahydropyridine-3-carboxamido)methyl)phenethyl methylcarbamate;

(S)-4-chloro-3-((N-cyclopropyl-4-(4-(2-(2,6-dichloro-4-methylphenoxy)ethoxy)phenyl)-2-(hydroxymethyl)-1,2,5,6-tetrahydropyridine-3-carboxamido)methyl)phenethyl methylcarbamate;

(S)-4-chloro-3-((N-cyclopropyl-4-(4-(2-(2,6-dichloro-4-methylphenoxy)ethoxy)phenyl)-2-((methoxymethoxy)methyl)-1,2,5,6-tetrahydropyridine-3-carboxamido)methyl)phenethyl methylcarbamate;

a tautomer of any one of the aforementioned compounds;

a stereoisomer of any one of the aforementioned compounds or tautomer; and a pharmaceutically acceptable salt of any one of the aforementioned compounds, tautomer or stereoisomer.

76. The compound, tautomer or pharmaceutically acceptable salt according to claim 1, wherein the compound is in the form of a pharmaceutically acceptable salt.

77. The compound, tautomer or pharmaceutically acceptable salt according to claim 1, wherein the compound is present in a mixture of stereoisomers.

78. The compound, tautomer or pharmaceutically acceptable salt according to claim 1, wherein the compound is a single stereoisomer.

79. A pharmaceutical composition comprising a compound, tautomer or pharmaceutically acceptable salt as defined in claim 1, and a pharmaceutically acceptable excipient.

80. A kit comprising:
a compound, tautomer or pharmaceutically acceptable salt as defined in claim 1; and
instructions comprising information about a disease state for which the compound is to be administered.

81. A method of treating a disease state in a subject, the method comprising administering to the subject a therapeutically effective amount of a compound, tautomer, stereoisomer or pharmaceutically acceptable salt as defined in claim 1, wherein the disease state is selected from the group consisting of hypertension, congestive heart failure, and myocardial infarction.

* * * * *